United States Patent [19]

MacDonald et al.

[11] Patent Number: 5,693,757
[45] Date of Patent: Dec. 2, 1997

[54] HUNTINGTIN DNA, PROTEIN AND USES THEREOF

[75] Inventors: Marcy E. MacDonald, Lexington; Christine M. Ambrose, Charlestown; Mabel P. Duyao, Cambridge; James F. Gusella, Framingham, all of Mass.

[73] Assignee: The General Hospital Corporation, Boston, Mass.

[21] Appl. No.: 453,265

[22] Filed: May 30, 1995

Related U.S. Application Data

[60] Division of Ser. No. 246,982, May 20, 1994, which is a continuation-in-part of Ser. No. 85,000, Jul. 1, 1993, abandoned, which is a continuation-in-part of Ser. No. 27,498, Mar. 5, 1993, abandoned.

[51] Int. Cl.$^6$ .............................. C07K 1/00; C12P 21/06; C12N 1/20; C12N 15/00
[52] U.S. Cl. ............... 530/350; 435/69.1; 435/252.3; 435/320.1
[58] Field of Search ............... 435/69.1, 320.1, 435/252.3; 530/350

[56] References Cited

U.S. PATENT DOCUMENTS

| | | | |
|---|---|---|---|
| 4,666,828 | 5/1987 | Gusella | 435/6 |
| 5,534,438 | 7/1996 | Hayden et al. | 435/320.1 |

OTHER PUBLICATIONS

Dodé, C., et al., "Huntington's Disease in French Families: CAG Repeat Expansion and Linkage Disequilibrium Analysis," *C.R. Acad. Sci. Paris III* 316(11):1374–1380 (Nov. 1993).

Laurent, B.C., et al., "The SNF5 Protein of *Saccharomyces cerevisiae* Is a Glutamine–and Proline–Rich Transcriptional Activator That Affects Expression of a Broad Spectrun of Genes," *Mol. Cell. Biol.* 10(11):5616–5625 (Nov. 1990).

Riess, O., et al., "Improved PCR Conditions for the Stretch of (CAG)$_n$ Repeats Causing Huntington's Disease," *Hum. Mol. Genet.* 2(6):637 (Jun. 1993).

Warner, J.P., et al., "A New Polymerase Chain Reaction (PCR) Assay for the Trinucleotide Repeat That is Unstable and Expanded on Huntington's Disease Chromosomes," *Mol. Cell. Probes* 7(3):235–239 (Jun. 1993).

A copy of the European Search Report for corresponding European Patent Application No. EP 94301587, EPO Publication No. 0 614 977.

Allitto, B.A. et al., "Increased recombination adjacent to the Huntington disease–linked D4S10 marker," *Genomics* 9:104–112 (1991).

Altherr, M.R. et al., "Radiation hybrid map spanning the Huntington disease gene region of chromosome 4," *Genomics* 13:1040–1046 (1992).

Altschul, S.F. et al., "Basic local alignment search tool," *J. Mol. Biol.* 215:403–410 (1990).

Ambrose, C. et al., "A novel G protein–coupled receptor kinase gene cloned from 4p16.3," *Hum. Mol. Genet.* 1(9):697–703 (1992).

Anderson, M.A. and Gusella, J.F., "Use of cyclosporin A in establishing Epstein–Barr virus–transformed human lymphoblastoid cell lines," *In Vitro* 20(11):856–858 (Nov. 1984).

Andrew, S.E. et al., "The relationship between trinucleotide (CAG) repeat length and clinical features of Huntington's Disease," *Nature Genet.* 4:398–403 (Aug. 1993).

Ashizawa, T. and Epstein, H.F., "Ethnic distribution of myotonic dystrophy gene," *Lancet* 338:642–643 (Sep. 7, 1991).

Aslanidis, C. et al., "Cloning of the essential myotonic dystrophy region and mapping of the putative defect," *Nature* 355:548–551 (Feb. 6, 1992).

Bates, G.P. et al., "Defined physical limits of the Huntington disease gene candidate region," *Am. J. Hum. Genet.* 49:7–16 (1991).

Bates, G.P. et al., "Characterization of a yeast artificial chromosome contig spanning the Huntington's disease gene candidate region," *Nature Genet.* 1:180–187 (Jun. 1992).

Bates, G.P. et al., "A yeast artificial chromosome telomere clone spanning a possible location of the Huntington disease gene," *Am. J. Hum. Genet.* 46:762–775 (1990).

Baxendale, S. et al., "The direct screening of cosmid libraries with YAC clones," *Nucleic Acids Res.* 19(23):6651 (1991).

Biancalana, V. et al., "Moderate instability of the trinucleotide repeat in spino bulbar muscular atrophy," *Hum. Mol. Genet.* 1(4):255–258 (1992).

Brook, J.D. et al., "Molecular basis of myotonic dystrophy: expansion of a trinucleotide (CTG) repeat at the 3' end of a transcript encoding a protein kinase family member," *Cell* 68:799–808 (Feb. 21, 1992).

Brunner, H.G. et al., "Brief report: reverse mutation in myotonic dystrophy," *N. Engl. J. Med.* 328:476–480 (Feb. 18, 1993).

Bucan, M. et al., "Physical maps of 4p16.3, the area expected to contain the Huntington disease mutation," *Genomics* 6:1–15 (1990).

Buckler, A.J. et al., "Exon amplification: a strategy to isolate mammalian genes based on RNA splicing," *Proc. Natl. Acad. Sci. USA* 88:4005–4009 (May 1991).

Buxton, J. et al., "Detection of an unstable fragment of DNA specific to individuals with myotonic dystrophy," *Nature* 355:547–548 (Feb. 6, 1992).

Cheng, S.V. et al., "Synteny on Mouse Chromosome 5 of Homologs for Human DNA Loci Linked to the Huntington Disease Gene," *Genomics* 5:304–308 (1989).

(List continued on next page.)

*Primary Examiner*—Robert A. Wax
*Assistant Examiner*—Tekchand Saidha
*Attorney, Agent, or Firm*—Sterne, Kessler, Goldstein & Fox PLLC

[57] ABSTRACT

A novel gene, huntingtin, is described, encoding huntingtin protein, recombinant vectors and hosts capable of expressing huntingtin. Methods for the diagnosis and treatment of Huntington's disease are also provided.

2 Claims, 50 Drawing Sheets

OTHER PUBLICATIONS

Conneally, P.M. et al., "Huntington disease: no evidence for locus heterogeneity," *Genomics* 5:304–308 (1989).

Daly, C.B., "Genetic cause is identified for Huntington's disease," *The Washington Post*, Mar. 24, 1993.

DeBoulle, K. et al., "A point mutation in the FMR-1 gene associated with fragile X mental retardation," *Nature Genet.* 3:31–35 (Jan. 1993).

Doucette-Stamm, L.A. et al., "Generation and characterization of irradiation hybrids of human chromosome 4," *Somat. Cell Mol. Genet.* 17(5):471–480 (1991).

Duyao, M. et al., "Trinucleotide repeat length instability and age of onset in Huntington's Disease," *Nature Genet.* 4:387–392 (Aug. 1993).

Fu Y.H. et al., "An unstable triplet repeat in a gene related to myotonic muscular dystrophy," *Science* 255:1256–1259 (Mar. 6, 1992).

Fu, Y.H. et al., "Variation of the CGG repeat at the fragile X site results in genetic instability: resolution of the Sherman paradox," *Cell* 67:1047–1058 (Dec. 20, 1991).

Goldberg, Y.P. et al., "Identification of an Alu retrotransposition event in close proximity to a strong candidate gene for Huntington's disease," *Nature* 362:370–373 (Mar. 25, 1993).

Goodfellow, P.N., "Planting alfalfa and cloning the Huntington's disease gene," *Cell* 72:817–818 (Mar. 26, 1993).

Gusella, J.F., "Chapter 3—Huntington's disease," *Adv. Hum. Genet.* 20:125–151 (1991).

Gusella, J.F., "Location cloning strategy for characterizing genetic defects in Huntington's disease and Alzheimer's disease," *FASEB J.* 3:2036–2041 (1989).

Gusella, J.F. and MacDonald, M.E., "Hunting for Huntington's Disease," in: Molecular Genetic Medicine, vol. 3 Academic Press, Inc., San Diego, CA, pp. 139–158 (Aug. 1993).

Gusella, J.F. et al. "DNA markers for nervous system diseases," *Science* 225:1320–1326 (Sep. 21, 1984).

Gusella, J.F. et al., "A polymorphic DNA marker genetically linked to Huntington's disease," *Nature* 306:234–238 (Nov. 17, 1983).

Gusella, J.F. et al., "Precise localization of human β–globin gene complex on chromosome 11," *Proc. Natl. Acad. Sci. USA* 76(10):5239–5243 (Oct. 1979).

Harley, H.G. et al., "Detection of linkage disequilibrium between the myotonic dystrophy and a new polymorphic DNA marker," *Am. J. Hum. Genet.* 49:68–75 (1991).

Harley, H.G. et al., "Expansion of an unstable DNA region and phenotypic variation in myotonic dystrophy," *Nature* 355:545–546 (Feb. 6, 1992).

Harley, H.G. et al., "Unstable DNA sequence in myotonic dystrophy," *Lancet* 339:1125–1128 (May 9, 1992).

Harper, P.S., "The epidemiology of Huntington's disease," *Hum. Genet.* 89:365–376 (1992).

Hoogeveen, A.T. et al., "Characterization and localization of the Huntington disease gene product," *Hum. Mol. Genet.* 2(12):2069–2073 (Dec. 1993).

Jerome, R., "Huntington's cornered," *The Sciences*, p. 7 (May/Jun. 1993).

Kremer, E.J. et al., "Mapping of DNA instability at the fragile X to a trinucleotide repeat sequence p(CCG)n," *Science* 252:1711–1714 (Jun. 21, 1991).

LaSpada, A.R. et al., "Androgen receptor gene mutations in X–linked spinal and bulbar muscular atrophy," *Nature* 352:77–79 (Jul. 4, 1991).

Lin, B. et al., "Differential 3' polyadenylation of the Huntington disease gene results in two mRNA species with variable tissue expression," *Hum. Mol. Genet.* 2(10):1541–1545 (Oct. 1993).

Lin, B. et al., "Sequence of the murine Huntington disease gene: evidence for conservation, and polymorphism in a triplet (CCG) repeat alternate splicing," *Hum. Mol. Genet.* 3(1):85–92 (1994).

Lin, C.S. et al., "New DNA markers in the Huntington's disease gene candidate region," *Somat. Cell Mol. Genet.* 17(5):481–488 (1991).

Little, P. "The end of the beginning," *Nature* 362:408–409 (Apr. 1, 1993).

MacDonald, M.E. et al., "Clustering of multiallele DNA markers near the Huntington's disease gene," *J. Clin. Inv.* 84:1013–1016 (Sep. 1989).

MacDonald, M.E. et al., "Complex patterns of linkage disequilibrium in the Huntington disease region," *Am. J. Hum. Genet.* 49:723–734 (1991).

MacDonald, M.E. et al., "Gametic but not somatic instability of CAG repeat length in Huntington's disease," *J. Med. Genet.* 30(12):982–986 (Dec. 1993).

MacDonald, M.E. et al., "The Huntington's disease candidate region exhibits many different haplotypes," *Nature Genet.* 1:99–103 (May 1992).

MacDonald, M.E. et al., "A Novel Gene Containing a Trinucleotide Repeat that is Expanded and Unstable on Huntington's Disease Chromosomes," *Cell* 72:971–983 (Mar. 26, 1993).

MacDonald, M.E et al., "Recombination events suggest potential sites for the Huntington's disease gene," *Neuron* 3:183–190 (Aug. 1989).

Mahadevan, M. et al., "Myotonic dystrophy mutation: an unstable CTG repeat in the 3' untranslated region of the gene," *Science* 255:1253–1255 (Mar. 6, 1992).

Martin, J.B. and Gusella, J.F., "Huntington's disease: pathogenesis and management," *N. Engl. J. Med.* 315(20):1267–1276 (Nov. 13, 1986).

McClatchey, A.I. et al., "The genomic structure of the human skeletal muscle sodium channel gene," *Hum. Mol. Genet.* 1(7):521–527 (1992).

Merrit, A.D. et al, "Juvenile Huntington's chorea," *Excerpta Medica*, Amsterdam, pp. 645–650 (1969).

Morell, V., "Huntington's gene finally found," *Science* 260:28–30 (Apr. 2, 1993).

Myers, R.H. et al., "Homozygote for Huntington disease," *Am. J. Hum. Genet.* 45:615–618 (1989).

Oudet, C. et al., "Linkage disequilibrium between the fragile X mutation and two closely linked CA repeats suggests that fragile X chromosomes are derived from a small number of founder chromosomes," *Am. J. Hum. Genet.* 52(2):297–304 (Feb. 1993).

Pieretti, M. et al., "Absence of expression of the FMR-1 gene in fragile X syndrome," *Cell* 66:817–822 (Aug. 23, 1991).

Pohl, T.M. et al., "Construction of a NotI linking library and isolation of new markers close to the Huntington's disease gene," *Nucleic Acids Res.* 6(19):9185–9198 (1988).

Pritchard, C. et al., "Recombination of 4p16 DNA markers in an unusual family with Huntington disease," *Am. J. Hum. Genet.* 50:1218–1230 (1992).

Richards R.I. et al., "Evidence of founder chromosomes in fragile X syndrome," *Nature Genet.* 1:257–260 (Jul. 1992).

Rubinstein, D.C. et al, "Site of (CCG) polymorphism i the HD gene," *Nature Genet.* 5:214–215 (Nov. 1993).

Sanger, T. et al., "DNA sequencing with chain-terminating inhibitors," *Proc. Natl. Acad. Sci. USA* 74(12) :5463–5467 (Dec. 1977).

Snell, R.G; et al., "Linkage disequilibrium in Huntington's disease: an improved localisation for the gene." *J. Med. Genet.* 26:673–675 (1989).

Snell, R.G. et al., "A recombination event that redefines the Huntington disease region," *Am. J. Hum. Genet.* 51:357–362 (1992).

Snell, R.G. et al., "Relationship between trinucleotide repeat expansion and phenotypic variation in Huntington's disease," *Nature Genet.* 4:393–397 (Aug. 1993).

Suthers, G.K. et al., "Instability versus predictability: the molecular diagnosis of myotonic dystrophy," *J. Med. Genet.* 29:761–765 (1992).

Taylor, S.A.M. et al., "Cloning of the α–adducin gene from the Huntington's disease candidate region of chromosome 4 by exon amplification," *Nature Genet.* 2:223–227 (Nov. 1992).

Theilman, J. et al., "Non–random association between alleles detected at D4S95 and D4S98 and the Huntington's disease gene," *J. Med. Genet.* 26:676–681 (1989).

Thompson, L.M. et al., "A gene encoding a fibroblast growth factor receptor isolated from the Huntington disease gene region of human chromosome 4," *Genomics* 11:1133–1142 (1991).

Tsilfidis, C. et al., "Correlation between CTG trinucleotide repeat length and frequency of severe congenital myotonic dystrophy," *Nature Genet.* 1:192–195 (Jun. 1992).

Verkerk, A.J.M.H. et al., "Identification of a gene (FMR–1) containing a CGG repeat coincident with a breakpoint cluster region exhibiting length variation in fragile X syndrome," *Cell* 65:904–914 (May 31, 1991).

Wexler, N.S. et al., "Homozygotes for Huntington's disease," *Nature* 326:194–197 (Mar. 12, 1987).

Whaley, W.L. et al., "Mapping of cosmid clones in Huntington's disease region of chromosome 4," *Somat. Cell Mol. Genet.* 17(1):83–91 (1991).

Wolff, G. et al., "New mutation to Huntington's disease," *J. Med. Genet.* 26:18–27 (1989).

Youngman, S. et al., "The telomeric 60 kb of chromosome arm 4p is homologous to telomeric regions on 13p, 15p, 21p, and 22p," *Genomics* 14:350–356 (1992).

Yu, S. et al., "Fragile–X syndrome: unique genetics of the heritable unstable element," *Am. J. Hum. Genet.* 50:968–980 (1992).

Hoogeveen, AT et al (1993) Hum. Mol. Gen (12)2:2069–2073, Oct. 22, 1993.

The Huntington's Disease Coll. Gp. (1993) *Cell* 72, 971–983, Mar. 26, 1993.

| | |
|---|---|
| TTGCTGTGTG AGGCAGAACC TGCGGGGGCA GGGGCGGGCT GGTTCCCTGG CCAGCCATTG | 60 |
| GCAGAGTCCG CAGGCTAGGG CTGTCAATCA TGCTGGCCGG CGTGGCCCCG CCTCCGCCGG | 120 |
| CGCCGCCCCG CCTCCGCCGG CGGACGTCTG GGACGCAAGG CGCCGTGGGG GCTGCCGGGA | 180 |
| CGGGTCCAAG ATGGACGGCC GCTCAGGTTC TGCTTTTACC TGCGGCCCAG AGCCCCATTC | 240 |
| ATTGCCCCGG TGCTGAGCGG CGCCGCGAGT CGGCCCGAGG CCTCCGGGGA CTGCCGTGCC | 300 |

```
GGGCGGGAGA CCGCC ATG GCG ACC CTG GAA AAG CTG ATG AAG GCC TTC GAG       351
            Met Ala Thr Leu Glu Lys Leu Met Lys Ala Phe Glu
              1           5                  10

TCC CTC AAG TCC TTC CAG CAG CAG CAG CAG CAG CAG CAG CAG CAG CAG        399
Ser Leu Lys Ser Phe Gln Gln Gln Gln Gln Gln Gln Gln Gln Gln Gln
             15              20                  25

CAG CAG CAG CAG CAG CAG CAG CAG CAG CAG CAA CAG CCG CCA CCG CCG        447
Gln Gln Gln Gln Gln Gln Gln Gln Gln Gln Gln Gln Pro Pro Pro Pro
     30                  35                  40

CCG CCG CCG CCG CCG CCT CCT CAG CTT CCT CAG CCG CCG CCG CAG GCA        495
Pro Pro Pro Pro Pro Pro Pro Gln Leu Pro Gln Pro Pro Pro Gln Ala
 45                  50                  55                  60

CAG CCG CTG CTG CCT CAG CCG CAG CCG CCC CCG CCG CCG CCC CCG CCG        543
Gln Pro Leu Leu Pro Gln Pro Gln Pro Pro Pro Pro Pro Pro Pro Pro
              65                  70                  75

CCA CCC GGC CCG GCT GTG GCT GAG GAG CCG CTG CAC CGA CCA AAG AAA        591
Pro Pro Gly Pro Ala Val Ala Glu Glu Pro Leu His Arg Pro Lys Lys
             80                  85                  90

GAA CTT TCA GCT ACC AAG AAA GAC CGT GTG AAT CAT TGT CTG ACA ATA        639
Glu Leu Ser Ala Thr Lys Lys Asp Arg Val Asn His Cys Leu Thr Ile
             95                  100                 105

TGT GAA AAC ATA GTG GCA CAG TCT GTC AGA AAT TCT CCA GAA TTT CAG        687
Cys Glu Asn Ile Val Ala Gln Ser Val Arg Asn Ser Pro Glu Phe Gln
     110                 115                 120
```

FIG.4A

| | |
|---|---|
| AAA CTT CTG GGC ATC GCT ATG GAA CTT TTT CTG CTG TGC AGT GAT GAC<br>Lys Leu Leu Gly Ile Ala Met Glu Leu Phe Leu Leu Cys Ser Asp Asp<br>125              130              135              140 | 735 |
| GCA GAG TCA GAT GTC AGG ATG GTG GCT GAC GAA TGC CTC AAC AAA GTT<br>Ala Glu Ser Asp Val Arg Met Val Ala Asp Glu Cys Leu Asn Lys Val<br>              145              150              155 | 783 |
| ATC AAA GCT TTG ATG GAT TCT AAT CTT CCA AGG TTA CAG CTC GAG CTC<br>Ile Lys Ala Leu Met Asp Ser Asn Leu Pro Arg Leu Gln Leu Glu Leu<br>              160              165              170 | 831 |
| TAT AAG GAA ATT AAA AAG AAT GGT GCC CCT CGG AGT TTG CGT GCT GCC<br>Tyr Lys Glu Ile Lys Lys Asn Gly Ala Pro Arg Ser Leu Arg Ala Ala<br>              175              180              185 | 879 |
| CTG TGG AGG TTT GCT GAG CTG GCT CAC CTG GTT CGG CCT CAG AAA TGC<br>Leu Trp Arg Phe Ala Glu Leu Ala His Leu Val Arg Pro Gln Lys Cys<br>    190              195              200 | 927 |
| AGG CCT TAC CTG GTG AAC CTT CTG CCG TGC CTG ACT CGA ACA AGC AAG<br>Arg Pro Tyr Leu Val Asn Leu Leu Pro Cys Leu Thr Arg Thr Ser Lys<br>205              210              215              220 | 975 |
| AGA CCC GAA GAA TCA GTC CAG GAG ACC TTG GCT GCA GCT GTT CCC AAA<br>Arg Pro Glu Glu Ser Val Gln Glu Thr Leu Ala Ala Ala Val Pro Lys<br>              225              230              235 | 1023 |
| ATT ATG GCT TCT TTT GGC AAT TTT GCA AAT GAC AAT GAA ATT AAG GTT<br>Ile Met Ala Ser Phe Gly Asn Phe Ala Asn Asp Asn Glu Ile Lys Val<br>              240              245              250 | 1071 |
| TTG TTA AAG GCC TTC ATA GCG AAC CTG AAG TCA AGC TCC CCC ACC ATT<br>Leu Leu Lys Ala Phe Ile Ala Asn Leu Lys Ser Ser Ser Pro Thr Ile<br>              255              260              265 | 1119 |
| CGG CGG ACA GCG GCT GGA TCA GCA GTG AGC ATC TGC CAG CAC TCA AGA<br>Arg Arg Thr Ala Ala Gly Ser Ala Val Ser Ile Cys Gln His Ser Arg<br>              270              275              280 | 1167 |

FIG.4B

```
AGG ACA CAA TAT TTC TAT AGT TGG CTA CTA AAT GTG CTC TTA GGC TTA       1215
Arg Thr Gln Tyr Phe Tyr Ser Trp Leu Leu Asn Val Leu Leu Gly Leu
285                 290             295             300

CTC GTT CCT GTC GAG GAT GAA CAC TCC ACT CTG CTG ATT CTT GGC GTG       1263
Leu Val Pro Val Glu Asp Glu His Ser Thr Leu Leu Ile Leu Gly Val
                305             310             315

CTG CTC ACC CTG AGG TAT TTG GTG CCC TTG CTG CAG CAG CAG GTC AAG       1311
Leu Leu Thr Leu Arg Tyr Leu Val Pro Leu Leu Gln Gln Gln Val Lys
            320             325             330

GAC ACA AGC CTG AAA GGC AGC TTC GGA GTC ACA AGG AAA GAA ATG GAA       1359
Asp Thr Ser Leu Lys Gly Ser Phe Gly Val Thr Arg Lys Glu Met Glu
            335             340             345

GTC TCT CCT TCT GCA GAG CAG CTT GTC CAG GTT TAT GAA CTG ACG TTA       1407
Val Ser Pro Ser Ala Glu Gln Leu Val Gln Val Tyr Glu Leu Thr Leu
    350             355             360

CAT CAT ACA CAG CAC CAA GAC CAC AAT GTT GTG ACC GGA GCC CTG GAG       1455
His His Thr Gln His Gln Asp His Asn Val Val Thr Gly Ala Leu Glu
365             370             375             380

CTG TTG CAG CAG CTC TTC AGA ACG CCT CCA CCC GAG CTT CTG CAA ACC       1503
Leu Leu Gln Gln Leu Phe Arg Thr Pro Pro Pro Glu Leu Leu Gln Thr
                385             390             395

CTG ACC GCA GTC GGG GGC ATT GGG CAG CTC ACC GCT GCT AAG GAG GAG       1551
Leu Thr Ala Val Gly Gly Ile Gly Gln Leu Thr Ala Ala Lys Glu Glu
                400             405             410

TCT GGT GGC CGA AGC CGT AGT GGG AGT ATT GTG GAA CTT ATA GCT GGA       1599
Ser Gly Gly Arg Ser Arg Ser Gly Ser Ile Val Glu Leu Ile Ala Gly
            415             420             425

GGG GGT TCC TCA TGC AGC CCT GTC CTT TCA AGA AAA CAA AAA GGC AAA       1647
Gly Gly Ser Ser Cys Ser Pro Val Leu Ser Arg Lys Gln Lys Gly Lys
        430             435             440
```

FIG.4C

```
GTG CTC TTA GGA GAA GAA GAA GCC TTG GAG GAT GAC TCT GAA TCG AGA      1695
Val Leu Leu Gly Glu Glu Glu Ala Leu Glu Asp Asp Ser Glu Ser Arg
445             450                 455                 460

TCG GAT GTC AGC AGC TCT GCC TTA ACA GCC TCA GTC AAG GAT GAG ATC      1743
Ser Asp Val Ser Ser Ser Ala Leu Thr Ala Ser Val Lys Asp Glu Ile
                465                 470                 475

AGT GGA GAG CTG GCT GCT TCT TCA GGG GTT TCC ACT CCA GGG TCA GCA      1791
Ser Gly Glu Leu Ala Ala Ser Ser Gly Val Ser Thr Pro Gly Ser Ala
                480                 485                 490

GGT CAT GAC ATC ATC ACA GAA CAG CCA CGG TCA CAG CAC ACA CTG CAG      1839
Gly His Asp Ile Ile Thr Glu Gln Pro Arg Ser Gln His Thr Leu Gln
                495                 500                 505

GCG GAC TCA CTG GAT CTG GCC AGC TGT GAC TTG ACA AGC TCT GCC ACT      1887
Ala Asp Ser Leu Asp Leu Ala Ser Cys Asp Leu Thr Ser Ser Ala Thr
                510                 515                 520

GAT GGG GAT GAG GAG GAT ATC TTG AGC CAC AGC TCC AGC CAG GTC AGC      1935
Asp Gly Asp Glu Glu Asp Ile Leu Ser His Ser Ser Ser Gln Val Ser
525                 530                 535                 540

GCC GTC CCA TCT GAC CCT GCC ATG GAC CTG AAT GAT GGG ACC CAG GCC      1983
Ala Val Pro Ser Asp Pro Ala Met Asp Leu Asn Asp Gly Thr Gln Ala
                545                 550                 555

TCG TCG CCC ATC AGC GAC AGC TCC CAG ACC ACC ACC GAA GGG CCT GAT      2031
Ser Ser Pro Ile Ser Asp Ser Ser Gln Thr Thr Thr Glu Gly Pro Asp
                560                 565                 570

TCA GCT GTT ACC CCT TCA GAC AGT TCT GAA ATT GTG TTA GAC GGT ACC      2079
Ser Ala Val Thr Pro Ser Asp Ser Ser Glu Ile Val Leu Asp Gly Thr
                575                 580                 585

GAC AAC CAG TAT TTG GGC CTG CAG ATT GGA CAG CCC CAG GAT GAA GAT      2127
Asp Asn Gln Tyr Leu Gly Leu Gln Ile Gly Gln Pro Gln Asp Glu Asp
                590                 595                 600
```

FIG.4D

```
GAG GAA GCC ACA GGT ATT CTT CCT GAT GAA GCC TCG GAG GCC TTC AGG        2175
Glu Glu Ala Thr Gly Ile Leu Pro Asp Glu Ala Ser Glu Ala Phe Arg
605             610             615             620

AAC TCT TCC ATG GCC CTT CAA CAG GCA CAT TTA TTG AAA AAC ATG AGT        2223
Asn Ser Ser Met Ala Leu Gln Gln Ala His Leu Leu Lys Asn Met Ser
            625             630             635

CAC TGC AGG CAG CCT TCT GAC AGC AGT GTT GAT AAA TTT GTG TTG AGA        2271
His Cys Arg Gln Pro Ser Asp Ser Ser Val Asp Lys Phe Val Leu Arg
        640             645             650

GAT GAA GCT ACT GAA CCG GGT GAT CAA GAA AAC AAG CCT TGC CGC ATC        2319
Asp Glu Ala Thr Glu Pro Gly Asp Gln Glu Asn Lys Pro Cys Arg Ile
        655             660             665

AAA GGT GAC ATT GGA CAG TCC ACT GAT GAT GAC TCT GCA CCT CTT GTC        2367
Lys Gly Asp Ile Gly Gln Ser Thr Asp Asp Asp Ser Ala Pro Leu Val
    670             675             680

CAT TCT GTC CGC CTT TTA TCT GCT TCG TTT TTG CTA ACA GGG GGA AAA        2415
His Ser Val Arg Leu Leu Ser Ala Ser Phe Leu Leu Thr Gly Gly Lys
685             690             695             700

AAT GTG CTG GTT CCC GAC AGG GAT GTG AGG GTC AGC GTG AAG GCC CTG        2463
Asn Val Leu Val Pro Asp Arg Asp Val Arg Val Ser Val Lys Ala Leu
            705             710             715

GCC CTC AGC TGT GTG GGA GCA GCT GTG GCC CTC CAC CCG GAA TCT TTC        2511
Ala Leu Ser Cys Val Gly Ala Ala Val Ala Leu His Pro Glu Ser Phe
        720             725             730

TTC AGC AAA CTC TAT AAA GTT CCT CTT GAC ACC ACG GAA TAC CCT GAG        2559
Phe Ser Lys Leu Tyr Lys Val Pro Leu Asp Thr Thr Glu Tyr Pro Glu
735             740             745
```

FIG.4E

```
GAA CAG TAT GTC TCA GAC ATC TTG AAC TAC ATC GAT CAT GGA GAC CCA         2607
Glu Gln Tyr Val Ser Asp Ile Leu Asn Tyr Ile Asp His Gly Asp Pro
        750                 755                 760

CAG GTT CGA GGA GCC ACT GCC ATT CTC TGT GGG ACC CTC ATC TGC TCC         2655
Gln Val Arg Gly Ala Thr Ala Ile Leu Cys Gly Thr Leu Ile Cys Ser
765                 770                 775                 780

ATC CTC AGC AGG TCC CGC TTC CAC GTG GGA GAT TGG ATG GGC ACC ATT         2703
Ile Leu Ser Arg Ser Arg Phe His Val Gly Asp Trp Met Gly Thr Ile
                785                 790                 795

AGA ACC CTC ACA GGA AAT ACA TTT TCT TTG GCG GAT TGC ATT CCT TTG         2751
Arg Thr Leu Thr Gly Asn Thr Phe Ser Leu Ala Asp Cys Ile Pro Leu
            800                 805                 810

CTG CGG AAA ACA CTG AAG GAT GAG TCT TCT GTT ACT TGC AAG TTA GCT         2799
Leu Arg Lys Thr Leu Lys Asp Glu Ser Ser Val Thr Cys Lys Leu Ala
        815                 820                 825

TGT ACA GCT GTG AGG AAC TGT GTC ATG AGT CTC TGC AGC AGC AGC TAC         2847
Cys Thr Ala Val Arg Asn Cys Val Met Ser Leu Cys Ser Ser Ser Tyr
830                 835                 840

AGT GAG TTA GGA CTG CAG CTG ATC ATC GAT GTG CTG ACT CTG AGG AAC         2895
Ser Glu Leu Gly Leu Gln Leu Ile Ile Asp Val Leu Thr Leu Arg Asn
845                 850                 855                 860

AGT TCC TAT TGG CTG GTG AGG ACA GAG CTT CTC GAA ACC CTT GCA GAG         2943
Ser Ser Tyr Trp Leu Val Arg Thr Glu Leu Leu Glu Thr Leu Ala Glu
                865                 870                 875

ATT GAC TTC AGG CTG GTG AGC TTT TTG GAG GCA AAA GCA GAA AAC TTA         2991
Ile Asp Phe Arg Leu Val Ser Phe Leu Glu Ala Lys Ala Glu Asn Leu
            880                 885                 890

CAC AGA GGG GCT CAT CAT TAT ACA GGG CTT TTA AAA CTC CAA GAA CGA         3039
His Arg Gly Ala His His Tyr Thr Gly Leu Leu Lys Leu Gln Glu Arg
        895                 900                 905
```

FIG.4F

```
GTC CTC AAT AAT GTT GTC ATC CAT TTG CTT GGA GAT GAA GAC CCC AGG        3087
Val Leu Asn Asn Val Val Ile His Leu Leu Gly Asp Glu Asp Pro Arg
    910                 915                 920

GTG CGA CAT GTT GCC GCA GCA TCA CTA ATT AGG CTT GTC CCA AAG CTG        3135
Val Arg His Val Ala Ala Ala Ser Leu Ile Arg Leu Val Pro Lys Leu
925                 930                 935                 940

TTT TAT AAA TGT GAC CAA GGA CAA GCT GAT CCA GTA GTG GCC GTG GCA        3183
Phe Tyr Lys Cys Asp Gln Gly Gln Ala Asp Pro Val Val Ala Val Ala
                945                 950                 955

AGA GAT CAA AGC AGT GTT TAC CTG AAA CTT CTC ATG CAT GAG ACC CAG        3231
Arg Asp Gln Ser Ser Val Tyr Leu Lys Leu Leu Met His Glu Thr Gln
            960                 965                 970

CCT CCA TCT CAT TTC TCC GTC AGC ACA ATA ACC AGA ATA TAT AGA GGC        3279
Pro Pro Ser His Phe Ser Val Ser Thr Ile Thr Arg Ile Tyr Arg Gly
            975                 980                 985

TAT AAC CTA CTA CCA AGC ATA ACA GAC GTC ACT ATG GAA AAT AAC CTT        3327
Tyr Asn Leu Leu Pro Ser Ile Thr Asp Val Thr Met Glu Asn Asn Leu
        990                 995                 1000

TCA AGA GTT ATT GCA GCA GTT TCT CAT GAA CTA ATC ACA TCA ACC ACC        3375
Ser Arg Val Ile Ala Ala Val Ser His Glu Leu Ile Thr Ser Thr Thr
1005                1010                1015                1020

AGA GCA CTC ACA TTT GGA TGC TGT GAA GCT TTG TGT CTT CTT TCC ACT        3423
Arg Ala Leu Thr Phe Gly Cys Cys Glu Ala Leu Cys Leu Leu Ser Thr
                1025                1030                1035

GCC TTC CCA GTT TGC ATT TGG AGT TTA GGT TGG CAC TGT GGA GTG CCT        3471
Ala Phe Pro Val Cys Ile Trp Ser Leu Gly Trp His Cys Gly Val Pro
                    1040                1045                1050

CCA CTG AGT GCC TCA GAT GAG TCT AGG AAG ACC TGT ACC GTT GGG ATG        3519
Pro Leu Ser Ala Ser Asp Glu Ser Arg Lys Ser Cys Thr Val Gly Met
        1055                1060                1065
```

FIG.4G

```
GCC ACA ATG ATT CTG ACC CTG CTC TCG TCA GCT TGG TTC CCA TTG GAT     3567
Ala Thr Met Ile Leu Thr Leu Leu Ser Ser Ala Trp Phe Pro Leu Asp
        1070            1075            1080

CTC TCA GCC CAT CAA GAT GCT TTG ATT TTG GCC GGA AAC TTG CTT GCA     3615
Leu Ser Ala His Gln Asp Ala Leu Ile Leu Ala Gly Asn Leu Leu Ala
1085            1090            1095            1100

GCC AGT GCT CCC AAA TCT CTG AGA AGT TCA TGG GCC TCT GAA GAA GAA     3663
Ala Ser Ala Pro Lys Ser Leu Arg Ser Ser Trp Ala Ser Glu Glu Glu
        1105            1110            1115

GCC AAC CCA GCA GCC ACC AAG CAA GAG GAG GTC TGG CCA GCC CTG GGG     3711
Ala Asn Pro Ala Ala Thr Lys Gln Glu Glu Val Trp Pro Ala Leu Gly
        1120            1125            1130

GAC CGG GCC CTG GTG CCC ATG GTG GAG CAG CTC TTC TCT CAC CTG CTG     3759
Asp Arg Ala Leu Val Pro Met Val Glu Gln Leu Phe Ser His Leu Leu
        1135            1140            1145

AAG GTG ATT AAC ATT TGT GCC CAC GTC CTG GAT GAC GTG GCT CCT GGA     3807
Lys Val Ile Asn Ile Cys Ala His Val Leu Asp Asp Val Ala Pro Gly
        1150            1155            1160

CCC GCA ATA AAG GCA GCC TTG CCT TCT CTA ACA AAC CCC CCT TCT CTA     3855
Pro Ala Ile Lys Ala Ala Leu Pro Ser Leu Thr Asn Pro Pro Ser Leu
1165            1170            1175            1180

AGT CCC ATC CGA CGA AAG GGG AAG GAG AAA GAA CCA GGA GAA CAA GCA     3903
Ser Pro Ile Arg Arg Lys Gly Lys Glu Lys Glu Pro Gly Glu Gln Ala
        1185            1190            1195

TCT GTA CCG TTG AGT CCC AAG AAA GGC AGT GAG GCC AGT GCA GCT TCT     3951
Ser Val Pro Leu Ser Pro Lys Lys Gly Ser Glu Ala Ser Ala Ala Ser
        1200            1205            1210

AGA CAA TCT GAT ACC TCA GGT CCT GTT ACA ACA AGT AAA TCC TCA TCA     3999
Arg Gln Ser Asp Thr Ser Gly Pro Val Thr Thr Ser Lys Ser Ser Ser
        1215            1220            1225
```

FIG.4H

```
CTG GGG AGT TTC TAT CAT CTT CCT TCA TAC CTC AGA CTG CAT GAT GTC    4047
Leu Gly Ser Phe Tyr His Leu Pro Ser Tyr Leu Arg Leu His Asp Val
        1230              1235              1240

CTG AAA GCT ACA CAC GCT AAC TAC AAG GTC ACG CTG GAT CTT CAG AAC    4095
Leu Lys Ala Thr His Ala Asn Tyr Lys Val Thr Leu Asp Leu Gln Asn
1245              1250              1255              1260

AGC ACG GAA AAG TTT GGA GGG TTT CTC CGC TCA GCC TTG GAT GTT CTT    4143
Ser Thr Glu Lys Phe Gly Gly Phe Leu Arg Ser Ala Leu Asp Val Leu
            1265              1270              1275

TCT CAG ATA CTA GAG CTG GCC ACA CTG CAG GAC ATT GGG AAG TGT GTT    4191
Ser Gln Ile Leu Glu Leu Ala Thr Leu Gln Asp Ile Gly Lys Cys Val
        1280              1285              1290

GAA GAG ATC CTA GGA TAC CTG AAA TCC TGC TTT AGT CGA GAA CCA ATG    4239
Glu Glu Ile Leu Gly Tyr Leu Lys Ser Cys Phe Ser Arg Glu Pro Met
        1295              1300              1305

ATG GCA ACT GTT TGT GTT CAA CAA TTG TTG AAG ACT CTC TTT GGC ACA    4287
Met Ala Thr Val Cys Val Gln Gln Leu Leu Lys Thr Leu Phe Gly Thr
        1310              1315              1320

AAC TTG GCC TCC CAG TTT GAT GGC TTA TCT TCC AAC CCC AGC AAG TCA    4335
Asn Leu Ala Ser Gln Phe Asp Gly Leu Ser Ser Asn Pro Ser Lys Ser
1325              1330              1335              1340

CAA GGC CGA GCA CAG CGC CTT GGC TCC TCC AGT GTG AGG CCA GGC TTG    4383
Gln Gly Arg Ala Gln Arg Leu Gly Ser Ser Ser Val Arg Pro Gly Leu
            1345              1350              1355

TAC CAC TAC TGC TTC ATG GCC CCG TAC ACC CAC TTC ACC CAG GCC CTC    4431
Tyr His Tyr Cys Phe Met Ala Pro Tyr Thr His Phe Thr Gln Ala Leu
        1360              1365              1370

GCT GAC GCC AGC CTG AGG AAC ATG GTG CAG GCG GAG CAG GAG AAC GAC    4479
Ala Asp Ala Ser Leu Arg Asn Met Val Gln Ala Glu Gln Glu Asn Asp
        1375              1380              1385
```

FIG.41

| | |
|---|---|
| ACC TCG GGA TGG TTT GAT GTC CTC CAG AAA GTG TCT ACC CAG TTG AAG<br>Thr Ser Gly Trp Phe Asp Val Leu Gln Lys Val Ser Thr Gln Leu Lys<br>1390                      1395                      1400 | 4527 |
| ACA AAC CTC ACG AGT GTC ACA AAG AAC CGT GCA GAT AAG AAT GCT ATT<br>Thr Asn Leu Thr Ser Val Thr Lys Asn Arg Ala Asp Lys Asn Ala Ile<br>1405                      1410                      1415                      1420 | 4575 |
| CAT AAT CAC ATT CGT TTG TTT GAA CCT CTT GTT ATA AAA GCT TTA AAA<br>His Asn His Ile Arg Leu Phe Glu Pro Leu Val Ile Lys Ala Leu Lys<br>                    1425                      1430                      1435 | 4623 |
| CAG TAC ACG ACT ACA ACA TGT GTG CAG TTA CAG AAG CAG GTT TTA GAT<br>Gln Tyr Thr Thr Thr Thr Cys Val Gln Leu Gln Lys Gln Val Leu Asp<br>                      1440                      1445                      1450 | 4671 |
| TTG CTG GCG CAG CTG GTT CAG TTA CGG GTT AAT TAC TGT CTT CTG GAT<br>Leu Leu Ala Gln Leu Val Gln Leu Arg Val Asn Tyr Cys Leu Leu Asp<br>                      1455                      1460                      1465 | 4719 |
| TCA GAT CAG GTC TTT ATT GGC TTT GTA TTG AAA CAG TTT GAA TAC ATT<br>Ser Asp Gln Val Phe Ile Gly Phe Val Leu Lys Gln Phe Glu Tyr Ile<br>                      1470                      1475                      1480 | 4767 |
| GAA GTG GGC CAG TTC AGG GAA TCA GAG GCA ATC ATT CCA AAC ATC TTT<br>Glu Val Gly Gln Phe Arg Glu Ser Glu Ala Ile Ile Pro Asn Ile Phe<br>1485                      1490                      1495                      1500 | 4815 |
| TTC TTC TTG GTA TTA CTA TCT TAT GAA CGC TAT CAT TCA AAA CAG ATC<br>Phe Phe Leu Val Leu Leu Ser Tyr Glu Arg Tyr His Ser Lys Gln Ile<br>                      1505                      1510                      1515 | 4863 |
| ATT GGA ATT CCT AAA ATC ATT CAG CTC TGT GAT GGC ATC ATG GCC AGT<br>Ile Gly Ile Pro Lys Ile Ile Gln Leu Cys Asp Gly Ile Met Ala Ser<br>                      1520                      1525                      1530 | 4911 |
| GGA ACG AAG GCT GTC ACA CAT GCC ATA CCG GCT CTG CAG CCC ATA GTC<br>Gly Arg Lys Ala Val Thr His Ala Ile Pro Ala Leu Gln Pro Ile Val<br>                      1535                      1540                      1545 | 4959 |

FIG.4J

```
CAC GAC CTC TTT GTA TTA AGA GGA ACA AAT AAA GCT GAT GCA GGA AAA         5007
His Asp Leu Phe Val Leu Arg Gly Thr Asn Lys Ala Asp Ala Gly Lys
    1550            1555            1560

GAG CTT GAA ACC CAA AAA GAG GTG GTG GTG TCA ATG TTA CTG AGA CTC         5055
Glu Leu Glu Thr Gln Lys Glu Val Val Val Ser Met Leu Leu Arg Leu
1565            1570            1575            1580

ATC CAG TAC CAT CAG GTG TTG GAG ATG TTC ATT CTT GTC CTG CAG CAG         5103
Ile Gln Tyr His Gln Val Leu Glu Met Phe Ile Leu Val Leu Gln Gln
            1585            1590            1595

TGC CAC AAG GAG AAT GAA GAC AAG TGG AAG CGA CTG TCT CGA CAG ATA         5151
Cys His Lys Glu Asn Glu Asp Lys Trp Lys Arg Leu Ser Arg Gln Ile
        1600            1605            1610

GCT GAC ATC ATC CTC CCA ATG TTA GCC AAA CAG CAG ATG CAC ATT GAC         5199
Ala Asp Ile Ile Leu Pro Met Leu Ala Lys Gln Gln Met His Ile Asp
        1615            1620            1625

TCT CAT GAA GCC CTT GGA GTG TTA AAT ACA TTA TTT GAG ATT TTG GCC         5247
Ser His Glu Ala Leu Gly Val Leu Asn Thr Leu Phe Glu Ile Leu Ala
    1630            1635            1640

CCT TCC TCC CTC CGT CCG GTA GAC ATG CTT TTA CGG AGT ATG TTC GTC         5295
Pro Ser Ser Leu Arg Pro Val Asp Met Leu Leu Arg Ser Met Phe Val
1645            1650            1655            1660

ACT CCA AAC ACA ATG GCG TCC GTG AGC ACT GTT CAA CTG TGG ATA TCG         5343
Thr Pro Asn Thr Met Ala Ser Val Ser Thr Val Gln Leu Trp Ile Ser
            1665            1670            1675

GGA ATT CTG GCC ATT TTG AGG GTT CTG ATT TCC CAG TCA ACT GAA GAT         5391
Gly Ile Leu Ala Ile Leu Arg Val Leu Ile Ser Gln Ser Thr Glu Asp
        1680            1685            1690

ATT GTT CTT TCT CGT ATT CAG GAG CTC TCC TTC TCT CCG TAT TTA ATC         5439
Ile Val Leu Ser Arg Ile Gln Glu Leu Ser Phe Ser Pro Tyr Leu Ile
        1695            1700            1705
```

FIG.4K

```
TCC TGT ACA GTA ATT AAT AGG TTA AGA GAT GGG GAC AGT ACT TCA ACG          5487
Ser Cys Thr Val Ile Asn Arg Leu Arg Asp Gly Asp Ser Thr Ser Thr
    1710            1715            1720

CTA GAA GAA CAC AGT GAA GGG AAA CAA ATA AAG AAT TTG CCA GAA GAA          5535
Leu Glu Glu His Ser Glu Gly Lys Gln Ile Lys Asn Leu Pro Glu Glu
1725            1730            1735            1740

ACA TTT TCA AGG TTT CTA TTA CAA CTG GTT GGT ATT CTT TTA GAA GAC          5583
Thr Phe Ser Arg Phe Leu Leu Gln Leu Val Gly Ile Leu Leu Glu Asp
        1745            1750            1755

ATT GTT ACA AAA CAG CTG AAG GTC GAA ATG AGT GAG CAG CAA CAT ACT          5631
Ile Val Thr Lys Gln Leu Lys Val Glu Met Ser Glu Gln Gln His Thr
            1760            1765            1770

TTC TAT TGC CAG GAA CTA GGC ACA CTG CTA ATG TGT CTG ATC CAC ATC          5679
Phe Tyr Cys Gln Glu Leu Gly Thr Leu Leu Met Cys Leu Ile His Ile
        1775            1780            1785

TTC AAG TCT GGA ATG TTC CGG AGA ATC ACA GCA GCT GCC ACT AGG CTG          5727
Phe Lys Ser Gly Met Phe Arg Arg Ile Thr Ala Ala Ala Thr Arg Leu
        1790            1795            1800

TTC CGC AGT GAT GGC TGT GGC GGC AGT TTC TAC ACC CTG GAC AGC TTG          5775
Phe Arg Ser Asp Gly Cys Gly Gly Ser Phe Tyr Thr Leu Asp Ser Leu
1805            1810            1815            1820

AAC TTG CGG GCT CGT TCC ATG ATC ACC ACC CAC CCG GCC CTG GTG CTG          5823
Asn Leu Arg Ala Arg Ser Met Ile Thr Thr His Pro Ala Leu Val Leu
            1825            1830            1835

CTC TGG TGT CAG ATA CTG CTG CTT GTC AAC CAC ACC GAC TAC CGC TGG          5871
Leu Trp Cys Gln Ile Leu Leu Leu Val Asn His Thr Asp Tyr Arg Trp
            1840            1845            1850
```

FIG.4L

```
TGG GCA GAA GTG CAG CAG ACC CCG AAA AGA CAC AGT CTG TCC AGC ACA            5919
Trp Ala Glu Val Gln Gln Thr Pro Lys Arg His Ser Leu Ser Ser Thr
        1855            1860            1865

AAG TTA CTT AGT CCC CAG ATG TCT GGA GAA GAG GAG GAT TCT GAC TTG            5967
Lys Leu Leu Ser Pro Gln Met Ser Gly Glu Glu Glu Asp Ser Asp Leu
        1870            1875            1880

GCA GCC AAA CTT GGA ATG TGC AAT AGA GAA ATA GTA CGA AGA GGG GCT            6015
Ala Ala Lys Leu Gly Met Cys Asn Arg Glu Ile Val Arg Arg Gly Ala
        1885            1890            1895            1900

CTC ATT CTC TTC TGT GAT TAT GTC TGT CAG AAC CTC CAT GAC TCC GAG            6063
Leu Ile Leu Phe Cys Asp Tyr Val Cys Gln Asn Leu His Asp Ser Glu
                1905            1910            1915

CAC TTA ACG TGG CTC ATT GTA AAT CAC ATT CAA GAT CTG ATC AGC CTT            6111
His Leu Thr Trp Leu Ile Val Asn His Ile Gln Asp Leu Ile Ser Leu
                1920            1925            1930

TCC CAC GAG CCT CCA GTA CAG GAC TTC ATC AGT GCC GTT CAT CGG AAC            6159
Ser His Glu Pro Pro Val Gln Asp Phe Ile Ser Ala Val His Arg Asn
        1935            1940            1945

TCT GCT GCC AGC GGC CTG TTC ATC CAG GCA ATT CAG TCT CGT TGT GAA            6207
Ser Ala Ala Ser Gly Leu Phe Ile Gln Ala Ile Gln Ser Arg Cys Glu
        1950            1955            1960

AAC CTT TCA ACT CCA ACC ATG CTG AAG AAA ACT CTT CAG TGC TTG GAG            6255
Asn Leu Ser Thr Pro Thr Met Leu Lys Lys Thr Leu Gln Cys Leu Glu
1965            1970            1975            1980

GGG ATC CAT CTC AGC CAG TCG GGA GCT GTG CTC ACG CTG TAT GTG GAC            6303
Gly Ile His Leu Ser Gln Ser Gly Ala Val Leu Thr Leu Tyr Val Asp
                1985            1990            1995

AGG CTT CTG TGC ACC CCT TTC CGT GTG CTG GCT CGC ATG GTC GAC ATC            6351
Arg Leu Leu Cys Thr Pro Phe Arg Val Leu Ala Arg Met Val Asp Ile
        2000            2005            2010
```

FIG.4M

```
CTT GCT TGT CGC CGG GTA GAA ATG CTT CTG GCT GCA AAT TTA CAG AGC          6399
Leu Ala Cys Arg Arg Val Glu Met Leu Leu Ala Ala Asn Leu Gln Ser
        2015            2020            2025

AGC ATG GCC CAG TTG CCA ATG GAA GAA CTC AAC AGA ATC CAG GAA TAC          6447
Ser Met Ala Gln Leu Pro Met Glu Glu Leu Asn Arg Ile Gln Glu Tyr
        2030            2035            2040

CTT CAG AGC AGC GGG CTC GCT CAG AGA CAC CAA AGG CTC TAT TCC CTG          6495
Leu Gln Ser Ser Gly Leu Ala Gln Arg His Gln Arg Leu Tyr Ser Leu
    2045            2050            2055            2060

CTG GAC AGG TTT CGT CTC TCC ACC ATG CAA GAC TCA CTT AGT CCC TCT          6543
Leu Asp Arg Phe Arg Leu Ser Thr Met Gln Asp Ser Leu Ser Pro Ser
                2065            2070            2075

CCT CCA GTC TCT TCC CAC CCG CTG GAC GGG GAT GGG CAC GTG TCA CTG          6591
Pro Pro Val Ser Ser His Pro Leu Asp Gly Asp Gly His Val Ser Leu
            2080            2085            2090

GAA ACA GTG AGT CCG GAC AAA GAC TGG TAC GTT CAT CTT GTC AAA TCC          6639
Glu Thr Val Ser Pro Asp Lys Asp Trp Tyr Val His Leu Val Lys Ser
            2095            2100            2105

CAG TGT TGG ACC AGG TCA GAT TCT GCA CTG CTG GAA GGT GCA GAG CTC          6687
Gln Cys Trp Thr Arg Ser Asp Ser Ala Leu Leu Glu Gly Ala Glu Leu
        2110            2115            2120

GTG AAT CGG ATT CCT GCT GAA GAT ATG AAT GCC TTC ATG ATG AAC TCG          6735
Val Asn Arg Ile Pro Ala Glu Asp Met Asn Ala Phe Met Met Asn Ser
    2125            2130            2135            2140

GAG TTC AAC CTA AGC CTG CTA GCT CCA TGC TTA AGC CTA GGG ATG AGT          6783
Glu Phe Asn Leu Ser Leu Leu Ala Pro Cys Leu Ser Leu Gly Met Ser
                2145            2150            2155

GAA ATT TCT GGT GCC CAG AAG AGT GCC CTT TTT GAA GCA GCC CGT GAG          6831
Glu Ile Ser Gly Gly Gln Lys Ser Ala Leu Phe Glu Ala Ala Arg Glu
        2160            2165            2170
```

FIG.4N

```
GTG ACT CTG GCC CGT GTG AGC GGC ACC GTG CAG CAG CTC CCT GCT GTC         6879
Val Thr Leu Ala Arg Val Ser Gly Thr Val Gln Gln Leu Pro Ala Val
        2175            2180            2185

CAT CAT GTC TTC CAG CCC GAG CTG CCT GCA GAG CCG GCG GCC TAC TGG         6927
His His Val Phe Gln Pro Glu Leu Pro Ala Glu Pro Ala Ala Tyr Trp
        2190            2195            2200

AGC AAG TTG AAT GAT CTG TTT GGG GAT GCT GCA CTG TAT CAG TCC CTG         6975
Ser Lys Leu Asn Asp Leu Phe Gly Asp Ala Ala Leu Tyr Gln Ser Leu
2205            2210            2215            2220

CCC ACT CTG GCC CGG GCC CTG GCA CAG TAC CTG GTG GTG GTC TCC AAA         7023
Pro Thr Leu Ala Arg Ala Leu Ala Gln Tyr Leu Val Val Val Ser Lys
            2225            2230            2235

CTG CCC AGT CAT TTG CAC CTT CCT CCT GAG AAA GAG AAG GAC ATT GTG         7071
Leu Pro Ser His Leu His Leu Pro Pro Glu Lys Glu Lys Asp Ile Val
        2240            2245            2250

AAA TTC GTG GTG GCA ACC CTT GAG GCC CTG TCC TGG CAT TTG ATC CAT         7119
Lys Phe Val Val Ala Thr Leu Glu Ala Leu Ser Trp His Leu Ile His
        2255            2260            2265

GAG CAG ATC CCG CTG AGT CTG GAT CTC CAG GCA GGG CTG GAC TGC TGC         7167
Glu Gln Ile Pro Leu Ser Leu Asp Leu Gln Ala Gly Leu Asp Cys Cys
        2270            2275            2280

TGC CTG GCC CTG CAG CTG CCT GGC CTC TGG AGC GTG GTC TCC TCC ACA         7215
Cys Leu Ala Leu Gln Leu Pro Gly Leu Trp Ser Val Val Ser Ser Thr
2285            2290            2295            2300

GAG TTT GTG ACC CAC GCC TGC TCC CTC ATC TAC TGT GTG CAC TTC ATC         7263
Glu Phe Val Thr His Ala Cys Ser Leu Ile Tyr Cys Val His Phe Ile
            2305            2310            2315

CTG GAG GCC GTT GCA GTG CAG CCT GGA GAG CAG CTT CTT AGT CCA GAA         7311
Leu Glu Ala Val Ala Val Gln Pro Gly Glu Gln Leu Leu Ser Pro Glu
        2320            2325            2330
```

FIG.40

```
AGA AGG ACA AAT ACC CCA AAA GCC ATC AGC GAG GAG GAG GAG GAA GTA      7359
Arg Arg Thr Asn Thr Pro Lys Ala Ile Ser Glu Glu Glu Glu Glu Val
        2335            2340                2345

GAT CCA AAC ACA CAG AAT CCT AAG TAT ATC ACT GCA GCC TGT GAG ATG      7407
Asp Pro Asn Thr Gln Asn Pro Lys Tyr Ile Thr Ala Ala Cys Glu Met
        2350            2355            2360

GTG GCA GAA ATG GTG GAG TCT CTG CAG TCG GTG TTG GCC TTG GGT CAT      7455
Val Ala Glu Met Val Glu Ser Leu Gln Ser Val Leu Ala Leu Gly His
2365            2370            2375            2380

AAA AGG AAT AGC GGC GTG CCG GCG TTT CTC ACG CCA TTC CTC AGG AAC      7503
Lys Arg Asn Ser Gly Val Pro Ala Phe Leu Thr Pro Leu Leu Arg Asn
            2385            2390            2395

ATC ATC ATC AGC CTG GCC CGC CTG CCC CTT GTC AAC AGC TAC ACA CGT      7551
Ile Ile Ile Ser Leu Ala Arg Leu Pro Leu Val Asn Ser Tyr Thr Arg
            2400            2405            2410

GTG CCC CCA CTG GTG TGG AAG CTT GGA TGC TCA CCC AAA CCG GGA GGG      7599
Val Pro Pro Leu Val Trp Lys Leu Gly Cys Ser Pro Lys Pro Gly Gly
            2415            2420            2425

GAT TTT GGC ACA GCA TTC CCT GAG ATC CCC GTG GAG TTC CTC CAG GAA      7647
Asp Phe Gly Thr Ala Phe Pro Glu Ile Pro Val Glu Phe Leu Gln Glu
        2430            2435            2440

AAG GAA GTC TTT AAG GAG TTC ATC TAC CGC ATC AAC ACA CTA GGC TGG      7695
Lys Glu Val Phe Lys Glu Phe Ile Tyr Arg Ile Asn Thr Leu Gly Trp
2445            2450            2455            2460

ACC AGT CGT ACT CAG TTT GAA GAA ACT TGG GCC ACC CTC CTT GGT GTC      7743
Thr Ser Arg Thr Gln Phe Glu Glu Thr Trp Ala Thr Leu Leu Gly Val
            2465            2470            2475

CTG GTG ACG CAG CCC CTC GTG ATG GAG CAG GAG GAG AGC CCA CCA GAA      7791
Leu Val Thr Gln Pro Leu Val Met Glu Gln Glu Glu Ser Pro Pro Glu
            2480            2485            2490
```

FIG.4P

```
GAA GAC ACA GAG AGG ACC CAG ATC AAC GTC CTG GCC GTG CAG GCC ATC      7839
Glu Asp Thr Glu Arg Thr Gln Ile Asn Val Leu Ala Val Gln Ala Ile
        2495            2500            2505

ACC TCA CTG GTG CTC AGT GCA ATG ACT GTG CCT GTG GCC GGC AAC CCA      7887
Thr Ser Leu Val Leu Ser Ala Met Thr Val Pro Val Ala Gly Asn Pro
        2510            2515            2520

GCT GTA AGC TGC TTG GAG CAG CAG CCC CGG AAC AAG CCT CTG AAA GCT      7935
Ala Val Ser Cys Leu Glu Gln Gln Pro Arg Asn Lys Pro Leu Lys Ala
2525            2530            2535            2540

CTC GAC ACC AGG TTT GGG AGG AAG CTG AGC ATT ATC AGA GGG ATT GTG      7983
Leu Asp Thr Arg Phe Gly Arg Lys Leu Ser Ile Ile Arg Gly Ile Val
            2545            2550            2555

GAG CAA GAG ATT CAA GCA ATG GTT TCA AAG AGA GAG AAT ATT GCC ACC      8031
Glu Gln Glu Ile Gln Ala Met Val Ser Lys Arg Glu Asn Ile Ala Thr
            2560            2565            2570

CAT CAT TTA TAT CAG GCA TGG GAT CCT GTC CCT TCT CTG TCT CCG GCT      8079
His His Leu Tyr Gln Ala Trp Asp Pro Val Pro Ser Leu Ser Pro Ala
            2575            2580            2585

ACT ACA GGT GCC CTC ATC AGC CAC GAG AAG CTG CTG CTA CAG ATC AAC      8127
Thr Thr Gly Ala Leu Ile Ser His Glu Lys Leu Leu Leu Gln Ile Asn
        2590            2595            2600

CCC GAG CGG GAG CTG GGG AGC ATG AGC TAC AAA CTC GGC CAG GTG TCC      8175
Pro Glu Arg Glu Leu Gly Ser Met Ser Tyr Lys Leu Gly Gln Val Ser
2605            2610            2615            2620

ATA CAC TCC GTG TGG CTG GGG AAC AGC ATC ACA CCC CTG AGG GAC GAG      8223
Ile His Ser Val Trp Leu Gly Asn Ser Ile Thr Pro Leu Arg Glu Glu
            2625            2630            2635

GAA TGG GAC GAG GAA GAG GAG GAG GAG GCC GAC GCC CCT GCA CCT TCC      8271
Glu Trp Asp Glu Glu Glu Glu Glu Glu Ala Asp Ala Pro Ala Pro Ser
            2640            2645            2650
```

FIG.4Q

```
TCA CCA CCC ACG TCT CCA GTC AAC TCC AGG AAA CAC CGG GCT GGA GTT      8319
Ser Pro Pro Thr Ser Pro Val Asn Ser Arg Lys His Arg Ala Gly Val
    2655                2660                2665

GAC ATC CAC TCC TGT TCG CAG TTT TTG CTT GAG TTG TAC AGC CGC TGG      8367
Asp Ile His Ser Cys Ser Gln Phe Leu Leu Glu Leu Tyr Ser Arg Trp
    2670                2675                2680

ATC CTG CCG TCC AGC TCA GCC AGG AGG ACC CCG GCC ATC CTG ATC AGT      8415
Ile Leu Pro Ser Ser Ser Ala Arg Arg Thr Pro Ala Ile Leu Ile Ser
2685                2690                2695                2700

GAG GTG GTC AGA TCC CTT CTA GTG GTC TCA GAC TTG TTC ACC GAG CGC      8463
Glu Val Val Arg Ser Leu Leu Val Val Ser Asp Leu Phe Thr Glu Arg
                2705                2710                2715

AAC CAG TTT GAG CTG ATG TAT GTG ACG CTG ACA GAA CTG CGA AGG GTG      8511
Asn Gln Phe Glu Leu Met Tyr Val Thr Leu Thr Glu Leu Arg Arg Val
            2720                2725                2730

CAC CCT TCA GAA GAC GAG ATC CTC GCT CAG TAC CTG GTG CCT GCC ACC      8559
His Pro Ser Glu Asp Glu Ile Leu Ala Gln Tyr Leu Val Pro Ala Thr
        2735                2740                2745

TGC AAG GCA GCT GCC GTC CTT GGG ATG GAC AAG GCC GTG GCG GAG CCT      8607
Cys Lys Ala Ala Ala Val Leu Gly Met Asp Lys Ala Val Ala Glu Pro
    2750                2755                2760

GTC AGC CGC CTG CTG GAG AGC ACG CTC AGG AGC AGC CAC CTG CCC AGC      8655
Val Ser Arg Leu Leu Glu Ser Thr Leu Arg Ser Ser His Leu Pro Ser
2765                2770                2775                2780

AGG GTT GGA GCC CTG CAC GGC ATC CTC TAT GTG CTG GAG TGC GAC CTG      8703
Arg Val Gly Ala Leu His Gly Ile Leu Tyr Val Leu Glu Cys Asp Leu
                2785                2790                2795

CTG GAC GAC ACT GCC AAG CAG CTC ATC CCG GTC ATC AGC GAC TAT CTC      8751
Leu Asp Asp Thr Ala Lys Gln Leu Ile Pro Val Ile Ser Asp Tyr Leu
            2800                2805                2810
```

FIG.4R

```
CTC TCC AAC CTG AAA GGG ATC GCC CAC TGC GTG AAC ATT CAC AGC CAG        8799
Leu Ser Asn Leu Lys Gly Ile Ala His Cys Val Asn Ile His Ser Gln
        2815            2820            2825

CAG CAC GTA CTG GTC ATG TGT GCC ACT GCG TTT TAC CTC ATT GAG AAC        8847
Gln His Val Leu Val Met Cys Ala Thr Ala Phe Tyr Leu Ile Glu Asn
        2830            2835            2840

TAT CCT CTG GAC GTA GGG CCG GAA TTT TCA GCA TCA ATA ATA CAG ATG        8895
Tyr Pro Leu Asp Val Gly Pro Glu Phe Ser Ala Ser Ile Ile Gln Met
2845            2850            2855            2860

TGT GGG GTG ATG CTG TCT GGA AGT GAG GAG TCC ACC CCC TCC ATC ATT        8943
Cys Gly Val Met Leu Ser Gly Ser Glu Glu Ser Thr Pro Ser Ile Ile
        2865            2870            2875

TAC CAC TGT GCC CTC AGA GGC CTG GAG CGC CTC CTG CTC TCT GAG CAG        8991
Tyr His Cys Ala Leu Arg Gly Leu Glu Arg Leu Leu Leu Ser Glu Gln
        2880            2885            2890

CTC TCC CGC CTG GAT GCA GAA TCG CTG GTC AAG CTG AGT GTG GAC AGA        9039
Leu Ser Arg Leu Asp Ala Glu Ser Leu Val Lys Leu Ser Val Asp Arg
        2895            2900            2905

GTG AAC GTG CAC AGC CCG CAC CGG GCC ATG GCG GCT CTG GGC CTG ATG        9087
Val Asn Val His Ser Pro His Arg Ala Met Ala Ala Leu Gly Leu Met
        2910            2915            2920

CTC ACC TGC ATG TAC ACA GGA AAG GAG AAA GTC AGT CCG GGT AGA ACT        9135
Leu Thr Cys Met Tyr Thr Gly Lys Glu Lys Val Ser Pro Gly Arg Thr
2925            2930            2935            2940

TCA GAC CCT AAT CCT GCA GCC CCC GAC AGC GAG TCA GTG ATT GTT GCT        9183
Ser Asp Pro Asn Pro Ala Ala Pro Asp Ser Glu Ser Val Ile Val Ala
        2945            2950            2955

ATG GAG CGG GTA TCT GTT CTT TTT GAT AGG ATC AGG AAA GGC TTT CCT        9231
Met Glu Arg Val Ser Val Leu Phe Asp Arg Ile Arg Lys Gly Phe Pro
        2960            2965            2970
```

FIG.4S

```
TGT GAA GCC AGA GTG GTG GCC AGG ATC CTG CCC CAG TTT CTA GAC GAC      9279
Cys Glu Ala Arg Val Val Ala Arg Ile Leu Pro Gln Phe Leu Asp Asp
        2975            2980            2985

TTC TTC CCA CCC CAG GAC ATC ATG AAC AAA GTC ATC GGA GAG TTT CTG      9327
Phe Phe Pro Pro Gln Asp Ile Met Asn Lys Val Ile Gly Glu Phe Leu
        2990            2995            3000

TCC AAC CAG CAG CCA TAC CCC CAG TTC ATG GCC ACC GTG GTG TAT AAG      9375
Ser Asn Gln Gln Pro Tyr Pro Gln Phe Met Ala Thr Val Val Tyr Lys
3005            3010            3015            3020

GTG TTT CAG ACT CTG CAC AGC ACC GGG CAG TCG TCC ATG GTC CGG GAC      9423
Val Phe Gln Thr Leu His Ser Thr Gly Gln Ser Ser Met Val Arg Asp
            3025            3030            3035

TGG GTC ATG CTG TCC CTC TCC AAC TTC ACG CAG AGG GCC CCG GTC GCC      9471
Trp Val Met Leu Ser Leu Ser Asn Phe Thr Gln Arg Ala Pro Val Ala
            3040            3045            3050

ATG GCC ACG TGG AGC CTC TCC TGC TTC TTT GTC AGC GCG TCC ACC AGC      9519
Met Ala Thr Trp Ser Leu Ser Cys Phe Phe Val Ser Ala Ser Thr Ser
        3055            3060            3065

CCG TGG GTC GCG GCG ATC CTC CCA CAT GTC ATC AGC AGG ATG GGC AAG      9567
Pro Trp Val Ala Ala Ile Leu Pro His Val Ile Ser Arg Met Gly Lys
        3070            3075            3080

CTG GAG CAG GTG GAC GTG AAC CTT TTC TGC CTG GTC GCC ACA GAC TTC      9615
Leu Glu Gln Val Asp Val Asn Leu Phe Cys Leu Val Ala Thr Asp Phe
3085            3090            3095            3100

TAC AGA CAC CAG ATA GAG GAG GAG CTC GAC CGC AGG GCC TTC CAG TCT      9663
Tyr Arg His Gln Ile Glu Glu Glu Leu Asp Arg Arg Ala Phe Gln Ser
            3105            3110            3115
```

FIG.4T

| | |
|---|---|
| GTG CTT GAG GTG GTT GCA GCC CCA GGA AGC CCA TAT CAC CGG CTG CTG<br>Val Leu Glu Val Val Ala Ala Pro Gly Ser Pro Tyr His Arg Leu Leu<br>           3120              3125             3130 | 9711 |
| ACT TGT TTA CGA AAT GTC CAC AAG GTC ACC ACC TGC T GAGCGCCATG<br>Thr Cys Leu Arg Asn Val His Lys Val Thr Thr Cys<br>       3135            3140 | 9758 |
| GTGGGAGAGA CTGTGAGGCG GCAGCTGGGG CCGGAGCCTT TGGAAGTCTG TGCCCTTGTG | 9818 |
| CCCTGCCTCC ACCGAGCCAG CTTGGTCCCT ATGGGCTTCC GCACATGCCG CGGGCGGCCA | 9878 |
| GGCAACGTGC GTGTCTCTGC CATGTGGCAG AAGTGCTCTT TGTGGCAGTG GCCAGGCAGG | 9938 |
| GAGTGTCTGC AGTCCTGGTG GGGCTGAGCC TGAGGCCTTC CAGAAAGCAG GAGCAGCTGT | 9998 |
| GCTGCACCCC ATGTGGGTGA CCAGGTCCTT TCTCCTGATA GTCACCTGCT GGTTGTTGCC | 10058 |
| AGGTTGCAGC TGCTCTTGCA TCTGGGCCAG AAGTCCTCCC TCCTGCAGGC TGGCTGTTGG | 10118 |
| CCCCTCTGCT GTCCTGCAGT AGAAGGTGCC GTGAGCAGGC TTTGGGAACA CTGGCCTGGG | 10178 |
| TCTCCCTGGT GGGGTGTGCA TGCCACGCCC CGTGTCTGGA TGCACAGATG CCATGGCCTG | 10238 |
| TGCTGGGCCA GTGGCTGGGG GTGCTAGACA CCCGGCACCA TTCTCCCTTC TCTCTTTTCT | 10298 |
| TCTCAGGATT TAAAATTTAA TTATATCAGT AAACAGATTA ATTTTAACGT AAAAAAAAAA | 10358 |
| AAAAAAAA | 10366 |

FIG.4U

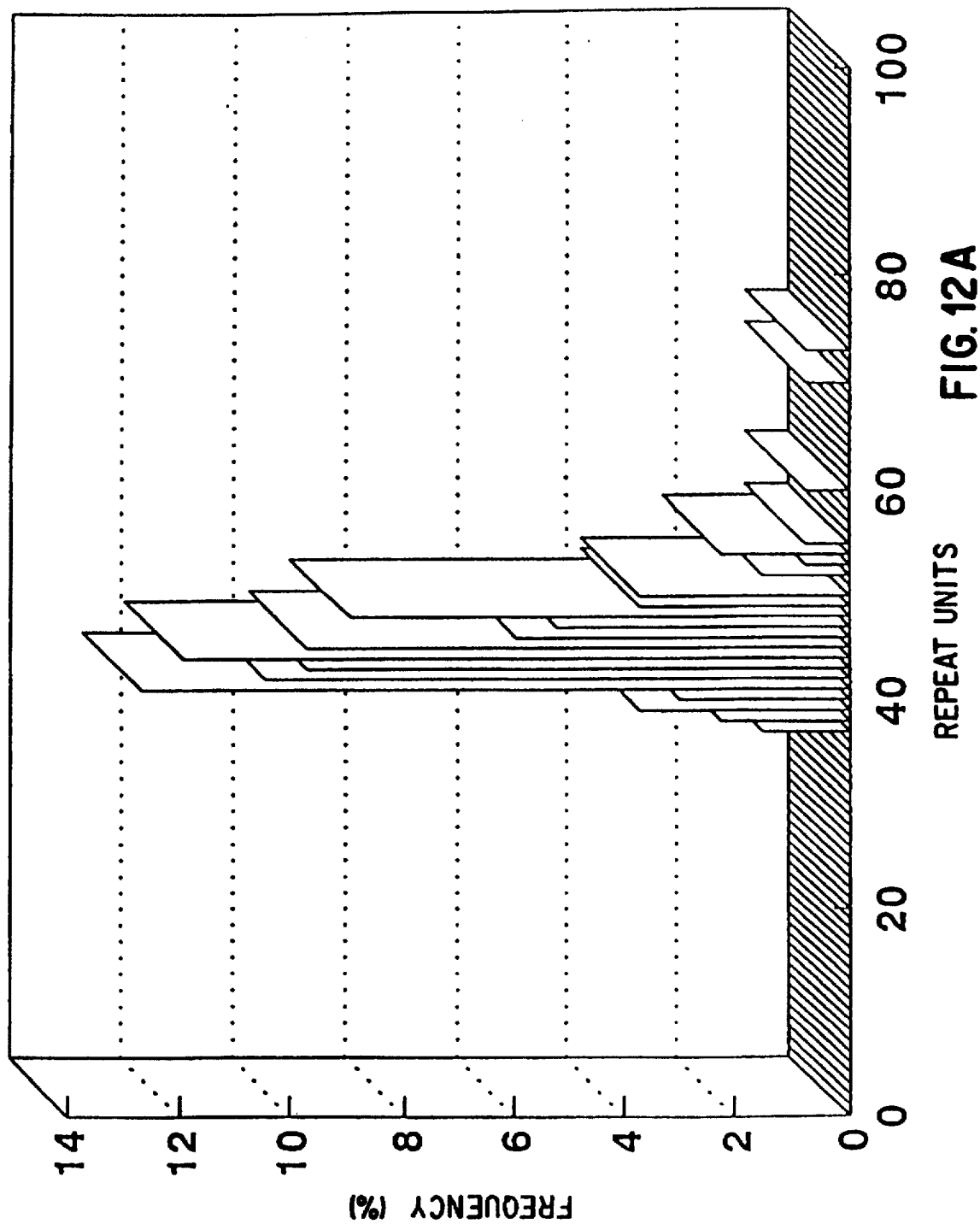

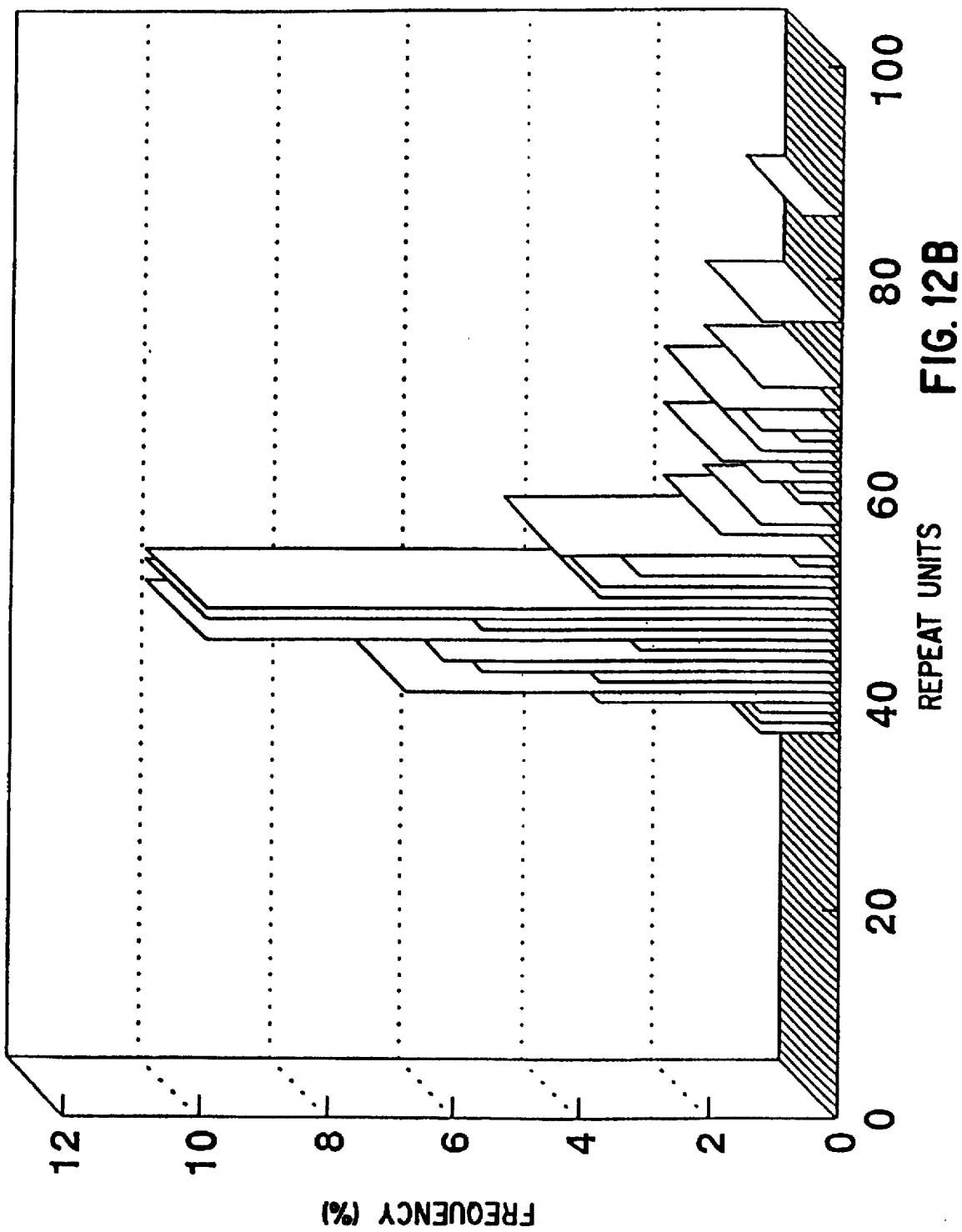

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 20 base pairs ( B ) TYPE: nucleic acid
( C ) STRANDEDNESS: single
( D ) TOPOLOGY: linear ( x i ) SEQUENCE DESCRIPTION: SEQ ID NO:1:

GGCGGGAGAC CGCCATGGCG                           20

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

AATACGACTC ACTATAG                              17

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

ATGAAGGCCT TCGAGTCCCT CAAGTCCTTC                 30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

AAACTCACGG TCGGTGCAGC GGCTCCTCAG                 30

( 2 ) INFORMATION FOR SEQ ID NO:5:

( i ) SEQUENCE CHARACTERISTICS:
        ( A ) LENGTH: 10366 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 316..9748

( x i ) SEQUENCE DESCRIPTION: SEQ ID NO:5:

TTGCTGTGTG AGGCAGAACC TGCGGGGGCA GGGGCGGGCT GGTTCCCTGG CCAGCCATTG     60

GCAGAGTCCG CAGGCTAGGG CTGTCAATCA TGCTGGCCGG CGTGGCCCCG CCTCCGCCGG    120

CGCGGCCCCG CCTCCGCCGG CGCACGTCTG GGACGCAAGG CGCCGTGGGG GCTGCCGGGA    180

CGGGTCCAAG ATGGACGGCC GCTCAGGTTC TGCTTTTACC TGCGGCCCAG AGCCCCATTC    240

ATTGCCCCGG TGCTGAGCGG CGCCGCGAGT CGGCCCGAGG CCTCCGGGGA CTGCCGTGCC    300

GGGCGGGAGA CCGCC ATG GCG ACC CTG GAA AAG CTG ATG AAG GCC TTC GAG    351
               Met Ala Thr Leu Glu Lys Leu Met Lys Ala Phe Glu
                1           5             10

TCC CTC AAG TCC TTC CAG CAG CAG CAG CAG CAG CAG CAG CAG CAG CAG    399
Ser Leu Lys Ser Phe Gln Gln Gln Gln Gln Gln Gln Gln Gln Gln Gln
     15            20             25

| | | | | | | | | | | | | | | | | |
|---|---|---|---|---|---|---|---|---|---|---|---|---|---|---|---|---|
| CAG | CAG | CAG | CAG | CAG | CAG | CAG | CAG | CAG | CAA | CAG | CCG | CCA | CCG | CCG | | 447 |
| Gln | Gln | Gln | Gln | Gln | Gln | Gln | Gln | Gln | Gln | Gln | Pro | Pro | Pro | Pro | | |
| | 30 | | | | 35 | | | | | 40 | | | | | | |
| CCG | CCG | CCG | CCG | CCG | CCT | CCT | CAG | CTT | CCT | CAG | CCG | CCG | CCG | CAG | GCA | 495 |
| Pro | Pro | Pro | Pro | Pro | Pro | Pro | Gln | Leu | Pro | Gln | Pro | Pro | Pro | Gln | Ala | |
| 45 | | | | | 50 | | | | | 55 | | | | | 60 | |
| CAG | CCG | CTG | CTG | CCT | CAG | CCG | CAG | CCG | CCC | CCG | CCG | CCG | CCC | CCG | CCG | 543 |
| Gln | Pro | Leu | Leu | Pro | Gln | Pro | Gln | Pro | Pro | Pro | Pro | Pro | Pro | Pro | Pro | |
| | | | | 65 | | | | | 70 | | | | | 75 | | |
| CCA | CCC | GGC | CCG | GCT | GTG | GCT | GAG | GAG | CCG | CTG | CAC | CGA | CCA | AAG | AAA | 591 |
| Pro | Pro | Gly | Pro | Ala | Val | Ala | Glu | Glu | Pro | Leu | His | Arg | Pro | Lys | Lys | |
| | | | 80 | | | | | 85 | | | | | 90 | | | |
| GAA | CTT | TCA | GCT | ACC | AAG | AAA | GAC | CGT | GTG | AAT | CAT | TGT | CTG | ACA | ATA | 639 |
| Glu | Leu | Ser | Ala | Thr | Lys | Lys | Asp | Arg | Val | Asn | His | Cys | Leu | Thr | Ile | |
| | | 95 | | | | | 100 | | | | | 105 | | | | |
| TGT | GAA | AAC | ATA | GTG | GCA | CAG | TCT | GTC | AGA | AAT | TCT | CCA | GAA | TTT | CAG | 687 |
| Cys | Glu | Asn | Ile | Val | Ala | Gln | Ser | Val | Arg | Asn | Ser | Pro | Glu | Phe | Gln | |
| | 110 | | | | | 115 | | | | | 120 | | | | | |
| AAA | CTT | CTG | GGC | ATC | GCT | ATG | GAA | CTT | TTT | CTG | TGC | AGT | GAT | GAC | | 735 |
| Lys | Leu | Leu | Gly | Ile | Ala | Met | Glu | Leu | Phe | Leu | Leu | Cys | Ser | Asp | Asp | |
| 125 | | | | | 130 | | | | | 135 | | | | | 140 | |
| GCA | GAG | TCA | GAT | GTC | AGG | ATG | GTG | GCT | GAC | GAA | TGC | CTC | AAC | AAA | GTT | 783 |
| Ala | Glu | Ser | Asp | Val | Arg | Met | Val | Ala | Asp | Glu | Cys | Leu | Asn | Lys | Val | |
| | | | | 145 | | | | | 150 | | | | | 155 | | |
| ATC | AAA | GCT | TTG | ATG | GAT | TCT | AAT | CTT | CCA | AGG | TTA | CAG | CTC | GAG | CTC | 831 |
| Ile | Lys | Ala | Leu | Met | Asp | Ser | Asn | Leu | Pro | Arg | Leu | Gln | Leu | Glu | Leu | |
| | | | | 160 | | | | | 165 | | | | | 170 | | |
| TAT | AAG | GAA | ATT | AAA | AAG | AAT | GGT | GCC | CCT | CGG | AGT | TTG | CGT | GCT | GCC | 879 |
| Tyr | Lys | Glu | Ile | Lys | Lys | Asn | Gly | Ala | Pro | Arg | Ser | Leu | Arg | Ala | Ala | |
| | | 175 | | | | | 180 | | | | | 185 | | | | |
| CTG | TGG | AGG | TTT | GCT | GAG | CTG | GCT | CAC | CTG | GTT | CGG | CCT | CAG | AAA | TGC | 927 |
| Leu | Trp | Arg | Phe | Ala | Glu | Leu | Ala | His | Leu | Val | Arg | Pro | Gln | Lys | Cys | |
| 190 | | | | | 195 | | | | | | | 200 | | | | |
| AGG | CCT | TAC | CTG | GTG | AAC | CTT | CTG | CCG | TGC | CTG | ACT | CGA | ACA | AGC | AAG | 975 |
| Arg | Pro | Tyr | Leu | Val | Asn | Leu | Leu | Pro | Cys | Leu | Thr | Arg | Thr | Ser | Lys | |
| 205 | | | | | 210 | | | | | 215 | | | | | 220 | |
| AGA | CCC | GAA | GAA | TCA | GTC | CAG | GAG | ACC | TTG | GCT | GCA | GCT | GTT | CCC | AAA | 1023 |
| Arg | Pro | Glu | Glu | Ser | Val | Gln | Glu | Thr | Leu | Ala | Ala | Ala | Val | Pro | Lys | |
| | | | | 225 | | | | | 230 | | | | | 235 | | |
| ATT | ATG | GCT | TCT | TTT | GGC | AAT | TTT | GCA | AAT | GAC | AAT | GAA | ATT | AAG | GTT | 1071 |
| Ile | Met | Ala | Ser | Phe | Gly | Asn | Phe | Ala | Asn | Asp | Asn | Glu | Ile | Lys | Val | |
| | | | 240 | | | | | 245 | | | | | 250 | | | |
| TTG | TTA | AAG | GCC | TTC | ATA | GCG | AAC | CTG | AAG | TCA | AGC | TCC | CCC | ACC | ATT | 1119 |
| Leu | Leu | Lys | Ala | Phe | Ile | Ala | Asn | Leu | Lys | Ser | Ser | Ser | Pro | Thr | Ile | |
| | | 255 | | | | | 260 | | | | | 265 | | | | |
| CGG | CGG | ACA | GCG | GCT | GGA | TCA | GCA | GTG | AGC | ATC | TGC | CAG | CAC | TCA | AGA | 1167 |
| Arg | Arg | Thr | Ala | Ala | Gly | Ser | Ala | Val | Ser | Ile | Cys | Gln | His | Ser | Arg | |
| | 270 | | | | | 275 | | | | | 280 | | | | | |
| AGG | ACA | CAA | TAT | TTC | TAT | AGT | TGG | CTA | CTA | AAT | GTG | CTC | TTA | GGC | TTA | 1215 |
| Arg | Thr | Gln | Tyr | Phe | Tyr | Ser | Trp | Leu | Leu | Asn | Val | Leu | Leu | Gly | Leu | |
| 285 | | | | | 290 | | | | | 295 | | | | | 300 | |
| CTC | GTT | CCT | GTC | GAG | GAT | GAA | CAC | TCC | ACT | CTG | CTG | ATT | CTT | GGC | GTG | 1263 |
| Leu | Val | Pro | Val | Glu | Asp | Glu | His | Ser | Thr | Leu | Leu | Ile | Leu | Gly | Val | |
| | | | | 305 | | | | | 310 | | | | | 315 | | |
| CTG | CTC | ACC | CTG | AGG | TAT | TTG | GTG | CCC | TTG | CTG | CAG | CAG | CAG | GTC | AAG | 1311 |
| Leu | Leu | Thr | Leu | Arg | Tyr | Leu | Val | Pro | Leu | Leu | Gln | Gln | Gln | Val | Lys | |
| | | | 320 | | | | | 325 | | | | | 330 | | | |
| GAC | ACA | AGC | CTG | AAA | GGC | AGC | TTC | GGA | GTG | ACA | AGG | AAA | GAA | ATG | GAA | 1359 |
| Asp | Thr | Ser | Leu | Lys | Gly | Ser | Phe | Gly | Val | Thr | Arg | Lys | Glu | Met | Glu | |
| | | 335 | | | | | 340 | | | | | 345 | | | | |

| | | | | | | | | | | | | | | | | |
|---|---|---|---|---|---|---|---|---|---|---|---|---|---|---|---|---|
| GTC | TCT | CCT | TCT | GCA | GAG | CAG | CTT | GTC | CAG | GTT | TAT | GAA | CTG | ACG | TTA | 1407 |
| Val | Ser 350 | Pro | Ser | Ala | Glu | Gln 355 | Leu | Val | Gln | Val | Tyr 360 | Glu | Leu | Thr | Leu | |
| CAT | CAT | ACA | CAG | CAC | CAA | GAC | CAC | AAT | GTT | GTG | ACC | GGA | GCC | CTG | GAG | 1455 |
| His 365 | His | Thr | Gln | His | Gln 370 | Asp | His | Asn | Val | Val 375 | Thr | Gly | Ala | Leu | Glu 380 | |
| CTG | TTG | CAG | CAG | CTC | TTC | AGA | ACG | CCT | CCA | CCC | GAG | CTT | CTG | CAA | ACC | 1503 |
| Leu | Leu | Gln | Gln | Leu 385 | Phe | Arg | Thr | Pro | Pro 390 | Pro | Glu | Leu | Leu | Gln 395 | Thr | |
| CTG | ACC | GCA | GTC | GGG | GGC | ATT | GGG | CAG | CTC | ACC | GCT | GCT | AAG | GAG | GAG | 1551 |
| Leu | Thr | Ala | Val 400 | Gly | Gly | Ile | Gly | Gln 405 | Leu | Thr | Ala | Ala | Lys 410 | Glu | Glu | |
| TCT | GGT | GGC | CGA | AGC | CGT | AGT | GGG | AGT | ATT | GTG | GAA | CTT | ATA | GCT | GGA | 1599 |
| Ser | Gly | Gly 415 | Arg | Ser | Arg | Ser | Gly 420 | Ser | Ile | Val | Glu | Leu 425 | Ile | Ala | Gly | |
| GGG | GGT | TCC | TCA | TGC | AGC | CCT | GTC | CTT | TCA | AGA | AAA | CAA | AAA | GGC | AAA | 1647 |
| Gly | Gly 430 | Ser | Ser | Cys | Ser | Pro 435 | Val | Leu | Ser | Arg | Lys 440 | Gln | Lys | Gly | Lys | |
| GTG | CTC | TTA | GGA | GAA | GAA | GAA | GCC | TTG | GAG | GAT | GAC | TCT | GAA | TCG | AGA | 1695 |
| Val 445 | Leu | Leu | Gly | Glu | Glu 450 | Glu | Ala | Leu | Glu | Asp 455 | Asp | Ser | Glu | Ser | Arg 460 | |
| TCG | GAT | GTC | AGC | AGC | TCT | GCC | TTA | ACA | GCC | TCA | GTG | AAG | GAT | GAG | ATC | 1743 |
| Ser | Asp | Val | Ser | Ser 465 | Ser | Ala | Leu | Thr | Ala 470 | Ser | Val | Lys | Asp | Glu 475 | Ile | |
| AGT | GGA | GAG | CTG | GCT | GCT | TCT | TCA | GGG | GTT | TCC | ACT | CCA | GGG | TCA | GCA | 1791 |
| Ser | Gly | Glu | Leu 480 | Ala | Ala | Ser | Ser | Val 485 | Ser | Thr | Pro | Gly 490 | Ser | Ala | | |
| GGT | CAT | GAC | ATC | ATC | ACA | GAA | CAG | CCA | CGG | TCA | CAG | CAC | ACA | CTG | CAG | 1839 |
| Gly | His | Asp 495 | Ile | Ile | Thr | Glu | Gln 500 | Pro | Arg | Ser | Gln | His 505 | Thr | Leu | Gln | |
| GCG | GAC | TCA | CTG | GAT | CTG | GCC | AGC | TGT | GAC | TTG | ACA | AGC | TCT | GCC | ACT | 1887 |
| Ala | Asp | Ser 510 | Leu | Asp | Leu | Ala | Ser 515 | Cys | Asp | Leu | Thr | Ser 520 | Ser | Ala | Thr | |
| GAT | GGG | GAT | GAG | GAG | GAT | ATC | TTG | AGC | CAC | AGC | TCC | AGC | CAG | GTC | AGC | 1935 |
| Asp 525 | Gly | Asp | Glu | Glu | Asp 530 | Ile | Leu | Ser | His | Ser 535 | Ser | Ser | Gln | Val | Ser 540 | |
| GCC | GTC | CCA | TCT | GAC | CCT | GCC | ATG | GAC | CTG | AAT | GAT | GGG | ACC | CAG | GCC | 1983 |
| Ala | Val | Pro | Ser | Asp 545 | Pro | Ala | Met | Asp | Leu 550 | Asn | Asp | Gly | Thr | Gln 555 | Ala | |
| TCG | TCG | CCC | ATC | AGC | GAC | AGC | TCC | CAG | ACC | ACC | ACC | GAA | GGG | CCT | GAT | 2031 |
| Ser | Ser | Pro | Ile 560 | Ser | Asp | Ser | Ser | Gln 565 | Thr | Thr | Thr | Glu | Gly 570 | Pro | Asp | |
| TCA | GCT | GTT | ACC | CCT | TCA | GAC | AGT | TCT | GAA | ATT | GTG | TTA | GAC | GGT | ACC | 2079 |
| Ser | Ala | Val 575 | Thr | Pro | Ser | Asp | Ser 580 | Ser | Glu | Ile | Val | Leu 585 | Asp | Gly | Thr | |
| GAC | AAC | CAG | TAT | TTG | GGC | CTG | CAG | ATT | GGA | CAG | CCC | CAG | GAT | GAA | GAT | 2127 |
| Asp | Asn | Gln | Tyr 590 | Leu | Gly | Leu | Gln | Ile 595 | Gly | Gln | Pro | Gln | Asp 600 | Glu | Asp | |
| GAG | GAA | GCC | ACA | GGT | ATT | CTT | CCT | GAT | GAA | GCC | TCG | GAG | GCC | TTC | AGG | 2175 |
| Glu 605 | Glu | Ala | Thr | Gly | Ile 610 | Leu | Pro | Asp | Glu | Ala 615 | Ser | Glu | Ala | Phe | Arg 620 | |
| AAC | TCT | TCC | ATG | GCC | CTT | CAA | CAG | GCA | CAT | TTA | TTG | AAA | AAC | ATG | AGT | 2223 |
| Asn | Ser | Ser | Met | Ala 625 | Leu | Gln | Gln | Ala | His 630 | Leu | Leu | Lys | Asn | Met 635 | Ser | |
| CAC | TGC | AGG | CAG | CCT | TCT | GAC | AGC | AGT | GTT | GAT | AAA | TTT | GTG | TTG | AGA | 2271 |
| His | Cys | Arg | Gln 640 | Pro | Ser | Asp | Ser | Ser 645 | Val | Asp | Lys | Phe | Val 650 | Leu | Arg | |
| GAT | GAA | GCT | ACT | GAA | CCG | GGT | GAT | CAA | GAA | AAC | AAG | CCT | TGC | CGC | ATC | 2319 |
| Asp | Glu | Ala | Thr 655 | Glu | Pro | Gly | Asp | Gln 660 | Glu | Asn | Lys | Pro | Cys 665 | Arg | Ile | |

| | | | | | | | | | | | | | | | | |
|---|---|---|---|---|---|---|---|---|---|---|---|---|---|---|---|---|
| AAA | GGT | GAC | ATT | GGA | CAG | TCC | ACT | GAT | GAT | GAC | TCT | GCA | CCT | CTT | GTC | 2367 |
| Lys | Gly 670 | Asp | Ile | Gly | Gln | Ser 675 | Thr | Asp | Asp | Asp | Ser 680 | Ala | Pro | Leu | Val | |
| CAT | TCT | GTC | CGC | CTT | TTA | TCT | GCT | TCG | TTT | TTG | CTA | ACA | GGG | GGA | AAA | 2415 |
| His 685 | Ser | Val | Arg | Leu 690 | Leu | Ser | Ala | Ser | Phe 695 | Leu | Leu | Thr | Gly | Gly | Lys 700 | |
| AAT | GTG | CTG | GTT | CCG | GAC | AGG | GAT | GTG | AGG | GTC | AGC | GTG | AAG | GCC | CTG | 2463 |
| Asn | Val | Leu | Val | Pro 705 | Asp | Arg | Asp | Val | Arg 710 | Val | Ser | Val | Lys 715 | Ala | Leu | |
| GCC | CTC | AGC | TGT | GTG | GGA | GCA | GCT | GTG | GCC | CTC | CAC | CCG | GAA | TCT | TTC | 2511 |
| Ala | Leu | Ser | Cys 720 | Val | Gly | Ala | Ala | Val 725 | Ala | Leu | His | Pro 730 | Glu | Ser | Phe | |
| TTC | AGC | AAA | CTC | TAT | AAA | GTT | CCT | CTT | GAC | ACC | ACG | GAA | TAC | CCT | GAG | 2559 |
| Phe | Ser | Lys 735 | Leu | Tyr | Lys | Val | Pro 740 | Leu | Asp | Thr | Thr | Glu 745 | Tyr | Pro | Glu | |
| GAA | CAG | TAT | GTC | TCA | GAC | ATC | TTG | AAC | TAC | ATC | GAT | CAT | GGA | GAC | CCA | 2607 |
| Glu | Gln | Tyr 750 | Val | Ser | Asp | Ile | Leu | Asn 755 | Tyr | Ile | Asp | His | Gly 760 | Asp | Pro | |
| CAG | GTT | CGA | GGA | GCC | ACT | GCC | ATT | CTC | TGT | GGG | ACC | CTC | ATC | TGC | TCC | 2655 |
| Gln 765 | Val | Arg | Gly | Ala | Thr 770 | Ala | Ile | Leu | Cys | Gly 775 | Thr | Leu | Ile | Cys | Ser 780 | |
| ATC | CTC | AGC | AGG | TCC | CGC | TTC | CAC | GTG | GGA | GAT | TGG | ATG | GGC | ACC | ATT | 2703 |
| Ile | Leu | Ser | Arg | Ser 785 | Arg | Phe | His | Val | Gly 790 | Asp | Trp | Met | Gly | Thr 795 | Ile | |
| AGA | ACC | CTC | ACA | GGA | AAT | ACA | TTT | TCT | TTG | GCG | GAT | TGC | ATT | CCT | TTG | 2751 |
| Arg | Thr | Leu | Thr 800 | Gly | Asn | Thr | Phe | Ser 805 | Leu | Ala | Asp | Cys | Ile 810 | Pro | Leu | |
| CTG | CGG | AAA | ACA | CTG | AAG | GAT | GAG | TCT | TCT | GTT | ACT | TGC | AAG | TTA | GCT | 2799 |
| Leu | Arg | Lys 815 | Thr | Leu | Lys | Asp | Glu 820 | Ser | Ser | Val | Thr | Cys 825 | Lys | Leu | Ala | |
| TGT | ACA | GCT | GTG | AGG | AAC | TGT | GTC | ATG | AGT | CTC | TGC | AGC | AGC | AGC | TAC | 2847 |
| Cys | Thr | Ala | Val 830 | Arg | Asn | Cys | Val | Met 835 | Ser | Leu | Cys | Ser | Ser 840 | Ser | Tyr | |
| AGT | GAG | TTA | GGA | CTG | CAG | CTG | ATC | ATC | GAT | GTG | CTG | ACT | CTG | AGG | AAC | 2895 |
| Ser 845 | Glu | Leu | Gly | Leu | Gln 850 | Leu | Ile | Ile | Asp | Val 855 | Leu | Thr | Leu | Arg | Asn 860 | |
| AGT | TCC | TAT | TGG | CTG | GTG | AGG | ACA | GAG | CTT | CTG | GAA | ACC | CTT | GCA | GAG | 2943 |
| Ser | Ser | Tyr | Trp | Leu 865 | Val | Arg | Thr | Glu | Leu 870 | Leu | Glu | Thr | Leu | Ala 875 | Glu | |
| ATT | GAC | TTC | AGG | CTG | GTG | AGC | TTT | TTG | GAG | GCA | AAA | GCA | GAA | AAC | TTA | 2991 |
| Ile | Asp | Phe | Arg 880 | Leu | Val | Ser | Phe | Leu 885 | Glu | Ala | Lys | Ala | Glu 890 | Asn | Leu | |
| CAC | AGA | GGG | GCT | CAT | CAT | TAT | ACA | GGG | CTT | TTA | AAA | CTG | CAA | GAA | CGA | 3039 |
| His | Arg | Gly 895 | Ala | His | His | Tyr | Thr 900 | Gly | Leu | Leu | Lys | Leu 905 | Gln | Glu | Arg | |
| GTG | CTC | AAT | AAT | GTT | GTC | ATC | CAT | TTG | CTT | GGA | GAT | GAA | GAC | CCC | AGG | 3087 |
| Val | Leu | Asn 910 | Asn | Val | Val | Ile | His 915 | Leu | Leu | Gly | Asp | Glu 920 | Asp | Pro | Arg | |
| GTG | CGA | CAT | GTT | GCC | GCA | GCA | TCA | CTA | ATT | AGG | CTT | GTC | CCA | AAG | CTG | 3135 |
| Val 925 | Arg | His | Val | Ala | Ala 930 | Ala | Ser | Leu | Ile | Arg 935 | Leu | Val | Pro | Lys 940 | Leu | |
| TTT | TAT | AAA | TGT | GAC | CAA | GGA | CAA | GCT | GAT | CCA | GTA | GTG | GCC | GTG | GCA | 3183 |
| Phe | Tyr | Lys | Cys | Asp 945 | Gln | Gly | Gln | Ala | Asp 950 | Pro | Val | Val | Ala | Val 955 | Ala | |
| AGA | GAT | CAA | AGC | AGT | GTT | TAC | CTG | AAA | CTT | CTC | ATG | CAT | GAG | ACG | CAG | 3231 |
| Arg | Asp | Gln | Ser 960 | Ser | Val | Tyr | Leu | Lys 965 | Leu | Leu | Met | His | Glu 970 | Thr | Gln | |
| CCT | CCA | TCT | CAT | TTC | TCC | GTC | AGC | ACA | ATA | ACC | AGA | ATA | TAT | AGA | GGC | 3279 |
| Pro | Pro | Ser | His 975 | Phe | Ser | Val | Ser | Thr 980 | Ile | Thr | Arg | Ile 985 | Tyr | Arg | Gly | |

```
TAT AAC CTA CTA CCA AGC ATA ACA GAC GTC ACT ATG GAA AAT AAC CTT      3327
Tyr Asn Leu Leu Pro Ser Ile Thr Asp Val Thr Met Glu Asn Asn Leu
    990             995                 1000

TCA AGA GTT ATT GCA GCA GTT TCT CAT GAA CTA ATC ACA TCA ACC ACC      3375
Ser Arg Val Ile Ala Ala Val Ser His Glu Leu Ile Thr Ser Thr Thr
1005            1010                1015                1020

AGA GCA CTC ACA TTT GGA TGC TGT GAA GCT TTG TGT CTT CTT TCC ACT      3423
Arg Ala Leu Thr Phe Gly Cys Cys Glu Ala Leu Cys Leu Leu Ser Thr
                1025                1030                1035

GCC TTC CCA GTT TGC ATT TGG AGT TTA GGT TGG CAC TGT GGA GTG CCT      3471
Ala Phe Pro Val Cys Ile Trp Ser Leu Gly Trp His Cys Gly Val Pro
            1040                1045                1050

CCA CTG AGT GCC TCA GAT GAG TCT AGG AAG AGC TGT ACC GTT GGG ATG      3519
Pro Leu Ser Ala Ser Asp Glu Ser Arg Lys Ser Cys Thr Val Gly Met
        1055                1060                1065

GCC ACA ATG ATT CTG ACC CTG CTC TCG TCA GCT TGG TTC CCA TTG GAT      3567
Ala Thr Met Ile Leu Thr Leu Leu Ser Ser Ala Trp Phe Pro Leu Asp
    1070                1075                1080

CTC TCA GCC CAT CAA GAT GCT TTG ATT TTG GCC GGA AAC TTG CTT GCA      3615
Leu Ser Ala His Gln Asp Ala Leu Ile Leu Ala Gly Asn Leu Leu Ala
1085            1090                1095                1100

GCC AGT GCT CCC AAA TCT CTG AGA AGT TCA TGG GCC TCT GAA GAA GAA      3663
Ala Ser Ala Pro Lys Ser Leu Arg Ser Ser Trp Ala Ser Glu Glu Glu
                1105                1110                1115

GCC AAC CCA GCA GCC ACC AAG CAA GAG GAG GTC TGG CCA GCC CTG GGG      3711
Ala Asn Pro Ala Ala Thr Lys Gln Glu Glu Val Trp Pro Ala Leu Gly
            1120                1125                1130

GAC CGG GCC CTG GTG CCC ATG GTG GAG CAG CTC TTC TCT CAC CTG CTG      3759
Asp Arg Ala Leu Val Pro Met Val Glu Gln Leu Phe Ser His Leu Leu
        1135                1140                1145

AAG GTG ATT AAC ATT TGT GCC CAC GTC CTG GAT GAC GTG GCT CCT GGA      3807
Lys Val Ile Asn Ile Cys Ala His Val Leu Asp Asp Val Ala Pro Gly
    1150                1155                1160

CCC GCA ATA AAG GCA GCC TTG CCT TCT CTA ACA AAC CCC CCT TCT CTA      3855
Pro Ala Ile Lys Ala Ala Leu Pro Ser Leu Thr Asn Pro Pro Ser Leu
1165            1170                1175                1180

AGT CCC ATC CGA CGA AAG GGG AAG GAG AAA GAA CCA GGA GAA CAA GCA      3903
Ser Pro Ile Arg Arg Lys Gly Lys Glu Lys Glu Pro Gly Glu Gln Ala
                1185                1190                1195

TCT GTA CCG TTG AGT CCC AAG AAA GGC AGT GAG GCC AGT GCA GCT TCT      3951
Ser Val Pro Leu Ser Pro Lys Lys Gly Ser Glu Ala Ser Ala Ala Ser
            1200                1205                1210

AGA CAA TCT GAT ACC TCA GGT CCT GTT ACA ACA AGT AAA TCC TCA TCA      3999
Arg Gln Ser Asp Thr Ser Gly Pro Val Thr Thr Ser Lys Ser Ser Ser
        1215                1220                1225

CTG GGG AGT TTC TAT CAT CTT CCT TCA TAC CTC AGA CTG CAT GAT GTC      4047
Leu Gly Ser Phe Tyr His Leu Pro Ser Tyr Leu Arg Leu His Asp Val
    1230                1235                1240

CTG AAA GCT ACA CAC GCT AAC TAC AAG GTC ACG CTG GAT CTT CAG AAC      4095
Leu Lys Ala Thr His Ala Asn Tyr Lys Val Thr Leu Asp Leu Gln Asn
1245            1250                1255                1260

AGC ACG GAA AAG TTT GGA GGG TTT CTC CGC TCA GCC TTG GAT GTT CTT      4143
Ser Thr Glu Lys Phe Gly Gly Phe Leu Arg Ser Ala Leu Asp Val Leu
                1265                1270                1275

TCT CAG ATA CTA GAG CTG GCC ACA CTG CAG GAC ATT GGG AAG TGT GTT      4191
Ser Gln Ile Leu Glu Leu Ala Thr Leu Gln Asp Ile Gly Lys Cys Val
            1280                1285                1290

GAA GAG ATC CTA GGA TAC CTG AAA TCC TGC TTT AGT CGA GAA CCA ATG      4239
Glu Glu Ile Leu Gly Tyr Leu Lys Ser Cys Phe Ser Arg Glu Pro Met
        1295                1300                1305
```

```
ATG GCA ACT GTT TGT GTT CAA CAA TTG TTG AAG ACT CTC TTT GGC ACA         4287
Met Ala Thr Val Cys Val Gln Gln Leu Leu Lys Thr Leu Phe Gly Thr
1310            1315                    1320

AAC TTG GCC TCC CAG TTT GAT GGC TTA TCT TCC AAC CCC AGC AAG TCA         4335
Asn Leu Ala Ser Gln Phe Asp Gly Leu Ser Ser Asn Pro Ser Lys Ser
1325            1330                1335                1340

CAA GGC CGA GCA CAG CGC CTT GGC TCC TCC AGT GTG AGG CCA GGC TTG         4383
Gln Gly Arg Ala Gln Arg Leu Gly Ser Ser Ser Val Arg Pro Gly Leu
                1345                1350                1355

TAC CAC TAC TGC TTC ATG GCC CCG TAC ACC CAC TTC ACC CAG GCC CTC         4431
Tyr His Tyr Cys Phe Met Ala Pro Tyr Thr His Phe Thr Gln Ala Leu
            1360                1365                1370

GCT GAC GCC AGC CTG AGG AAC ATG GTG CAG GCG GAG CAG GAG AAC GAC         4479
Ala Asp Ala Ser Leu Arg Asn Met Val Gln Ala Glu Gln Glu Asn Asp
1375                1380                1385

ACC TCG GGA TGG TTT GAT GTC CTC CAG AAA GTG TCT ACC CAG TTG AAG         4527
Thr Ser Gly Trp Phe Asp Val Leu Gln Lys Val Ser Thr Gln Leu Lys
1390                1395                1400

ACA AAC CTC ACG AGT GTC ACA AAG AAC CGT GCA GAT AAG AAT GCT ATT         4575
Thr Asn Leu Thr Ser Val Thr Lys Asn Arg Ala Asp Lys Asn Ala Ile
1405                1410                1415                1420

CAT AAT CAC ATT CGT TTG TTT GAA CCT CTT GTT ATA AAA GCT TTA AAA         4623
His Asn His Ile Arg Leu Phe Glu Pro Leu Val Ile Lys Ala Leu Lys
                    1425                1430                1435

CAG TAC ACG ACT ACA ACA TGT GTG CAG TTA CAG AAG CAG GTT TTA GAT         4671
Gln Tyr Thr Thr Thr Thr Cys Val Gln Leu Gln Lys Gln Val Leu Asp
                1440                1445                1450

TTG CTG GCG CAG CTG GTT CAG TTA CGG GTT AAT TAC TGT CTT CTG GAT         4719
Leu Leu Ala Gln Leu Val Gln Leu Arg Val Asn Tyr Cys Leu Leu Asp
            1455                1460                1465

TCA GAT CAG GTG TTT ATT GGC TTT GTA TTG AAA CAG TTT GAA TAC ATT         4767
Ser Asp Gln Val Phe Ile Gly Phe Val Leu Lys Gln Phe Glu Tyr Ile
        1470                1475                1480

GAA GTG GGC CAG TTC AGG GAA TCA GAG GCA ATC ATT CCA AAC ATC TTT         4815
Glu Val Gly Gln Phe Arg Glu Ser Glu Ala Ile Ile Pro Asn Ile Phe
1485                1490                1495                1500

TTC TTC TTG GTA TTA CTA TCT TAT GAA CGC TAT CAT TCA AAA CAG ATC         4863
Phe Phe Leu Val Leu Leu Ser Tyr Glu Arg Tyr His Ser Lys Gln Ile
                    1505                1510                1515

ATT GGA ATT CCT AAA ATC ATT CAG CTC TGT GAT GGC ATC ATG GCC AGT         4911
Ile Gly Ile Pro Lys Ile Ile Gln Leu Cys Asp Gly Ile Met Ala Ser
                1520                1525                1530

GGA AGG AAG GCT GTG ACA CAT GCC ATA CCG GCT CTG CAG CCC ATA GTC         4959
Gly Arg Lys Ala Val Thr His Ala Ile Pro Ala Leu Gln Pro Ile Val
            1535                1540                1545

CAC GAC CTC TTT GTA TTA AGA GGA ACA AAT AAA GCT GAT GCA GGA AAA         5007
His Asp Leu Phe Val Leu Arg Gly Thr Asn Lys Ala Asp Ala Gly Lys
        1550                1555                1560

GAG CTT GAA ACC CAA AAA GAG GTG GTG GTG TCA ATG TTA CTG AGA CTC         5055
Glu Leu Glu Thr Gln Lys Glu Val Val Val Ser Met Leu Leu Arg Leu
1565                1570                1575                1580

ATC CAG TAC CAT CAG GTG TTG GAG ATG TTC ATT CTT GTC CTG CAG CAG         5103
Ile Gln Tyr His Gln Val Leu Glu Met Phe Ile Leu Val Leu Gln Gln
                    1585                1590                1595

TGC CAC AAG GAG AAT GAA GAC AAG TGG AAG CGA CTG TCT CGA CAG ATA         5151
Cys His Lys Glu Asn Glu Asp Lys Trp Lys Arg Leu Ser Arg Gln Ile
                1600                1605                1610

GCT GAC ATC ATC CTC CCA ATG TTA GCC AAA CAG CAG ATG CAC ATT GAC         5199
Ala Asp Ile Ile Leu Pro Met Leu Ala Lys Gln Gln Met His Ile Asp
            1615                1620                1625
```

| | | | | | | | | | | | | | | | | |
|---|---|---|---|---|---|---|---|---|---|---|---|---|---|---|---|---|
| TCT | CAT | GAA | GCC | CTT | GGA | GTG | TTA | AAT | ACA | TTA | TTT | GAG | ATT | TTG | GCC | 5247 |
| Ser | His | Glu | Ala | Leu | Gly | Val | Leu | Asn | Thr | Leu | Phe | Glu | Ile | Leu | Ala | |
| | 1630 | | | | 1635 | | | | | 1640 | | | | | | |
| CCT | TCC | TCC | CTC | CGT | CCG | GTA | GAC | ATG | CTT | TTA | CGG | AGT | ATG | TTC | GTC | 5295 |
| Pro | Ser | Ser | Leu | Arg | Pro | Val | Asp | Met | Leu | Leu | Arg | Ser | Met | Phe | Val | |
| 1645 | | | | | 1650 | | | | | 1655 | | | | | 1660 | |
| ACT | CCA | AAC | ACA | ATG | GCG | TCC | GTG | AGC | ACT | GTT | CAA | CTG | TGG | ATA | TCG | 5343 |
| Thr | Pro | Asn | Thr | Met | Ala | Ser | Val | Ser | Thr | Val | Gln | Leu | Trp | Ile | Ser | |
| | | | | 1665 | | | | | 1670 | | | | | 1675 | | |
| GGA | ATT | CTG | GCC | ATT | TTG | AGG | GTT | CTG | ATT | TCC | CAG | TCA | ACT | GAA | GAT | 5391 |
| Gly | Ile | Leu | Ala | Ile | Leu | Arg | Val | Leu | Ile | Ser | Gln | Ser | Thr | Glu | Asp | |
| | | | 1680 | | | | | 1685 | | | | | 1690 | | | |
| ATT | GTT | CTT | TCT | CGT | ATT | CAG | GAG | CTC | TCC | TTC | TCT | CCG | TAT | TTA | ATC | 5439 |
| Ile | Val | Leu | Ser | Arg | Ile | Gln | Glu | Leu | Ser | Phe | Ser | Pro | Tyr | Leu | Ile | |
| | | | 1695 | | | | | 1700 | | | | | 1705 | | | |
| TCC | TGT | ACA | GTA | ATT | AAT | AGG | TTA | AGA | GAT | GGG | GAC | AGT | ACT | TCA | ACG | 5487 |
| Ser | Cys | Thr | Val | Ile | Asn | Arg | Leu | Arg | Asp | Gly | Asp | Ser | Thr | Ser | Thr | |
| | 1710 | | | | | 1715 | | | | | 1720 | | | | | |
| CTA | GAA | GAA | CAC | AGT | GAA | GGG | AAA | CAA | ATA | AAG | AAT | TTG | CCA | GAA | GAA | 5535 |
| Leu | Glu | Glu | His | Ser | Glu | Gly | Lys | Gln | Ile | Lys | Asn | Leu | Pro | Glu | Glu | |
| 1725 | | | | | 1730 | | | | | 1735 | | | | | 1740 | |
| ACA | TTT | TCA | AGG | TTT | CTA | TTA | CAA | CTG | GTT | GGT | ATT | CTT | TTA | GAA | GAC | 5583 |
| Thr | Phe | Ser | Arg | Phe | Leu | Leu | Gln | Leu | Val | Gly | Ile | Leu | Leu | Glu | Asp | |
| | | | | 1745 | | | | | 1750 | | | | | 1755 | | |
| ATT | GTT | ACA | AAA | CAG | CTG | AAG | GTG | GAA | ATG | AGT | GAG | CAG | CAA | CAT | ACT | 5631 |
| Ile | Val | Thr | Lys | Gln | Leu | Lys | Val | Glu | Met | Ser | Glu | Gln | Gln | His | Thr | |
| | | | 1760 | | | | | 1765 | | | | | 1770 | | | |
| TTC | TAT | TGC | CAG | GAA | CTA | GGC | ACA | CTG | CTA | ATG | TGT | CTG | ATC | CAC | ATC | 5679 |
| Phe | Tyr | Cys | Gln | Glu | Leu | Gly | Thr | Leu | Leu | Met | Cys | Leu | Ile | His | Ile | |
| | | 1775 | | | | | 1780 | | | | | 1785 | | | | |
| TTC | AAG | TCT | GGA | ATG | TTC | CGG | AGA | ATC | ACA | GCA | GCT | GCC | ACT | AGG | CTG | 5727 |
| Phe | Lys | Ser | Gly | Met | Phe | Arg | Arg | Ile | Thr | Ala | Ala | Ala | Thr | Arg | Leu | |
| | 1790 | | | | | 1795 | | | | | 1800 | | | | | |
| TTC | CGC | AGT | GAT | GGC | TGT | GGC | GGC | AGT | TTC | TAC | ACC | CTG | GAC | AGC | TTG | 5775 |
| Phe | Arg | Ser | Asp | Gly | Cys | Gly | Gly | Ser | Phe | Tyr | Thr | Leu | Asp | Ser | Leu | |
| 1805 | | | | 1810 | | | | | 1815 | | | | | 1820 | | |
| AAC | TTG | CGG | GCT | CGT | TCC | ATG | ATC | ACC | ACC | CAC | CCG | GCC | CTG | GTG | CTG | 5823 |
| Asn | Leu | Arg | Ala | Arg | Ser | Met | Ile | Thr | Thr | His | Pro | Ala | Leu | Val | Leu | |
| | | | | 1825 | | | | | 1830 | | | | | 1835 | | |
| CTC | TGG | TGT | CAG | ATA | CTG | CTG | CTT | GTC | AAC | CAC | ACC | GAC | TAC | CGC | TGG | 5871 |
| Leu | Trp | Cys | Gln | Ile | Leu | Leu | Leu | Val | Asn | His | Thr | Asp | Tyr | Arg | Trp | |
| | | | 1840 | | | | | 1845 | | | | | 1850 | | | |
| TGG | GCA | GAA | GTG | CAG | CAG | ACC | CCG | AAA | AGA | CAC | AGT | CTG | TCC | AGC | ACA | 5919 |
| Trp | Ala | Glu | Val | Gln | Gln | Thr | Pro | Lys | Arg | His | Ser | Leu | Ser | Ser | Thr | |
| | | 1855 | | | | | 1860 | | | | | 1865 | | | | |
| AAG | TTA | CTT | AGT | CCC | CAG | ATG | TCT | GGA | GAA | GAG | GAG | GAT | TCT | GAC | TTG | 5967 |
| Lys | Leu | Leu | Ser | Pro | Gln | Met | Ser | Gly | Glu | Glu | Glu | Asp | Ser | Asp | Leu | |
| | 1870 | | | | | 1875 | | | | | 1880 | | | | | |
| GCA | GCC | AAA | CTT | GGA | ATG | TGC | AAT | AGA | GAA | ATA | GTA | CGA | AGA | GGG | GCT | 6015 |
| Ala | Ala | Lys | Leu | Gly | Met | Cys | Asn | Arg | Glu | Ile | Val | Arg | Arg | Gly | Ala | |
| 1885 | | | | 1890 | | | | | 1895 | | | | | 1900 | | |
| CTC | ATT | CTC | TTC | TGT | GAT | TAT | GTC | TGT | CAG | AAC | CTC | CAT | GAC | TCC | GAG | 6063 |
| Leu | Ile | Leu | Phe | Cys | Asp | Tyr | Val | Cys | Gln | Asn | Leu | His | Asp | Ser | Glu | |
| | | | | 1905 | | | | | 1910 | | | | | 1915 | | |
| CAC | TTA | ACG | TGG | CTC | ATT | GTA | AAT | CAC | ATT | CAA | GAT | CTG | ATC | AGC | CTT | 6111 |
| His | Leu | Thr | Trp | Leu | Ile | Val | Asn | His | Ile | Gln | Asp | Leu | Ile | Ser | Leu | |
| | | | 1920 | | | | | 1925 | | | | | 1930 | | | |
| TCC | CAC | GAG | CCT | CCA | GTA | CAG | GAC | TTC | ATC | AGT | GCC | GTT | CAT | CGG | AAC | 6159 |
| Ser | His | Glu | Pro | Pro | Val | Gln | Asp | Phe | Ile | Ser | Ala | Val | His | Arg | Asn | |
| | 1935 | | | | | 1940 | | | | | 1945 | | | | | |

| | | | | | | | | | | | | | | | | |
|---|---|---|---|---|---|---|---|---|---|---|---|---|---|---|---|---|
| TCT | GCT | GCC | AGC | GGC | CTG | TTC | ATC | CAG | GCA | ATT | CAG | TCT | CGT | TGT | GAA | 6207 |
| Ser | Ala | Ala | Ser | Gly | Leu | Phe | Ile | Gln | Ala | Ile | Gln | Ser | Arg | Cys | Glu | |
| | | 1950 | | | 1955 | | | | | 1960 | | | | | | |
| AAC | CTT | TCA | ACT | CCA | ACC | ATG | CTG | AAG | AAA | ACT | CTT | CAG | TGC | TTG | GAG | 6255 |
| Asn | Leu | Ser | Thr | Pro | Thr | Met | Leu | Lys | Lys | Thr | Leu | Gln | Cys | Leu | Glu | |
| 1965 | | | | | 1970 | | | | 1975 | | | | | | 1980 | |
| GGG | ATC | CAT | CTC | AGC | CAG | TCG | GGA | GCT | GTG | CTC | ACG | CTG | TAT | GTG | GAC | 6303 |
| Gly | Ile | His | Leu | Ser | Gln | Ser | Gly | Ala | Val | Leu | Thr | Leu | Tyr | Val | Asp | |
| | | | | 1985 | | | | | 1990 | | | | | | 1995 | |
| AGG | CTT | CTG | TGC | ACC | CCT | TTC | CGT | GTG | CTG | GCT | CGC | ATG | GTC | GAC | ATC | 6351 |
| Arg | Leu | Leu | Cys | Thr | Pro | Phe | Arg | Val | Leu | Ala | Arg | Met | Val | Asp | Ile | |
| | | | 2000 | | | | | 2005 | | | | | 2010 | | | |
| CTT | GCT | TGT | CGC | CGG | GTA | GAA | ATG | CTT | CTG | GCT | GCA | AAT | TTA | CAG | AGC | 6399 |
| Leu | Ala | Cys | Arg | Arg | Val | Glu | Met | Leu | Leu | Ala | Ala | Asn | Leu | Gln | Ser | |
| | | 2015 | | | | | 2020 | | | | | 2025 | | | | |
| AGC | ATG | GCC | CAG | TTG | CCA | ATG | GAA | GAA | CTC | AAC | AGA | ATC | CAG | GAA | TAC | 6447 |
| Ser | Met | Ala | Gln | Leu | Pro | Met | Glu | Glu | Leu | Asn | Arg | Ile | Gln | Glu | Tyr | |
| | 2030 | | | | | 2035 | | | | | 2040 | | | | | |
| CTT | CAG | AGC | AGC | GGG | CTC | GCT | CAG | AGA | CAC | CAA | AGG | CTC | TAT | TCC | CTG | 6495 |
| Leu | Gln | Ser | Ser | Gly | Leu | Ala | Gln | Arg | His | Gln | Arg | Leu | Tyr | Ser | Leu | |
| 2045 | | | | | 2050 | | | | | 2055 | | | | | 2060 | |
| CTG | GAC | AGG | TTT | CGT | CTC | TCC | ACC | ATG | CAA | GAC | TCA | CTT | AGT | CCC | TCT | 6543 |
| Leu | Asp | Arg | Phe | Arg | Leu | Ser | Thr | Met | Gln | Asp | Ser | Leu | Ser | Pro | Ser | |
| | | | | 2065 | | | | | 2070 | | | | | 2075 | | |
| CCT | CCA | GTC | TCT | TCC | CAC | CCG | CTG | GAC | GGG | GAT | GGG | CAC | GTG | TCA | CTG | 6591 |
| Pro | Pro | Val | Ser | Ser | His | Pro | Leu | Asp | Gly | Asp | Gly | His | Val | Ser | Leu | |
| | | | 2080 | | | | | 2085 | | | | | 2090 | | | |
| GAA | ACA | GTG | AGT | CCG | GAC | AAA | GAC | TGG | TAC | GTT | CAT | CTT | GTC | AAA | TCC | 6639 |
| Glu | Thr | Val | Ser | Pro | Asp | Lys | Asp | Trp | Tyr | Val | His | Leu | Val | Lys | Ser | |
| | | 2095 | | | | | 2100 | | | | | 2105 | | | | |
| CAG | TGT | TGG | ACC | AGG | TCA | GAT | TCT | GCA | CTG | CTG | GAA | GGT | GCA | GAG | CTG | 6687 |
| Gln | Cys | Trp | Thr | Arg | Ser | Asp | Ser | Ala | Leu | Leu | Glu | Gly | Ala | Glu | Leu | |
| | 2110 | | | | | 2115 | | | | | 2120 | | | | | |
| GTG | AAT | CGG | ATT | CCT | GCT | GAA | GAT | ATG | AAT | GCC | TTC | ATG | ATG | AAC | TCG | 6735 |
| Val | Asn | Arg | Ile | Pro | Ala | Glu | Asp | Met | Asn | Ala | Phe | Met | Met | Asn | Ser | |
| 2125 | | | | 2130 | | | | | 2135 | | | | | | 2140 | |
| GAG | TTC | AAC | CTA | AGC | CTG | CTA | GCT | CCA | TGC | TTA | AGC | CTA | GGG | ATG | AGT | 6783 |
| Glu | Phe | Asn | Leu | Ser | Leu | Leu | Ala | Pro | Cys | Leu | Ser | Leu | Gly | Met | Ser | |
| | | | | 2145 | | | | | 2150 | | | | | 2155 | | |
| GAA | ATT | TCT | GGT | GGC | CAG | AAG | AGT | GCC | CTT | TTT | GAA | GCA | GCC | CGT | GAG | 6831 |
| Glu | Ile | Ser | Gly | Gly | Gln | Lys | Ser | Ala | Leu | Phe | Glu | Ala | Ala | Arg | Glu | |
| | | | 2160 | | | | | 2165 | | | | | 2170 | | | |
| GTG | ACT | CTG | GCC | CGT | GTG | AGC | GGC | ACC | GTG | CAG | CAG | CTC | CCT | GCT | GTC | 6879 |
| Val | Thr | Leu | Ala | Arg | Val | Ser | Gly | Thr | Val | Gln | Gln | Leu | Pro | Ala | Val | |
| | | 2175 | | | | | 2180 | | | | | 2185 | | | | |
| CAT | CAT | GTC | TTC | CAG | CCC | GAG | CTG | CCT | GCA | GAG | CCG | GCG | GCC | TAC | TGG | 6927 |
| His | His | Val | Phe | Gln | Pro | Glu | Leu | Pro | Ala | Glu | Pro | Ala | Ala | Tyr | Trp | |
| | 2190 | | | | | 2195 | | | | | 2200 | | | | | |
| AGC | AAG | TTG | AAT | GAT | CTG | TTT | GGG | GAT | GCT | GCA | CTG | TAT | CAG | TCC | CTG | 6975 |
| Ser | Lys | Leu | Asn | Asp | Leu | Phe | Gly | Asp | Ala | Ala | Leu | Tyr | Gln | Ser | Leu | |
| 2205 | | | | 2210 | | | | | 2215 | | | | | 2220 | | |
| CCC | ACT | CTG | GCC | CGG | GCC | CTG | GCA | CAG | TAC | CTG | GTG | GTG | GTC | TCC | AAA | 7023 |
| Pro | Thr | Leu | Ala | Arg | Ala | Leu | Ala | Gln | Tyr | Leu | Val | Val | Val | Ser | Lys | |
| | | | | 2225 | | | | | 2230 | | | | | 2235 | | |
| CTG | CCC | AGT | CAT | TTG | CAC | CTT | CCT | CCT | GAG | AAA | GAG | AAG | GAC | ATT | GTG | 7071 |
| Leu | Pro | Ser | His | Leu | His | Leu | Pro | Pro | Glu | Lys | Glu | Lys | Asp | Ile | Val | |
| | | | 2240 | | | | | 2245 | | | | | 2250 | | | |
| AAA | TTC | GTG | GTG | GCA | ACC | CTT | GAG | GCC | CTG | TCC | TGG | CAT | TTG | ATC | CAT | 7119 |
| Lys | Phe | Val | Val | Ala | Thr | Leu | Glu | Ala | Leu | Ser | Trp | His | Leu | Ile | His | |
| | | 2255 | | | | | 2260 | | | | | 2265 | | | | |

| | | | | | | | | | | | | | | | | |
|---|---|---|---|---|---|---|---|---|---|---|---|---|---|---|---|---|
| GAG | CAG | ATC | CCG | CTG | AGT | CTG | GAT | CTC | CAG | GCA | GGG | CTG | GAC | TGC | TGC | 7167 |
| Glu | Gln | Ile | Pro | Leu | Ser | Leu | Asp | Leu | Gln | Ala | Gly | Leu | Asp | Cys | Cys | |
| | | 2270 | | | 2275 | | | | | 2280 | | | | | | |
| TGC | CTG | GCC | CTG | CAG | CTG | CCT | GGC | CTC | TGG | AGC | GTG | GTC | TCC | TCC | ACA | 7215 |
| Cys | Leu | Ala | Leu | Gln | Leu | Pro | Gly | Leu | Trp | Ser | Val | Val | Ser | Ser | Thr | |
| 2285 | | | | 2290 | | | | | 2295 | | | | | | 2300 | |
| GAG | TTT | GTG | ACC | CAC | GCC | TGC | TCC | CTC | ATC | TAC | TGT | GTG | CAC | TTC | ATC | 7263 |
| Glu | Phe | Val | Thr | His | Ala | Cys | Ser | Leu | Ile | Tyr | Cys | Val | His | Phe | Ile | |
| | | | | 2305 | | | | | 2310 | | | | | 2315 | | |
| CTG | GAG | GCC | GTT | GCA | GTG | CAG | CCT | GGA | GAG | CAG | CTT | CTT | AGT | CCA | GAA | 7311 |
| Leu | Glu | Ala | Val | Ala | Val | Gln | Pro | Gly | Glu | Gln | Leu | Leu | Ser | Pro | Glu | |
| | | | 2320 | | | | | 2325 | | | | | 2330 | | | |
| AGA | AGG | ACA | AAT | ACC | CCA | AAA | GCC | ATC | AGC | GAG | GAG | GAG | GAG | GAA | GTA | 7359 |
| Arg | Arg | Thr | Asn | Thr | Pro | Lys | Ala | Ile | Ser | Glu | Glu | Glu | Glu | Glu | Val | |
| | | 2335 | | | | | 2340 | | | | | 2345 | | | | |
| GAT | CCA | AAC | ACA | CAG | AAT | CCT | AAG | TAT | ATC | ACT | GCA | GCC | TGT | GAG | ATG | 7407 |
| Asp | Pro | Asn | Thr | Gln | Asn | Pro | Lys | Tyr | Ile | Thr | Ala | Ala | Cys | Glu | Met | |
| 2350 | | | | | 2355 | | | | | 2360 | | | | | | |
| GTG | GCA | GAA | ATG | GTG | GAG | TCT | CTG | CAG | TCG | GTG | TTG | GCC | TTG | GGT | CAT | 7455 |
| Val | Ala | Glu | Met | Val | Glu | Ser | Leu | Gln | Ser | Val | Leu | Ala | Leu | Gly | His | |
| 2365 | | | | 2370 | | | | | 2375 | | | | | 2380 | | |
| AAA | AGG | AAT | AGC | GGC | GTG | CCG | GCG | TTT | CTC | ACG | CCA | TTG | CTC | AGG | AAC | 7503 |
| Lys | Arg | Asn | Ser | Gly | Val | Pro | Ala | Phe | Leu | Thr | Pro | Leu | Leu | Arg | Asn | |
| | | | | 2385 | | | | | 2390 | | | | | 2395 | | |
| ATC | ATC | ATC | AGC | CTG | GCC | CGC | CTG | CCC | CTT | GTC | AAC | AGC | TAC | ACA | CGT | 7551 |
| Ile | Ile | Ile | Ser | Leu | Ala | Arg | Leu | Pro | Leu | Val | Asn | Ser | Tyr | Thr | Arg | |
| | | | 2400 | | | | | 2405 | | | | | 2410 | | | |
| GTG | CCC | CCA | CTG | GTG | TGG | AAG | CTT | GGA | TGG | TCA | CCC | AAA | CCG | GGA | GGG | 7599 |
| Val | Pro | Pro | Leu | Val | Trp | Lys | Leu | Gly | Trp | Ser | Pro | Lys | Pro | Gly | Gly | |
| | | 2415 | | | | | 2420 | | | | | 2425 | | | | |
| GAT | TTT | GGC | ACA | GCA | TTC | CCT | GAG | ATC | CCC | GTG | GAG | TTC | CTC | CAG | GAA | 7647 |
| Asp | Phe | Gly | Thr | Ala | Phe | Pro | Glu | Ile | Pro | Val | Glu | Phe | Leu | Gln | Glu | |
| | 2430 | | | | | 2435 | | | | | 2440 | | | | | |
| AAG | GAA | GTC | TTT | AAG | GAG | TTC | ATC | TAC | CGC | ATC | AAC | ACA | CTA | GGC | TGG | 7695 |
| Lys | Glu | Val | Phe | Lys | Glu | Phe | Ile | Tyr | Arg | Ile | Asn | Thr | Leu | Gly | Trp | |
| 2445 | | | | 2450 | | | | | 2455 | | | | | 2460 | | |
| ACC | AGT | CGT | ACT | CAG | TTT | GAA | GAA | ACT | TGG | GCC | ACC | CTC | CTT | GGT | GTC | 7743 |
| Thr | Ser | Arg | Thr | Gln | Phe | Glu | Glu | Thr | Trp | Ala | Thr | Leu | Leu | Gly | Val | |
| | | | | 2465 | | | | | 2470 | | | | | 2475 | | |
| CTG | GTG | ACG | CAG | CCC | CTC | GTG | ATG | GAG | CAG | GAG | AGC | CCA | CCA | GAA | | 7791 |
| Leu | Val | Thr | Gln | Pro | Leu | Val | Met | Glu | Gln | Glu | Ser | Pro | Pro | Glu | | |
| | | | 2480 | | | | | 2485 | | | | | 2490 | | | |
| GAA | GAC | ACA | GAG | AGG | ACC | CAG | ATC | AAC | GTC | CTG | GCC | GTG | CAG | GCC | ATC | 7839 |
| Glu | Asp | Thr | Glu | Arg | Thr | Gln | Ile | Asn | Val | Leu | Ala | Val | Gln | Ala | Ile | |
| | | 2495 | | | | | 2500 | | | | | 2505 | | | | |
| ACC | TCA | CTG | GTG | CTC | AGT | GCA | ATG | ACT | GTG | CCT | GTG | GCC | GGC | AAC | CCA | 7887 |
| Thr | Ser | Leu | Val | Leu | Ser | Ala | Met | Thr | Val | Pro | Val | Ala | Gly | Asn | Pro | |
| | 2510 | | | | | 2515 | | | | | 2520 | | | | | |
| GCT | GTA | AGC | TGC | TTG | GAG | CAG | CAG | CCC | CGG | AAC | AAG | CCT | CTG | AAA | GCT | 7935 |
| Ala | Val | Ser | Cys | Leu | Glu | Gln | Gln | Pro | Arg | Asn | Lys | Pro | Leu | Lys | Ala | |
| 2525 | | | | 2530 | | | | | 2535 | | | | | 2540 | | |
| CTC | GAC | ACC | AGG | TTT | GGG | AGG | AAG | CTG | AGC | ATT | ATC | AGA | GGG | ATT | GTG | 7983 |
| Leu | Asp | Thr | Arg | Phe | Gly | Arg | Lys | Leu | Ser | Ile | Ile | Arg | Gly | Ile | Val | |
| | | | | 2545 | | | | | 2550 | | | | | 2555 | | |
| GAG | CAA | GAG | ATT | CAA | GCA | ATG | GTT | TCA | AAG | AGA | GAG | AAT | ATT | GCC | ACC | 8031 |
| Glu | Gln | Glu | Ile | Gln | Ala | Met | Val | Ser | Lys | Arg | Glu | Asn | Ile | Ala | Thr | |
| | | | 2560 | | | | | 2565 | | | | | 2570 | | | |
| CAT | CAT | TTA | TAT | CAG | GCA | TGG | GAT | CCT | GTC | CCT | TCT | CTG | TCT | CCG | GCT | 8079 |
| His | His | Leu | Tyr | Gln | Ala | Trp | Asp | Pro | Val | Pro | Ser | Leu | Ser | Pro | Ala | |
| | | 2575 | | | | | 2580 | | | | | 2585 | | | | |

| | | | | | | | | | | | | | | | | |
|---|---|---|---|---|---|---|---|---|---|---|---|---|---|---|---|---|
| ACT | ACA | GGT | GCC | CTC | ATC | AGC | CAC | GAG | AAG | CTG | CTG | CTA | CAG | ATC | AAC | 8127 |
| Thr | Thr | Gly | Ala | Leu | Ile | Ser | His | Glu | Lys | Leu | Leu | Leu | Gln | Ile | Asn | |
| | | 2590 | | | | 2595 | | | | 2600 | | | | | | |
| CCC | GAG | CGG | GAG | CTG | GGG | AGC | ATG | AGC | TAC | AAA | CTC | GGC | CAG | GTG | TCC | 8175 |
| Pro | Glu | Arg | Glu | Leu | Gly | Ser | Met | Ser | Tyr | Lys | Leu | Gly | Gln | Val | Ser | |
| 2605 | | | | 2610 | | | | 2615 | | | | | | | 2620 | |
| ATA | CAC | TCC | GTG | TGG | CTG | GGG | AAC | AGC | ATC | ACA | CCC | CTG | AGG | GAG | GAG | 8223 |
| Ile | His | Ser | Val | Trp | Leu | Gly | Asn | Ser | Ile | Thr | Pro | Leu | Arg | Glu | Glu | |
| | | | | 2625 | | | | | 2630 | | | | | 2635 | | |
| GAA | TGG | GAC | GAG | GAA | GAG | GAG | GAG | GAG | GCC | GAC | GCC | CCT | GCA | CCT | TCG | 8271 |
| Glu | Trp | Asp | Glu | Glu | Glu | Glu | Glu | Glu | Ala | Asp | Ala | Pro | Ala | Pro | Ser | |
| | | | 2640 | | | | | 2645 | | | | | 2650 | | | |
| TCA | CCA | CCC | ACG | TCT | CCA | GTC | AAC | TCC | AGG | AAA | CAC | CGG | GCT | GGA | GTT | 8319 |
| Ser | Pro | Pro | Thr | Ser | Pro | Val | Asn | Ser | Arg | Lys | His | Arg | Ala | Gly | Val | |
| | | 2655 | | | | | 2660 | | | | | 2665 | | | | |
| GAC | ATC | CAC | TCC | TGT | TCG | CAG | TTT | TTG | CTT | GAG | TTG | TAC | AGC | CGC | TGG | 8367 |
| Asp | Ile | His | Ser | Cys | Ser | Gln | Phe | Leu | Leu | Glu | Leu | Tyr | Ser | Arg | Trp | |
| | | 2670 | | | | | 2675 | | | | | 2680 | | | | |
| ATC | CTG | CCG | TCC | AGC | TCA | GCC | AGG | AGG | ACC | CCG | GCC | ATC | CTG | ATC | AGT | 8415 |
| Ile | Leu | Pro | Ser | Ser | Ser | Ala | Arg | Arg | Thr | Pro | Ala | Ile | Leu | Ile | Ser | |
| 2685 | | | | | 2690 | | | | | 2695 | | | | | 2700 | |
| GAG | GTG | GTC | AGA | TCC | CTT | CTA | GTG | GTC | TCA | GAC | TTG | TTC | ACC | GAG | CGC | 8463 |
| Glu | Val | Val | Arg | Ser | Leu | Leu | Val | Val | Ser | Asp | Leu | Phe | Thr | Glu | Arg | |
| | | | | 2705 | | | | | 2710 | | | | | 2715 | | |
| AAC | CAG | TTT | GAG | CTG | ATG | TAT | GTG | ACG | CTG | ACA | GAA | CTG | CGA | AGG | GTG | 8511 |
| Asn | Gln | Phe | Glu | Leu | Met | Tyr | Val | Thr | Leu | Thr | Glu | Leu | Arg | Arg | Val | |
| | | | 2720 | | | | | 2725 | | | | | 2730 | | | |
| CAC | CCT | TCA | GAA | GAC | GAG | ATC | CTC | GCT | CAG | TAC | CTG | GTG | CCT | GCC | ACC | 8559 |
| His | Pro | Ser | Glu | Asp | Glu | Ile | Leu | Ala | Gln | Tyr | Leu | Val | Pro | Ala | Thr | |
| | | 2735 | | | | | 2740 | | | | | 2745 | | | | |
| TGC | AAG | GCA | GCT | GCC | GTC | CTT | GGG | ATG | GAC | AAG | GCC | GTG | GCG | GAG | CCT | 8607 |
| Cys | Lys | Ala | Ala | Ala | Val | Leu | Gly | Met | Asp | Lys | Ala | Val | Ala | Glu | Pro | |
| | | 2750 | | | | | 2755 | | | | | 2760 | | | | |
| GTC | AGC | CGC | CTG | CTG | GAG | AGC | ACG | CTC | AGG | AGC | AGC | CAC | CTG | CCC | AGC | 8655 |
| Val | Ser | Arg | Leu | Leu | Glu | Ser | Thr | Leu | Arg | Ser | Ser | His | Leu | Pro | Ser | |
| 2765 | | | | | 2770 | | | | | 2775 | | | | | 2780 | |
| AGG | GTT | GGA | GCC | CTG | CAC | GGC | ATC | CTC | TAT | GTG | CTG | GAG | TGC | GAC | CTG | 8703 |
| Arg | Val | Gly | Ala | Leu | His | Gly | Ile | Leu | Tyr | Val | Leu | Glu | Cys | Asp | Leu | |
| | | | | 2785 | | | | | 2790 | | | | | 2795 | | |
| CTG | GAC | GAC | ACT | GCC | AAG | CAG | CTC | ATC | CCG | GTC | ATC | AGC | GAC | TAT | CTC | 8751 |
| Leu | Asp | Asp | Thr | Ala | Lys | Gln | Leu | Ile | Pro | Val | Ile | Ser | Asp | Tyr | Leu | |
| | | | 2800 | | | | | 2805 | | | | | 2810 | | | |
| CTC | TCC | AAC | CTG | AAA | GGG | ATC | GCC | CAC | TGC | GTG | AAC | ATT | CAC | AGC | CAG | 8799 |
| Leu | Ser | Asn | Leu | Lys | Gly | Ile | Ala | His | Cys | Val | Asn | Ile | His | Ser | Gln | |
| | | 2815 | | | | | 2820 | | | | | 2825 | | | | |
| CAG | CAC | GTA | CTG | GTC | ATG | TGT | GCC | ACT | GCG | TTT | TAC | CTC | ATT | GAG | AAC | 8847 |
| Gln | His | Val | Leu | Val | Met | Cys | Ala | Thr | Ala | Phe | Tyr | Leu | Ile | Glu | Asn | |
| | | 2830 | | | | | 2835 | | | | | 2840 | | | | |
| TAT | CCT | CTG | GAC | GTA | GGG | CCG | GAA | TTT | TCA | GCA | TCA | ATA | ATA | CAG | ATG | 8895 |
| Tyr | Pro | Leu | Asp | Val | Gly | Pro | Glu | Phe | Ser | Ala | Ser | Ile | Ile | Gln | Met | |
| 2845 | | | | 2850 | | | | | 2855 | | | | | | 2860 | |
| TGT | GGG | GTG | ATG | CTG | TCT | GGA | AGT | GAG | GAG | TCC | ACC | CCC | TCC | ATC | ATT | 8943 |
| Cys | Gly | Val | Met | Leu | Ser | Gly | Ser | Glu | Glu | Ser | Thr | Pro | Ser | Ile | Ile | |
| | | | | 2865 | | | | | 2870 | | | | | 2875 | | |
| TAC | CAC | TGT | GCC | CTC | AGA | GGC | CTG | GAG | CGC | CTC | CTG | CTC | TCT | GAG | CAG | 8991 |
| Tyr | His | Cys | Ala | Leu | Arg | Gly | Leu | Glu | Arg | Leu | Leu | Leu | Ser | Glu | Gln | |
| | | | | 2880 | | | | | 2885 | | | | | 2890 | | |
| CTC | TCC | CGC | CTG | GAT | GCA | GAA | TCG | CTG | GTC | AAG | CTG | AGT | GTG | GAC | AGA | 9039 |
| Leu | Ser | Arg | Leu | Asp | Ala | Glu | Ser | Leu | Val | Lys | Leu | Ser | Val | Asp | Arg | |
| | | 2895 | | | | | 2900 | | | | | 2905 | | | | |

| | | | | | | | | | | | | | | | | |
|---|---|---|---|---|---|---|---|---|---|---|---|---|---|---|---|---|
| GTG | AAC | GTG | CAC | AGC | CCG | CAC | CGG | GCC | ATG | GCG | GCT | CTG | GGC | CTG | ATG | 9087 |
| Val | Asn | Val | His | Ser | Pro | His | Arg | Ala | Met | Ala | Ala | Leu | Gly | Leu | Met | |
| | | 2910 | | | | 2915 | | | | 2920 | | | | | | |
| CTC | ACC | TGC | ATG | TAC | ACA | GGA | AAG | GAG | AAA | GTC | AGT | CCG | GGT | AGA | ACT | 9135 |
| Leu | Thr | Cys | Met | Tyr | Thr | Gly | Lys | Glu | Lys | Val | Ser | Pro | Gly | Arg | Thr | |
| 2925 | | | | | 2930 | | | | | 2935 | | | | | 2940 | |
| TCA | GAC | CCT | AAT | CCT | GCA | GCC | CCC | GAC | AGC | GAG | TCA | GTG | ATT | GTT | GCT | 9183 |
| Ser | Asp | Pro | Asn | Pro | Ala | Ala | Pro | Asp | Ser | Glu | Ser | Val | Ile | Val | Ala | |
| | | | | 2945 | | | | | 2950 | | | | | 2955 | | |
| ATG | GAG | CGG | GTA | TCT | GTT | CTT | TTT | GAT | AGG | ATC | AGG | AAA | GGC | TTT | CCT | 9231 |
| Met | Glu | Arg | Val | Ser | Val | Leu | Phe | Asp | Arg | Ile | Arg | Lys | Gly | Phe | Pro | |
| | | 2960 | | | | | 2965 | | | | | 2970 | | | | |
| TGT | GAA | GCC | AGA | GTG | GTG | GCC | AGG | ATC | CTG | CCC | CAG | TTT | CTA | GAC | GAC | 9279 |
| Cys | Glu | Ala | Arg | Val | Val | Ala | Arg | Ile | Leu | Pro | Gln | Phe | Leu | Asp | Asp | |
| | | 2975 | | | | | 2980 | | | | | 2985 | | | | |
| TTC | TTC | CCA | CCC | CAG | GAC | ATC | ATG | AAC | AAA | GTC | ATC | GGA | GAG | TTT | CTG | 9327 |
| Phe | Phe | Pro | Pro | Gln | Asp | Ile | Met | Asn | Lys | Val | Ile | Gly | Glu | Phe | Leu | |
| | 2990 | | | | | 2995 | | | | | 3000 | | | | | |
| TCC | AAC | CAG | CAG | CCA | TAC | CCC | CAG | TTC | ATG | GCC | ACC | GTG | GTG | TAT | AAG | 9375 |
| Ser | Asn | Gln | Gln | Pro | Tyr | Pro | Gln | Phe | Met | Ala | Thr | Val | Val | Tyr | Lys | |
| 3005 | | | | | 3010 | | | | | 3015 | | | | | 3020 | |
| GTG | TTT | CAG | ACT | CTG | CAC | AGC | ACC | GGG | CAG | TCG | TCC | ATG | GTC | CGG | GAC | 9423 |
| Val | Phe | Gln | Thr | Leu | His | Ser | Thr | Gly | Gln | Ser | Ser | Met | Val | Arg | Asp | |
| | | | | 3025 | | | | | 3030 | | | | | 3035 | | |
| TGG | GTC | ATG | CTG | TCC | CTC | TCC | AAC | TTC | ACG | CAG | AGG | GCC | CCG | GTC | GCC | 9471 |
| Trp | Val | Met | Leu | Ser | Leu | Ser | Asn | Phe | Thr | Gln | Arg | Ala | Pro | Val | Ala | |
| | | | 3040 | | | | | 3045 | | | | | 3050 | | | |
| ATG | GCC | ACG | TGG | AGC | CTC | TCC | TGC | TTC | TTT | GTC | AGC | GCG | TCC | ACC | AGC | 9519 |
| Met | Ala | Thr | Trp | Ser | Leu | Ser | Cys | Phe | Phe | Val | Ser | Ala | Ser | Thr | Ser | |
| | | 3055 | | | | | 3060 | | | | | 3065 | | | | |
| CCG | TGG | GTC | GCG | GCG | ATC | CTC | CCA | CAT | GTC | ATC | AGC | AGG | ATG | GGC | AAG | 9567 |
| Pro | Trp | Val | Ala | Ala | Ile | Leu | Pro | His | Val | Ile | Ser | Arg | Met | Gly | Lys | |
| 3070 | | | | | 3075 | | | | | 3080 | | | | | | |
| CTG | GAG | CAG | GTG | GAC | GTG | AAC | CTT | TTC | TGC | CTG | GTC | GCC | ACA | GAC | TTC | 9615 |
| Leu | Glu | Gln | Val | Asp | Val | Asn | Leu | Phe | Cys | Leu | Val | Ala | Thr | Asp | Phe | |
| 3085 | | | | | 3090 | | | | | 3095 | | | | | 3100 | |
| TAC | AGA | CAC | CAG | ATA | GAG | GAG | GAG | CTC | GAC | CGC | AGG | GCC | TTC | CAG | TCT | 9663 |
| Tyr | Arg | His | Gln | Ile | Glu | Glu | Glu | Leu | Asp | Arg | Arg | Ala | Phe | Gln | Ser | |
| | | | | 3105 | | | | | 3110 | | | | | 3115 | | |
| GTG | CTT | GAG | GTG | GTT | GCA | GCC | CCA | GGA | AGC | CCA | TAT | CAC | CGG | CTG | CTG | 9711 |
| Val | Leu | Glu | Val | Val | Ala | Ala | Pro | Gly | Ser | Pro | Tyr | His | Arg | Leu | Leu | |
| | | | 3120 | | | | | 3125 | | | | | 3130 | | | |
| ACT | TGT | TTA | CGA | AAT | GTC | CAC | AAG | GTC | ACC | ACC | TGC | T | GAGCGCCATG | | | 9758 |
| Thr | Cys | Leu | Arg | Asn | Val | His | Lys | Val | Thr | Thr | Cys | | | | | |
| | | 3135 | | | | | 3140 | | | | | | | | | |

| | | | | |
|---|---|---|---|---|
| GTGGGAGAGA | CTGTGAGGCG | GCAGCTGGGG | CCGGAGCCTT | TGGAAGTCTG | TGCCCTTGTG | 9818 |
| CCCTGCCTCC | ACCGAGCCAG | CTTGGTCCCT | ATGGGCTTCC | GCACATGCCG | CGGGCGGCCA | 9878 |
| GGCAACGTGC | GTGTCTCTGC | CATGTGGCAG | AAGTGCTCTT | TGTGGCAGTG | GCCAGGCAGG | 9938 |
| GAGTGTCTGC | AGTCCTGGTG | GGGCTGAGCC | TGAGGCCTTC | CAGAAAGCAG | GAGCAGCTGT | 9998 |
| GCTGCACCCC | ATGTGGGTGA | CCAGGTCCTT | TCTCCTGATA | GTCACCTGCT | GGTTGTTGCC | 10058 |
| AGGTTGCAGC | TGCTCTTGCA | TCTGGGCCAG | AAGTCCTCCC | TCCTGCAGGC | TGGCTGTTGG | 10118 |
| CCCCTCTGCT | GTCCTGCAGT | AGAAGGTGCC | GTGAGCAGGC | TTTGGGAACA | CTGGCCTGGG | 10178 |
| TCTCCCTGGT | GGGGTGTGCA | TGCCACGCCC | CGTGTCTGGA | TGCACAGATG | CCATGGCCTG | 10238 |
| TGCTGGGCCA | GTGGCTGGGG | GTGCTAGACA | CCCGGCACCA | TTCTCCCTTC | TCTCTTTTCT | 10298 |
| TCTCAGGATT | TAAAATTTAA | TTATATCAGT | AAAGAGATTA | ATTTTAACGT | AAAAAAAAAA | 10358 |

(2) INFORMATION FOR SEQ ID NO:6:

(i) SEQUENCE CHARACTERISTICS:
       (A) LENGTH: 3144 amino acids
       (B) TYPE: amino acid
       (D) TOPOLOGY: linear (ii) MOLECULE TYPE: protein (xi) SEQUENCE DESCRIPTION: SEQ ID NO:6:

| Met | Ala | Thr | Leu | Glu | Lys | Leu | Met | Lys | Ala | Phe | Glu | Ser | Leu | Lys | Ser |
|---|---|---|---|---|---|---|---|---|---|---|---|---|---|---|---|
| 1 | | | | 5 | | | | 10 | | | | | | 15 | |
| Phe | Gln | Gln | Gln | Gln | Gln | Gln | Gln | Gln | Gln | Gln | Gln | Gln | Gln | Gln | Gln |
| | | | 20 | | | | | 25 | | | | | 30 | | |
| Gln | Gln | Gln | Gln | Gln | Gln | Gln | Gln | Pro | Pro | Pro | Pro | Pro | Pro | Pro | Pro |
| | | | 35 | | | | | 40 | | | | | 45 | | |
| Pro | Pro | Pro | Gln | Leu | Pro | Gln | Pro | Pro | Pro | Gln | Ala | Gln | Pro | Leu | Leu |
| | 50 | | | | | 55 | | | | | 60 | | | | |
| Pro | Gln | Pro | Gln | Pro | Pro | Pro | Pro | Pro | Pro | Pro | Pro | Pro | Pro | Gly | Pro |
| 65 | | | | | 70 | | | | | 75 | | | | | 80 |
| Ala | Val | Ala | Glu | Glu | Pro | Leu | His | Arg | Pro | Lys | Lys | Glu | Leu | Ser | Ala |
| | | | | 85 | | | | | 90 | | | | | 95 | |
| Thr | Lys | Lys | Asp | Arg | Val | Asn | His | Cys | Leu | Thr | Ile | Cys | Glu | Asn | Ile |
| | | | 100 | | | | | 105 | | | | | 110 | | |
| Val | Ala | Gln | Ser | Val | Arg | Asn | Ser | Pro | Glu | Phe | Gln | Lys | Leu | Leu | Gly |
| | | | 115 | | | | | 120 | | | | | 125 | | |
| Ile | Ala | Met | Glu | Leu | Phe | Leu | Leu | Cys | Ser | Asp | Asp | Ala | Glu | Ser | Asp |
| | | 130 | | | | | 135 | | | | | 140 | | | |
| Val | Arg | Met | Val | Ala | Asp | Glu | Cys | Leu | Asn | Lys | Val | Ile | Lys | Ala | Leu |
| 145 | | | | | 150 | | | | | 155 | | | | | 160 |
| Met | Asp | Ser | Asn | Leu | Pro | Arg | Leu | Gln | Leu | Glu | Leu | Tyr | Lys | Glu | Ile |
| | | | | 165 | | | | | 170 | | | | | 175 | |
| Lys | Lys | Asn | Gly | Ala | Pro | Arg | Ser | Leu | Arg | Ala | Ala | Leu | Trp | Arg | Phe |
| | | | 180 | | | | | 185 | | | | | 190 | | |
| Ala | Glu | Leu | Ala | His | Leu | Val | Arg | Pro | Gln | Lys | Cys | Arg | Pro | Tyr | Leu |
| | | 195 | | | | | 200 | | | | | 205 | | | |
| Val | Asn | Leu | Leu | Pro | Cys | Leu | Thr | Arg | Thr | Ser | Lys | Arg | Pro | Glu | Glu |
| | 210 | | | | | 215 | | | | | 220 | | | | |
| Ser | Val | Gln | Glu | Thr | Leu | Ala | Ala | Ala | Val | Pro | Lys | Ile | Met | Ala | Ser |
| 225 | | | | | 230 | | | | | 235 | | | | | 240 |
| Phe | Gly | Asn | Phe | Ala | Asn | Asp | Asn | Glu | Ile | Lys | Val | Leu | Leu | Lys | Ala |
| | | | | 245 | | | | | 250 | | | | | 255 | |
| Phe | Ile | Ala | Asn | Leu | Lys | Ser | Ser | Ser | Pro | Thr | Ile | Arg | Arg | Thr | Ala |
| | | | 260 | | | | | 265 | | | | | 270 | | |
| Ala | Gly | Ser | Ala | Val | Ser | Ile | Cys | Gln | His | Ser | Arg | Arg | Thr | Gln | Tyr |
| | | 275 | | | | | 280 | | | | | 285 | | | |
| Phe | Tyr | Ser | Trp | Leu | Leu | Asn | Val | Leu | Leu | Gly | Leu | Leu | Val | Pro | Val |
| | 290 | | | | | 295 | | | | | 300 | | | | |
| Glu | Asp | Glu | His | Ser | Thr | Leu | Leu | Ile | Leu | Gly | Val | Leu | Leu | Thr | Leu |
| 305 | | | | | 310 | | | | | 315 | | | | | 320 |
| Arg | Tyr | Leu | Val | Pro | Leu | Leu | Gln | Gln | Gln | Val | Lys | Asp | Thr | Ser | Leu |
| | | | | 325 | | | | | 330 | | | | | 335 | |
| Lys | Gly | Ser | Phe | Gly | Val | Thr | Arg | Lys | Glu | Met | Glu | Val | Ser | Pro | Ser |
| | | | 340 | | | | | 345 | | | | | 350 | | |

| | | | | | | | | | | | | | |
|---|---|---|---|---|---|---|---|---|---|---|---|---|---|
|Ala|Glu|Gln<br>355|Leu|Val|Gln|Val|Tyr<br>360|Glu|Leu|Thr|Leu<br>365|His|His|Thr|Gln|
|His|Gln<br>370|Asp|His|Asn|Val|Val<br>375|Thr|Gly|Ala|Leu|Glu<br>380|Leu|Leu|Gln|Gln|
|Leu<br>385|Phe|Arg|Thr|Pro|Pro<br>390|Pro|Glu|Leu|Leu|Gln<br>395|Thr|Leu|Thr|Ala|Val<br>400|
|Gly|Gly|Ile|Gly|Gln<br>405|Leu|Thr|Ala|Ala|Lys<br>410|Glu|Glu|Ser|Gly|Gly<br>415|Arg|
|Ser|Arg|Ser|Gly<br>420|Ser|Ile|Val|Glu|Leu<br>425|Ile|Ala|Gly|Gly<br>430|Ser|Ser|
|Cys|Ser|Pro<br>435|Val|Leu|Ser|Arg|Lys<br>440|Gln|Lys|Gly|Lys|Val<br>445|Leu|Leu|Gly|
|Glu|Glu<br>450|Glu|Ala|Leu|Glu|Asp<br>455|Asp|Ser|Glu|Ser|Arg<br>460|Ser|Asp|Val|Ser|
|Ser<br>465|Ser|Ala|Leu|Thr|Ala<br>470|Ser|Val|Lys|Asp|Glu<br>475|Ile|Ser|Gly|Glu|Leu<br>480|
|Ala|Ala|Ser|Ser|Gly<br>485|Val|Ser|Thr|Pro|Gly<br>490|Ser|Ala|Gly|His|Asp<br>495|Ile|
|Ile|Thr|Glu|Gln<br>500|Pro|Arg|Ser|Gln|His<br>505|Thr|Leu|Gln|Ala|Asp<br>510|Ser|Leu|
|Asp|Leu|Ala|Ser<br>515|Cys|Asp|Leu|Thr<br>520|Ser|Ser|Ala|Thr|Asp<br>525|Gly|Asp|Glu|
|Glu|Asp<br>530|Ile|Leu|Ser|His|Ser<br>535|Ser|Ser|Gln|Val|Ser<br>540|Ala|Val|Pro|Ser|
|Asp<br>545|Pro|Ala|Met|Asp|Leu<br>550|Asn|Asp|Gly|Thr|Gln<br>555|Ala|Ser|Ser|Pro|Ile<br>560|
|Ser|Asp|Ser|Ser|Gln<br>565|Thr|Thr|Thr|Glu|Gly<br>570|Pro|Asp|Ser|Ala|Val<br>575|Thr|
|Pro|Ser|Asp|Ser<br>580|Ser|Glu|Ile|Val|Leu<br>585|Asp|Gly|Thr|Asp|Asn<br>590|Gln|Tyr|
|Leu|Gly|Leu|Gln<br>595|Ile|Gly|Gln|Pro<br>600|Gln|Asp|Glu|Asp<br>605|Glu|Ala|Thr|
|Gly|Ile|Leu<br>610|Pro|Asp|Glu|Ala|Ser<br>615|Glu|Ala|Phe|Arg|Asn<br>620|Ser|Ser|Met|
|Ala|Leu|Gln|Gln|Ala|His<br>630|Leu|Leu|Lys|Asn|Met<br>635|Ser|His|Cys|Arg|Gln<br>640|
|Pro|Ser|Asp|Ser|Ser<br>645|Val|Asp|Lys|Phe|Val<br>650|Leu|Arg|Asp|Glu|Ala<br>655|Thr|
|Glu|Pro|Gly|Asp<br>660|Gln|Glu|Asn|Lys|Pro<br>665|Cys|Arg|Ile|Lys|Gly<br>670|Asp|Ile|
|Gly|Gln|Ser|Thr<br>675|Asp|Asp|Asp|Ser|Ala<br>680|Pro|Leu|Val|His|Ser<br>685|Val|Arg|
|Leu|Leu|Ser<br>690|Ala|Ser|Phe|Leu|Leu<br>695|Thr|Gly|Gly|Lys<br>700|Asn|Val|Leu|Val|
|Pro|Asp<br>705|Arg|Asp|Val|Arg<br>710|Val|Ser|Val|Lys|Ala<br>715|Leu|Ala|Leu|Ser|Cys<br>720|
|Val|Gly|Ala|Ala|Val<br>725|Ala|Leu|His|Pro|Glu<br>730|Ser|Phe|Phe|Ser|Lys<br>735|Leu|
|Tyr|Lys|Val|Pro<br>740|Leu|Asp|Thr|Thr|Glu<br>745|Tyr|Pro|Glu|Glu|Gln<br>750|Tyr|Val|
|Ser|Asp|Ile<br>755|Leu|Asn|Tyr|Ile|Asp<br>760|His|Gly|Asp|Pro|Gln<br>765|Val|Arg|Gly|
|Ala|Thr<br>770|Ala|Ile|Leu|Cys|Gly<br>775|Thr|Leu|Ile|Cys|Ser<br>780|Ile|Leu|Ser|Arg|

```
Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
                805                 810                 815

Leu Lys Asp Glu Ser Ser Val Thr Cys Lys Leu Ala Cys Thr Ala Val
            820                 825                 830

Arg Asn Cys Val Met Ser Leu Cys Ser Ser Ser Tyr Ser Glu Leu Gly
        835                 840                 845

Leu Gln Leu Ile Ile Asp Val Leu Thr Leu Arg Asn Ser Ser Tyr Trp
850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
                885                 890                 895

His His Tyr Thr Gly Leu Leu Lys Leu Gln Glu Arg Val Leu Asn Asn
            900                 905                 910

Val Val Ile His Leu Leu Gly Asp Glu Asp Pro Arg Val Arg His Val
        915                 920                 925

Ala Ala Ala Ser Leu Ile Arg Leu Val Pro Lys Leu Phe Tyr Lys Cys
930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
                965                 970                 975

Phe Ser Val Ser Thr Ile Thr Arg Ile Tyr Arg Gly Tyr Asn Leu Leu
            980                 985                 990

Pro Ser Ile Thr Asp Val Thr Met Glu Asn Asn Leu Ser Arg Val Ile
        995                 1000                1005

Ala Ala Val Ser His Glu Leu Ile Thr Ser Thr Arg Ala Leu Thr
1010                1015                1020

Phe Gly Cys Cys Glu Ala Leu Cys Leu Leu Ser Thr Ala Phe Pro Val
1025                1030                1035                1040

Cys Ile Trp Ser Leu Gly Trp His Cys Gly Val Pro Pro Leu Ser Ala
                1045                1050                1055

Ser Asp Glu Ser Arg Lys Ser Cys Thr Val Gly Met Ala Thr Met Ile
            1060                1065                1070

Leu Thr Leu Leu Ser Ser Ala Trp Phe Pro Leu Asp Leu Ser Ala His
        1075                1080                1085

Gln Asp Ala Leu Ile Leu Ala Gly Asn Leu Leu Ala Ala Ser Ala Pro
1090                1095                1100

Lys Ser Leu Arg Ser Ser Trp Ala Ser Glu Glu Glu Ala Asn Pro Ala
1105                1110                1115                1120

Ala Thr Lys Gln Glu Glu Val Trp Pro Ala Leu Gly Asp Arg Ala Leu
                1125                1130                1135

Val Pro Met Val Glu Gln Leu Phe Ser His Leu Leu Lys Val Ile Asn
            1140                1145                1150

Ile Cys Ala His Val Leu Asp Asp Val Ala Pro Gly Pro Ala Ile Lys
        1155                1160                1165

Ala Ala Leu Pro Ser Leu Thr Asn Pro Pro Ser Leu Ser Pro Ile Arg
1170                1175                1180

Arg Lys Gly Lys Glu Lys Glu Pro Gly Glu Gln Ala Ser Val Pro Leu
1185                1190                1195                1200

Ser Pro Lys Lys Gly Ser Glu Ala Ser Ala Ala Ser Arg Gln Ser Asp
```

```
              1205                    1210                    1215
Thr Ser Gly Pro Val Thr Thr Ser Lys Ser Ser Ser Leu Gly Ser Phe
          1220                    1225                    1230
Tyr His Leu Pro Ser Tyr Leu Arg Leu His Asp Val Leu Lys Ala Thr
          1235                    1240                    1245
His Ala Asn Tyr Lys Val Thr Leu Asp Leu Gln Asn Ser Thr Glu Lys
          1250                    1255                    1260
Phe Gly Gly Phe Leu Arg Ser Ala Leu Asp Val Leu Ser Gln Ile Leu
1265                    1270                    1275                    1280
Glu Leu Ala Thr Leu Gln Asp Ile Gly Lys Cys Val Glu Glu Ile Leu
                1285                    1290                    1295
Gly Tyr Leu Lys Ser Cys Phe Ser Arg Glu Pro Met Met Ala Thr Val
                1300                    1305                    1310
Cys Val Gln Gln Leu Leu Lys Thr Leu Phe Gly Thr Asn Leu Ala Ser
          1315                    1320                    1325
Gln Phe Asp Gly Leu Ser Ser Asn Pro Ser Lys Ser Gln Gly Arg Ala
          1330                    1335                    1340
Gln Arg Leu Gly Ser Ser Ser Val Arg Pro Gly Leu Tyr His Tyr Cys
1345                    1350                    1355                    1360
Phe Met Ala Pro Tyr Thr His Phe Thr Gln Ala Leu Ala Asp Ala Ser
                1365                    1370                    1375
Leu Arg Asn Met Val Gln Ala Glu Gln Glu Asn Asp Thr Ser Gly Trp
                1380                    1385                    1390
Phe Asp Val Leu Gln Lys Val Ser Thr Gln Leu Lys Thr Asn Leu Thr
          1395                    1400                    1405
Ser Val Thr Lys Asn Arg Ala Asp Lys Asn Ala Ile His Asn His Ile
          1410                    1415                    1420
Arg Leu Phe Glu Pro Leu Val Ile Lys Ala Leu Lys Gln Tyr Thr Thr
1425                    1430                    1435                    1440
Thr Thr Cys Val Gln Leu Gln Lys Gln Val Leu Asp Leu Leu Ala Gln
                1445                    1450                    1455
Leu Val Gln Leu Arg Val Asn Tyr Cys Leu Leu Asp Ser Asp Gln Val
                1460                    1465                    1470
Phe Ile Gly Phe Val Leu Lys Gln Phe Glu Tyr Ile Glu Val Gly Gln
          1475                    1480                    1485
Phe Arg Glu Ser Glu Ala Ile Ile Pro Asn Ile Phe Phe Phe Leu Val
1490                    1495                    1500
Leu Leu Ser Tyr Glu Arg Tyr His Ser Lys Gln Ile Ile Gly Ile Pro
1505                    1510                    1515                    1520
Lys Ile Ile Gln Leu Cys Asp Gly Ile Met Ala Ser Gly Arg Lys Ala
                1525                    1530                    1535
Val Thr His Ala Ile Pro Ala Leu Gln Pro Ile Val His Asp Leu Phe
          1540                    1545                    1550
Val Leu Arg Gly Thr Asn Lys Ala Asp Ala Gly Lys Glu Leu Glu Thr
          1555                    1560                    1565
Gln Lys Glu Val Val Val Ser Met Leu Leu Arg Leu Ile Gln Tyr His
1570                    1575                    1580
Gln Val Leu Glu Met Phe Ile Leu Val Leu Gln Gln Cys His Lys Glu
1585                    1590                    1595                    1600
Asn Glu Asp Lys Trp Lys Arg Leu Ser Arg Gln Ile Ala Asp Ile Ile
                1605                    1610                    1615
Leu Pro Met Leu Ala Lys Gln Gln Met His Ile Asp Ser His Glu Ala
                1620                    1625                    1630
```

Leu Gly Val Leu Asn Thr Leu Phe Glu Ile Leu Ala Pro Ser Ser Leu
            1635                1640                1645

Arg Pro Val Asp Met Leu Leu Arg Ser Met Phe Val Thr Pro Asn Thr
1650                1655                1660

Met Ala Ser Val Ser Thr Val Gln Leu Trp Ile Ser Gly Ile Leu Ala
1665                1670                1675                1680

Ile Leu Arg Val Leu Ile Ser Gln Ser Thr Glu Asp Ile Val Leu Ser
            1685                1690                1695

Arg Ile Gln Glu Leu Ser Phe Ser Pro Tyr Leu Ile Ser Cys Thr Val
            1700                1705                1710

Ile Asn Arg Leu Arg Asp Gly Asp Ser Thr Ser Thr Leu Glu Glu His
            1715                1720                1725

Ser Glu Gly Lys Gln Ile Lys Asn Leu Pro Glu Glu Thr Phe Ser Arg
            1730                1735                1740

Phe Leu Leu Gln Leu Val Gly Ile Leu Leu Glu Asp Ile Val Thr Lys
1745                1750                1755                1760

Gln Leu Lys Val Glu Met Ser Glu Gln Gln His Thr Phe Tyr Cys Gln
            1765                1770                1775

Glu Leu Gly Thr Leu Leu Met Cys Leu Ile His Ile Phe Lys Ser Gly
            1780                1785                1790

Met Phe Arg Arg Ile Thr Ala Ala Ala Thr Arg Leu Phe Arg Ser Asp
            1795                1800                1805

Gly Cys Gly Gly Ser Phe Tyr Thr Leu Asp Ser Leu Asn Leu Arg Ala
            1810                1815                1820

Arg Ser Met Ile Thr Thr His Pro Ala Leu Val Leu Leu Trp Cys Gln
1825                1830                1835                1840

Ile Leu Leu Leu Val Asn His Thr Asp Tyr Arg Trp Trp Ala Glu Val
            1845                1850                1855

Gln Gln Thr Pro Lys Arg His Ser Leu Ser Ser Thr Lys Leu Leu Ser
            1860                1865                1870

Pro Gln Met Ser Gly Glu Glu Glu Asp Ser Asp Leu Ala Ala Lys Leu
            1875                1880                1885

Gly Met Cys Asn Arg Glu Ile Val Arg Arg Gly Ala Leu Ile Leu Phe
            1890                1895                1900

Cys Asp Tyr Val Cys Gln Asn Leu His Asp Ser Glu His Leu Thr Trp
1905                1910                1915                1920

Leu Ile Val Asn His Ile Gln Asp Leu Ile Ser Leu Ser His Glu Pro
            1925                1930                1935

Pro Val Gln Asp Phe Ile Ser Ala Val His Arg Asn Ser Ala Ala Ser
            1940                1945                1950

Gly Leu Phe Ile Gln Ala Ile Gln Ser Arg Cys Glu Asn Leu Ser Thr
            1955                1960                1965

Pro Thr Met Leu Lys Lys Thr Leu Gln Cys Leu Glu Gly Ile His Leu
            1970                1975                1980

Ser Gln Ser Gly Ala Val Leu Thr Leu Tyr Val Asp Arg Leu Leu Cys
1985                1990                1995                2000

Thr Pro Phe Arg Val Leu Ala Arg Met Val Asp Ile Leu Ala Cys Arg
            2005                2010                2015

Arg Val Glu Met Leu Leu Ala Ala Asn Leu Gln Ser Ser Met Ala Gln
            2020                2025                2030

Leu Pro Met Glu Glu Leu Asn Arg Ile Gln Glu Tyr Leu Gln Ser Ser
            2035                2040                2045

Gly Leu Ala Gln Arg His Gln Arg Leu Tyr Ser Leu Leu Asp Arg Phe
            2050                2055                2060

```
Arg Leu Ser Thr Met Gln Asp Ser Leu Ser Pro Ser Pro Pro Val Ser
2065                2070            2075            2080

Ser His Pro Leu Asp Gly Asp Gly His Val Ser Leu Glu Thr Val Ser
            2085            2090            2095

Pro Asp Lys Asp Trp Tyr Val His Leu Val Lys Ser Gln Cys Trp Thr
        2100            2105            2110

Arg Ser Asp Ser Ala Leu Leu Glu Gly Ala Glu Leu Val Asn Arg Ile
        2115            2120            2125

Pro Ala Glu Asp Met Asn Ala Phe Met Met Asn Ser Glu Phe Asn Leu
        2130            2135            2140

Ser Leu Leu Ala Pro Cys Leu Ser Leu Gly Met Ser Glu Ile Ser Gly
2145            2150            2155            2160

Gly Gln Lys Ser Ala Leu Phe Glu Ala Ala Arg Glu Val Thr Leu Ala
            2165            2170            2175

Arg Val Ser Gly Thr Val Gln Gln Leu Pro Ala Val His His Val Phe
            2180            2185            2190

Gln Pro Glu Leu Pro Ala Glu Pro Ala Ala Tyr Trp Ser Lys Leu Asn
        2195            2200            2205

Asp Leu Phe Gly Asp Ala Ala Leu Tyr Gln Ser Leu Pro Thr Leu Ala
        2210            2215            2220

Arg Ala Leu Ala Gln Tyr Leu Val Val Val Ser Lys Leu Pro Ser His
2225            2230            2235            2240

Leu His Leu Pro Pro Glu Lys Glu Lys Asp Ile Val Lys Phe Val Val
                2245            2250            2255

Ala Thr Leu Glu Ala Leu Ser Trp His Leu Ile His Glu Gln Ile Pro
                2260            2265            2270

Leu Ser Leu Asp Leu Gln Ala Gly Leu Asp Cys Cys Cys Leu Ala Leu
        2275            2280            2285

Gln Leu Pro Gly Leu Trp Ser Val Val Ser Ser Thr Glu Phe Val Thr
        2290            2295            2300

His Ala Cys Ser Leu Ile Tyr Cys Val His Phe Ile Leu Glu Ala Val
2305            2310            2315            2320

Ala Val Gln Pro Gly Glu Gln Leu Leu Ser Pro Glu Arg Arg Thr Asn
            2325            2330            2335

Thr Pro Lys Ala Ile Ser Glu Glu Glu Glu Val Asp Pro Asn Thr
            2340            2345            2350

Gln Asn Pro Lys Tyr Ile Thr Ala Ala Cys Glu Met Val Ala Glu Met
        2355            2360            2365

Val Glu Ser Leu Gln Ser Val Leu Ala Leu Gly His Lys Arg Asn Ser
2370            2375            2380

Gly Val Pro Ala Phe Leu Thr Pro Leu Leu Arg Asn Ile Ile Ile Ser
2385            2390            2395            2400

Leu Ala Arg Leu Pro Leu Val Asn Ser Tyr Thr Arg Val Pro Pro Leu
            2405            2410            2415

Val Trp Lys Leu Gly Trp Ser Pro Lys Pro Gly Gly Asp Phe Gly Thr
            2420            2425            2430

Ala Phe Pro Glu Ile Pro Val Glu Phe Leu Gln Glu Lys Glu Val Phe
        2435            2440            2445

Lys Glu Phe Ile Tyr Arg Ile Asn Thr Leu Gly Trp Thr Ser Arg Thr
        2450            2455            2460

Gln Phe Glu Glu Thr Trp Ala Thr Leu Leu Gly Val Leu Val Thr Gln
2465            2470            2475            2480

Pro Leu Val Met Glu Gln Glu Glu Ser Pro Pro Glu Glu Asp Thr Glu
```

```
              2485                    2490                    2495
Arg Thr Gln Ile Asn Val Leu Ala Val Gln Ala Ile Thr Ser Leu Val
                2500                    2505                    2510
Leu Ser Ala Met Thr Val Pro Val Ala Gly Asn Pro Ala Val Ser Cys
                2515                    2520                    2525
Leu Glu Gln Gln Pro Arg Asn Lys Pro Leu Lys Ala Leu Asp Thr Arg
                2530                    2535                    2540
Phe Gly Arg Lys Leu Ser Ile Ile Arg Gly Ile Val Glu Gln Glu Ile
2545                    2550                    2555                    2560
Gln Ala Met Val Ser Lys Arg Glu Asn Ile Ala Thr His His Leu Tyr
                2565                    2570                    2575
Gln Ala Trp Asp Pro Val Pro Ser Leu Ser Pro Ala Thr Thr Gly Ala
                2580                    2585                    2590
Leu Ile Ser His Glu Lys Leu Leu Leu Gln Ile Asn Pro Glu Arg Glu
                2595                    2600                    2605
Leu Gly Ser Met Ser Tyr Lys Leu Gly Gln Val Ser Ile His Ser Val
                2610                    2615                    2620
Trp Leu Gly Asn Ser Ile Thr Pro Leu Arg Glu Glu Glu Trp Asp Glu
2625                    2630                    2635                    2640
Glu Glu Glu Glu Glu Ala Asp Ala Pro Ala Pro Ser Ser Pro Pro Thr
                2645                    2650                    2655
Ser Pro Val Asn Ser Arg Lys His Arg Ala Gly Val Asp Ile His Ser
                2660                    2665                    2670
Cys Ser Gln Phe Leu Leu Glu Leu Tyr Ser Arg Trp Ile Leu Pro Ser
                2675                    2680                    2685
Ser Ser Ala Arg Arg Thr Pro Ala Ile Leu Ile Ser Glu Val Val Arg
                2690                    2695                    2700
Ser Leu Leu Val Val Ser Asp Leu Phe Thr Glu Arg Asn Gln Phe Glu
2705                    2710                    2715                    2720
Leu Met Tyr Val Thr Leu Thr Glu Leu Arg Arg Val His Pro Ser Glu
                2725                    2730                    2735
Asp Glu Ile Leu Ala Gln Tyr Leu Val Pro Ala Thr Cys Lys Ala Ala
                2740                    2745                    2750
Ala Val Leu Gly Met Asp Lys Ala Val Ala Glu Pro Val Ser Arg Leu
                2755                    2760                    2765
Leu Glu Ser Thr Leu Arg Ser Ser His Leu Pro Ser Arg Val Gly Ala
                2770                    2775                    2780
Leu His Gly Ile Leu Tyr Val Leu Glu Cys Asp Leu Leu Asp Asp Thr
2785                    2790                    2795                    2800
Ala Lys Gln Leu Ile Pro Val Ile Ser Asp Tyr Leu Leu Ser Asn Leu
                2805                    2810                    2815
Lys Gly Ile Ala His Cys Val Asn Ile His Ser Gln Gln His Val Leu
                2820                    2825                    2830
Val Met Cys Ala Thr Ala Phe Tyr Leu Ile Glu Asn Tyr Pro Leu Asp
                2835                    2840                    2845
Val Gly Pro Glu Phe Ser Ala Ser Ile Ile Gln Met Cys Gly Val Met
                2850                    2855                    2860
Leu Ser Gly Ser Glu Glu Ser Thr Pro Ser Ile Ile Tyr His Cys Ala
2865                    2870                    2875                    2880
Leu Arg Gly Leu Glu Arg Leu Leu Leu Ser Glu Gln Leu Ser Arg Leu
                2885                    2890                    2895
Asp Ala Glu Ser Leu Val Lys Leu Ser Val Asp Arg Val Asn Val His
                2900                    2905                    2910
```

-continued

| | | | | | | | | | | | | | | |
|---|---|---|---|---|---|---|---|---|---|---|---|---|---|---|
| Ser | Pro | His | Arg | Ala | Met | Ala | Ala | Leu | Gly | Leu | Met | Leu | Thr | Cys | Met |
| | | 2915 | | | | | 2920 | | | | 2925 | | | | |
| Tyr | Thr | Gly | Lys | Glu | Lys | Val | Ser | Pro | Gly | Arg | Thr | Ser | Asp | Pro | Asn |
| | | 2930 | | | | | 2935 | | | | 2940 | | | | |
| Pro | Ala | Ala | Pro | Asp | Ser | Glu | Ser | Val | Ile | Val | Ala | Met | Glu | Arg | Val |
| 2945 | | | | | 2950 | | | | 2955 | | | | | | 2960 |
| Ser | Val | Leu | Phe | Asp | Arg | Ile | Arg | Lys | Gly | Phe | Pro | Cys | Glu | Ala | Arg |
| | | | | 2965 | | | | 2970 | | | | | 2975 | | |
| Val | Val | Ala | Arg | Ile | Leu | Pro | Gln | Phe | Leu | Asp | Asp | Phe | Phe | Pro | Pro |
| | | | 2980 | | | | 2985 | | | | | 2990 | | | |
| Gln | Asp | Ile | Met | Asn | Lys | Val | Ile | Gly | Glu | Phe | Leu | Ser | Asn | Gln | Gln |
| | | 2995 | | | | | 3000 | | | | | 3005 | | | |
| Pro | Tyr | Pro | Gln | Phe | Met | Ala | Thr | Val | Val | Tyr | Lys | Val | Phe | Gln | Thr |
| | | 3010 | | | | | 3015 | | | | 3020 | | | | |
| Leu | His | Ser | Thr | Gly | Gln | Ser | Ser | Met | Val | Arg | Asp | Trp | Val | Met | Leu |
| 3025 | | | | | 3030 | | | | | 3035 | | | | | 3040 |
| Ser | Leu | Ser | Asn | Phe | Thr | Gln | Arg | Ala | Pro | Val | Ala | Met | Ala | Thr | Trp |
| | | | | 3045 | | | | | 3050 | | | | | 3055 | |
| Ser | Leu | Ser | Cys | Phe | Phe | Val | Ser | Ala | Ser | Thr | Ser | Pro | Trp | Val | Ala |
| | | | 3060 | | | | | 3065 | | | | | 3070 | | |
| Ala | Ile | Leu | Pro | His | Val | Ile | Ser | Arg | Met | Gly | Lys | Leu | Glu | Gln | Val |
| | | | 3075 | | | | | 3080 | | | | 3085 | | | |
| Asp | Val | Asn | Leu | Phe | Cys | Leu | Val | Ala | Thr | Asp | Phe | Tyr | Arg | His | Gln |
| | | 3090 | | | | | 3095 | | | | | 3100 | | | |
| Ile | Glu | Glu | Glu | Leu | Asp | Arg | Arg | Ala | Phe | Gln | Ser | Val | Leu | Glu | Val |
| 3105 | | | | | 3110 | | | | | 3115 | | | | | 3120 |
| Val | Ala | Ala | Pro | Gly | Ser | Pro | Tyr | His | Arg | Leu | Leu | Thr | Cys | Leu | Arg |
| | | | | 3125 | | | | | 3130 | | | | | 3135 | |
| Asn | Val | His | Lys | Val | Thr | Thr | Cys | | | | | | | | |
| | | | | 3140 | | | | | | | | | | | |

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:7:

GAAAAGCTGA TGAAGGCT                                              18

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:8:

CTGCTGAAAC GACTTGAG                                              18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:9:

CACCGCCGCT GCCAGGTC 18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:10:

GGTCGGTGCA GCGGTTCC 18

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:11:

CTGATGAAGG CTTTCGAGTC GCTCAAGTCG 30

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:12:

CCTTCTTTGG TCGGTGCAGC GGTTCCTCTG 30

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:13:

AGUAGUAGUA GAUCAAGCTT ATCGATACC 29

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:14:

AUGAUGAUGA UGAUCGAATT CCTGCAGCC 29

( 2 ) INFORMATION FOR SEQ ID NO:15:

( i ) SEQUENCE CHARACTERISTICS:
        ( A ) LENGTH: 9997 base pairs
        ( B ) TYPE: nucleic acid
        ( C ) STRANDEDNESS: both
        ( D ) TOPOLOGY: linear ( i x ) FEATURE:
        ( A ) NAME/KEY: CDS ( B ) LOCATION: 90..9446

( x i ) SEQUENCE DESCRIPTION: SEQ ID NO:15:

```
                                   CCCA TTCATTGCCT TGCTGCTAAG TGGCGCCGCG TAGTGCCAGT        44

AGGCTCCAAG TCTTCAGGGT CTGTCCCATC GGGCAGGAAG CCGTC ATG GCA ACC                              98
                                                       Met Ala Thr
                                                       1

CTG GAA AAG CTG ATG AAG GCT TTC GAG TCG CTC AAG TCG TTT CAG CAG                           146
Leu Glu Lys Leu Met Lys Ala Phe Glu Ser Leu Lys Ser Phe Gln Gln
        5               10                  15

CAA CAG CAG CAG CAG CCA CCG CCG CAG CCG CCG CCA CCG CCG CCG CCG                           194
Gln Gln Gln Gln Gln Pro Pro Pro Gln Pro Pro Pro Pro Pro Pro Pro
 20                  25                  30                  35

CCT CCG CCT CAA CCC CCT CAG CCG CCG CCT CAG GGG CAG CCG CCG CCG                           242
Pro Pro Pro Gln Pro Pro Gln Pro Pro Pro Gln Gly Gln Pro Pro Pro
                40                  45                  50

CCA CCA CCG CCG CTG CCA GGT CCG GCA GAG GAA CCG CTG CAC CGA CCA                           290
Pro Pro Pro Pro Leu Pro Gly Pro Ala Glu Glu Pro Leu His Arg Pro
            55                  60                  65

AAG AAG GAA CTC TCA GCC ACC AAG AAA GAC CGT GTG AAT CAT TGT CTA                           338
Lys Lys Glu Leu Ser Ala Thr Lys Lys Asp Arg Val Asn His Cys Leu
        70                  75                  80

ACA ATA TGT GAA AAC ATT GTG GCA CAG TCT CTC AGA AAT TCT CCA GAA                           386
Thr Ile Cys Glu Asn Ile Val Ala Gln Ser Leu Arg Asn Ser Pro Glu
 85                  90                  95

TTT CAG AAA CTC TTG GGC ATC GCT ATG GAA CTG TTT CTG CTG TGC AGT                           434
Phe Gln Lys Leu Leu Gly Ile Ala Met Glu Leu Phe Leu Leu Cys Ser
100                 105                 110                 115

GAC GAT GCG GAG TCA GAT GTC AGA ATG GTG GCT GAT GAG TGC CTC AAC                           482
Asp Asp Ala Glu Ser Asp Val Arg Met Val Ala Asp Glu Cys Leu Asn
                120                 125                 130

AAA GTC ATC AAA GCT TTG ATG GAT TCT AAT CTT CCA AGG CTA CAG TTA                           530
Lys Val Ile Lys Ala Leu Met Asp Ser Asn Leu Pro Arg Leu Gln Leu
            135                 140                 145

GAA CTC TAT AAG GAA ATT AAA AAG AAT GGT GCT CCT CGA AGT TTG CGT                           578
Glu Leu Tyr Lys Glu Ile Lys Lys Asn Gly Ala Pro Arg Ser Leu Arg
        150                 155                 160

GCT GCC CTG TGG AGG TTT GCT GAG CTG GCT CAC CTG GTT CGA CCT CAG                           626
Ala Ala Leu Trp Arg Phe Ala Glu Leu Ala His Leu Val Arg Pro Gln
165                 170                 175

AAG TGC AGG CCT TAC CTG GTG AAT CTT CTT CCA TGC CTG ACC CGA ACA                           674
Lys Cys Arg Pro Tyr Leu Val Asn Leu Leu Pro Cys Leu Thr Arg Thr
180                 185                 190                 195

AGC AAA AGA CCG GAG GAA TCA GTT CAG GAG ACC TTG GCT GCA GCT GTT                           722
Ser Lys Arg Pro Glu Glu Ser Val Gln Glu Thr Leu Ala Ala Ala Val
                200                 205                 210

CCT AAA ATT ATG GCT TCT TTT GGC AAT TTC GCA AAT GAC AAT GAA ATT                           770
Pro Lys Ile Met Ala Ser Phe Gly Asn Phe Ala Asn Asp Asn Glu Ile
            215                 220                 225

AAG GTT CTG TTG AAA GCT TTC ATA GCA AAT CTG AAG TCA AGC TCT CCC                           818
Lys Val Leu Leu Lys Ala Phe Ile Ala Asn Leu Lys Ser Ser Ser Pro
        230                 235                 240

ACC GTG CGG CGG ACA GCA GCC GGC TCA GCC GTG AGC ATC TGC CAA CAT                           866
Thr Val Arg Arg Thr Ala Ala Gly Ser Ala Val Ser Ile Cys Gln His
245                 250                 255

TCT AGG AGG ACA CAG TAC TTC TAC AAC TGG CTC CTT AAT GTC CTC CTA                           914
Ser Arg Arg Thr Gln Tyr Phe Tyr Asn Trp Leu Leu Asn Val Leu Leu
260                 265                 270                 275

GGT CTG CTG GTT CCC ATG GAA GAA GAG CAC TCC ACT CTC CTG ATC CTC                           962
Gly Leu Leu Val Pro Met Glu Glu Glu His Ser Thr Leu Leu Ile Leu
```

|     |     |     |     |     |     | 280 |     |     |     |     |     | 285 |     |     |     |     |     | 290 |     |     |     |
|-----|-----|-----|-----|-----|-----|-----|-----|-----|-----|-----|-----|-----|-----|-----|-----|-----|-----|-----|-----|-----|-----|

```
GGT GTG TTG CTC ACA TTG AGG TGT CTA GTG CCC TTG CTC CAG CAG CAG        1010
Gly Val Leu Leu Thr Leu Arg Cys Leu Val Pro Leu Leu Gln Gln Gln
            295                 300                 305

GTC AAG GAC ACA AGT CTA AAA GGC AGC TTT GGG GTG ACA CGG AAA GAA        1058
Val Lys Asp Thr Ser Leu Lys Gly Ser Phe Gly Val Thr Arg Lys Glu
        310                 315                 320

ATG GAA GTC TCT CCT TCT ACA GAG CAG CTT GTC CAG GTT TAT GAA CTG        1106
Met Glu Val Ser Pro Ser Thr Glu Gln Leu Val Gln Val Tyr Glu Leu
    325                 330                 335

ACT TTG CAT CAT ACT CAG CAC CAA GAC CAC AAT GTG GTG ACA GGG GCA        1154
Thr Leu His His Thr Gln His Gln Asp His Asn Val Val Thr Gly Ala
340                 345                 350                 355

CTG GAG CTC CTG CAG CAG CTC TTC CGT ACC CCT CCA CCT GAA CTC CTG        1202
Leu Glu Leu Leu Gln Gln Leu Phe Arg Thr Pro Pro Pro Glu Leu Leu
                360                 365                 370

CAA GCA CTG ACC ACA CCA GGA GGG CTT GGG CAG CTC ACT CTG GTT CAA        1250
Gln Ala Leu Thr Thr Pro Gly Gly Leu Gly Gln Leu Thr Leu Val Gln
            375                 380                 385

GAA GAG GCC CGG GGC CGA GGC CGC AGC GGG AGC ATC GTG GAG CTT TTA        1298
Glu Glu Ala Arg Gly Arg Gly Arg Ser Gly Ser Ile Val Glu Leu Leu
            390                 395                 400

GCT GGA GGG GGT TCC TCG TGC AGC CCT GTC CTC TCA AGA AAG CAG AAA        1346
Ala Gly Gly Gly Ser Ser Cys Ser Pro Val Leu Ser Arg Lys Gln Lys
405                 410                 415

GGC AAA GTG CTC TTA GGA GAG GAA GAA GCC TTG GAA GAT GAC TCG GAG        1394
Gly Lys Val Leu Leu Gly Glu Glu Glu Ala Leu Glu Asp Asp Ser Glu
420                 425                 430                 435

TCC AGA TCA GAT GTC AGC AGC TCA GCC TTT GCA GCC TCT GTG AAG AGT        1442
Ser Arg Ser Asp Val Ser Ser Ser Ala Phe Ala Ala Ser Val Lys Ser
                440                 445                 450

GAG ATT GGT GGA GAG CTC GCT GCT TCT TCA GGT GTT TCC ACT CCT GGT        1490
Glu Ile Gly Gly Glu Leu Ala Ala Ser Ser Gly Val Ser Thr Pro Gly
            455                 460                 465

TCT GTT GGT CAC GAC ATC ATC ACT GAG CAG CCT AGA TCC CAG CAC ACA        1538
Ser Val Gly His Asp Ile Ile Thr Glu Gln Pro Arg Ser Gln His Thr
            470                 475                 480

CTT CAA GCA GAC TCT GTG GAT TTG TCC GGC TGT GAC CTG ACC AGT GCT        1586
Leu Gln Ala Asp Ser Val Asp Leu Ser Gly Cys Asp Leu Thr Ser Ala
            485                 490                 495

GCT ACT GAT GGG GAT GAG GAG GAC ATC TTG AGC CAC AGC TCC AGC CAG        1634
Ala Thr Asp Gly Asp Glu Glu Asp Ile Leu Ser His Ser Ser Ser Gln
500                 505                 510                 515

TTC AGT GCT GTC CCA TCC GAC CCT GCC ATG GAC CTG AAT GAT GGG ACC        1682
Phe Ser Ala Val Pro Ser Asp Pro Ala Met Asp Leu Asn Asp Gly Thr
                520                 525                 530

CAG GCC TCC TCA CCC ATC AGT GAC AGT TCT CAG ACC ACC ACT GAA GGA        1730
Gln Ala Ser Ser Pro Ile Ser Asp Ser Ser Gln Thr Thr Thr Glu Gly
            535                 540                 545

CCT GAT TCA GCT GTG ACT CCT TCG GAC AGT TCT GAA ATT GTG TTA GAT        1778
Pro Asp Ser Ala Val Thr Pro Ser Asp Ser Ser Glu Ile Val Leu Asp
            550                 555                 560

GGT GCC GAT AGC CAG TAT TTA GGC ATG CAG ATA GGA CAG CCA CAG GAG        1826
Gly Ala Asp Ser Gln Tyr Leu Gly Met Gln Ile Gly Gln Pro Gln Glu
            565                 570                 575

GAC GAT GAG GAG GGA GCT GCA GGT GTT CTT TCT GGT GAA GTC TCA GAT        1874
Asp Asp Glu Glu Gly Ala Ala Gly Val Leu Ser Gly Glu Val Ser Asp
580                 585                 590                 595

GTT TTC AGA AAC TCT TCT CTG GCC CTT CAA CAG GCA CAC TTG TTG GAA        1922
Val Phe Arg Asn Ser Ser Leu Ala Leu Gln Gln Ala His Leu Leu Glu
```

-continued

| | | | | | | 600 | | | | | 605 | | | | | 610 | | | |
|---|---|---|---|---|---|---|---|---|---|---|---|---|---|---|---|---|---|---|---|
| AGA | ATG | GGC | CAT | AGC | AGG | CAG | CCT | TCC | GAC | AGC | AGT | ATA | GAT | AAG | TAT | | | | 1970 |
| Arg | Met | Gly | His | Ser | Arg | Gln | Pro | Ser | Asp | Ser | Ser | Ile | Asp | Lys | Tyr | | | | |
| | | 615 | | | | | | 620 | | | | | 625 | | | | | | |
| GTA | ACA | AGA | GAT | GAG | GTT | GCT | GAA | GCC | AGT | GAT | CCA | GAA | AGC | AAG | CCT | | | | 2018 |
| Val | Thr | Arg | Asp | Glu | Val | Ala | Glu | Ala | Ser | Asp | Pro | Glu | Ser | Lys | Pro | | | | |
| | | 630 | | | | | 635 | | | | | 640 | | | | | | | |
| TGC | CGA | ATC | AAA | GGT | GAC | ATA | GGA | CAG | CCT | AAT | GAT | GAT | GAT | TCT | GCT | | | | 2066 |
| Cys | Arg | Ile | Lys | Gly | Asp | Ile | Gly | Gln | Pro | Asn | Asp | Asp | Asp | Ser | Ala | | | | |
| | 645 | | | | | 650 | | | | | 655 | | | | | | | | |
| CCT | CTG | GTA | CAT | TGT | GTC | CGT | CTT | TTA | TCT | GCT | TCC | TTT | TTG | TTA | ACT | | | | 2114 |
| Pro | Leu | Val | His | Cys | Val | Arg | Leu | Leu | Ser | Ala | Ser | Phe | Leu | Leu | Thr | | | | |
| 660 | | | | | 665 | | | | | 670 | | | | | 675 | | | | |
| GGT | GAA | AAG | AAA | GCA | CTG | GTT | CCA | GAC | AGA | GAC | GTG | AGA | GTC | AGT | GTG | | | | 2162 |
| Gly | Glu | Lys | Lys | Ala | Leu | Val | Pro | Asp | Arg | Asp | Val | Arg | Val | Ser | Val | | | | |
| | | | | 680 | | | | | 685 | | | | | 690 | | | | | |
| AAG | GCC | CTG | GCC | CTC | AGC | TGC | ATT | GGT | GCG | GCT | GTG | GCC | CTT | CAT | CCA | | | | 2210 |
| Lys | Ala | Leu | Ala | Leu | Ser | Cys | Ile | Gly | Ala | Ala | Val | Ala | Leu | His | Pro | | | | |
| | | 695 | | | | | 700 | | | | | 705 | | | | | | | |
| GAG | TCG | TTC | TTC | AGC | AGA | CTG | TAC | AAA | GTA | CCT | CTT | AAT | ACC | ACG | GAA | | | | 2258 |
| Glu | Ser | Phe | Phe | Ser | Arg | Leu | Tyr | Lys | Val | Pro | Leu | Asn | Thr | Thr | Glu | | | | |
| | | 710 | | | | | 715 | | | | | 720 | | | | | | | |
| AGT | ACT | GAG | GAA | CAG | TAT | GTT | TCT | GAC | ATC | TTG | AAC | TAC | ATC | GAT | CAT | | | | 2306 |
| Ser | Thr | Glu | Glu | Gln | Tyr | Val | Ser | Asp | Ile | Leu | Asn | Tyr | Ile | Asp | His | | | | |
| | 725 | | | | | 730 | | | | | 735 | | | | | | | | |
| GGA | GAC | CCA | CAG | GTC | CGA | GGA | GCT | ACT | GCC | ATT | CTC | TGT | GGG | ACC | CTT | | | | 2354 |
| Gly | Asp | Pro | Gln | Val | Arg | Gly | Ala | Thr | Ala | Ile | Leu | Cys | Gly | Thr | Leu | | | | |
| 740 | | | | | 745 | | | | | 750 | | | | | 755 | | | | |
| GTC | TAC | TCC | ATC | CTC | AGT | AGG | TCC | CGT | CTC | CGT | GTT | GGT | GAG | TGG | CTG | | | | 2402 |
| Val | Tyr | Ser | Ile | Leu | Ser | Arg | Ser | Arg | Leu | Arg | Val | Gly | Glu | Trp | Leu | | | | |
| | | | | 760 | | | | | 765 | | | | | 770 | | | | | |
| GGC | AAC | ATC | AGA | ACC | CTG | ACA | GGA | AAT | ACA | TTT | TCT | CTG | GTG | GAC | TGC | | | | 2450 |
| Gly | Asn | Ile | Arg | Thr | Leu | Thr | Gly | Asn | Thr | Phe | Ser | Leu | Val | Asp | Cys | | | | |
| | | | 775 | | | | | 780 | | | | | 785 | | | | | | |
| ATT | CCT | TTA | CTG | CAG | AAA | ACG | TTG | AAG | GAT | GAA | TCT | TCT | GTT | ACT | TGC | | | | 2498 |
| Ile | Pro | Leu | Leu | Gln | Lys | Thr | Leu | Lys | Asp | Glu | Ser | Ser | Val | Thr | Cys | | | | |
| | | 790 | | | | | 795 | | | | | 800 | | | | | | | |
| AAG | TTG | GCT | TGT | ACA | GCT | GTG | AGG | CAC | TGT | GTC | CTG | AGT | CTT | TGC | AGC | | | | 2546 |
| Lys | Leu | Ala | Cys | Thr | Ala | Val | Arg | His | Cys | Val | Leu | Ser | Leu | Cys | Ser | | | | |
| | 805 | | | | | 810 | | | | | 815 | | | | | | | | |
| AGC | AGC | TAC | AGT | GAC | TTG | GGA | TTA | CAA | CTG | CTT | ATT | GAT | ATG | CTG | CCT | | | | 2594 |
| Ser | Ser | Tyr | Ser | Asp | Leu | Gly | Leu | Gln | Leu | Leu | Ile | Asp | Met | Leu | Pro | | | | |
| 820 | | | | | 825 | | | | | 830 | | | | | 835 | | | | |
| CTG | AAG | AAC | AGC | TCC | TAC | TGG | CTG | GTG | AGG | ACC | GAA | CTG | CTG | GAC | ACT | | | | 2642 |
| Leu | Lys | Asn | Ser | Ser | Tyr | Trp | Leu | Val | Arg | Thr | Glu | Leu | Leu | Asp | Thr | | | | |
| | | | | 840 | | | | | 845 | | | | | 850 | | | | | |
| CTG | GCA | GAG | ATT | GAC | TTC | AGG | CTC | GTG | AGT | TTT | TTG | GAG | GCA | AAA | GCA | | | | 2690 |
| Leu | Ala | Glu | Ile | Asp | Phe | Arg | Leu | Val | Ser | Phe | Leu | Glu | Ala | Lys | Ala | | | | |
| | | | 855 | | | | | 860 | | | | | 865 | | | | | | |
| GAA | AGT | TTA | CAC | CGA | GGG | GCT | CAT | CAT | TAT | ACA | GGG | TTT | CTA | AAA | CTA | | | | 2738 |
| Glu | Ser | Leu | His | Arg | Gly | Ala | His | His | Tyr | Thr | Gly | Phe | Leu | Lys | Leu | | | | |
| | | 870 | | | | | 875 | | | | | 880 | | | | | | | |
| CAA | GAA | CGA | GTA | CTC | AAT | AAT | GTG | GTC | ATT | TAT | TTG | CTT | GGA | GAT | GAA | | | | 2786 |
| Gln | Glu | Arg | Val | Leu | Asn | Asn | Val | Val | Ile | Tyr | Leu | Leu | Gly | Asp | Glu | | | | |
| | 885 | | | | | 890 | | | | | 895 | | | | | | | | |
| GAC | CCC | AGG | GTT | CGA | CAT | GTT | GCT | GCA | ACA | TCA | TTA | ACA | AGG | CTT | GTC | | | | 2834 |
| Asp | Pro | Arg | Val | Arg | His | Val | Ala | Ala | Thr | Ser | Leu | Thr | Arg | Leu | Val | | | | |
| 900 | | | | | 905 | | | | | 910 | | | | | 915 | | | | |
| CCA | AAG | CTG | TTT | TAC | AAG | TGT | GAC | CAA | GGA | CAA | GCT | GAT | CCA | GTT | GTG | | | | 2882 |
| Pro | Lys | Leu | Phe | Tyr | Lys | Cys | Asp | Gln | Gly | Gln | Ala | Asp | Pro | Val | Val | | | | |

| | | | |
|---|---|---|---|
| GCT Ala | GTA Val | GCG Ala | AGG Arg 935 | GAT Asp | CAG Gln | AGC Ser | AGT Ser 940 | GTC Val | TAC Tyr | CTG Leu | AAG Lys 945 | CTC Leu | CTC Leu | ATG Met | CAT His | 2930 |

```
GCT GTA GCG AGG GAT CAG AGC AGT GTC TAC CTG AAG CTC CTC ATG CAT    2930
Ala Val Ala Arg Asp Gln Ser Ser Val Tyr Leu Lys Leu Leu Met His
            935             940             945

GAG ACC CAG CCA CCA TCA CAC TTT TCT GTC AGC ACC ATC ACC AGA ATC    2978
Glu Thr Gln Pro Pro Ser His Phe Ser Val Ser Thr Ile Thr Arg Ile
        950             955             960

TAT AGA GGC TAT AGC TTA CTG CCA AGT ATA ACA GAT GTC ACC ATG GAA    3026
Tyr Arg Gly Tyr Ser Leu Leu Pro Ser Ile Thr Asp Val Thr Met Glu
965             970             975

AAC AAT CTC TCA AGA GTT GTT GCC GCA GTT TCT CAT GAA CTC ATT ACG    3074
Asn Asn Leu Ser Arg Val Val Ala Ala Val Ser His Glu Leu Ile Thr
980             985             990             995

TCA ACA ACA CGG GCA CTC ACA TTT GGA TGC TGT GAA GCC TTG TGT CTT    3122
Ser Thr Thr Arg Ala Leu Thr Phe Gly Cys Cys Glu Ala Leu Cys Leu
            1000            1005            1010

CTC TCA GCA GCC TTT CCA GTT TGC ACT TGG AGT TTA GGA TGG CAC TGT    3170
Leu Ser Ala Ala Phe Pro Val Cys Thr Trp Ser Leu Gly Trp His Cys
            1015            1020            1025

GGA GTG CCC CCA CTG AGT GCC TCT GAT GAG TCC AGG AAG AGC TGC ACT    3218
Gly Val Pro Pro Leu Ser Ala Ser Asp Glu Ser Arg Lys Ser Cys Thr
        1030            1035            1040

GTT GGG ATG GCC TCC ATG ATT CTC ACC TTG CTT TCA TCA GCT TGG TTC    3266
Val Gly Met Ala Ser Met Ile Leu Thr Leu Leu Ser Ser Ala Trp Phe
    1045            1050            1055

CCA CTG GAT CTC TCA GCC CAT CAG GAT GCC TTG ATT TTG GCT GGA AAC    3314
Pro Leu Asp Leu Ser Ala His Gln Asp Ala Leu Ile Leu Ala Gly Asn
1060            1065            1070            1075

TTG CTA GCA GCG AGT GCC CCC AAG TCT CTG AGA AGT TCA TGG ACC TCT    3362
Leu Leu Ala Ala Ser Ala Pro Lys Ser Leu Arg Ser Ser Trp Thr Ser
            1080            1085            1090

GAA GAA GAA GCC AAC TCA GCA GCC ACC AGA CAG GAG GAA ATC TGG CCT    3410
Glu Glu Glu Ala Asn Ser Ala Ala Thr Arg Gln Glu Glu Ile Trp Pro
            1095            1100            1105

GCT CTG GGG GAT CGG ACT CTA GTG CCC TTG GTG GAG CAG CTT TTC TCC    3458
Ala Leu Gly Asp Arg Thr Leu Val Pro Leu Val Glu Gln Leu Phe Ser
        1110            1115            1120

CAC CTG CTG AAG GTG ATC AAT ATC TGT GCT CAT GTC TTG GAC GAT GTG    3506
His Leu Leu Lys Val Ile Asn Ile Cys Ala His Val Leu Asp Asp Val
        1125            1130            1135

ACT CCT GGA CCA GCA ATC AAG GCA GCC TTG CCT TCT CTA ACA AAC CCC    3554
Thr Pro Gly Pro Ala Ile Lys Ala Ala Leu Pro Ser Leu Thr Asn Pro
1140            1145            1150            1155

CCT TCT CTA AGT CCT ATT CGA CGG AAA GGG AAG GAG AAA GAA CCT GGA    3602
Pro Ser Leu Ser Pro Ile Arg Arg Lys Gly Lys Glu Lys Glu Pro Gly
            1160            1165            1170

GAA CAA GCT TCT ACT CCA ATG AGT CCC AAG AAA GTT GGT GAG GCC AGT    3650
Glu Gln Ala Ser Thr Pro Met Ser Pro Lys Lys Val Gly Glu Ala Ser
            1175            1180            1185

GCA GCC TCT CGA CAA TCA GAC ACC TCA GGA CCT GTC ACA GCA AGT AAA    3698
Ala Ala Ser Arg Gln Ser Asp Thr Ser Gly Pro Val Thr Ala Ser Lys
            1190            1195            1200

TCA TCC TCA CTG GGG AGT TTC TAC CAT CTC CCC TCC TAC CTC AAA CTG    3746
Ser Ser Ser Leu Gly Ser Phe Tyr His Leu Pro Ser Tyr Leu Lys Leu
1205            1210            1215

CAT GAT GTC CTG AAA GCC ACT CAC GCC AAC TAT AAG GTC ACC TTA GAT    3794
His Asp Val Leu Lys Ala Thr His Ala Asn Tyr Lys Val Thr Leu Asp
1220            1225            1230            1235

CTT CAG AAC AGC ACT GAA AAG TTT GGG GGG TTC CTG CGC TCT GCC TTG    3842
Leu Gln Asn Ser Thr Glu Lys Phe Gly Gly Phe Leu Arg Ser Ala Leu
```

```
                        1240                        1245                        1250
GAC  GTC  CTT  TCT  CAG  ATT  CTA  GAG  CTG  GCG  ACA  CTG  CAG  GAC  ATT  GGA       3890
Asp  Val  Leu  Ser  Gln  Ile  Leu  Glu  Leu  Ala  Thr  Leu  Gln  Asp  Ile  Gly
               1255                          1260                     1265

AAG  TGT  GTT  GAA  GAG  GTC  CTT  GGA  TAC  CTG  AAA  TCC  TGC  TTT  AGT  CGA       3938
Lys  Cys  Val  Glu  Glu  Val  Leu  Gly  Tyr  Leu  Lys  Ser  Cys  Phe  Ser  Arg
          1270                     1275                     1280

GAA  CCA  ATG  ATG  GCA  ACT  GTC  TGT  GTG  CAG  CAG  CTA  TTG  AAG  ACT  CTC       3986
Glu  Pro  Met  Met  Ala  Thr  Val  Cys  Val  Gln  Gln  Leu  Leu  Lys  Thr  Leu
          1285                     1290                     1295

TTT  GGG  ACA  AAC  TTA  GCC  TCA  CAG  TTT  GAT  GGC  TTA  TCT  TCC  AAC  CCC       4034
Phe  Gly  Thr  Asn  Leu  Ala  Ser  Gln  Phe  Asp  Gly  Leu  Ser  Ser  Asn  Pro
1300                     1305                     1310                     1315

AGC  AAG  TCT  CAG  TGC  CGA  GCT  CAG  CGC  CTT  GGC  TCT  TCA  AGT  GTG  AGG       4082
Ser  Lys  Ser  Gln  Cys  Arg  Ala  Gln  Arg  Leu  Gly  Ser  Ser  Ser  Val  Arg
                    1320                     1325                     1330

CCC  GGC  TTA  TAT  CAC  TAC  TGC  TTC  ATG  GCA  CCA  TAC  ACG  CAC  TTC  ACA       4130
Pro  Gly  Leu  Tyr  His  Tyr  Cys  Phe  Met  Ala  Pro  Tyr  Thr  His  Phe  Thr
                         1335                     1340                     1345

CAG  GCC  TTG  GCT  GAC  GCA  AGC  CTG  AGG  AAC  ATG  GTG  CAG  GCG  GAG  CAG       4178
Gln  Ala  Leu  Ala  Asp  Ala  Ser  Leu  Arg  Asn  Met  Val  Gln  Ala  Glu  Gln
               1350                     1355                     1360

GAG  CGT  GAT  GCC  TCG  GGG  TGG  TTT  GAT  GTA  CTC  CAG  AAA  GTG  TCT  GCC       4226
Glu  Arg  Asp  Ala  Ser  Gly  Trp  Phe  Asp  Val  Leu  Gln  Lys  Val  Ser  Ala
          1365                     1370                     1375

CAA  TTG  AAG  ACG  AAC  CTA  ACA  AGC  GTC  ACA  AAG  AAC  CGT  GCA  GAT  AAG       4274
Gln  Leu  Lys  Thr  Asn  Leu  Thr  Ser  Val  Thr  Lys  Asn  Arg  Ala  Asp  Lys
1380                     1385                     1390                     1395

AAT  GCT  ATT  CAT  AAT  CAC  ATT  AGG  TTA  TTT  GAG  CCT  CTT  GTT  ATA  AAA       4322
Asn  Ala  Ile  His  Asn  His  Ile  Arg  Leu  Phe  Glu  Pro  Leu  Val  Ile  Lys
                    1400                     1405                     1410

GCA  TTG  AAG  CAG  TAC  ACC  ACG  ACA  ACA  TCT  GTA  CAA  TTG  CAG  AAG  CAG       4370
Ala  Leu  Lys  Gln  Tyr  Thr  Thr  Thr  Thr  Ser  Val  Gln  Leu  Gln  Lys  Gln
               1415                     1420                     1425

GTT  TTG  GAT  TTG  CTG  GCA  CAG  CTG  GTT  CAG  CTA  CGG  GTC  AAT  TAC  TGT       4418
Val  Leu  Asp  Leu  Leu  Ala  Gln  Leu  Val  Gln  Leu  Arg  Val  Asn  Tyr  Cys
          1430                     1435                     1440

CTA  CTG  GAT  TCA  GAC  CAG  GTG  TTC  ATC  GGG  TTT  GTG  CTG  AAG  CAG  TTT       4466
Leu  Leu  Asp  Ser  Asp  Gln  Val  Phe  Ile  Gly  Phe  Val  Leu  Lys  Gln  Phe
     1445                     1450                     1455

GAG  TAC  ATT  GAA  GTG  GGC  CAG  TTC  AGG  GAA  TCA  GAG  GCA  ATT  ATT  CCA       4514
Glu  Tyr  Ile  Glu  Val  Gly  Gln  Phe  Arg  Glu  Ser  Glu  Ala  Ile  Ile  Pro
1460                     1465                     1470                     1475

AAT  ATA  TTT  TTC  TTC  CTG  GTA  TTA  CTG  TCT  TAT  GAG  CGC  TAC  CAT  TCA       4562
Asn  Ile  Phe  Phe  Phe  Leu  Val  Leu  Leu  Ser  Tyr  Glu  Arg  Tyr  His  Ser
                    1480                     1485                     1490

AAA  CAG  ATC  ATT  GGA  ATT  CCT  AAA  ATC  ATC  CAG  CTG  TGT  GAT  GGC  ATC       4610
Lys  Gln  Ile  Ile  Gly  Ile  Pro  Lys  Ile  Ile  Gln  Leu  Cys  Asp  Gly  Ile
               1495                     1500                     1505

ATG  GCC  AGT  GGA  AGG  AAG  GCC  GTT  ACA  CAT  GCT  ATA  CCT  GCT  CTG  CAG       4658
Met  Ala  Ser  Gly  Arg  Lys  Ala  Val  Thr  His  Ala  Ile  Pro  Ala  Leu  Gln
          1510                     1515                     1520

CCC  ATT  GTC  CAT  GAC  CTC  TTT  GTG  TTA  CGA  GGA  ACA  AAT  AAA  GCT  GAT       4706
Pro  Ile  Val  His  Asp  Leu  Phe  Val  Leu  Arg  Gly  Thr  Asn  Lys  Ala  Asp
     1525                     1530                     1535

GCA  GGG  AAA  GAG  CTT  GAG  ACA  CAG  AAG  GAG  GTG  GTG  GTC  TCC  ATG  CTG       4754
Ala  Gly  Lys  Glu  Leu  Glu  Thr  Gln  Lys  Glu  Val  Val  Val  Ser  Met  Leu
1540                     1545                     1550                     1555

TTA  CGA  CTC  ATC  CAG  TAC  CAT  CAG  GTG  CTG  GAG  ATG  TTC  ATC  CTT  GTC       4802
Leu  Arg  Leu  Ile  Gln  Tyr  His  Gln  Val  Leu  Glu  Met  Phe  Ile  Leu  Val
```

```
                    1560                        1565                        1570

CTG CAG CAG TGC CAC AAG GAG AAT GAG GAC AAG TGG AAA CGG CTC TCT                 4850
Leu Gln Gln Cys His Lys Glu Asn Glu Asp Lys Trp Lys Arg Leu Ser
            1575                1580                1585

CGG CAG GTC GCA GAC ATC ATC CTG CCC ATG TTG GCC AAG CAG CAG ATG                 4898
Arg Gln Val Ala Asp Ile Ile Leu Pro Met Leu Ala Lys Gln Gln Met
        1590                1595                1600

CAT ATT GAC TCT CAT GAA GCC CTT GGA GTG TTA AAT ACC TTG TTT GAG                 4946
His Ile Asp Ser His Glu Ala Leu Gly Val Leu Asn Thr Leu Phe Glu
1605                1610                1615

ATT TTG GCT CCT TCC TCC CTA CGT CCT GTG GAC ATG CTT TTG CGG AGT                 4994
Ile Leu Ala Pro Ser Ser Leu Arg Pro Val Asp Met Leu Leu Arg Ser
1620                1625                1630                1635

ATG TTC ATC ACT CCA AGC ACA ATG GCA TCT GTA AGC ACT GTG CAG CTG                 5042
Met Phe Ile Thr Pro Ser Thr Met Ala Ser Val Ser Thr Val Gln Leu
            1640                1645                1650

TGG ATA TCT GGA ATC CTC GCC ATT CTG AGG GTT CTC ATT TCC CAG TCA                 5090
Trp Ile Ser Gly Ile Leu Ala Ile Leu Arg Val Leu Ile Ser Gln Ser
            1655                1660                1665

ACC GAG GAC ATT GTT CTT TGT CGT ATT CAG GAG CTC TCC TTC TCT CCA                 5138
Thr Glu Asp Ile Val Leu Cys Arg Ile Gln Glu Leu Ser Phe Ser Pro
        1670                1675                1680

CAC TTG CTC TCC TGT CCA GTG ATT AAC AGG TTA AGG GGT GGA GGC GGT                 5186
His Leu Leu Ser Cys Pro Val Ile Asn Arg Leu Arg Gly Gly Gly Gly
        1685                1690                1695

AAT GTA ACA CTA GGA GAA TGC AGC GAA GGG AAA CAA AAG AGT TTG CCA                 5234
Asn Val Thr Leu Gly Glu Cys Ser Glu Gly Lys Gln Lys Ser Leu Pro
1700                1705                1710                1715

GAA GAT ACA TTC TCA AGG TTT CTT TTA CAG CTG GTT GGT ATT CTT CTA                 5282
Glu Asp Thr Phe Ser Arg Phe Leu Leu Gln Leu Val Gly Ile Leu Leu
                1720                1725                1730

GAA GAC ATC GTT ACA AAA CAG CTC AAA GTG GAC ATG AGT GAA CAG CAG                 5330
Glu Asp Ile Val Thr Lys Gln Leu Lys Val Asp Met Ser Glu Gln Gln
            1735                1740                1745

CAT ACG TTC TAC TGC CAA GAG CTA GGC ACA CTG CTC ATG TGT CTG ATC                 5378
His Thr Phe Tyr Cys Gln Glu Leu Gly Thr Leu Leu Met Cys Leu Ile
        1750                1755                1760

CAC ATA TTC AAA TCT GGA ATG TTC CGG AGA ATC ACA GCA GCT GCC ACT                 5426
His Ile Phe Lys Ser Gly Met Phe Arg Arg Ile Thr Ala Ala Ala Thr
        1765                1770                1775

AGA CTC TTC ACC AGT GAT GGC TGT GAA GGC AGC TTC TAT ACT CTA GAG                 5474
Arg Leu Phe Thr Ser Asp Gly Cys Glu Gly Ser Phe Tyr Thr Leu Glu
1780                1785                1790                1795

AGC CTG AAT GCA CGG GTC CGA TCC ATG GTG CCC ACG CAC CCA GCC CTG                 5522
Ser Leu Asn Ala Arg Val Arg Ser Met Val Pro Thr His Pro Ala Leu
                1800                1805                1810

GTA CTG CTC TGG TGT CAG ATC CTA CTT CTC ATC AAC CAC ACT GAC CAC                 5570
Val Leu Leu Trp Cys Gln Ile Leu Leu Leu Ile Asn His Thr Asp His
            1815                1820                1825

CGG TGG TGG GCA GAG GTG CAG CAG ACA CCC AAG AGA CAC AGT CTG TCC                 5618
Arg Trp Trp Ala Glu Val Gln Gln Thr Pro Lys Arg His Ser Leu Ser
        1830                1835                1840

TGC ACG AAG TCA CTT AAC CCC CAG AAG TCT GGC GAA GAG GAG GAT TCT                 5666
Cys Thr Lys Ser Leu Asn Pro Gln Lys Ser Gly Glu Glu Glu Asp Ser
1845                1850                1855

GGC TCG GCA GCT CAG CTG GGA ATG TGC AAT AGA GAA ATA GTG CGA AGA                 5714
Gly Ser Ala Ala Gln Leu Gly Met Cys Asn Arg Glu Ile Val Arg Arg
1860                1865                1870                1875

GGG GCC CTT ATT CTC TTC TGT GAT TAT GTC TGT CAG AAT CTC CAT GAC                 5762
Gly Ala Leu Ile Leu Phe Cys Asp Tyr Val Cys Gln Asn Leu His Asp
```

```
                    1880                        1885                        1890
TCA GAA CAC TTA ACA TGG CTC ATT GTG AAT CAC ATT CAA GAT CTG ATC         5810
Ser Glu His Leu Thr Trp Leu Ile Val Asn His Ile Gln Asp Leu Ile
                1895                    1900                    1905

AGC TTG TCT CAT GAG CCT CCA GTA CAA GAC TTT ATT AGT GCC ATT CAT         5858
Ser Leu Ser His Glu Pro Pro Val Gln Asp Phe Ile Ser Ala Ile His
                1910                    1915                    1920

CGT AAT TCT GCA GCT AGT GGT CTT TTT ATC CAG GCA ATT CAG TCT CGC         5906
Arg Asn Ser Ala Ala Ser Gly Leu Phe Ile Gln Ala Ile Gln Ser Arg
                1925                    1930                    1935

TGT GAA AAT CTT TCA ACG CCA ACC ACT CTG AAG AAA ACA CTT CAG TGC         5954
Cys Glu Asn Leu Ser Thr Pro Thr Thr Leu Lys Lys Thr Leu Gln Cys
1940                    1945                    1950                    1955

TTG GAA GGC ATC CAT CTC AGC CAG TCT GGT GCT GTG CTC ACA CTA TAT         6002
Leu Glu Gly Ile His Leu Ser Gln Ser Gly Ala Val Leu Thr Leu Tyr
                1960                    1965                    1970

GTG GAC AGG CTC CTG GGC ACC CCC TTC CGT GCG CTG GCT CGC ATG GTC         6050
Val Asp Arg Leu Leu Gly Thr Pro Phe Arg Ala Leu Ala Arg Met Val
                1975                    1980                    1985

GAC ACC CTG GCC TGT CGC CGG GTA GAA ATG CTT TTG GCT GCA AAT TTA         6098
Asp Thr Leu Ala Cys Arg Arg Val Glu Met Leu Leu Ala Ala Asn Leu
                1990                    1995                    2000

CAG AGC AGC ATG GCC CAG TTG CCA GAG GAG GAA CTA AAC AGA ATC CAA         6146
Gln Ser Ser Met Ala Gln Leu Pro Glu Glu Glu Leu Asn Arg Ile Gln
                2005                    2010                    2015

GAA CAC CTC CAG AAC AGT GGG CTT GCA CAA AGA CAC CAA AGG CTC TAT         6194
Glu His Leu Gln Asn Ser Gly Leu Ala Gln Arg His Gln Arg Leu Tyr
2020                    2025                    2030                    2035

TCA CTG CTG GAC AGA TTC CGA CTC TCT ACT GTG CAG GAC TCA CTT AGC         6242
Ser Leu Leu Asp Arg Phe Arg Leu Ser Thr Val Gln Asp Ser Leu Ser
                2040                    2045                    2050

CCC TTG CCC CCA GTC ACT TCC CAC CCA CTG GAT GGG GAT GGG CAC ACA         6290
Pro Leu Pro Pro Val Thr Ser His Pro Leu Asp Gly Asp Gly His Thr
                2055                    2060                    2065

TCT CTG GAA ACA GTG AGT CCA GAC AAA GAC TGG TAC CTC CAG CTT GTC         6338
Ser Leu Glu Thr Val Ser Pro Asp Lys Asp Trp Tyr Leu Gln Leu Val
                2070                    2075                    2080

AGA TCC CAG TGT TGG ACC AGA TCA GAT TCT GCA CTG CTG GAA GGT GCA         6386
Arg Ser Gln Cys Trp Thr Arg Ser Asp Ser Ala Leu Leu Glu Gly Ala
                2085                    2090                    2095

GAG CTG GTC AAC CGT ATC CCT GCT GAA GAT ATG AAT GAC TTC ATG ATG         6434
Glu Leu Val Asn Arg Ile Pro Ala Glu Asp Met Asn Asp Phe Met Met
2100                    2105                    2110                    2115

AGC TCG GAG TTC AAC CTA AGC CTT TTG GCT CCC TGT TTA AGC CTT GGC         6482
Ser Ser Glu Phe Asn Leu Ser Leu Leu Ala Pro Cys Leu Ser Leu Gly
                2120                    2125                    2130

ATG AGC GAG ATT GCT AAT GGC CAA AAG AGT CCC CTC TTT GAA GCA GCC         6530
Met Ser Glu Ile Ala Asn Gly Gln Lys Ser Pro Leu Phe Glu Ala Ala
                2135                    2140                    2145

CGT GGG GTG ATT CTG AAC CGG GTG ACC AGT GTT GTT CAG CAG CTT CCT         6578
Arg Gly Val Ile Leu Asn Arg Val Thr Ser Val Val Gln Gln Leu Pro
                2150                    2155                    2160

GCT GTC CAT CAA GTC TTC CAG CCC TTC CTG CCT ATA GAG CCC ACG GCC         6626
Ala Val His Gln Val Phe Gln Pro Phe Leu Pro Ile Glu Pro Thr Ala
                2165                    2170                    2175

TAC TGG AAC AAG TTG AAT GAT CTG CTT GGT GAT ACC ACA TCA TAC CAG         6674
Tyr Trp Asn Lys Leu Asn Asp Leu Leu Gly Asp Thr Thr Ser Tyr Gln
                2180                    2185                    2190                    2195

TCT CTG ACC ATA CTT GCC CGT GCC CTG GCA CAG TAC CTG GTG GTG CTC         6722
Ser Leu Thr Ile Leu Ala Arg Ala Leu Ala Gln Tyr Leu Val Val Leu
```

```
                    2200                              2205                              2210

TCC AAA GTG CCT GCT CAT TTG CAC CTT CCT CCT GAG AAG GAG GGG GAC        6770
Ser Lys Val Pro Ala His Leu His Leu Pro Pro Glu Lys Glu Gly Asp
        2215                    2220                    2225

ACG GTG AAG TTT GTG GTA ATG ACA GTT GAG GCC CTG TCA TGG CAT TTG        6818
Thr Val Lys Phe Val Val Met Thr Val Glu Ala Leu Ser Trp His Leu
    2230                    2235                    2240

ATC CAT GAG CAG ATC CCA CTG AGT CTG GAC CTC CAA GCC GGG CTA GAC        6866
Ile His Glu Gln Ile Pro Leu Ser Leu Asp Leu Gln Ala Gly Leu Asp
2245                    2250                    2255

TGC TGC TGC CTG GCA CTA CAG GTG CCT GGC CTC TGG GGG GTG CTG TCC        6914
Cys Cys Cys Leu Ala Leu Gln Val Pro Gly Leu Trp Gly Val Leu Ser
2260                    2265                    2270                    2275

TCC CCA GAG TAC GTG ACT CAT GCC TGC TCC CTC ATC CAT TGT GTG CGA        6962
Ser Pro Glu Tyr Val Thr His Ala Cys Ser Leu Ile His Cys Val Arg
            2280                    2285                    2290

TTC ATC CTG GAA GCC ATT GCA GTA CAA CCT GGA GAC CAG CTT CTC GGT        7010
Phe Ile Leu Glu Ala Ile Ala Val Gln Pro Gly Asp Gln Leu Leu Gly
        2295                    2300                    2305

CCT GAA AGC AGG TCA CAT ACT CCA AGA GCT GTC AGA AAG GAG GAA GTA        7058
Pro Glu Ser Arg Ser His Thr Pro Arg Ala Val Arg Lys Glu Glu Val
            2310                    2315                    2320

GAC TCA GAT ATA CAA AAC CTC AGT CAT GTC ACT TCG GCC TGC GAG ATG        7106
Asp Ser Asp Ile Gln Asn Leu Ser His Val Thr Ser Ala Cys Glu Met
        2325                    2330                    2335

GTG GCA GAC ATG GTG GAA TCC CTG CAG TCA GTG CTG GCC TTG GGC CAC        7154
Val Ala Asp Met Val Glu Ser Leu Gln Ser Val Leu Ala Leu Gly His
2340                    2345                    2350                    2355

AAG AGG AAC AGC ACC CTG CCT TCA TTT CTC ACA GCT GTG CTG AAG AAC        7202
Lys Arg Asn Ser Thr Leu Pro Ser Phe Leu Thr Ala Val Leu Lys Asn
                2360                    2365                    2370

ATT GTT ATC AGT CTG GCC CGA CTC CCC CTA GTT AAC AGC TAT ACT CGT        7250
Ile Val Ile Ser Leu Ala Arg Leu Pro Leu Val Asn Ser Tyr Thr Arg
            2375                    2380                    2385

GTG CCT CCT CTG GTA TGG AAA CTC GGG TGG TCA CCC AAG CCT GGA GGG        7298
Val Pro Pro Leu Val Trp Lys Leu Gly Trp Ser Pro Lys Pro Gly Gly
        2390                    2395                    2400

GAT TTT GGC ACA GTG TTT CCT GAG ATC CCT GTA GAG TTC CTC CAG GAG        7346
Asp Phe Gly Thr Val Phe Pro Glu Ile Pro Val Glu Phe Leu Gln Glu
    2405                    2410                    2415

AAG GAG ATC CTC AAG GAG TTC ATC TAC CGC ATC AAC ACC CTA GGG TGG        7394
Lys Glu Ile Leu Lys Glu Phe Ile Tyr Arg Ile Asn Thr Leu Gly Trp
2420                    2425                    2430                    2435

ACC AAT CGT ACC CAG TTC GAA GAA ACT TGG GCC ACC CTC CTT GGT GTC        7442
Thr Asn Arg Thr Gln Phe Glu Glu Thr Trp Ala Thr Leu Leu Gly Val
            2440                    2445                    2450

CTG GTG ACT CAG CCC CTG GTG ATG GAA CAG GAA GAG AGC CCA CCA GAG        7490
Leu Val Thr Gln Pro Leu Val Met Glu Gln Glu Glu Ser Pro Pro Glu
        2455                    2460                    2465

GAA GAC ACA GAA AGA ACC CAG ATC CAT GTC CTG GCT GTG CAG GCC ATC        7538
Glu Asp Thr Glu Arg Thr Gln Ile His Val Leu Ala Val Gln Ala Ile
            2470                    2475                    2480

ACC TCT CTA GTG CTC AGT GCA ATG ACC GTG CCT GTG GCT GGC AAT CCA        7586
Thr Ser Leu Val Leu Ser Ala Met Thr Val Pro Val Ala Gly Asn Pro
    2485                    2490                    2495

GCT GTA AGC TGC TTG GAG CAA CAG CCC CGG AAC AAG CCA CTG AAG GCT        7634
Ala Val Ser Cys Leu Glu Gln Gln Pro Arg Asn Lys Pro Leu Lys Ala
2500                    2505                    2510                    2515

CTC GAT ACC AGA TTT GGA AGA AAG CTG AGC ATG ATC AGA GGG ATT GTA        7682
Leu Asp Thr Arg Phe Gly Arg Lys Leu Ser Met Ile Arg Gly Ile Val
```

|  |  |
|---|---|
| GAA CAA GAA ATC CAA GAG ATG GTT TCC CAG AGA GAG AAT ACT GCC ACT<br>Glu Gln Glu Ile Gln Glu Met Val Ser Gln Arg Glu Asn Thr Ala Thr<br>2535                                2540                              2545 | 7730 |
| CAC CAT TCT CAC CAG GCG TGG GAT CCT GTC CCT TCT CTG TTA CCA GCT<br>His His Ser His Gln Ala Trp Asp Pro Val Pro Ser Leu Leu Pro Ala<br>2550                               2555                            2560 | 7778 |
| ACT ACA GGT GCT CTT ATC AGC CAT GAC AAG CTG CTG CTG CAG ATC AAC<br>Thr Thr Gly Ala Leu Ile Ser His Asp Lys Leu Leu Leu Gln Ile Asn<br>2565                               2570                            2575 | 7826 |
| CCA GAG CGG GAG CCA GGC AAC ATG AGC TAC AAG CTG GGC CAG GTG TCC<br>Pro Glu Arg Glu Pro Gly Asn Met Ser Tyr Lys Leu Gly Gln Val Ser<br>2580                               2585                           2590                            2595 | 7874 |
| ATA CAC TCC GTG TGG CTG GGA AAT AAC ATC ACA CCC CTG AGA GAG GAG<br>Ile His Ser Val Trp Leu Gly Asn Asn Ile Thr Pro Leu Arg Glu Glu<br>2600                               2605                            2610 | 7922 |
| GAA TGG GAT GAG GAA GAA GAG GAA GAA AGT GAT GTC CCT GCA CCA ACG<br>Glu Trp Asp Glu Glu Glu Glu Glu Glu Ser Asp Val Pro Ala Pro Thr<br>2615                               2620                            2625 | 7970 |
| TCA CCA CCT GTG TCT CCA GTC AAT TCC AGA AAA CAC CGT GCC GGG GTT<br>Ser Pro Pro Val Ser Pro Val Asn Ser Arg Lys His Arg Ala Gly Val<br>2630                               2635                            2640 | 8018 |
| GAT ATT CAC TCC TGT TCG CAG TTT CTG CTT GAA TTG TAC AGC CGA TGG<br>Asp Ile His Ser Cys Ser Gln Phe Leu Leu Glu Leu Tyr Ser Arg Trp<br>2645                               2650                            2655 | 8066 |
| ATC CTG CCA TCC AGT GCA GCC AGA AGG ACC CCC GTC ATC CTG ATC AGT<br>Ile Leu Pro Ser Ser Ala Ala Arg Arg Thr Pro Val Ile Leu Ile Ser<br>2660                               2665                            2670                            2675 | 8114 |
| GAA GTG GTT CGA TCT CTT CTT GTA GTG TCA GAC TTA TTC ACC GAA CGT<br>Glu Val Val Arg Ser Leu Leu Val Val Ser Asp Leu Phe Thr Glu Arg<br>2680                               2685                            2690 | 8162 |
| ACC CAG TTT GAA ATG ATG TAT CTG ACG CTG ACA GAA CTA CGG AGA GTG<br>Thr Gln Phe Glu Met Met Tyr Leu Thr Leu Thr Glu Leu Arg Arg Val<br>2695                               2700                            2705 | 8210 |
| CAC CCT TCA GAA GAT GAG ATC CTC ATT CAG TAC CTG GTG CCT GCC ACC<br>His Pro Ser Glu Asp Glu Ile Leu Ile Gln Tyr Leu Val Pro Ala Thr<br>2710                               2715                            2720 | 8258 |
| TGT AAG GCA GCT GCT GTC CTT GGA ATG GAC AAA ACT GTG GCA GAG CCA<br>Cys Lys Ala Ala Ala Val Leu Gly Met Asp Lys Thr Val Ala Glu Pro<br>2725                               2730                            2735 | 8306 |
| GTC AGC CGC CTA CTG GAG AGC ACA CTG AGG AGC AGC CAC CTG CCC AGC<br>Val Ser Arg Leu Leu Glu Ser Thr Leu Arg Ser Ser His Leu Pro Ser<br>2740                               2745                            2750                            2755 | 8354 |
| CAG ATC GGA GCC CTG CAC GGC ATC CTC TAT GTG TTG GAG TGT GAC CTC<br>Gln Ile Gly Ala Leu His Gly Ile Leu Tyr Val Leu Glu Cys Asp Leu<br>2760                               2765                            2770 | 8402 |
| TTG GAT GAC ACT GCA AAG CAG CTC ATT CCA GTT GTT AGT GAC TAT CTG<br>Leu Asp Asp Thr Ala Lys Gln Leu Ile Pro Val Val Ser Asp Tyr Leu<br>2775                               2780                            2785 | 8450 |
| CTG TCC AAC CTC AAA GGA ATA GCC CAC TGC GTG AAC ATT CAC AGC CAG<br>Leu Ser Asn Leu Lys Gly Ile Ala His Cys Val Asn Ile His Ser Gln<br>2790                               2795                            2800 | 8498 |
| CAG CAT GTG CTG GTA ATG TGT GCC ACT GCT TTC TAC CTG ATG GAA AAC<br>Gln His Val Leu Val Met Cys Ala Thr Ala Phe Tyr Leu Met Glu Asn<br>2805                               2810                            2815 | 8546 |
| TAC CCT CTG GAT GTG GGA CCA GAA TTT TCA GCA TCT GTG ATA CAG ATG<br>Tyr Pro Leu Asp Val Gly Pro Glu Phe Ser Ala Ser Val Ile Gln Met<br>2820                               2825                            2830                            2835 | 8594 |
| TGT GGA GTA ATG CTG TCT GGA AGT GAG GAG TCC ACC CCC TCC ATC ATT<br>Cys Gly Val Met Leu Ser Gly Ser Glu Glu Ser Thr Pro Ser Ile Ile | 8642 |

```
                    2840                        2845                        2850
TAC  CAC  TGT  GCC  CTC  CGG  GGT  CTG  GAG  CGG  CTC  CTG  CTG  TCT  GAG  CAG     8690
Tyr  His  Cys  Ala  Leu  Arg  Gly  Leu  Glu  Arg  Leu  Leu  Leu  Ser  Glu  Gln
               2855                        2860                        2865

CTA  TCT  CGG  CTA  GAC  ACA  GAG  TCC  TTG  GTC  AAG  CTA  AGT  GTG  GAC  AGA     8738
Leu  Ser  Arg  Leu  Asp  Thr  Glu  Ser  Leu  Val  Lys  Leu  Ser  Val  Asp  Arg
               2870                        2875                        2880

GTG  AAT  GTA  CAA  AGC  CCA  CAC  AGG  GCC  ATG  GCA  GCC  CTA  GGC  CTG  ATG     8786
Val  Asn  Val  Gln  Ser  Pro  His  Arg  Ala  Met  Ala  Ala  Leu  Gly  Leu  Met
               2885                        2890                        2895

CTC  ACC  TGC  ATG  TAC  ACA  GGA  AAG  GAA  AAA  GCC  AGT  CCA  GGC  AGA  GCT     8834
Leu  Thr  Cys  Met  Tyr  Thr  Gly  Lys  Glu  Lys  Ala  Ser  Pro  Gly  Arg  Ala
2900                2905                        2910                        2915

TCT  GAC  CCC  AGC  CCT  GCT  ACA  CCT  GAC  AGC  GAG  TCT  GTG  ATT  GTA  GCT     8882
Ser  Asp  Pro  Ser  Pro  Ala  Thr  Pro  Asp  Ser  Glu  Ser  Val  Ile  Val  Ala
               2920                        2925                        2930

ATG  GAG  CGA  GTG  TCT  GTT  CTC  TTT  GAT  AGG  ATC  CGC  AAG  GGA  TTT  CCC     8930
Met  Glu  Arg  Val  Ser  Val  Leu  Phe  Asp  Arg  Ile  Arg  Lys  Gly  Phe  Pro
               2935                        2940                        2945

TGT  GAA  GCC  AGG  GTT  GTG  GCA  AGG  ATC  CTG  CCT  CAG  TTC  CTA  GAT  GAC     8978
Cys  Glu  Ala  Arg  Val  Val  Ala  Arg  Ile  Leu  Pro  Gln  Phe  Leu  Asp  Asp
               2950                        2955                        2960

TTC  TTT  CCA  CCT  CAA  GAT  GTC  ATG  AAC  AAA  GTC  ATT  GGA  GAG  TTC  CTG     9026
Phe  Phe  Pro  Pro  Gln  Asp  Val  Met  Asn  Lys  Val  Ile  Gly  Glu  Phe  Leu
               2965                        2970                        2975

TCC  AAT  CAG  CAG  CCA  TAC  CCA  CAG  TTC  ATG  GCC  ACT  GTA  GTT  TAC  AAG     9074
Ser  Asn  Gln  Gln  Pro  Tyr  Pro  Gln  Phe  Met  Ala  Thr  Val  Val  Tyr  Lys
2980                2985                        2990                        2995

GTT  TTT  CAG  ACT  CTG  CAC  AGT  GCT  GGG  CAG  TCA  TCC  ATG  GTC  CGG  GAC     9122
Val  Phe  Gln  Thr  Leu  His  Ser  Ala  Gly  Gln  Ser  Ser  Met  Val  Arg  Asp
               3000                        3005                        3010

TGG  GTC  ATG  CTG  TCC  CTG  TCC  AAC  TTC  ACA  CAA  AGA  ACT  CCA  GTT  GCC     9170
Trp  Val  Met  Leu  Ser  Leu  Ser  Asn  Phe  Thr  Gln  Arg  Thr  Pro  Val  Ala
               3015                        3020                        3025

ATG  GCC  ATG  TGG  AGC  CTC  TCC  TGC  TTC  CTT  GTT  AGC  GCA  TCT  ACC  AGC     9218
Met  Ala  Met  Trp  Ser  Leu  Ser  Cys  Phe  Leu  Val  Ser  Ala  Ser  Thr  Ser
               3030                        3035                        3040

CCA  TGG  GTT  TCT  GCG  ATC  CTT  CCA  CAT  GTC  ATC  AGC  AGG  ATG  GGC  AAA     9266
Pro  Trp  Val  Ser  Ala  Ile  Leu  Pro  His  Val  Ile  Ser  Arg  Met  Gly  Lys
               3045                        3050                        3055

CTG  GAA  CAG  GTG  GAT  GTG  AAC  CTT  TTC  TGC  CTG  GTT  GCC  ACA  GAC  TTC     9314
Leu  Glu  Gln  Val  Asp  Val  Asn  Leu  Phe  Cys  Leu  Val  Ala  Thr  Asp  Phe
3060                3065                        3070                        3075

TAC  AGA  CAC  CAG  ATA  GAG  GAG  GAA  TTC  GAC  CGC  AGG  GCT  TTC  CAG  TCT     9362
Tyr  Arg  His  Gln  Ile  Glu  Glu  Glu  Phe  Asp  Arg  Arg  Ala  Phe  Gln  Ser
               3080                        3085                        3090

GTG  TTT  GAG  GTG  GTG  GCT  GCA  CCA  GGA  AGT  CCA  TAC  CAC  AGG  CTG  CTT     9410
Val  Phe  Glu  Val  Val  Ala  Ala  Pro  Gly  Ser  Pro  Tyr  His  Arg  Leu  Leu
               3095                        3100                        3105

GCT  TGT  TTG  CAA  AAT  GTT  CAC  AAG  GTC  ACC  ACC  TGC  TGAGTAGTGC              9456
Ala  Cys  Leu  Gln  Asn  Val  His  Lys  Val  Thr  Thr  Cys
               3110                        3115

CTGTGGGACA  AAAGGCTGAA  AGAAGGCAGC  TGCTGGGGCC  TGAGCCTCCA  GGAGCCTGCT     9516
CCAAGCTTCT  GCTGGGGCTG  CCTTGGCCGT  GCAGGCTTCA  CTTGTGTCAA  GTGGACAGCC     9576
AGGCAATGGC  AGGAGTGCTT  TGCAATGAGG  GCTATGCAGG  GAACATGCAC  TATGTTGGGG     9636
TTGAGCCTGA  GTCCTGGGTC  CTGGCCTCGC  TGCAGCTGGT  GACAGTGCTA  GGTTGACCAG     9696
GTGTTTGTCT  TTTTCCTAGT  GTTCCCCTGG  CCATAGTCGC  CAGGTTGCAG  CTGCCCTGGT     9756
```

```
ATGTGGATCA GAAGTCCTAG CTCCTGCCAG ATGGTTCTGA GCCGCCTGCT CCACTGGGCT      9816

GGAGAGCTCC CTCCCACATT TACCCAGTAG GCATACCTGC CACACCAGTG TCTGGACACA      9876

AATGAATGGT GTGTGGGGCT GGGAACTGGG GCTGCCAGGT GTCCAGCACC ATTTTCCTTT      9936

CTGTGTTTTC TTCTCAGGAG TTAAAATTTA ATTATATCAG TAAAGAGATT AATTTTAATG      9996

T                                                                     9997
```

( 2 ) INFORMATION FOR SEQ ID NO:16:

( i ) SEQUENCE CHARACTERISTICS:
        ( A ) LENGTH: 3119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met  Ala  Thr  Leu  Glu  Lys  Leu  Met  Lys  Ala  Phe  Glu  Ser  Leu  Lys  Ser
 1              5                   10                  15

Phe  Gln  Gln  Gln  Gln  Gln  Gln  Gln  Pro  Pro  Gln  Pro  Pro  Pro  Pro
            20                  25                  30

Pro  Pro  Pro  Pro  Pro  Pro  Gln  Pro  Pro  Gln  Pro  Pro  Gln  Gly  Gln
        35                  40                  45

Pro  Pro  Pro  Pro  Pro  Pro  Pro  Leu  Pro  Gly  Pro  Ala  Glu  Glu  Pro  Leu
        50                  55                  60

His  Arg  Pro  Lys  Lys  Glu  Leu  Ser  Ala  Thr  Lys  Lys  Asp  Arg  Val  Asn
65                  70                  75                  80

His  Cys  Leu  Thr  Ile  Cys  Glu  Asn  Ile  Val  Ala  Gln  Ser  Leu  Arg  Asn
                85                  90                  95

Ser  Pro  Glu  Phe  Gln  Lys  Leu  Leu  Gly  Ile  Ala  Met  Glu  Leu  Phe  Leu
            100                 105                 110

Leu  Cys  Ser  Asp  Asp  Ala  Glu  Ser  Asp  Val  Arg  Met  Val  Ala  Asp  Glu
            115                 120                 125

Cys  Leu  Asn  Lys  Val  Ile  Lys  Ala  Leu  Met  Asp  Ser  Asn  Leu  Pro  Arg
     130                 135                 140

Leu  Gln  Leu  Glu  Leu  Tyr  Lys  Glu  Ile  Lys  Lys  Asn  Gly  Ala  Pro  Arg
145                 150                 155                 160

Ser  Leu  Arg  Ala  Ala  Leu  Trp  Arg  Phe  Ala  Glu  Leu  Ala  His  Leu  Val
                165                 170                 175

Arg  Pro  Gln  Lys  Cys  Arg  Pro  Tyr  Leu  Val  Asn  Leu  Leu  Pro  Cys  Leu
            180                 185                 190

Thr  Arg  Thr  Ser  Lys  Arg  Pro  Glu  Glu  Ser  Val  Gln  Glu  Thr  Leu  Ala
            195                 200                 205

Ala  Ala  Val  Pro  Lys  Ile  Met  Ala  Ser  Phe  Gly  Asn  Phe  Ala  Asn  Asp
     210                 215                 220

Asn  Glu  Ile  Lys  Val  Leu  Leu  Lys  Ala  Phe  Ile  Ala  Asn  Leu  Lys  Ser
225                 230                 235                 240

Ser  Ser  Pro  Thr  Val  Arg  Arg  Thr  Ala  Ala  Gly  Ser  Ala  Val  Ser  Ile
            245                 250                 255

Cys  Gln  His  Ser  Arg  Arg  Thr  Gln  Tyr  Phe  Tyr  Asn  Trp  Leu  Leu  Asn
            260                 265                 270

Val  Leu  Leu  Gly  Leu  Leu  Val  Pro  Met  Glu  Glu  Glu  His  Ser  Thr  Leu
            275                 280                 285

Leu  Ile  Leu  Gly  Val  Leu  Leu  Thr  Leu  Arg  Cys  Leu  Val  Pro  Leu  Leu
            290                 295                 300

Gln  Gln  Gln  Val  Lys  Asp  Thr  Ser  Leu  Lys  Gly  Ser  Phe  Gly  Val  Thr
```

|   |   |   |   |   |   |   |   |   |   |   |   |   |   |   |   |
|---|---|---|---|---|---|---|---|---|---|---|---|---|---|---|---|
| 305 |   |   |   |   | 310 |   |   |   |   | 315 |   |   |   |   | 320 |
| Arg | Lys | Glu | Met | Glu | Val | Ser | Pro | Ser | Thr | Glu | Gln | Leu | Val | Gln | Val |
|   |   |   |   | 325 |   |   |   |   | 330 |   |   |   |   | 335 |   |
| Tyr | Glu | Leu | Thr | Leu | His | His | Thr | Gln | His | Gln | Asp | His | Asn | Val | Val |
|   |   |   | 340 |   |   |   |   | 345 |   |   |   |   | 350 |   |   |
| Thr | Gly | Ala | Leu | Glu | Leu | Leu | Gln | Gln | Leu | Phe | Arg | Thr | Pro | Pro | Pro |
|   |   | 355 |   |   |   |   | 360 |   |   |   |   | 365 |   |   |   |
| Glu | Leu | Leu | Gln | Ala | Leu | Thr | Thr | Pro | Gly | Gly | Leu | Gly | Gln | Leu | Thr |
|   | 370 |   |   |   |   | 375 |   |   |   |   | 380 |   |   |   |   |
| Leu | Val | Gln | Glu | Glu | Ala | Arg | Gly | Arg | Gly | Arg | Ser | Gly | Ser | Ile | Val |
| 385 |   |   |   |   | 390 |   |   |   |   | 395 |   |   |   |   | 400 |
| Glu | Leu | Leu | Ala | Gly | Gly | Ser | Ser | Cys | Ser | Pro | Val | Leu | Ser | Arg |   |
|   |   |   |   | 405 |   |   |   | 410 |   |   |   |   | 415 |   |   |
| Lys | Gln | Lys | Gly | Lys | Val | Leu | Leu | Gly | Glu | Glu | Ala | Leu | Glu | Asp |   |
|   |   |   | 420 |   |   |   |   | 425 |   |   |   |   | 430 |   |   |
| Asp | Ser | Glu | Ser | Arg | Ser | Asp | Val | Ser | Ser | Ser | Ala | Phe | Ala | Ala | Ser |
|   |   | 435 |   |   |   |   | 440 |   |   |   |   | 445 |   |   |   |
| Val | Lys | Ser | Glu | Ile | Gly | Gly | Glu | Leu | Ala | Ala | Ser | Ser | Gly | Val | Ser |
|   | 450 |   |   |   |   | 455 |   |   |   |   | 460 |   |   |   |   |
| Thr | Pro | Gly | Ser | Val | Gly | His | Asp | Ile | Ile | Thr | Glu | Gln | Pro | Arg | Ser |
| 465 |   |   |   |   | 470 |   |   |   |   | 475 |   |   |   |   | 480 |
| Gln | His | Thr | Leu | Gln | Ala | Asp | Ser | Val | Asp | Leu | Ser | Gly | Cys | Asp | Leu |
|   |   |   |   | 485 |   |   |   |   | 490 |   |   |   |   | 495 |   |
| Thr | Ser | Ala | Ala | Thr | Asp | Gly | Asp | Glu | Glu | Asp | Ile | Leu | Ser | His | Ser |
|   |   |   | 500 |   |   |   |   | 505 |   |   |   |   | 510 |   |   |
| Ser | Ser | Gln | Phe | Ser | Ala | Val | Pro | Ser | Asp | Pro | Ala | Met | Asp | Leu | Asn |
|   |   | 515 |   |   |   |   | 520 |   |   |   |   | 525 |   |   |   |
| Asp | Gly | Thr | Gln | Ala | Ser | Ser | Pro | Ile | Ser | Asp | Ser | Ser | Gln | Thr | Thr |
|   | 530 |   |   |   |   | 535 |   |   |   |   | 540 |   |   |   |   |
| Thr | Glu | Gly | Pro | Asp | Ser | Ala | Val | Thr | Pro | Ser | Asp | Ser | Ser | Glu | Ile |
| 545 |   |   |   |   | 550 |   |   |   |   | 555 |   |   |   |   | 560 |
| Val | Leu | Asp | Gly | Ala | Asp | Ser | Gln | Tyr | Leu | Gly | Met | Gln | Ile | Gly | Gln |
|   |   |   |   | 565 |   |   |   |   | 570 |   |   |   |   | 575 |   |
| Pro | Gln | Glu | Asp | Asp | Glu | Glu | Gly | Ala | Ala | Gly | Val | Leu | Ser | Gly | Glu |
|   |   |   | 580 |   |   |   |   | 585 |   |   |   |   | 590 |   |   |
| Val | Ser | Asp | Val | Phe | Arg | Asn | Ser | Ser | Leu | Ala | Leu | Gln | Gln | Ala | His |
|   |   | 595 |   |   |   |   | 600 |   |   |   |   | 605 |   |   |   |
| Leu | Leu | Glu | Arg | Met | Gly | His | Ser | Arg | Gln | Pro | Ser | Asp | Ser | Ser | Ile |
|   | 610 |   |   |   |   | 615 |   |   |   |   | 620 |   |   |   |   |
| Asp | Lys | Tyr | Val | Thr | Arg | Asp | Glu | Val | Ala | Glu | Ala | Ser | Asp | Pro | Glu |
| 625 |   |   |   |   | 630 |   |   |   |   | 635 |   |   |   |   | 640 |
| Ser | Lys | Pro | Cys | Arg | Ile | Lys | Gly | Asp | Ile | Gly | Gln | Pro | Asn | Asp | Asp |
|   |   |   |   | 645 |   |   |   |   | 650 |   |   |   |   | 655 |   |
| Asp | Ser | Ala | Pro | Leu | Val | His | Cys | Val | Arg | Leu | Leu | Ser | Ala | Ser | Phe |
|   |   |   | 660 |   |   |   |   | 665 |   |   |   |   | 670 |   |   |
| Leu | Leu | Thr | Gly | Glu | Lys | Lys | Ala | Leu | Val | Pro | Asp | Arg | Asp | Val | Arg |
|   |   | 675 |   |   |   |   | 680 |   |   |   |   | 685 |   |   |   |
| Val | Ser | Val | Lys | Ala | Leu | Ala | Leu | Ser | Cys | Ile | Gly | Ala | Ala | Val | Ala |
|   | 690 |   |   |   |   | 695 |   |   |   |   | 700 |   |   |   |   |
| Leu | His | Pro | Glu | Ser | Phe | Phe | Ser | Arg | Leu | Tyr | Lys | Val | Pro | Leu | Asn |
| 705 |   |   |   |   | 710 |   |   |   |   | 715 |   |   |   |   | 720 |
| Thr | Thr | Glu | Ser | Thr | Glu | Glu | Gln | Tyr | Val | Ser | Asp | Ile | Leu | Asn | Tyr |
|   |   |   |   | 725 |   |   |   |   | 730 |   |   |   |   | 735 |   |

```
Ile  Asp  His  Gly  Asp  Pro  Gln  Val  Arg  Gly  Ala  Thr  Ala  Ile  Leu  Cys
               740                    745                    750

Gly  Thr  Leu  Val  Tyr  Ser  Ile  Leu  Ser  Arg  Ser  Arg  Leu  Arg  Val  Gly
          755                    760                    765

Glu  Trp  Leu  Gly  Asn  Ile  Arg  Thr  Leu  Thr  Gly  Asn  Thr  Phe  Ser  Leu
     770                    775                    780

Val  Asp  Cys  Ile  Pro  Leu  Leu  Gln  Lys  Thr  Leu  Lys  Asp  Glu  Ser  Ser
785                      790                    795                         800

Val  Thr  Cys  Lys  Leu  Ala  Cys  Thr  Ala  Val  Arg  His  Cys  Val  Leu  Ser
               805                    810                         815

Leu  Cys  Ser  Ser  Ser  Tyr  Ser  Asp  Leu  Gly  Leu  Gln  Leu  Leu  Ile  Asp
               820                    825                    830

Met  Leu  Pro  Leu  Lys  Asn  Ser  Ser  Tyr  Trp  Leu  Val  Arg  Thr  Glu  Leu
          835                    840                    845

Leu  Asp  Thr  Leu  Ala  Glu  Ile  Asp  Phe  Arg  Leu  Val  Ser  Phe  Leu  Glu
     850                    855                    860

Ala  Lys  Ala  Glu  Ser  Leu  His  Arg  Gly  Ala  His  His  Tyr  Thr  Gly  Phe
865                      870                    875                         880

Leu  Lys  Leu  Gln  Glu  Arg  Val  Leu  Asn  Asn  Val  Val  Ile  Tyr  Leu  Leu
                    885                    890                         895

Gly  Asp  Glu  Asp  Pro  Arg  Val  Arg  His  Val  Ala  Ala  Thr  Ser  Leu  Thr
               900                    905                    910

Arg  Leu  Val  Pro  Lys  Leu  Phe  Tyr  Lys  Cys  Asp  Gln  Gly  Gln  Ala  Asp
          915                    920                    925

Pro  Val  Val  Ala  Val  Ala  Arg  Asp  Gln  Ser  Ser  Val  Tyr  Leu  Lys  Leu
     930                    935                    940

Leu  Met  His  Glu  Thr  Gln  Pro  Pro  Ser  His  Phe  Ser  Val  Ser  Thr  Ile
945                      950                    955                         960

Thr  Arg  Ile  Tyr  Arg  Gly  Tyr  Ser  Leu  Leu  Pro  Ser  Ile  Thr  Asp  Val
               965                    970                    975

Thr  Met  Glu  Asn  Asn  Leu  Ser  Arg  Val  Ala  Ala  Val  Ser  His  Glu
               980                    985                    990

Leu  Ile  Thr  Ser  Thr  Thr  Arg  Ala  Leu  Thr  Phe  Gly  Cys  Cys  Glu  Ala
          995                    1000                   1005

Leu  Cys  Leu  Leu  Ser  Ala  Ala  Phe  Pro  Val  Cys  Thr  Trp  Ser  Leu  Gly
     1010                   1015                   1020

Trp  His  Cys  Gly  Val  Pro  Pro  Leu  Ser  Ala  Ser  Asp  Glu  Ser  Arg  Lys
1025                     1030                   1035                        1040

Ser  Cys  Thr  Val  Gly  Met  Ala  Ser  Met  Ile  Leu  Thr  Leu  Leu  Ser  Ser
               1045                   1050                   1055

Ala  Trp  Phe  Pro  Leu  Asp  Leu  Ser  Ala  His  Gln  Asp  Ala  Leu  Ile  Leu
          1060                   1065                   1070

Ala  Gly  Asn  Leu  Leu  Ala  Ala  Ser  Ala  Pro  Lys  Ser  Leu  Arg  Ser  Ser
     1075                   1080                   1085

Trp  Thr  Ser  Glu  Glu  Glu  Ala  Asn  Ser  Ala  Ala  Thr  Arg  Gln  Glu  Glu
     1090                   1095                   1100

Ile  Trp  Pro  Ala  Leu  Gly  Asp  Arg  Thr  Leu  Val  Pro  Leu  Val  Glu  Gln
1105                     1110                   1115                        1120

Leu  Phe  Ser  His  Leu  Leu  Lys  Val  Ile  Asn  Ile  Cys  Ala  His  Val  Leu
               1125                   1130                   1135

Asp  Asp  Val  Thr  Pro  Gly  Pro  Ala  Ile  Lys  Ala  Ala  Leu  Pro  Ser  Leu
               1140                   1145                   1150

Thr  Asn  Pro  Pro  Ser  Leu  Ser  Pro  Ile  Arg  Arg  Lys  Gly  Lys  Glu  Lys
          1155                   1160                   1165
```

```
Glu Pro Gly Glu Gln Ala Ser Thr Pro Met Ser Pro Lys Lys Val Gly
    1170                1175            1180

Glu Ala Ser Ala Ala Ser Arg Gln Ser Asp Thr Ser Gly Pro Val Thr
1185            1190                1195                    1200

Ala Ser Lys Ser Ser Ser Leu Gly Ser Phe Tyr His Leu Pro Ser Tyr
            1205                1210                1215

Leu Lys Leu His Asp Val Leu Lys Ala Thr His Ala Asn Tyr Lys Val
            1220                1225                1230

Thr Leu Asp Leu Gln Asn Ser Thr Glu Lys Phe Gly Gly Phe Leu Arg
            1235                1240            1245

Ser Ala Leu Asp Val Leu Ser Gln Ile Leu Glu Leu Ala Thr Leu Gln
1250                1255                1260

Asp Ile Gly Lys Cys Val Glu Glu Val Leu Gly Tyr Leu Lys Ser Cys
1265                1270                1275                1280

Phe Ser Arg Glu Pro Met Met Ala Thr Val Cys Val Gln Gln Leu Leu
                1285                1290                1295

Lys Thr Leu Phe Gly Thr Asn Leu Ala Ser Gln Phe Asp Gly Leu Ser
            1300                1305                1310

Ser Asn Pro Ser Lys Ser Gln Cys Arg Ala Gln Arg Leu Gly Ser Ser
            1315                1320                1325

Ser Val Arg Pro Gly Leu Tyr His Tyr Cys Phe Met Ala Pro Tyr Thr
            1330                1335                1340

His Phe Thr Gln Ala Leu Ala Asp Ala Ser Leu Arg Asn Met Val Gln
1345                1350                1355                1360

Ala Glu Gln Glu Arg Asp Ala Ser Gly Trp Phe Asp Val Leu Gln Lys
                1365                1370                1375

Val Ser Ala Gln Leu Lys Thr Asn Leu Thr Ser Val Thr Lys Asn Arg
            1380                1385                1390

Ala Asp Lys Asn Ala Ile His Asn His Ile Arg Leu Phe Glu Pro Leu
            1395                1400                1405

Val Ile Lys Ala Leu Lys Gln Tyr Thr Thr Thr Thr Ser Val Gln Leu
            1410                1415                1420

Gln Lys Gln Val Leu Asp Leu Leu Ala Gln Leu Val Gln Leu Arg Val
1425                1430                1435                1440

Asn Tyr Cys Leu Leu Asp Ser Asp Gln Val Phe Ile Gly Phe Val Leu
                1445                1450                1455

Lys Gln Phe Glu Tyr Ile Glu Val Gly Gln Phe Arg Glu Ser Glu Ala
                1460                1465                1470

Ile Ile Pro Asn Ile Phe Phe Leu Val Leu Leu Ser Tyr Glu Arg
            1475                1480                1485

Tyr His Ser Lys Gln Ile Ile Gly Ile Pro Lys Ile Ile Gln Leu Cys
            1490                1495                1500

Asp Gly Ile Met Ala Ser Gly Arg Lys Ala Val Thr His Ala Ile Pro
1505                1510                1515                1520

Ala Leu Gln Pro Ile Val His Asp Leu Phe Val Leu Arg Gly Thr Asn
                1525                1530                1535

Lys Ala Asp Ala Gly Lys Glu Leu Glu Thr Gln Lys Glu Val Val Val
            1540                1545                1550

Ser Met Leu Leu Arg Leu Ile Gln Tyr His Gln Val Leu Glu Met Phe
            1555                1560                1565

Ile Leu Val Leu Gln Gln Cys His Lys Glu Asn Glu Asp Lys Trp Lys
            1570                1575                1580

Arg Leu Ser Arg Gln Val Ala Asp Ile Ile Leu Pro Met Leu Ala Lys
```

| | | | |
|---|---|---|---|
| 1585 | 1590 | 1595 | 1600 |

Gln Gln Met His Ile Asp Ser His Glu Ala Leu Gly Val Leu Asn Thr
       1605                    1610                    1615

Leu Phe Glu Ile Leu Ala Pro Ser Ser Leu Arg Pro Val Asp Met Leu
       1620                    1625                    1630

Leu Arg Ser Met Phe Ile Thr Pro Ser Thr Met Ala Ser Val Ser Thr
       1635                    1640                    1645

Val Gln Leu Trp Ile Ser Gly Ile Leu Ala Ile Leu Arg Val Leu Ile
       1650                    1655                    1660

Ser Gln Ser Thr Glu Asp Ile Val Leu Cys Arg Ile Gln Glu Leu Ser
1665                    1670                    1675                    1680

Phe Ser Pro His Leu Leu Ser Cys Pro Val Ile Asn Arg Leu Arg Gly
              1685                    1690                    1695

Gly Gly Gly Asn Val Thr Leu Gly Glu Cys Ser Glu Gly Lys Gln Lys
       1700                    1705                    1710

Ser Leu Pro Glu Asp Thr Phe Ser Arg Phe Leu Leu Gln Leu Val Gly
       1715                    1720                    1725

Ile Leu Leu Glu Asp Ile Val Thr Lys Gln Leu Lys Val Asp Met Ser
       1730                    1735                    1740

Glu Gln Gln His Thr Phe Tyr Cys Gln Glu Leu Gly Thr Leu Leu Met
1745                    1750                    1755                    1760

Cys Leu Ile His Ile Phe Lys Ser Gly Met Phe Arg Arg Ile Thr Ala
              1765                    1770                    1775

Ala Ala Thr Arg Leu Phe Thr Ser Asp Gly Cys Glu Gly Ser Phe Tyr
       1780                    1785                    1790

Thr Leu Glu Ser Leu Asn Ala Arg Val Arg Ser Met Val Pro Thr His
       1795                    1800                    1805

Pro Ala Leu Val Leu Leu Trp Cys Gln Ile Leu Leu Leu Ile Asn His
       1810                    1815                    1820

Thr Asp His Arg Trp Trp Ala Glu Val Gln Gln Thr Pro Lys Arg His
1825                    1830                    1835                    1840

Ser Leu Ser Cys Thr Lys Ser Leu Asn Pro Gln Lys Ser Gly Glu Glu
              1845                    1850                    1855

Glu Asp Ser Gly Ser Ala Ala Gln Leu Gly Met Cys Asn Arg Glu Ile
       1860                    1865                    1870

Val Arg Arg Gly Ala Leu Ile Leu Phe Cys Asp Tyr Val Cys Gln Asn
       1875                    1880                    1885

Leu His Asp Ser Glu His Leu Thr Trp Leu Ile Val Asn His Ile Gln
       1890                    1895                    1900

Asp Leu Ile Ser Leu Ser His Glu Pro Pro Val Gln Asp Phe Ile Ser
1905                    1910                    1915                    1920

Ala Ile His Arg Asn Ser Ala Ala Ser Gly Leu Phe Ile Gln Ala Ile
              1925                    1930                    1935

Gln Ser Arg Cys Glu Asn Leu Ser Thr Pro Thr Thr Leu Lys Lys Thr
       1940                    1945                    1950

Leu Gln Cys Leu Glu Gly Ile His Leu Ser Gln Ser Gly Ala Val Leu
       1955                    1960                    1965

Thr Leu Tyr Val Asp Arg Leu Leu Gly Thr Pro Phe Arg Ala Leu Ala
       1970                    1975                    1980

Arg Met Val Asp Thr Leu Ala Cys Arg Arg Val Glu Met Leu Leu Ala
1985                    1990                    1995                    2000

Ala Asn Leu Gln Ser Ser Met Ala Gln Leu Pro Glu Glu Glu Leu Asn
              2005                    2010                    2015

```
Arg Ile Gln Glu His Leu Gln Asn Ser Gly Leu Ala Gln Arg His Gln
            2020                2025                2030
Arg Leu Tyr Ser Leu Leu Asp Arg Phe Arg Leu Ser Thr Val Gln Asp
        2035                2040                2045
Ser Leu Ser Pro Leu Pro Pro Val Thr Ser His Pro Leu Asp Gly Asp
    2050                2055                2060
Gly His Thr Ser Leu Glu Thr Val Ser Pro Asp Lys Asp Trp Tyr Leu
2065                2070                2075                2080
Gln Leu Val Arg Ser Gln Cys Trp Thr Arg Ser Asp Ser Ala Leu Leu
                2085                2090                2095
Glu Gly Ala Glu Leu Val Asn Arg Ile Pro Ala Glu Asp Met Asn Asp
            2100                2105                2110
Phe Met Met Ser Ser Glu Phe Asn Leu Ser Leu Leu Ala Pro Cys Leu
            2115                2120                2125
Ser Leu Gly Met Ser Glu Ile Ala Asn Gly Gln Lys Ser Pro Leu Phe
        2130                2135                2140
Glu Ala Ala Arg Gly Val Ile Leu Asn Arg Val Thr Ser Val Val Gln
2145                2150                2155                2160
Gln Leu Pro Ala Val His Gln Val Phe Gln Pro Phe Leu Pro Ile Glu
                2165                2170                2175
Pro Thr Ala Tyr Trp Asn Lys Leu Asn Asp Leu Leu Gly Asp Thr Thr
            2180                2185                2190
Ser Tyr Gln Ser Leu Thr Ile Leu Ala Arg Ala Leu Ala Gln Tyr Leu
        2195                2200                2205
Val Val Leu Ser Lys Val Pro Ala His Leu His Leu Pro Pro Glu Lys
        2210                2215                2220
Glu Gly Asp Thr Val Lys Phe Val Val Met Thr Val Glu Ala Leu Ser
2225                2230                2235                2240
Trp His Leu Ile His Glu Gln Ile Pro Leu Ser Leu Asp Leu Gln Ala
                2245                2250                2255
Gly Leu Asp Cys Cys Cys Leu Ala Leu Gln Val Pro Gly Leu Trp Gly
            2260                2265                2270
Val Leu Ser Ser Pro Glu Tyr Val Thr His Ala Cys Ser Leu Ile His
    2275                2280                2285
Cys Val Arg Phe Ile Leu Glu Ala Ile Ala Val Gln Pro Gly Asp Gln
2290                2295                2300
Leu Leu Gly Pro Glu Ser Arg Ser His Thr Pro Arg Ala Val Arg Lys
2305                2310                2315                2320
Glu Glu Val Asp Ser Asp Ile Gln Asn Leu Ser His Val Thr Ser Ala
            2325                2330                2335
Cys Glu Met Val Ala Asp Met Val Glu Ser Leu Gln Ser Val Leu Ala
        2340                2345                2350
Leu Gly His Lys Arg Asn Ser Thr Leu Pro Ser Phe Leu Thr Ala Val
        2355                2360                2365
Leu Lys Asn Ile Val Ile Ser Leu Ala Arg Leu Pro Leu Val Asn Ser
    2370                2375                2380
Tyr Thr Arg Val Pro Pro Leu Val Trp Lys Leu Gly Trp Ser Pro Lys
2385                2390                2395                2400
Pro Gly Gly Asp Phe Gly Thr Val Phe Pro Glu Ile Pro Val Glu Phe
                2405                2410                2415
Leu Gln Glu Lys Glu Ile Leu Lys Glu Phe Ile Tyr Arg Ile Asn Thr
            2420                2425                2430
Leu Gly Trp Thr Asn Arg Thr Gln Phe Glu Glu Thr Trp Ala Thr Leu
            2435                2440                2445
```

```
Leu Gly Val Leu Val Thr Gln Pro Leu Val Met Glu Gln Glu Glu Ser
        2450                2455            2460
Pro Pro Glu Glu Asp Thr Glu Arg Thr Gln Ile His Val Leu Ala Val
2465            2470            2475                        2480
Gln Ala Ile Thr Ser Leu Val Leu Ser Ala Met Thr Val Pro Val Ala
                2485                2490                2495
Gly Asn Pro Ala Val Ser Cys Leu Glu Gln Gln Pro Arg Asn Lys Pro
            2500                2505                2510
Leu Lys Ala Leu Asp Thr Arg Phe Gly Arg Lys Leu Ser Met Ile Arg
        2515                2520                2525
Gly Ile Val Glu Gln Glu Ile Gln Glu Met Val Ser Gln Arg Glu Asn
    2530                2535                2540
Thr Ala Thr His His Ser His Gln Ala Trp Asp Pro Val Pro Ser Leu
2545            2550                2555                    2560
Leu Pro Ala Thr Thr Gly Ala Leu Ile Ser His Asp Lys Leu Leu Leu
                2565                2570                2575
Gln Ile Asn Pro Glu Arg Glu Pro Gly Asn Met Ser Tyr Lys Leu Gly
            2580                2585                2590
Gln Val Ser Ile His Ser Val Trp Leu Gly Asn Asn Ile Thr Pro Leu
        2595                2600                2605
Arg Glu Glu Glu Trp Asp Glu Glu Glu Glu Glu Ser Asp Val Pro
2610                2615                2620
Ala Pro Thr Ser Pro Pro Val Ser Pro Val Asn Ser Arg Lys His Arg
2625            2630                2635                    2640
Ala Gly Val Asp Ile His Ser Cys Ser Gln Phe Leu Leu Glu Leu Tyr
                2645                2650                2655
Ser Arg Trp Ile Leu Pro Ser Ser Ala Ala Arg Arg Thr Pro Val Ile
            2660                2665                2670
Leu Ile Ser Glu Val Val Arg Ser Leu Leu Val Val Ser Asp Leu Phe
        2675                2680                2685
Thr Glu Arg Thr Gln Phe Glu Met Met Tyr Leu Thr Leu Thr Glu Leu
    2690                2695                2700
Arg Arg Val His Pro Ser Glu Asp Glu Ile Leu Ile Gln Tyr Leu Val
2705            2710                2715                    2720
Pro Ala Thr Cys Lys Ala Ala Ala Val Leu Gly Met Asp Lys Thr Val
                2725                2730                2735
Ala Glu Pro Val Ser Arg Leu Leu Glu Ser Thr Leu Arg Ser Ser His
            2740                2745                2750
Leu Pro Ser Gln Ile Gly Ala Leu His Gly Ile Leu Tyr Val Leu Glu
        2755                2760                2765
Cys Asp Leu Leu Asp Asp Thr Ala Lys Gln Leu Ile Pro Val Val Ser
    2770                2775                2780
Asp Tyr Leu Leu Ser Asn Leu Lys Gly Ile Ala His Cys Val Asn Ile
2785            2790                2795                    2800
His Ser Gln Gln His Val Leu Val Met Cys Ala Thr Ala Phe Tyr Leu
                2805                2810                2815
Met Glu Asn Tyr Pro Leu Asp Val Gly Pro Glu Phe Ser Ala Ser Val
            2820                2825                2830
Ile Gln Met Cys Gly Val Met Leu Ser Gly Ser Glu Glu Ser Thr Pro
        2835                2840                2845
Ser Ile Ile Tyr His Cys Ala Leu Arg Gly Leu Glu Arg Leu Leu Leu
    2850                2855                2860
Ser Glu Gln Leu Ser Arg Leu Asp Thr Glu Ser Leu Val Lys Leu Ser
```

|  |  |  |  |
|---|---|---|---|
| 2865 | 2870 | 2875 | 2880 |

Val Asp Arg Val Asn Val Gln Ser Pro His Arg Ala Met Ala Ala Leu
                    2885              2890              2895

Gly Leu Met Leu Thr Cys Met Tyr Thr Gly Lys Glu Lys Ala Ser Pro
                    2900              2905              2910

Gly Arg Ala Ser Asp Pro Ser Pro Ala Thr Pro Asp Ser Glu Ser Val
                    2915              2920              2925

Ile Val Ala Met Glu Arg Val Ser Val Leu Phe Asp Arg Ile Arg Lys
                    2930              2935              2940

Gly Phe Pro Cys Glu Ala Arg Val Val Ala Arg Ile Leu Pro Gln Phe
2945                2950              2955              2960

Leu Asp Asp Phe Phe Pro Pro Gln Asp Val Met Asn Lys Val Ile Gly
                    2965              2970              2975

Glu Phe Leu Ser Asn Gln Gln Pro Tyr Pro Gln Phe Met Ala Thr Val
                    2980              2985              2990

Val Tyr Lys Val Phe Gln Thr Leu His Ser Ala Gly Gln Ser Ser Met
                    2995              3000              3005

Val Arg Asp Trp Val Met Leu Ser Leu Ser Asn Phe Thr Gln Arg Thr
3010                3015              3020

Pro Val Ala Met Ala Met Trp Ser Leu Ser Cys Phe Leu Val Ser Ala
3025                3030              3035              3040

Ser Thr Ser Pro Trp Val Ser Ala Ile Leu Pro His Val Ile Ser Arg
                    3045              3050              3055

Met Gly Lys Leu Glu Gln Val Asp Val Asn Leu Phe Cys Leu Val Ala
                    3060              3065              3070

Thr Asp Phe Tyr Arg His Gln Ile Glu Glu Glu Phe Asp Arg Arg Ala
                    3075              3080              3085

Phe Gln Ser Val Phe Glu Val Val Ala Ala Pro Gly Ser Pro Tyr His
                    3090              3095              3100

Arg Leu Leu Ala Cys Leu Gln Asn Val His Lys Val Thr Thr Cys
3105                3110              3115

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GGGAACAGCA TCACACCC                                                18

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GTTGCGCTCG GTGAACA                                                17

( 2 ) INFORMATION FOR SEQ ID NO:19:

( i ) SEQUENCE CHARACTERISTICS:
        ( A ) LENGTH: 22 base pairs
        ( B ) TYPE: nucleic acid
        ( C ) STRANDEDNESS: single (D) TOPOLOGY: linear (x i) SEQUENCE DESCRIPTION: SEQ ID NO:19:

GCTGGGGAAC AGCATCACAC CC    22

(2) INFORMATION FOR SEQ ID NO:20:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (x i) SEQUENCE DESCRIPTION: SEQ ID NO:20:

CCTGGAGTTG ACTGGAGACG TG    22

(2) INFORMATION FOR SEQ ID NO:21:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (x i) SEQUENCE DESCRIPTION: SEQ ID NO:21:

CAGGTACTGA GCGAGGAT    18

(2) INFORMATION FOR SEQ ID NO:22:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (x i) SEQUENCE DESCRIPTION: SEQ ID NO:22:

GGAGAACACA GTCGTCTGTG    20

(2) INFORMATION FOR SEQ ID NO:23:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (x i) SEQUENCE DESCRIPTION: SEQ ID NO:23:

CGTGTAAAGT ATGTGAATCG C    21

(2) INFORMATION FOR SEQ ID NO:24:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (x i) SEQUENCE DESCRIPTION: SEQ ID NO:24:

CTTCAACGCT AGAAGAAC    18

(2) INFORMATION FOR SEQ ID NO:25:

(i) SEQUENCE CHARACTERISTICS:
    (A) LENGTH: 20 base pairs
    (B) TYPE: nucleic acid
    (C) STRANDEDNESS: single
    (D) TOPOLOGY: linear ( x i ) SEQUENCE DESCRIPTION: SEQ ID NO:25:

CAGACTTGAA GATGTGGATC 20

HUNTINGTIN DNA, PROTEIN AND USES THEREOF

Cross-Reference to Related Application

This application is a division of application Ser. No. 08/246,982, filed May 20, 1994, (status: pending) which is a continuation-in-part of 08/085,000, filed Jul. 1, 1993 (status: abandoned) which is a continuation-in-part of Ser. No. 08/027,498, filed Mar. 5, 1993 (status: abandoned).

Part of the work performed during development of this invention utilized U.S. Government funds; the U.S. Government has certain rights in this invention.

FIELD OF THE INVENTION

The invention is in the field of the detection and treatment of genetic diseases. Specifically, the invention is directed to the huntingtin gene (also called the IT15 gene), huntingtin protein encoded by such gene, and the use of this gene and protein in assays (1) for the detection of a predisposition to develop Huntington's disease, (2) for the diagnosis of Huntington's disease (3) for the treatment of Huntington's disease, and (4) for monitoring the course of treatment of such treatment.

BACKGROUND OF THE INVENTION

Huntington's disease (HD) is a progressive neurodegenerative disorder characterized by motor disturbance, cognitive loss and psychiatric manifestations (Martin and Gusella, N. Engl. J. Med. 315:1267–1276 (1986). It is inherited in an autosomal dominant fashion, and affects about 1/10,000 individuals in most populations of European origin (Harper, P. S. et al., in Huntington's disease, W. B. Saunders, Philadelphia, 1991). The hallmark of HD is a distinctive choreic movement disorder that typically has a subtle, insidious onset in the fourth to fifth decade of life and gradually worsens over a course of 10 to 20 years until death. Occasionally, HD is expressed in juveniles typically manifesting with more severe symptoms including rigidity and a more rapid course. Juvenile onset of HD is associated with a preponderance of paternal transmission of the disease allele. The neuropathology of HD also displays a distinctive pattern, with selective loss of neurons that is most severe in the caudate and putamen regions of the brain. The biochemical basis for neuronal death in HD has not yet been explained, and there is consequently no treatment effective in delaying or preventing the onset and progression of this devastating disorder.

The genetic defect causing HD was assigned to chromosome 4 in 1983 in one of the first successes of linkage analysis using polymorphic DNA markers in man (Gusella et al., Nature 306:234–238 (1983). Since that time, we have pursued a location cloning approach to isolating and characterizing the HD gene based on progressively refining its localization (Gusella, FASEB J. 3:2036–2041 (1989); Gusella, Adv. Hum. Genet. 20:125–151 (1991)). Among other work, this has involved the generation of new genetic markers in the region by a number of techniques (Pohl et al., Nucleic Acids Res. 16:9185–9198 (1988); Whaley et al., Somat. Cell. Mol. Genet. 17:83–91 (1991); MacDonald et al., J. Clin. Inv. 84:1013–1016 (1989)), the establishment of genetic (MacDonald et al., Neuron 3:183–190 (1989); Allitto et al., Genomics 9:104–112 (1991)) and physical maps of the implicated regions (Bucan et al., Genomics 6:1–15 (1990); Bates et al., Nature Genet. 1:180–187 (1992); Doucette-Stamm et al., Somat. Cell Mol. Genet. 17:471–480 (1991); Altherr et al., Genomics 13:1040–1046 (1992)), the cloning of the 4p telomere of an HD chromosome in a YAC clone (Bates et al., Am. J. Hum. Genet. 46:762–775 (1990); Youngman et al., Genomics 14:350–356 (1992)), the establishment of YAC [yeast artificial chromosome] (Bates et al., Nature Genet. 1:180–187 (1992)) and cosmid (Baxendale. et al., in preparation) contigs (a series of overlapping clones which together form a whole sequence) of the candidate region, as well as the analysis and characterization of a number of candidate genes from the region (Thompson et al., Genomics 11:1133–1142 (1991); Taylor et al., Nature Genet. 2:223–227 (1992); Ambrose et al., Hum. Mol. Genet. 1:697–703 (1992)). Analysis of recombination events in HD kindreds has identified a candidate region of 2.2 Mb, between D4S10 and D4S98 in 4p16.3, as the most likely position of the HD gene (MacDonald et al., Neuron 3:183–190 (1989); Bates et al., Am. J. Hum. Genet. 49:7–16 (1991); Snell et al., Am. J. Hum. Genet. 51:357–362 (1992)). Investigations of linkage disequilibrium between HD and DNA markers in 4p16.3 (Snell et al., J. Med. Genet. 26:673–675 (1989); Theilman et al., J. Med. Genet. 26:676–681 (1989)) have suggested that multiple mutations have occurred to cause the disorder (MacDonald et al., Am. J. Hum. Genet. 49:723–734 (1991)). However, haplotype analysis using multi-allele markers has indicated that at least ⅓ of HD chromosomes are ancestrally related (MacDonald et al., Nature Genet. 1:99–103 (1992)). The haplotype shared by these HD chromosomes points to a 500 kb segment between D4S180 and D4S182 as the most likely site of the genetic defect.

Targeting this 500 kb region for saturation with gene transcripts, exon amplification has been used as a rapid method for obtaining candidate coding sequences (Buckler et al., Proc. Natl. Acad. Sci. USA 88:4005–4009 (1991)). This strategy has previously identified three genes: the a-adducin gene (ADDA) (Taylor et al., Nature Genet. 2:223–227 (1992)); a putative novel transporter gene (IT10C3) in the distal portion of this segment; and a novel G protein-coupled receptor kinase gene (IT11) in the central portion (Ambrose et al., Hum. Mol. Genet. 1:697–703 (1992)). However, no defects implicating any of these genes as the HD locus have been found.

SUMMARY OF THE INVENTION

A large gene, termed herein "huntingtin" or "IT15," has been identified that spans about 210 kb and encodes a previously undescribed protein of about 348 kDa. The huntingtin reading frame contains a polymorphic $(CAG)_n$ trinucleotide repeat with at least 17 alleles in the normal population, varying from 11 to about 34 CAG copies. On HD chromosomes, the length of the trinucleotide repeat is substantially increased, for example, about 37 to at least 73 copies, and shows an apparent correlation with age of onset, the longest segments are detected in juvenile HD cases. The instability in length of the repeat is reminiscent of similar trinucleotide repeats in the fragile X syndrome and in myotonic dystrophy (Suthers et al., J. Med. Genet. 29:761–765 (1992)). The presence of an unstable, expandable trinucleotide repeat on HD chromosomes in the region of strongest linkage disequilibrium with the disorder suggests that this alteration underlies the dominant phenotype of HD, and that huntingtin encodes the HD gene.

The invention is directed to the protein huntingtin, DNA and RNA encoding this protein, and uses thereof.

Accordingly, in a first embodiment, the invention is directed to purified preparations of the protein huntingtin.

In a further embodiment, the invention is directed to a recombinant construct containing DNA or RNA encoding huntingtin.

In a further embodiment, the invention is directed to a vector containing such huntingtin-encoding nucleic acid.

In a further embodiment, the invention is directed to a host transformed with such vector.

In a further embodiment, the invention is directed to a method for producing huntingtin from such recombinant host.

In a further embodiment, the invention is direct to a method for diagnosing Huntington's disease using such huntingtin DNA, RNA and/or protein.

In a further embodiment, the invention is directed to a method for treating Huntington's disease using such huntingtin DNA, RNA and/or protein.

In a further embodiment, the invention is directed to a method of gene therapy of a symptomatic or presymptomatic patient, such method comprising providing a functional huntingtin gene with a $(CAG)_n$ repeat of the normal range of 11–34 copies to the desired cell of such patient in need of such treatment, in a manner that permits the expression of the huntingtin protein provided by such gene, for a time and in a quantity sufficient to provide the huntingtin function to the cells of such patient.

In a further embodiment, the invention is directed to a method of gene therapy of a symptomatic or presymptomatic patient, such method comprising providing a functional huntingtin antisense gene to the desired cells of such patient in need of such treatment, in a manner that permits the expression of huntingtin antisense RNA provided by such gene, for a time and in a quantity sufficient to inhibit huntingtin mRNA expression in the cells of such patient.

In a further embodiment, the invention is directed to a method of gene therapy of a symptomatic or presymptomatic patient, such method comprising providing a functional huntingtin gene to the cells of such patient in need of such gene; in one embodiment the functional huntingtin gene contains a $(CAG)_n$ repeat size between 11–34 copies.

In a further embodiment, the invention is directed to a method for diagnosing Huntington's disease or a predisposition to develop Huntington's disease in a patient, such method comprising determining the number of $(CAG)_n$ repeats present in the huntingtin gene in such patient and especially in the affected tissue of such patient.

In a further embodiment, the invention is directed to a method for treating Huntington's disease in a patient, such method comprising decreasing the number of huntingtin $(CAG)_n$ repeats in the huntingtin gene in the desired cells of such patient.

The composite sequence was derived as follows. From 22 bases 3' to the putative initiator Met ATG, the sequence was compiled from the cDNA clones and exons shown. There are 9 bases of sequence intervening between the 3' end of IT16B and the 5' end of IT15B. These were by PCR amplification of first strand cDNA and sequencing of the PCR product. At the 5' end of the composite sequence, the cDNA clone IT16C terminates 27 bases upstream of the $(CAG)_n$. However, when IT16C was identified, we had already generated genomic sequence surrounding the $(CAG)_n$ in an attempt to generate new polymorphisms. This sequence matched the IT16C sequence, and extended it 337 bases upstream, including the apparent Met initiation codon.

FIG. 4. Composite sequence of huntingtin (IT15)(SEQ ID NO:5 and SEQ ID NO:6). The composite DNA sequence of huntingtin (IT15) is shown (SEQ ID NO:5). The predicted protein product (SEQ ID NO:6) is shown below the DNA sequence, based on the assumption that translation begins at the first in-frame methionine of the long open reading frame.

Figure 5:
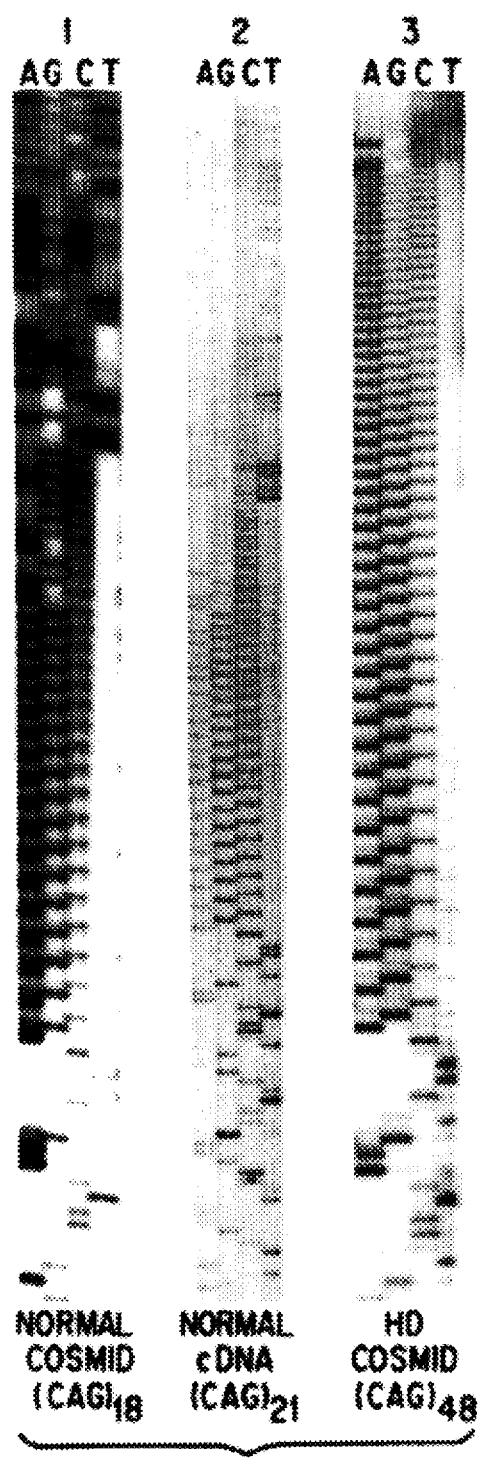

FIG. 5. DNA sequence analysis of the $(CAG)_n$ repeat. DNA sequence shown in panels 1, 2 and 3, demonstrates the variation in the $(CAG)_n$ repeat detected in normal cosmid L191F1 (1), cDNA IT16C (2), and HD cosmid GUS72-2130. Panels 1 and 3 were generated by direct sequencing of cosmid subclones using the following primer (SEQ ID NO:1):

5' GGC GGG AGA CCG CCA TGG CG 3'.

Panel 2 was generated using the pBSKII T7 primer (SEQ ID NO:2):

5' AAT ACG ACT CAC TAT AG 3'.

Figure 6:
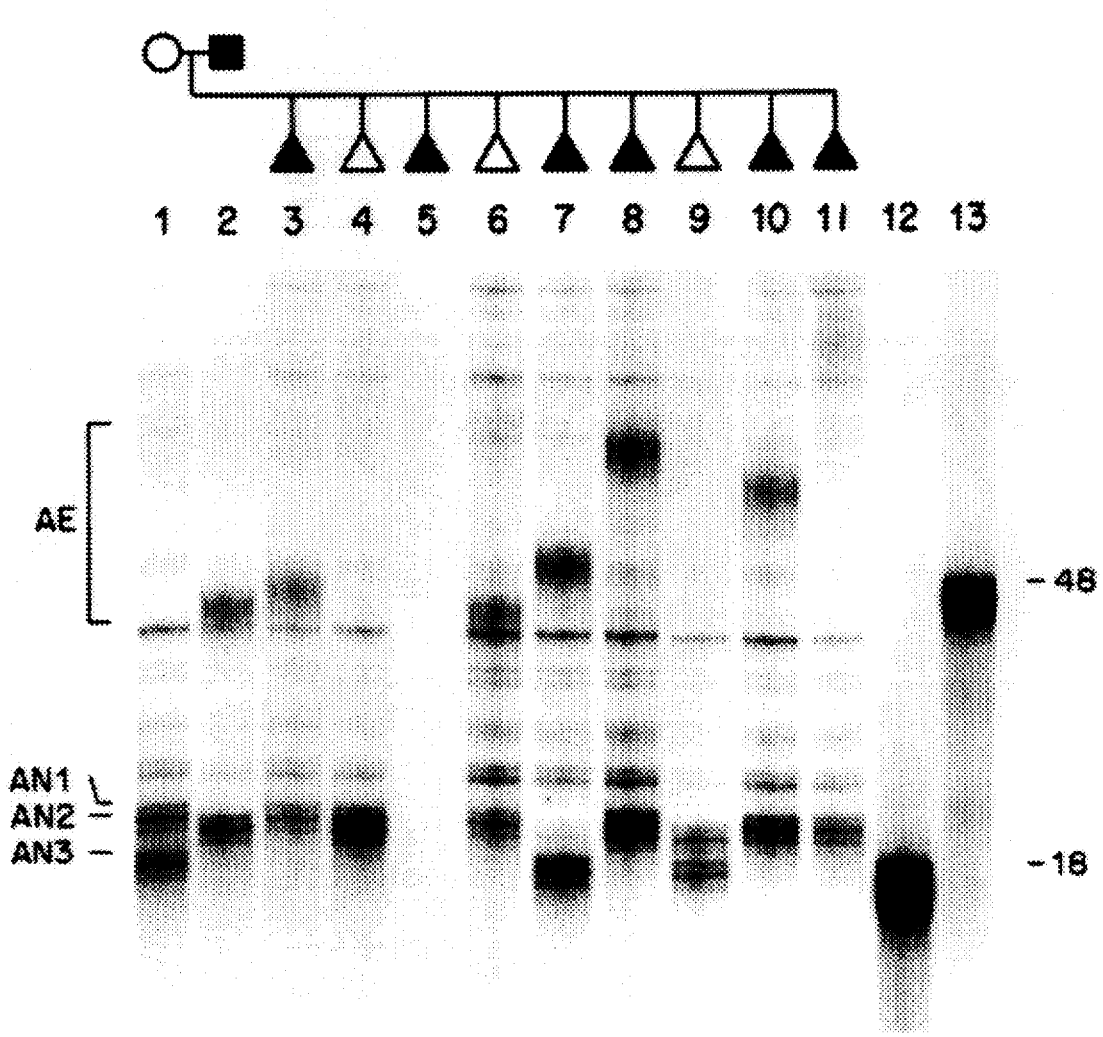

FIG. 6. PCR analysis of the $(CAG)_n$ repeat in a Venezuelan HD sibship with some offspring displaying juvenile onset. Results of PCR analysis of a sibship in the Venezuela HD pedigree are shown. Affected individuals are represented by shaded symbols. Progeny are shown as triangles for confidentiality. AN1, AN2 and AN3 mark the positions of the allelic products from normal chromosomes. AE marks the range of PCR products from the HD chromosome. The intensity of background constant bands, which represent a useful reference for comparison of the above PCR products, varies with slight differences in PCR conditions. The PCR products from cosmids L191F1 and GUS72-2130 are loaded in lanes 12 and 13 and have 18 and 48 CAG repeats, respectively.

Figure 7:
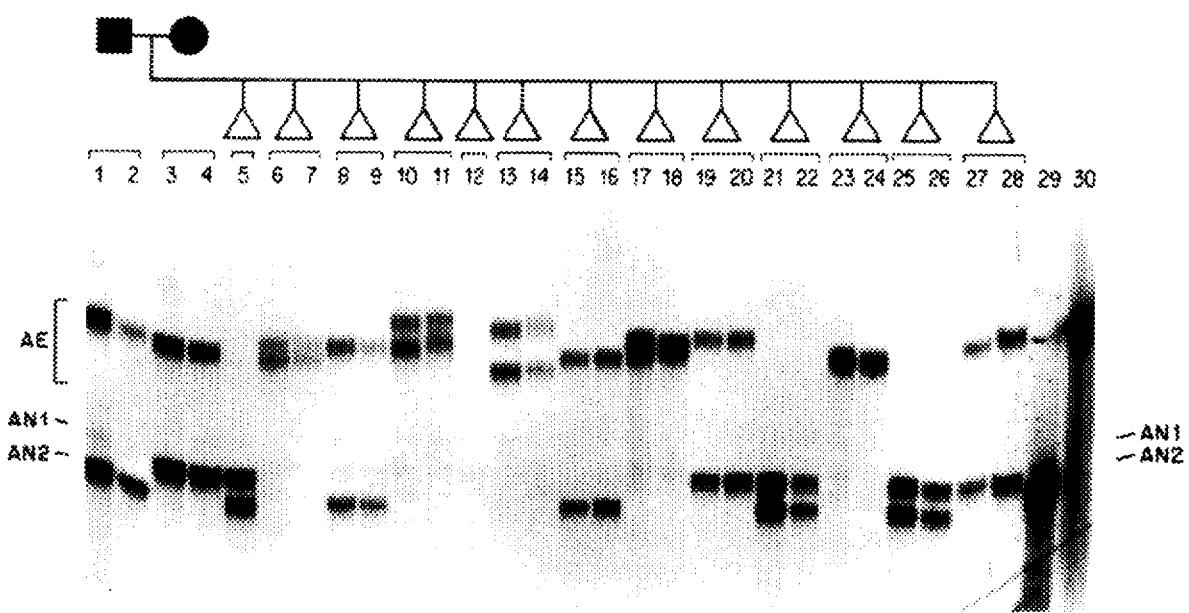

FIG. 7. PCR analysis of the $(CAG)_n$ repeat in a Venezuelan HD sibship with offspring homozygous for the same HD haplotype. Result of PCR analysis of a sibship from the Venezuela HD pedigree in which both parents are affected by HD are shown. Progeny are shown as triangles for confidentiality and no HD diagnostic information is given to preserve the blind status of investigators in the Venezuelan Collaborative Group. AN 1 and AN2 mark the positions of the allelic products from normal parental chromosomes. AE marks the range of PCR products from the HD chromosome. The PCR products from cosmids L191F1 and GUS72-2130 are loaded in lanes 29 and 30 and have 18 and 48 CAG repeats, respectively.

Figure 8:
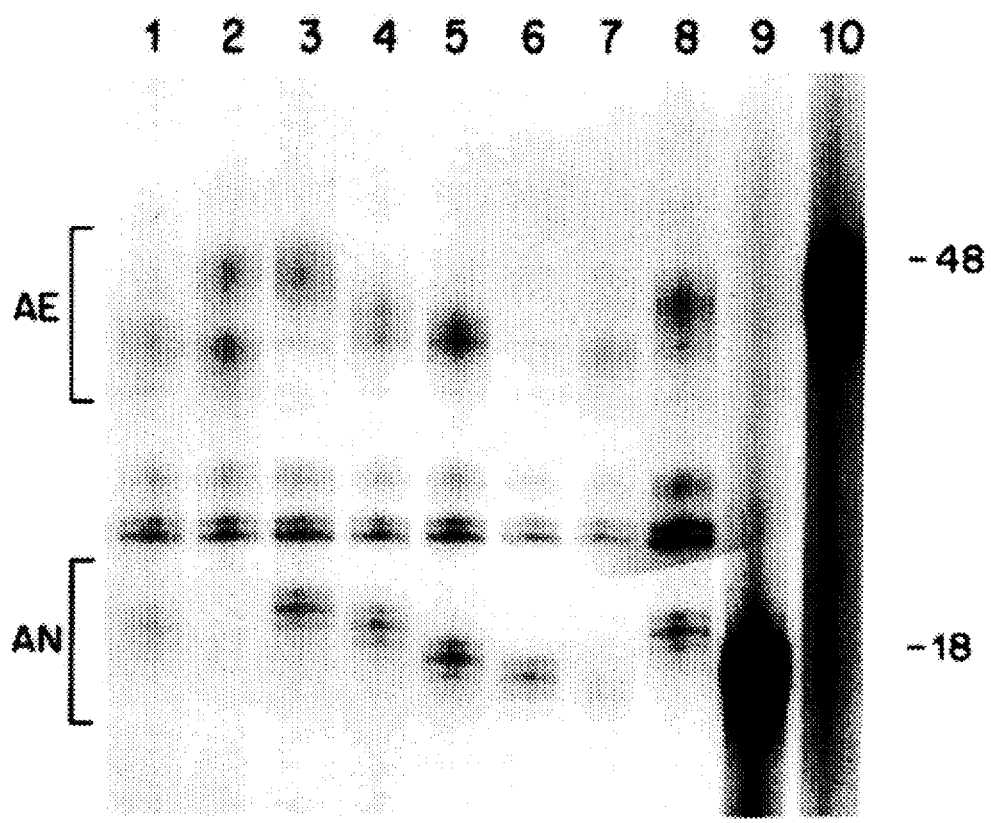

FIG. 8. PCR analysis of the $(CAG)_n$ repeat in members of an American family with an individual homozygous for the major HD haplotype. Results of PCR analysis of members of an American family segregating the major HD haplotype. AN marks the range of normal alleles; AE marks the range of HD alleles. Lanes 1, 3, 4, 5, 7 and 8 represent PCR products from related HD heterozygotes. Lane 2 contains the PCR products from a member of the family homozygous for the same HD chromosome. Lane 6 contains PCR products from a normal individual. Pedigree relationships and affected status are not presented to preserve confidentiality. The PCR products from cosmids L191F1 and GUS72-2130 (which was derived from the individual represented in lane 2) are loaded in lanes 9 and 10 and have 18 and 48 CAG repeats, respectively.

Figure 9:
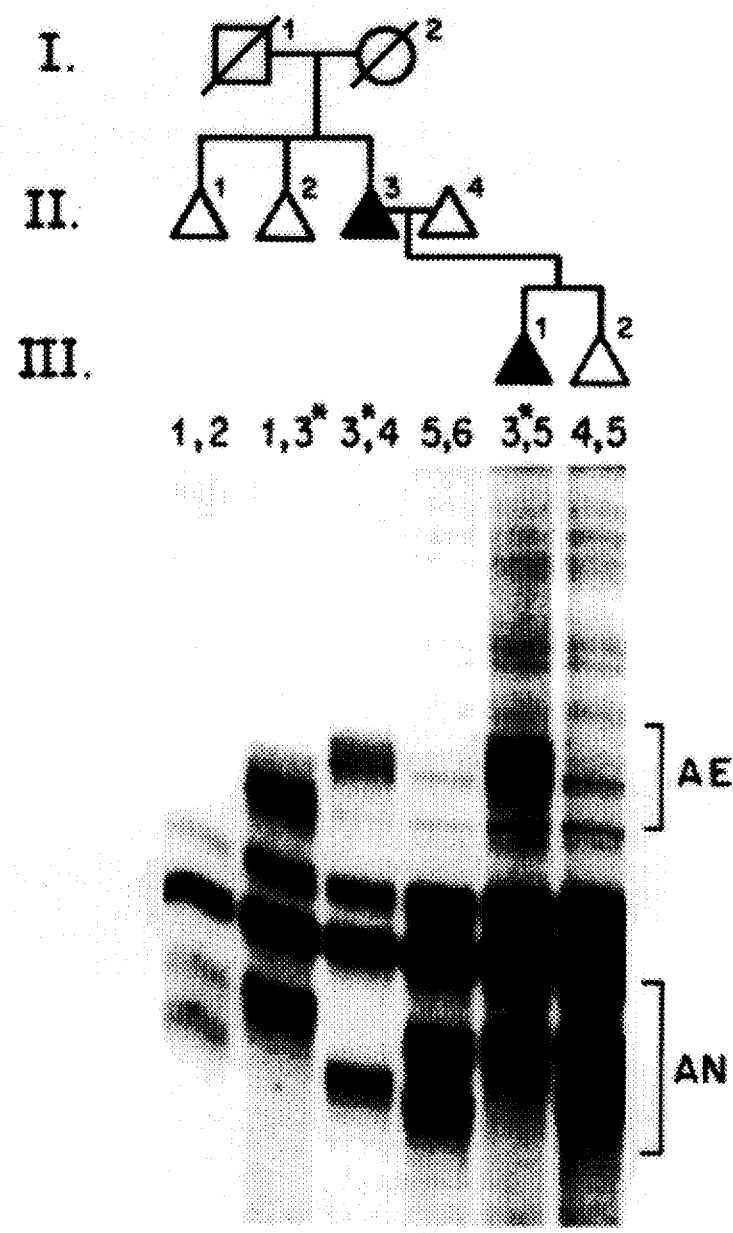
Figure 10:
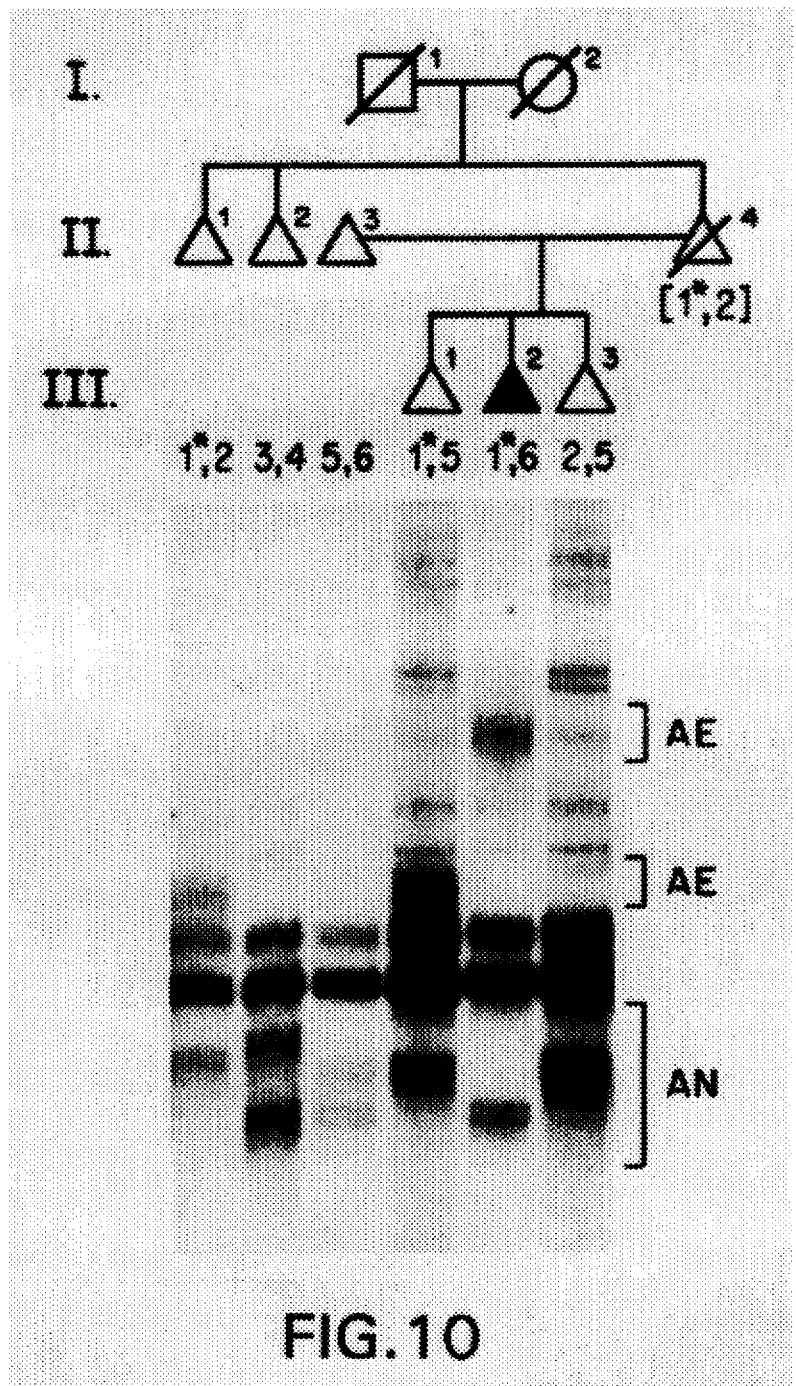

FIGS. 9 and 10. PCR analysis of the $(CAG)_n$ repeat in two families with supposed new mutation causing HD. Results of PCR analysis of two families in which sporadic HD cases representing putative new mutants are shown. Individuals in each pedigree are numbered by generation (Roman numerals) and order in the pedigree. Triangles are used to protect confidentiality. Filled symbols indicate symptomatic individuals. The different chromosomes segregating in the pedigree have been distinguished by extensive typing with polymorphic markers in 4p16.3 and have been assigned arbitrary numbers shown above the gel lanes. The starred chromosomes (3 in FIG. 9, 1 in FIG. 10) represent the presumed HD chromosome. AN denotes the range of normal alleles; AE denotes the range of alleles present in affected individuals and in their unaffected relatives bearing the same chromosomes.

Figure 11:
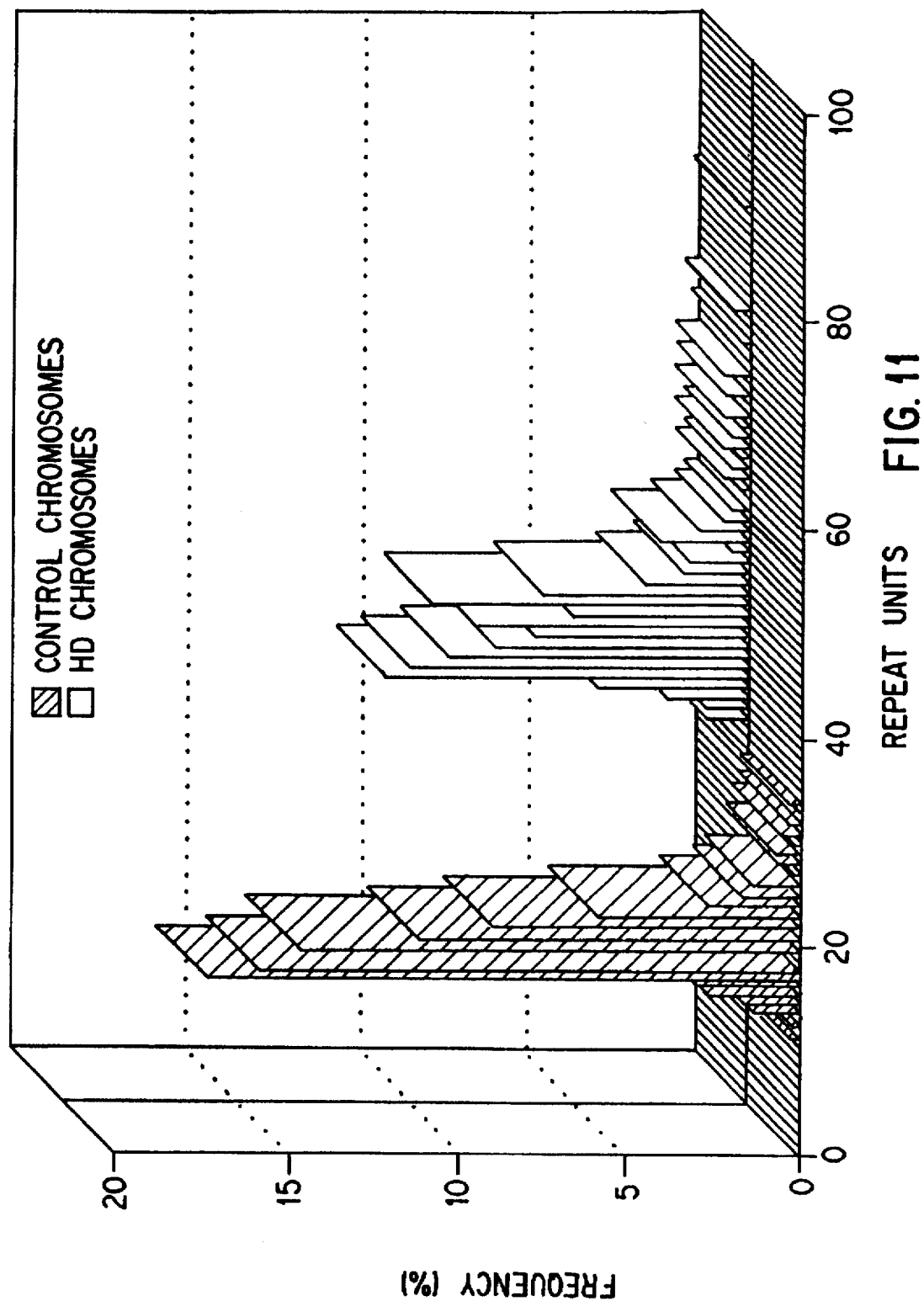

FIG. 11. Comparison of $(CAG)_n$ Repeat Unit Number on Control and HD Chromosomes. Frequency distributions are shown for the number of $(CAG)_n$ repeat units observed on 425 HD chromosomes from 150 independent families, and from 545 control chromosomes.

FIG. 12. Comparison of $(CAG)_n$ Repeat Unit Number on Maternally and Paternally Transmitted HD Chromosomes. Frequency distributions are shown for the 134 and 161 HD chromosomes from FIG. 11 known to have been transmitted from the mother (Panel A) and father (Panel B), respectively. The two distributions differ significantly based on a t-test ($t_{272.3}$=5.34, $p<0.0001$).

Figure 13A:
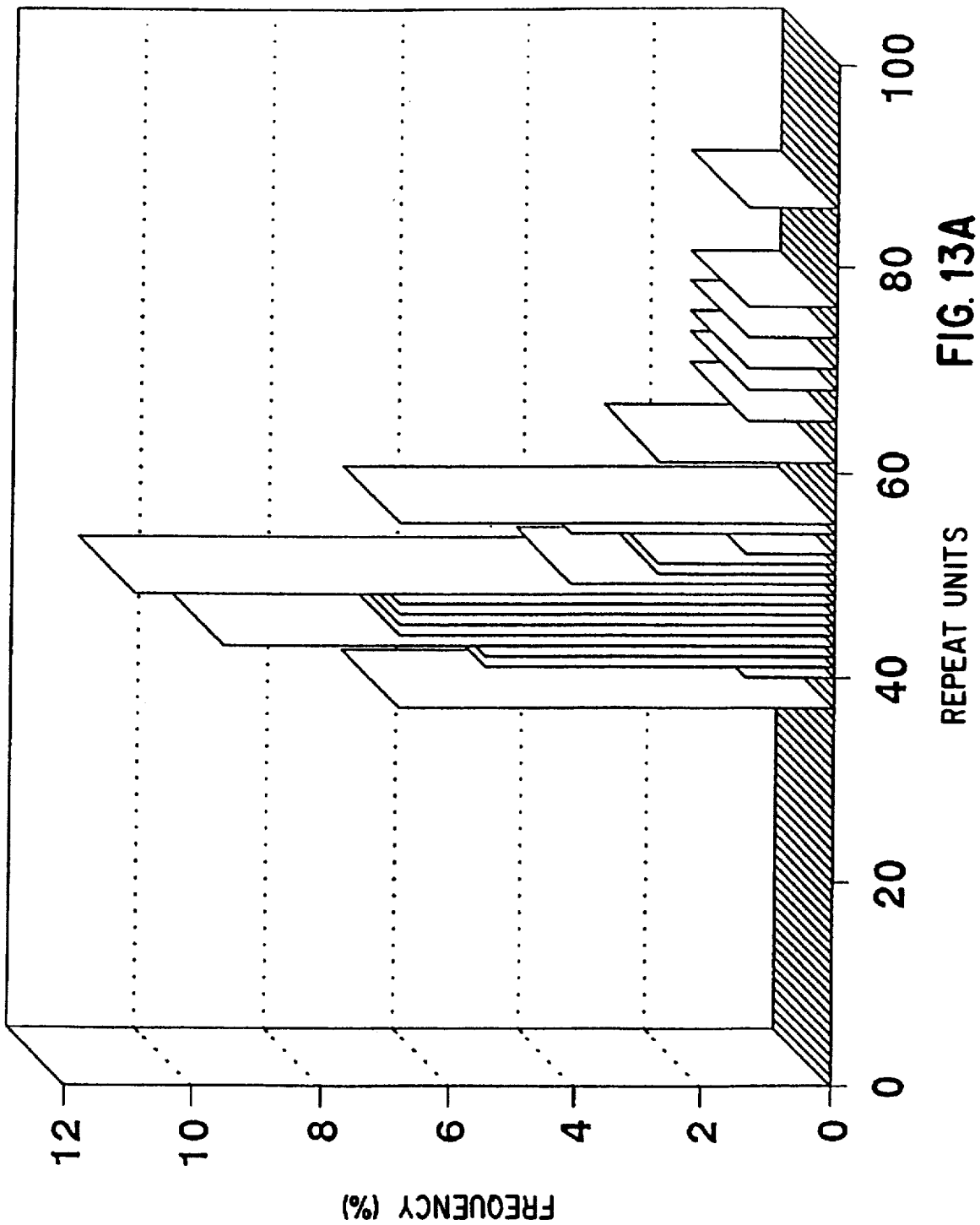
Figure 13B:
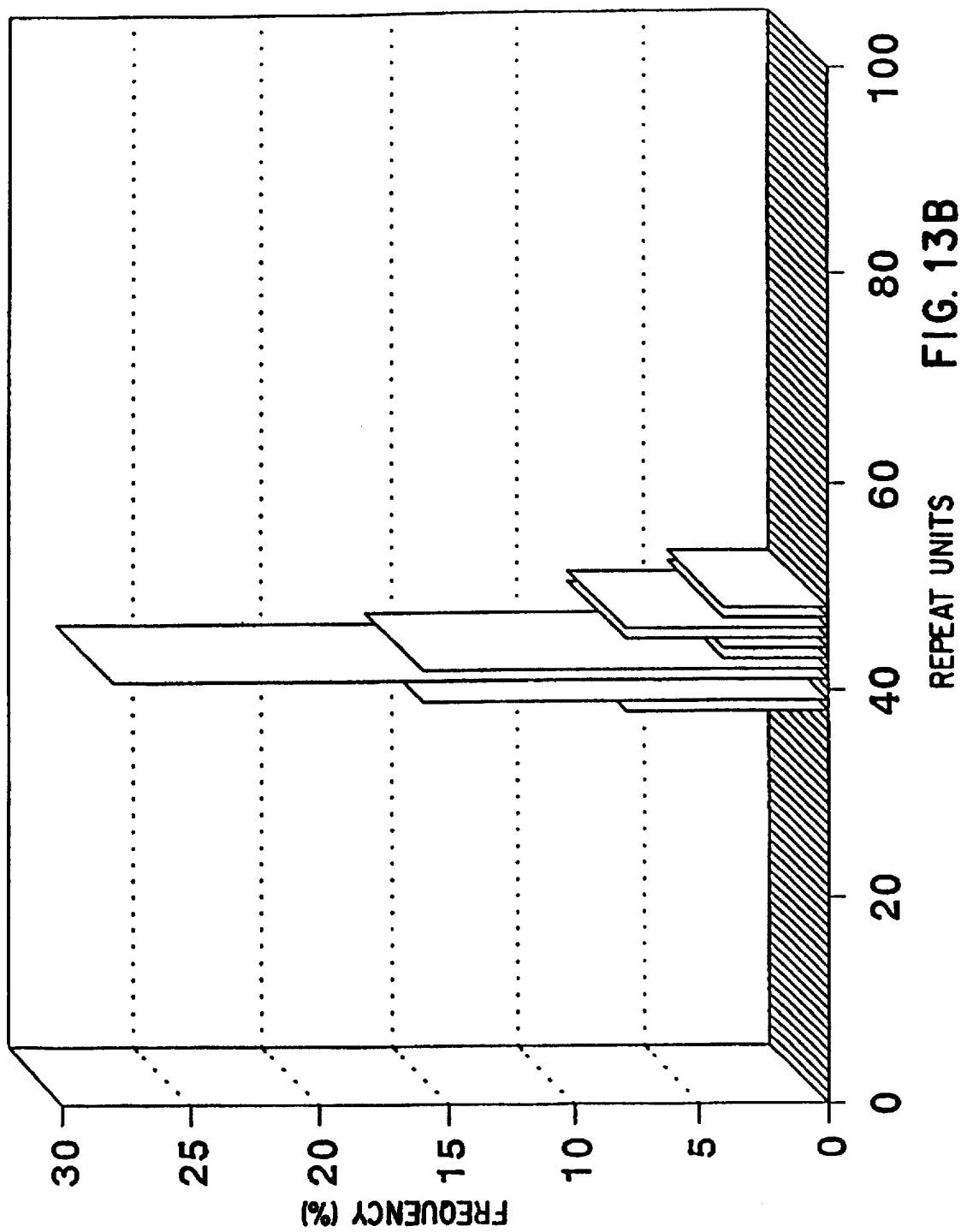
Figure 13C:
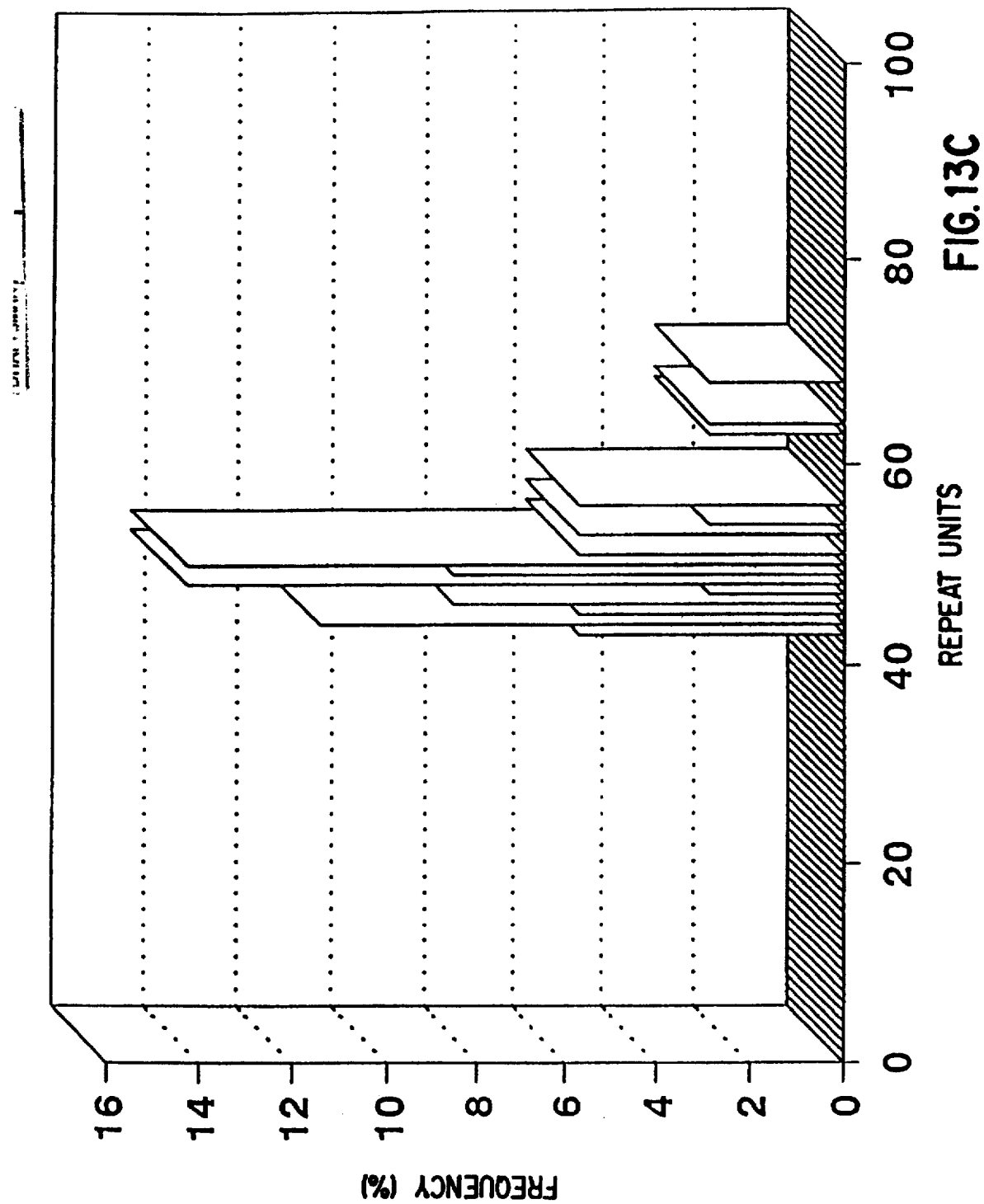

FIG. 13. Comparison of $(CAG)_n$ Repeat Unit Number on HD Chromosomes from Three Large Families with Different HD Founders. Frequency distributions are shown for 75, 25 and 35 HD chromosomes from the Venezuelan HD family (Panel A) (Gusella, J. F., et al., Nature 306:234–238 (1983); Wexler, N. S., et al., Nature 326:194–197 (1987)), Family Z (Panel B) and Family D (Panel C) (Folstein, S. E., et al., Science 229:776–779 (1985)), respectively. The Venezuelan distribution did not differ from the overall HD chromosome distribution in FIG. 11 ($t_{79,7}$=1.58, $p<0.12$). Both Family Z and Family D did produce distributions significantly different from the overall HD distribution ($t_{42.2}$=6.73, $p<0.0001$ and $t_{458}$=2.90, $p<0.004$, respectively).

Figure 14A:
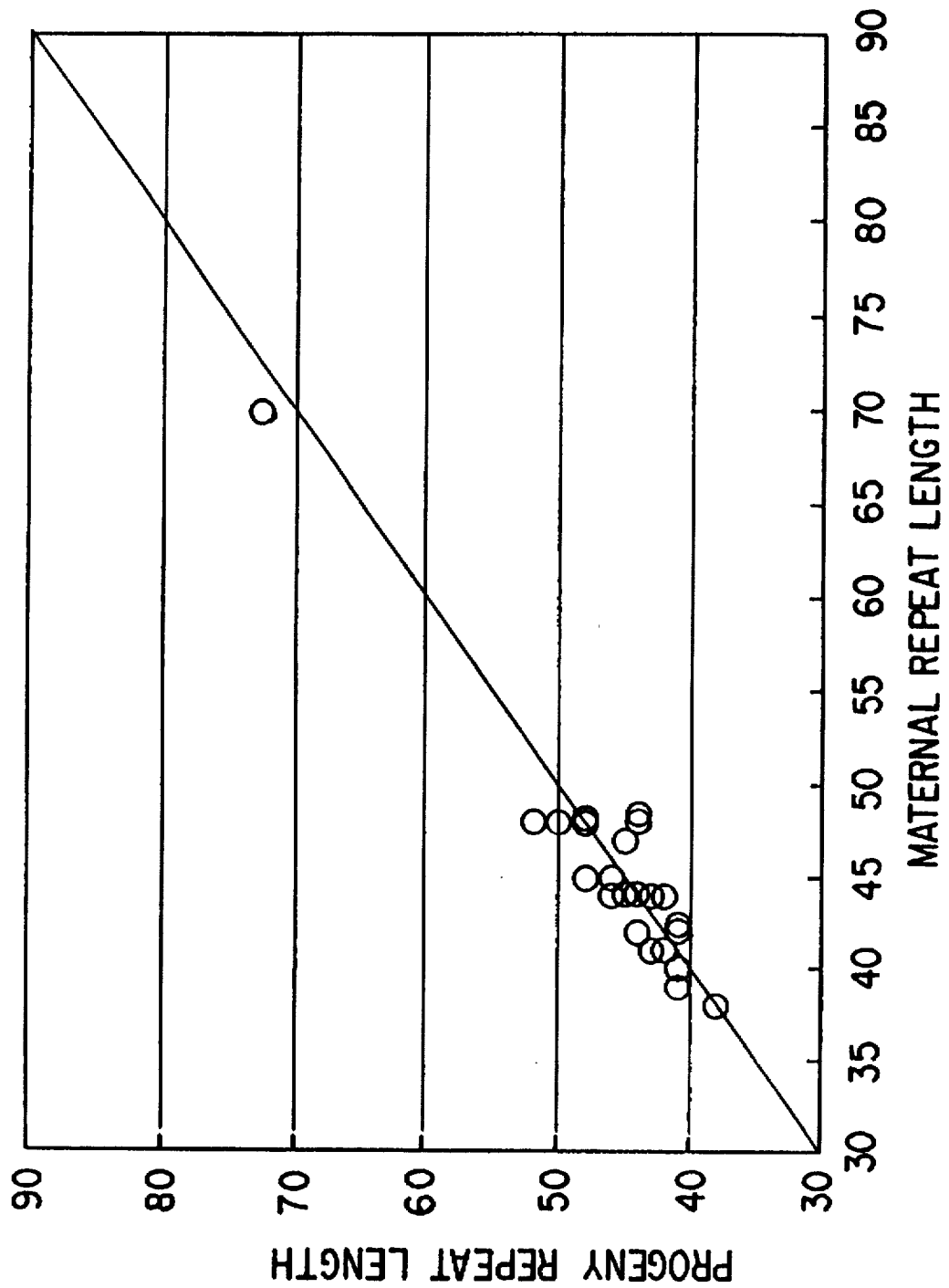
Figure 14B:
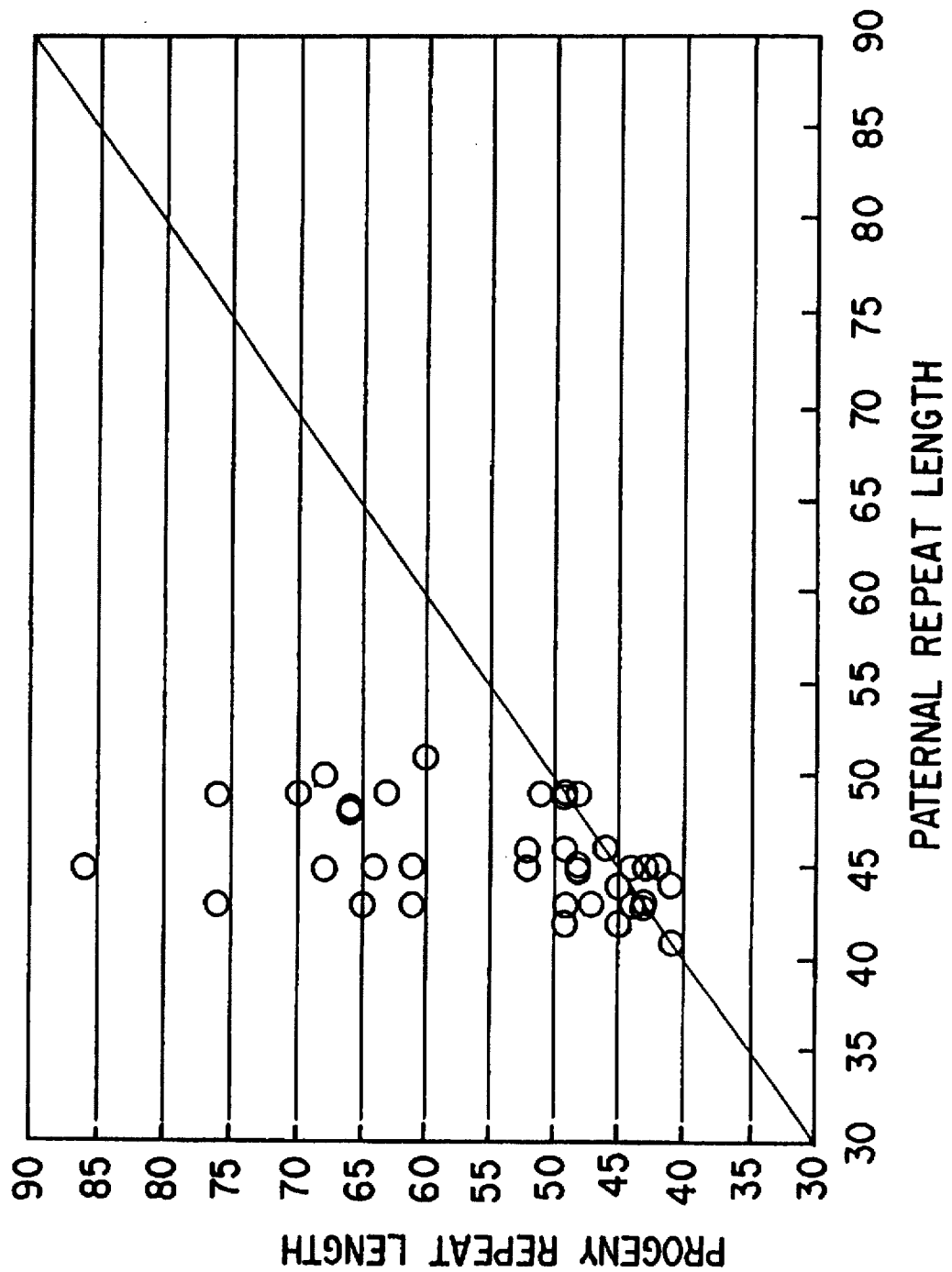

FIG. 14. Relationship of $(CAG)_n$ Repeat Length in Parents and Corresponding Progeny. Repeat length on the HD chromosome in mothers (Panel A) or fathers (Panel B) is plotted against the repeat length in the corresponding offspring. A total of 25 maternal transmissions and 37 paternal transmissions were available for typing.

Figure 15:
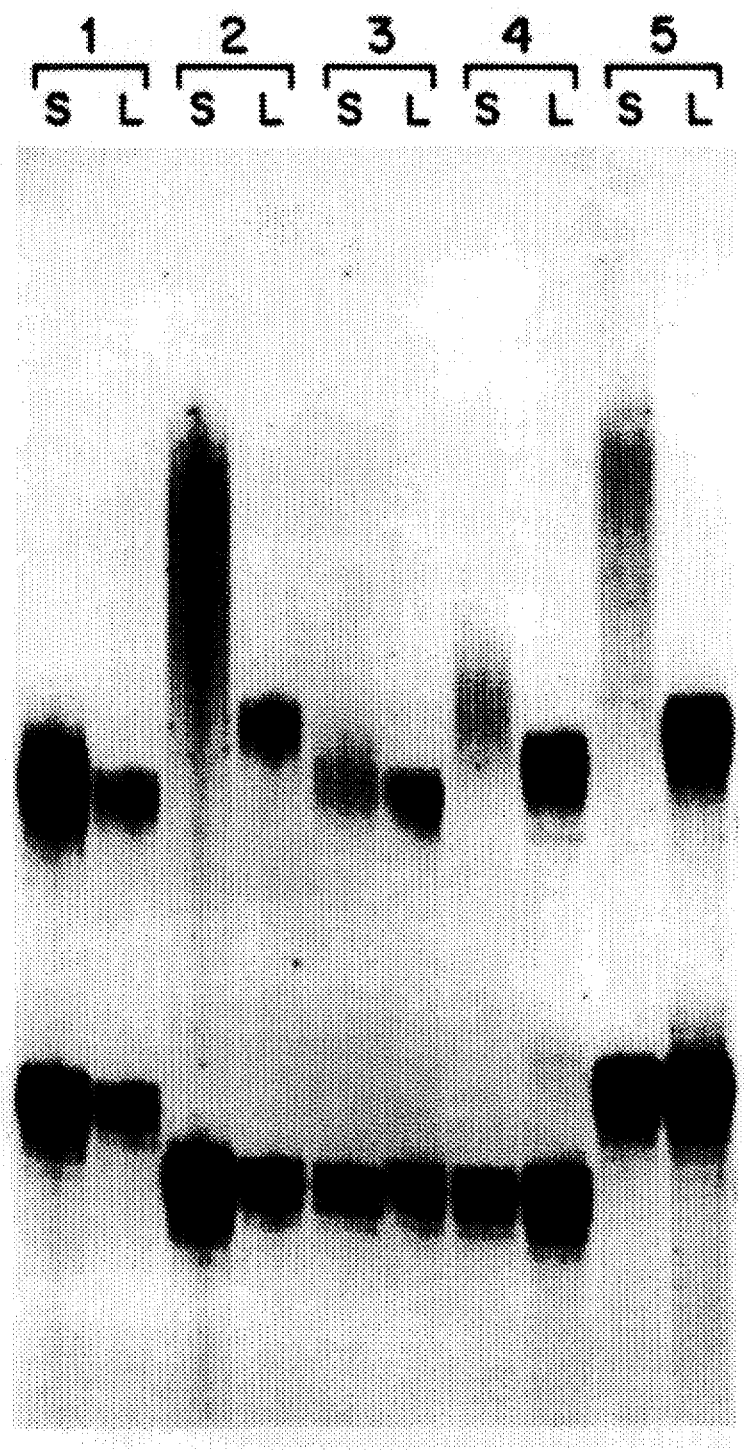

FIG. 15. Amplification of the HD $(CAG)_n$ Repeat From Sperm and Lymphoblast DNA. DNA from sperm (S) and lymphoblasts (L) for 5 members (pairs 1–5) of the Venezuelan HD pedigree aged 24–30 were used for PCR amplification of the HD $(CAG)_n$ repeat. The lower band in each lane derives from the normal chromosome.

Figure 16:
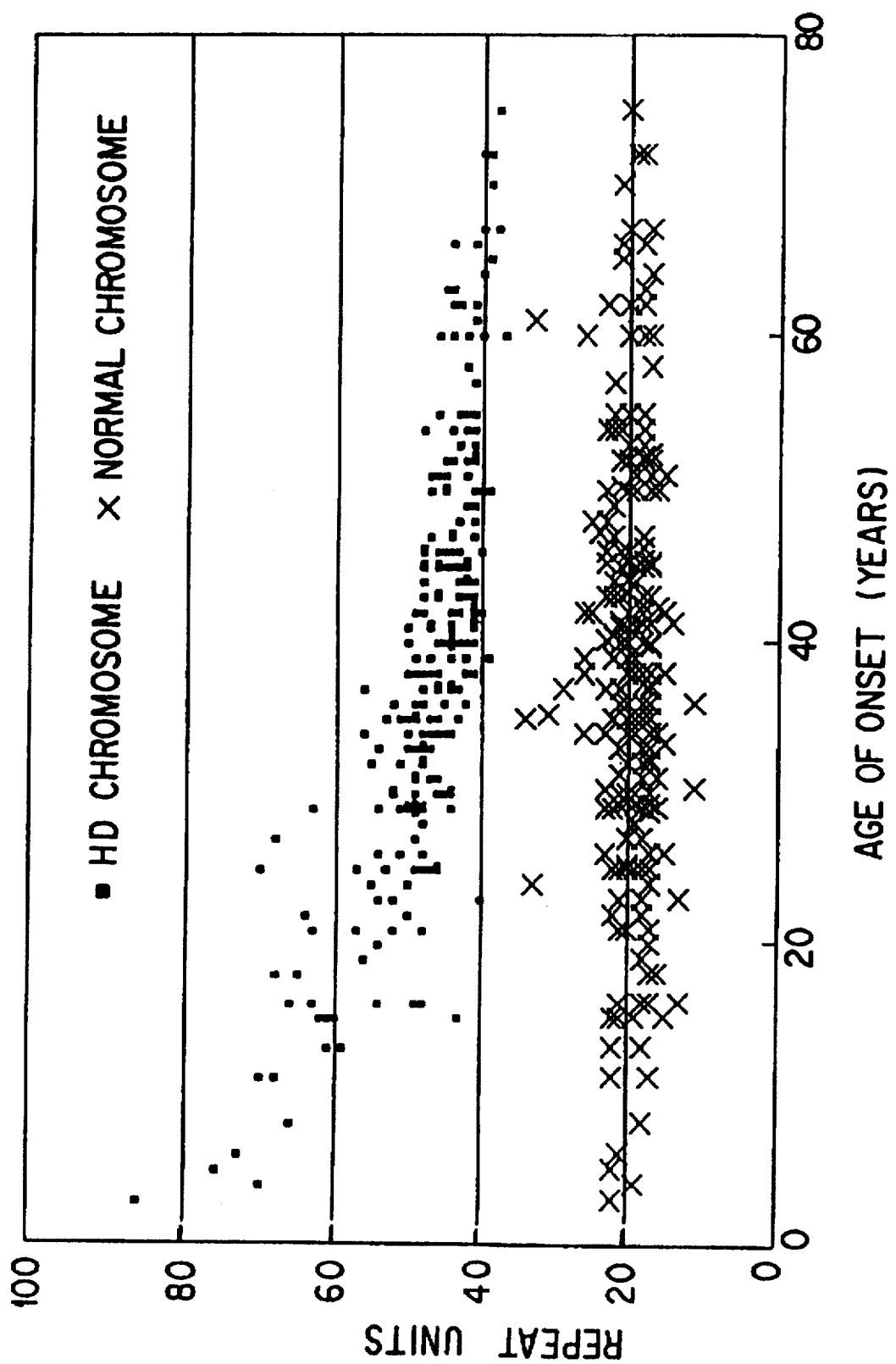

FIG. 16. Relationship of Repeat Unit Length with Age of Onset. Age of onset was established for 234 diagnosed HD gene carriers and plotted against the repeat length observed on both the HD and normal chromosomes in the corresponding lymphoblast lines.

Figure 17:
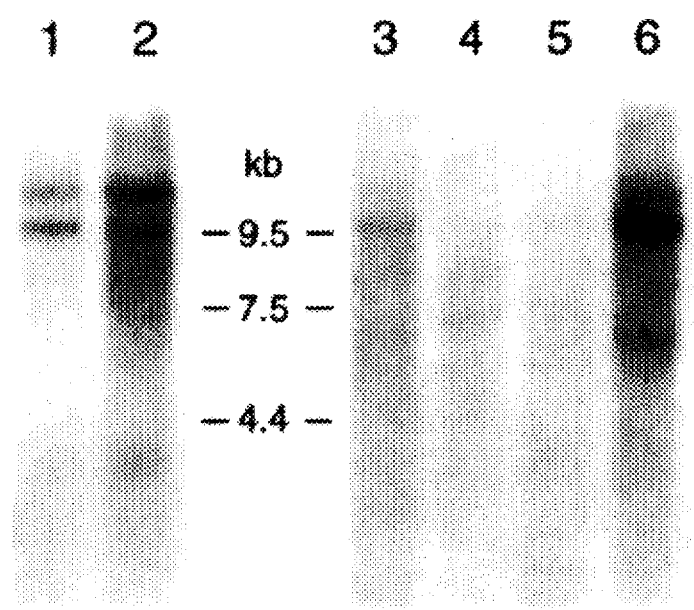

FIG. 17. Northern Blots Analysis of Mouse Hdh mRNAs. Northern blots containing 2 µg of polyA$^+$ mRNA from various adult mouse tissues were hybridized with human IT15B.1. Transcript sizes were estimated from RNA size markers ns shown. Lanes: 1, heart; 2, brain; 3, liver; 4, skeletal muscle; 5, kidney, 6, testis.

Figure 18:
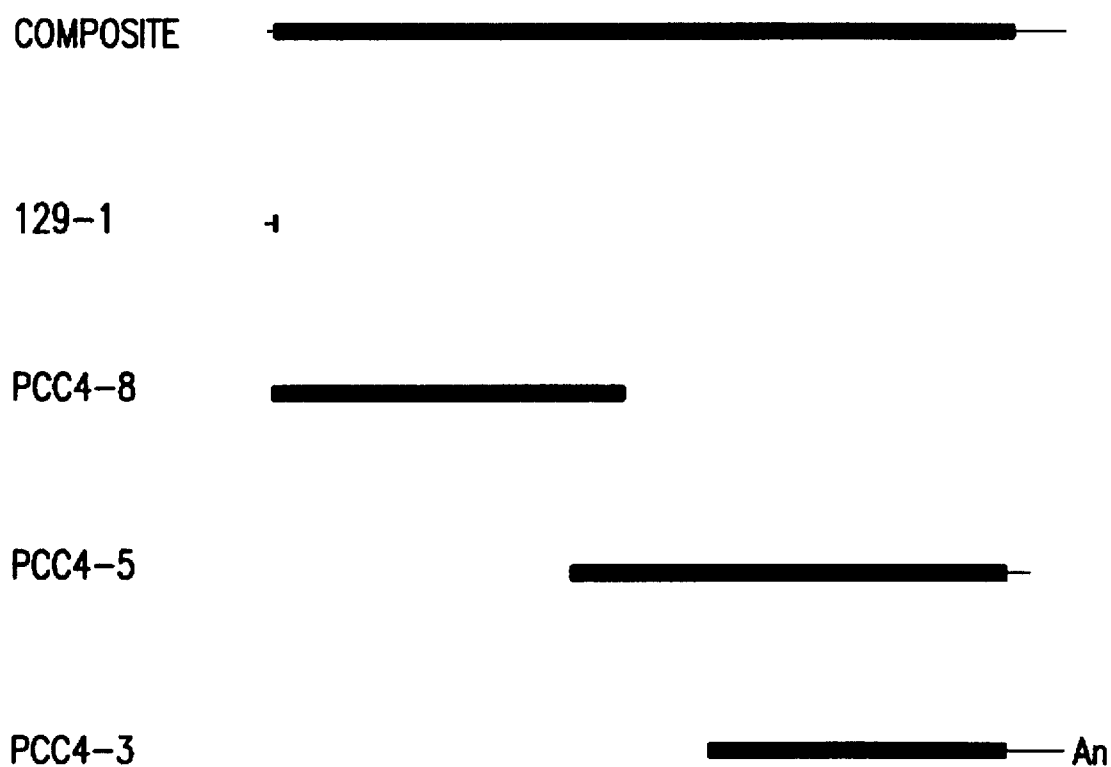

FIG. 18. Schematic Diagram of Mouse Hdh Clones. The composite mouse Hdh cDNA sequence deposited in GenBank as accession #L28827 is shown schematically over the clones from which it was derived. The 5' UTR and 3' UTR sequences are shown as thin lines, while the predicted coding sequence is depicted as a filled box. The sequences provided by each clone are: 129-1 genomic phage, nt 1-133; cDNA PCC4-8, nt 102-4469; PCC4-5, nt 3906-9765; and PCC4-3, nt 5781-9998. Only the latter clone displayed a polyA tail.

Figure 19:
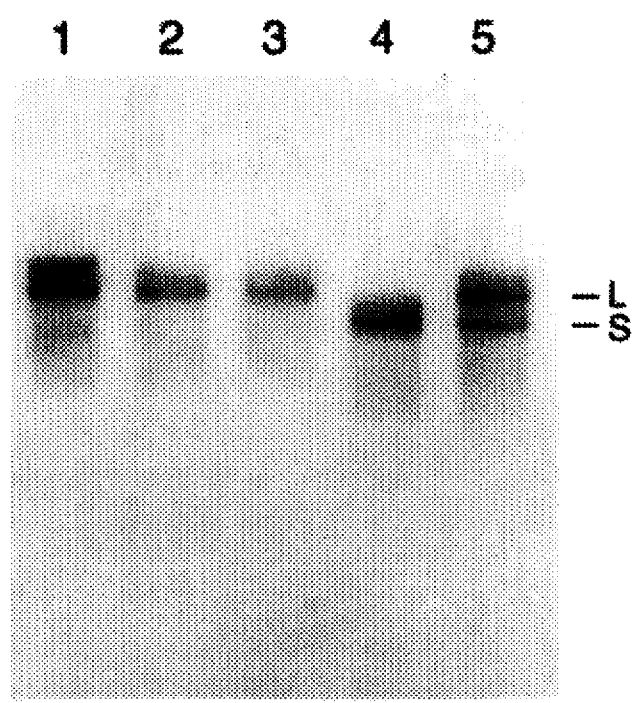

FIG. 19. CCG Polymorphism in Mus spretus. Mouse genomic or cloned DNA was amplified using PCR primers flanking the CAG-CCG rich region near the 5' end of the Hdh gene. Products were displayed on a 6% denaturing polyacrylamide gel. Lanes: 1: PCC4-8 cDNA; 2, C57BL/6J; 3, CBA/J; 4, M. spretus; 5, C57BL/6J+M. spretus. The laboratory mouse (L=190 bp) and M. spretus (S=187 bp) products differ by one CCG repeat unit as confirmed by DNA sequence analysis.

Figure 20:
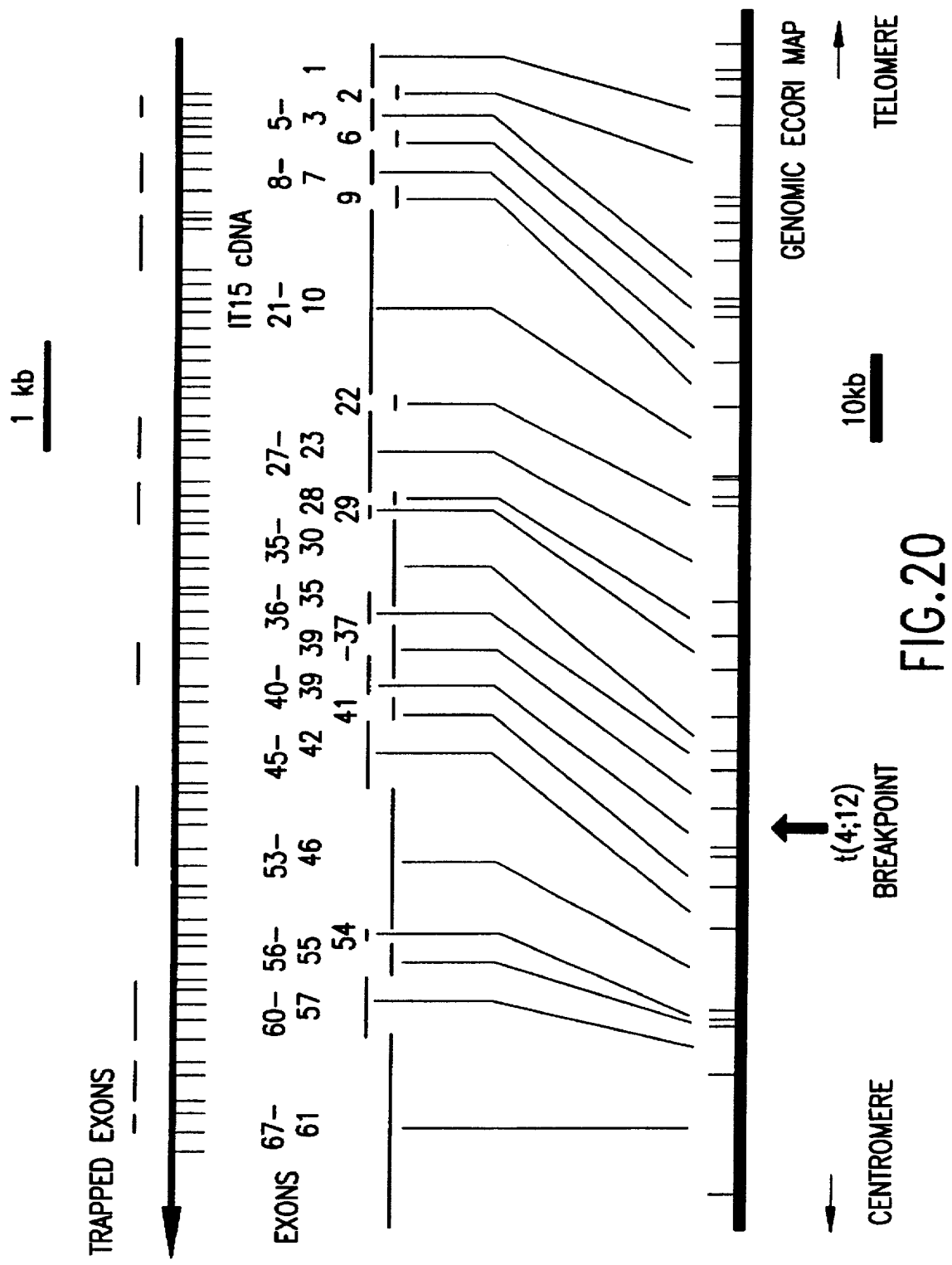

FIG. 20. Exon Structure of the HD Gene. A schematic of the IT15 cDNA is shown (top) with an arrow to denote the direction of transcription. Vertical lines below the cDNA correspond to exon junctions. Horizontal lines above the cDNA span those exons that were recovered from genomic DNA as cloned products in the exon amplification procedure. The genomic EcoRI map of the HD region of 4p16.3 (bottom) is shown, with vertical lines denoting EcoRI sites and centromere-telomere orientation provided below (Baxendale, S. et al., Nature Genet. 4:181–186 (1993)). Between the cDNA and the genomic map, exons 1–67 are shown as horizontal lines under the corresponding exon number. Contiguous horizontal lines denote exons which map to the same genomic EcoRI fragment as demonstrated by the vertical lines connecting to the physical map. The position of the t(4;12) breakpoint between exons 40 and 41 is shown by the vertical arrow below the genomic map.

Figure 21A:
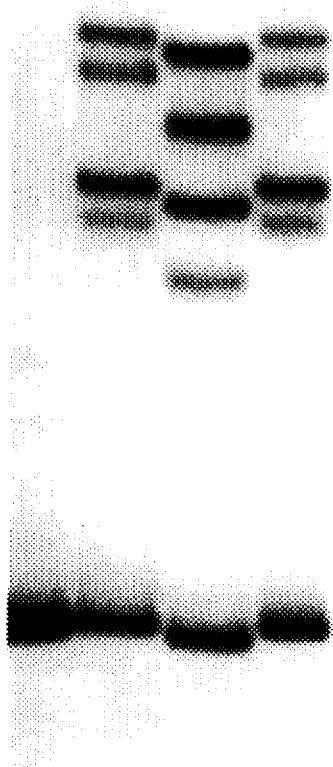

FIG. 21. The Δ2642 codon loss polymorphism.

A. SSCP analysis by RT-PCR of mRNA

First strand oligo (dT)-primed cDNA was amplified with primers 5' GGGAACAGCATCACACCC 3' (SEQ ID NO:17) and 5' GTTGCGCTCGGTGAACA 3' (SEQ ID NO:t8) and the ~273 bp PCR products were analyzed under SSCP Conditions (Orita, M. et al., *Genomics* 5:874–879 (1989); Ambrose, C. et al., *Hum. Mol. Genet.* 1:697–703 (1992)). Lane 1=undenatured product from a normal individual; lane 2=denatured product from the same normal individual; lane 3=denatured product from an HD homozygote of the most common haplotype representing ⅓ of HD chromosomes (MacDonald, M. E. et al., *Nature Genet.* 1:99–103 (1992)); lane 4=denatured product from an HD homozygote of another less frequent haplotype.

B. Genomic PCR assay for the Δ2642 codon loss polymorphism

The region of the polymorphism was amplified from 10 ng of genomic DNA using primers within exon 58, 5' GCTGGGGAACAGCATCACACCC 3' (SEQ ID NO:19) and 5' CCTGGAGTTGACTGGAGACGTG 3' (SEQ ID NO:20), and the following amplification program: 2'@94° C., 30 cycles of 1'@58° C., 1'@72° C., followed by 10'@72° C. The products were displayed on a 6% denaturing urea-polyacrylamide gel. Lanes 1, 3 and 5 contain PCR products from HD heterozygotes of the major haplotype; lanes 2 and 4 contain PCR products from normal individuals bearing other 4p16.3 haplotypes. A1 denotes presence of codon 2642 (112 bp product); A2 denotes absence of codon 2642 (109 bp product).

Figure 21B:
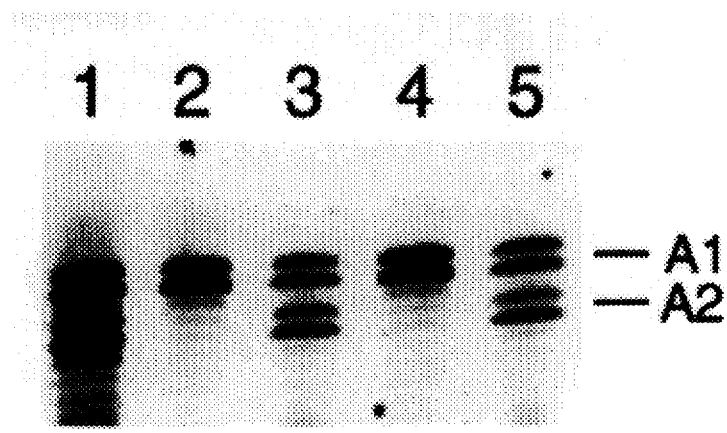
Figure 22:
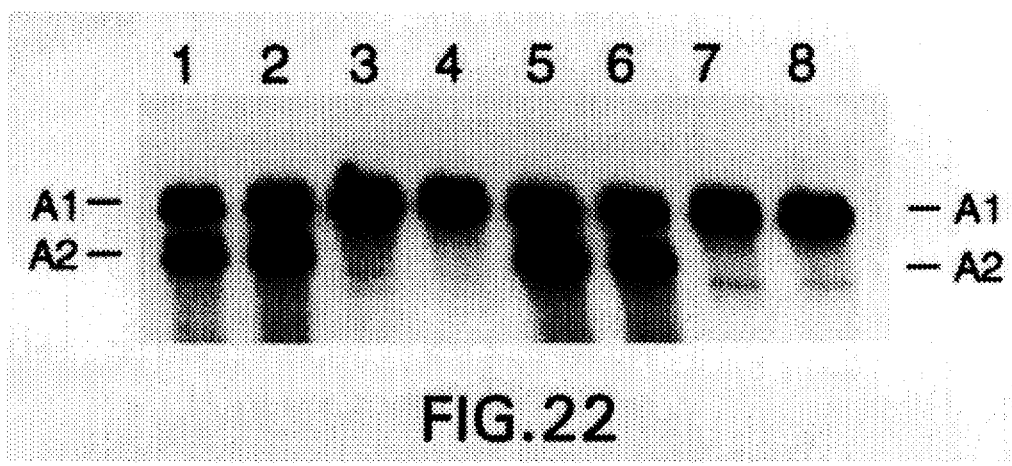
Figure 23A:
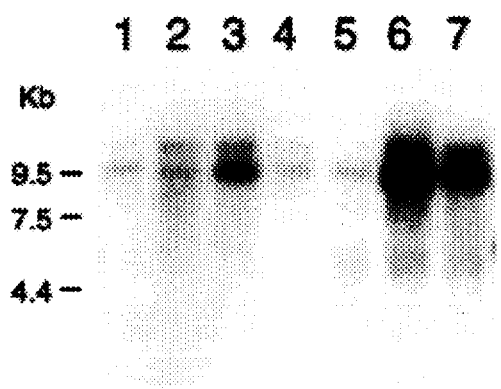
Figure 23B:
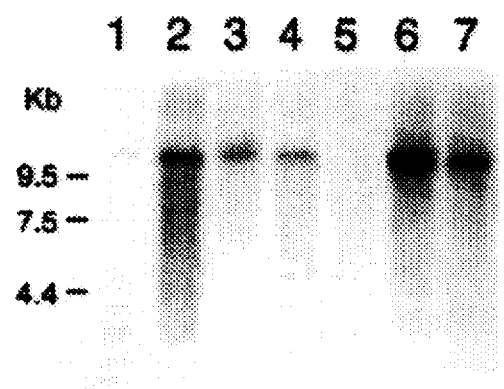
Figure 23C:
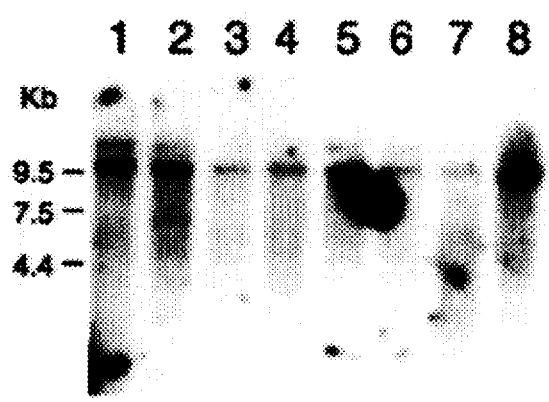
Figure 23D:
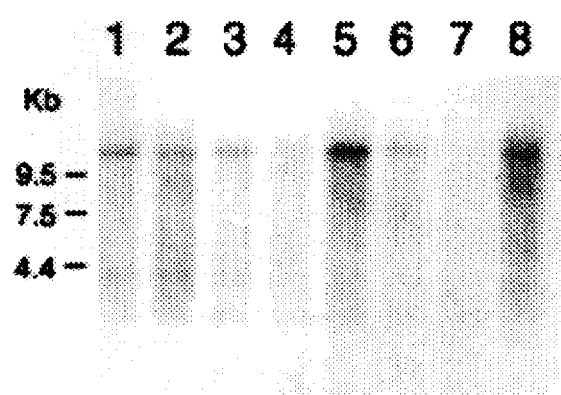

FIG. 22. Expression of both normal and HD alleles in mRNA. First strand cDNA primed with oligo(dT) (lanes 1–4) or an IT15 specific primer (5' CAGGTACTGAGCGAGGAT 3') (SEQ ID NO:21) (lanes 5–8) was amplified using the same primers described in FIG. 21B. The PCR products spanning the Δ2642 codon polymorphism were resolved on a 6% denaturing urea-polyacrylamide gel. Lanes 1,5 and 2,6 represent 2 different HD heterozygotes with the major HD haplotype; lanes 3,7 and 4,8 represent 2 different HD heterozygotes with 2 other HD haplotypes. A1 denotes presence of codon 2642 (112 bp product); A2 denotes the absence of codon 2642 (109 bp product).

FIG. 23. Northern blot survey of HD gene transcripts in adult tissues. Northern blots containing 2 μg of polyA⁺ mRNA from various adult human tissues were hybridized with two probes. Panels A and C were hybridized with coding region 2,841 bp probe made by EcoRI digestion of cDNA clone IT15B. This probe spans nucleotides 2,028 to 4,868 of the published IT15 sequence (MacDonald, M. E. et al., *Cell* 72:971–983 (1993)). Panels B and D represent the same blots hybridized with a 292 bp genomic probe produced by PCR of cosmid L120D5 DNA using primers 5' GGAGAACACAGTCGTCTGTG 3' (SEQ ID NO:22) and 5' CGTGTAAAGTATGTGAATCGC 3' (SEQ ID NO:23). This probe derives from the sequence immediately 3' to the end of the 3'UTR reported in the published IT15 sequence. Panels A and B lanes: 1, heart; 2, brain; 3, placenta; 4, lung; 5, liver; 6, skeletal muscle; 7, kidney; Panels C and D lanes: 1, spleen; 2, thymus; 3, prostrate; 4, testis; 5, ovary; 6, small intestine; 7, colon; 8, peripheral blood leukocyte. Transcript sizes were estimated from RNA size markers as shown.

Figures 24A, 24B:
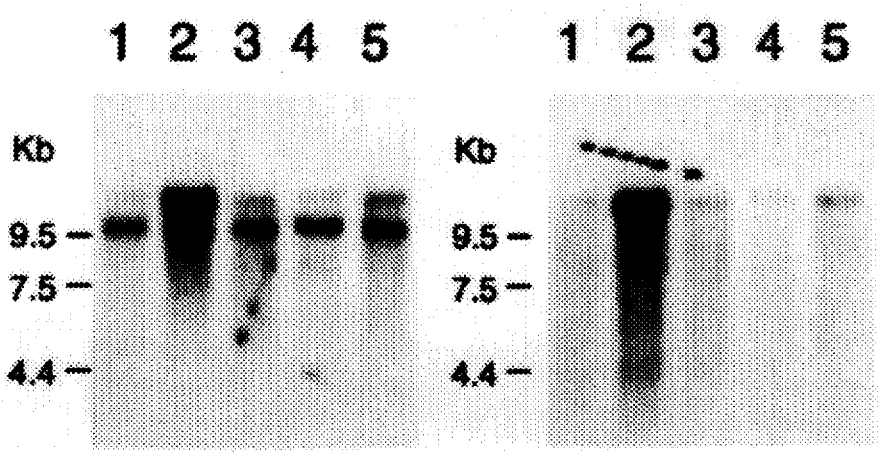

FIG. 24. Northern blot survey of HD gene transcripts in fetal tissues. Northern blot containing 2 ug of polyA⁺ mRNA from various fetal human tissues were hybridized sequentially with the same two probes described in FIG. 4 (left and right, respectively). Lanes: 1, heart; 2, brain; 3, lung; 4, liver; 5, kidney.

Figure 25A:
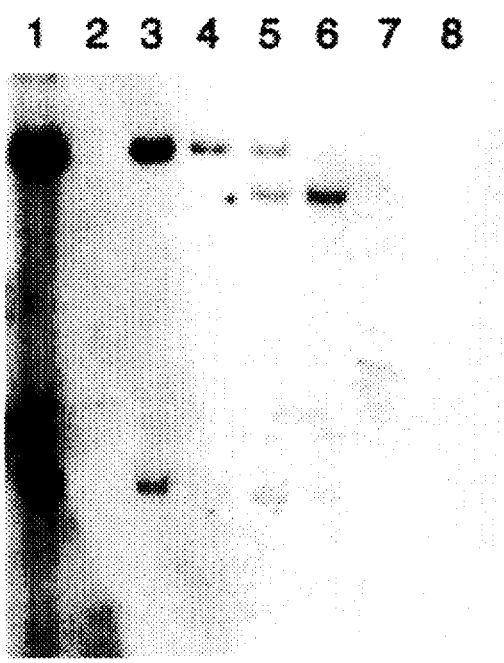
Figure 25B:

FIG. 25. The t(4;12) translocation disrupts the HD gene. Southern blots of HindIII (Panel A) and EcoRI (panel B) digested DNAs were hybridized with a 210 bp probe consisting of all of exon 40 and that portion of exon 39 3' to the EcoRI site contained with this exon. The probe was made by PCR from the cDNA using primers 5' CTTCAACGCTAGAAGAAC 3' (SEQ ID NO:24) and 5' CAGACTTGAAGATGTGGATC 3' (SEQ ID NO:25). Lane 1=normal human genomic lymphoblastoid cell DNA; lane 2 =hamster DNA; lane 3=DNA from human-hamster hybrid HHW416 containing only human chromosome 4; lane 4=DNA from human-hamster hybrid HHW661 containing only a human t(4p15;5p15.1) chromosome; lane 5=DNA from lymphoblast line CV066 from the balanced t(4p16.3;12p13.3) carrier (McKeown, C. et al., *J. Med. Genet.* 24:410–412 (1987)); lane 6=DNA from human-hamster hybrid HHW1071 containing the der(12) from CV066; lane 7=DNA from human-hamster hybrid HHW842 containing a chromosome 4 with an interstitial deletion that removes the entire HD gene; lane 8=DNA from human-hamster hybrid HHW847 containing a t(4;12) chromosome from which all of 4p16.3 is missing (Smith, B. et al., *Am. J. Hum. Genet.* 42:335–344 (1988); Lin, C. S. et al., *Somat. Cell Mol. Genet.* 17:481–488 (1991)). Both EcoRI and HindIII fragments are altered in CV066 and HHW1071. Since exons 39 and 40 reside on the same EcoRI fragment but different HindIII fragments (the small unaltered HindIII fragment is detected by exon 39), the t(4;12) breakpoint must map within the EcoRI fragment but proximal to both exons.

DETAILED DESCRIPTION OF THE INVENTION

In the following description, reference will be made to various methodologies known to those of skill in the art of molecular genetics and biology. Publications and other materials setting forth such known methodologies to which reference is made are incorporated herein by reference in their entireties as though set forth in full.

The IT15 gene described herein is a gene from the proximal portion of the 500 kb segment between human chromosome 4 markers D4S180 and D4S182. The huntingtin gene spans about 210 kb of DNA and encodes a previously undescribed protein of about 348 kDa. The huntingtin reading frame contains a polymorphic (CAG)ₙ trinucleotide repeat with at least 17 alleles in the normal human population, where the repeat number varies from 11 to about 34 CAG copies in such alleles. This is the gene of the human chromosome that, as shown herein, suffers the presence of an unstable, expanded number of CAG trinucleotide repeats in Huntington's disease patients, such that the number of CAG repeats in the huntingtin gene increases to a range of 37 to at least 86 copies. These results are the basis of a conclusion that the huntingtin gene encodes a protein called "huntingtin," and that in such huntingtin gene the increase in the number of CAG repeats to a range of greater than about 37 repeats is the alteration that underlies the dominant phenotype of Huntington's disease. As used herein huntingtin gene is also called the Huntington's disease gene.

It is to be understood that the description below is applicable to any gene in which a CAG repeat within the gene is amplified in an aberrant manner resulting in a change in the regulation, localization, stability or translatability of the mRNA containing such amplified CAG repeat that is transcribed from such gene.

I. Cloning Of Huntingtin DNA And Expression Of Huntingtin Protein

The identification of huntingtin DNA and protein as the altered gene in Huntington's disease patients is exemplified below. In addition to utilizing the exemplified methods and results for the identification of deletions of the huntingtin gene in Huntington's disease patients, and for the isolation of the native human huntingtin gene, the sequence information presented in FIG. 4 represents a nucleic acid and protein sequence, that, when inserted into a linear or circular recombinant nucleic acid construct such as a vector, and used to transform a host cell, will provide copies of huntingtin DNA and huntingtin protein that are useful sources for the native huntingtin DNA and huntingtin protein for the methods of the invention. Such methods are known in the art and are briefly outlined below.

The process for genetically engineering the huntingtin coding sequence, for expression under a desired promoter, is facilitated through the cloning of genetic sequences which are capable of encoding such huntingtin protein. Such cloning technologies can utilize techniques known in the art for construction of a DNA sequence encoding the huntingtin protein, such as, for example, polymerase chain reaction technologies utilizing the huntingtin sequence disclosed herein to isolate the huntingtin gene anew, or an allele thereof that varies in the number of CAG repeats in such gene, or polynucleotide synthesis methods for constructing the nucleotide sequence using chemical methods. Expression of the cloned huntingtin DNA provides huntingtin protein.

As used herein, the term "genetic sequences" is intended to refer to a nucleic acid molecule of DNA or RNA, preferably DNA. Genetic sequences that are capable of being operably linked to DNA encoding huntingtin protein, so as to provide for its expression and maintenance in a host cell are obtained from a variety of sources, including commercial sources, genomic DNA, cDNA, synthetic DNA, and combinations thereof. Since the genetic code is universal, it is to be expected that any DNA encoding the huntingtin amino acid sequence of the invention will be useful to express huntingtin protein in any host, including prokaryotic (bacterial) hosts, eukaryotic hosts (plants, mammals (especially human), insects, yeast, and especially any cultured cell populations).

If it is desired to select anew a gene encoding huntingtin from a library that is thought to contain a huntingtin gene, such library can be screened and the desired gene sequence identified by any means which specifically selects for a sequence coding for the huntingtin gene or expressed huntingtin protein such as, for example, a) by hybridization (under stringent conditions for DNA:DNA hybridization) with an appropriate huntingtin DNA probe(s) containing a sequence specific for the DNA of this protein, such sequence being that provided in FIG. 4 or a functional derivative thereof that is, a shortened form that is of sufficient length to identify a clone containing the huntingtin gene, or b) by hybridization-selected translational analysis in which native huntingtin mRNA which hybridizes to the done in question is translated in vitro and the translation products are further characterized for the presence of a biological activity of huntingtin, or c) by immunoprecipitation of a translated huntingtin protein product from the host expressing the huntingtin protein.

When a human allele does not encode the identical sequence to that of FIG. 4, it can be isolated and identified as being huntingtin DNA using the same techniques used herein, and especially PCR techniques to amplify the appropriate gene with primers based on the sequences disclosed herein. Many polymorphic probes useful in the fine localization of genes on chromosome 4 are known and available (see, for example, "ATCC/NIH Repository Catalogue of Human and Mouse DNA Probes and Libraries," fifth edition, 1991, pages 4–6. For example, a useful D4S10 probe is clone designation pTV20 (ATCC 57605 and 57604); H5.52 (ATCC 61107 and 61106) and F5.53 (ATCC 61108).

Human chromosome 4-specific libraries are known in the art and available from the ATCC for the isolation of probes ("ATCC/NIH Repository Catalogue of Human and Mouse DNA Probes and Libraries," fifth edition, 1991, pages 72–73), for example, LL04NS01 and LL04NS02 (ATCC 57719 and ATCC57718) are useful for these purposes.

It is not necessary to utilize the exact vector constructs exemplified in the invention; equivalent vectors can be constructed using techniques known in the art. For example, the sequence of the huntingtin DNA is provided herein, (see FIG. 4) and this sequence provides the specificity for the huntingtin gene; it is only necessary that a desired probe contain this sequence, or a portion thereof sufficient to provide a positive indication of the presence of the huntingtin gene.

Huntingtin genomic DNA may or may not include naturally occurring introns. Moreover, such genomic DNA can be obtained in association with the native huntingtin 5' promoter region of the gene sequences and/or with the native huntingtin 3' transcriptional termination region.

Such huntingtin genomic DNA can also be obtained in association with the genetic sequences which encode the 5' non-translated region of the huntingtin mRNA and/or with the genetic sequences which encode the huntingtin 3' non-translated region. To the extent that a host cell can recognize the transcriptional and/or translational regulatory signals associated with the expression of huntingtin mRNA and protein, then the 5' and/or 3' non-transcribed regions of the native huntingtin gene, and/or, the 5' and/or 3' non-translated regions of the huntingtin mRNA can be retained and employed for transcriptional and translational regulation.

Genomic DNA can be extracted and purified from any host cell, especially a human host cell possessing chromosome 4, by means well known in the art. Genomic DNA can be shortened by means known in the art, such as physical shearing or restriction digestion, to isolate the desired huntingtin gene from a chromosomal region that otherwise would contain more information than necessary for the utilization of the huntingtin gene in the hosts of the invention. For example, restriction digestion can be utilized to cleave the full-length sequence at a desired location. Alternatively, or in addition, nucleases that cleave from the 3'-end of a DNA molecule can be used to digest a certain sequence to a shortened form, the desired length then being identified and purified by polymerase chain reaction technologies, gel electrophoresis, and DNA sequencing. Such nucleases include, for example, Exonuclease III and Bal31. Other nucleases are well known in the art.

Alternatively, if it is known that a certain host cell population expresses huntingtin protein, then cDNA techniques known in the art can be utilized to synthesize a cDNA copy of the huntingtin mRNA present in such population.

For cloning the genomic or cDNA nucleic acid that encodes the amino acid sequence of the huntingtin protein into a vector, the DNA preparation can be ligated into an appropriate vector. The DNA sequence encoding huntingtin protein can be inserted into a DNA vector in accordance with conventional techniques, including blunt-ending or staggered-ending termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are well known in the art.

When the huntingtin DNA coding sequence and an operably linked promoter are introduced into a recipient eukaryotic cell (preferably a human host cell) as a non-replicating, non-integrating, molecule, the expression of the encoded huntingtin protein can occur through the transient (nonstable) expression of the introduced sequence.

Preferably the coding sequence is introduced on a DNA molecule, such as a closed circular or linear molecule that is capable of autonomous replication. If integration into the host chromosome is desired, it is preferable to use a linear molecule. If stable maintenance of the huntingtin gene is desired on an extrachromosomal element, then it is preferable to use a circular plasmid form, with the appropriate plasmid element for autonomous replication in the desired host.

The desired gene construct, providing a gene coding for the huntingtin protein, and the necessary regulatory elements operably linked thereto, can be introduced into a desired host cells by transformation, transfection, or any method capable of providing the construct to the host cell. A marker gene for the detection of a host cell that has accepted the huntingtin DNA can be on the same vector as the huntingtin DNA or on a separate construct for co-transformation with the huntingtin coding sequence construct into the host cell. The nature of the vector will depend on the host organism.

Suitable selection markers will depend upon the host cell. For example, the marker can provide biocide resistance, e.g., resistance to antibiotics, or heavy metals, such as copper, or the like.

Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species.

When it is desired to use *S. cerevisiae* as a host for a shuttle vector, preferred *S. cerevisiae* yeast plasmids include those containing the 2-micron circle, etc., or their derivatives. Such plasmids are well known in the art and are commercially available.

Oligonucleotide probes specific for the huntingtin sequence can be used to identify clones to huntingtin and can be designed de novo from the knowledge of the amino acid sequence of the protein as provided herein in FIG. 4 or from the knowledge of the nucleic acid sequence of the DNA encoding such protein as provided herein in FIG. 4 or of a related protein. Alternatively, antibodies can be raised against the huntingtin protein and used to identify the presence of unique protein determinants in transformants that express the desired cloned protein.

A nucleic acid molecule, such as DNA, is said to be "capable of expressing" a huntingtin protein if that nucleic acid contains expression control sequences which contain transcriptional regulatory information and such sequences are "operably linked" to the huntingtin nucleotide sequence which encode the huntingtin polypeptide.

An operable linkage is a linkage in which a sequence is connected to a regulatory sequence (or sequences) in such a way as to place expression of the sequence under the influence or control of the regulatory sequence. If the two DNA sequences are a coding sequence and a promoter region sequence linked to the 5' end of the coding sequence, they are operably linked if induction of promoter function results in the transcription of mRNA encoding the desired protein and if the nature of the linkage between the two DNA sequences does not (1) result in the introduction of a frame-shift mutation, (2) interfere with the ability of the expression regulatory sequences to direct the expression of the protein, antisense RNA, or (3) interfere with the ability of the DNA template to be transcribed. Thus, a promoter region would be operably linked to a DNA sequence if the promoter was capable of effecting transcription of that DNA sequence.

The precise nature of the regulatory regions needed for gene expression can vary between species or cell types, but shall in general include, as necessary, 5' non-transcribing and 5' non-translating (non-coding) sequences involved with initiation of transcription and translation respectively, such as the TATA box, capping sequence, CAAT sequence, and the like, with those elements necessary for the promoter sequence being provided by the promoters of the invention. Such transcriptional control sequences can also include enhancer sequences or upstream activator sequences, as desired.

The vectors of the invention can further comprise other operably linked regulatory elements such as DNA elements which confer antibiotic resistance, or origins of replication for maintenance of the vector in one or more host cells.

In another embodiment, especially for maintenance of the vectors of the invention in prokaryotic cells, or in yeast *S. cerevisiae* cells, the introduced sequence is incorporated into a plasmid or viral vector capable of autonomous replication in the recipient host. Any of a wide variety of vectors can be employed for this purpose. In Bacillus hosts, integration of the desired DNA can be necessary.

Expression of a protein in eukaryotic hosts such as a human cell requires the use of regulatory regions functional in such hosts. A wide variety of transcriptional and translational regulatory sequences can be employed, depending upon the nature of the host. Preferably, these regulatory signals are associated in their native state with a particular gene which is capable of a high level of expression in the specific host cell, such as a specific human tissue type. In eukaryotes, where transcription is not linked to translation, such control regions may or may not provide an initiator methionine (AUG) codon, depending on whether the cloned sequence contains such a methionine. Such regions will, in general, include a promoter region sufficient to direct the initiation of RNA synthesis in the host cell.

If desired, the non-transcribed and/or non-translated regions 3' to the sequence coding for the huntingtin protein can be obtained by the above-described cloning methods. The 3'-non-transcribed region of the native human huntingtin gene can be retained for its transcriptional termination regulatory sequence elements, or for those elements which direct polyadenylation in eukaryotic cells. Where the native expression control sequences signals do not function satisfactorily in a host cell, then sequences functional in the host cell can be substituted.

It may be desired to construct a fusion product that contains a partial coding sequence (usually at the amino terminal end) of a first protein or small peptide and a second coding sequence (partial or complete) of the huntingtin protein at the carboxyl end. The coding sequence of the first protein can, for example, function as a signal sequence for secretion of the huntingtin protein from the host cell. Such first protein can also provide for tissue targeting or localization of the huntingtin protein if it is to be made in one cell type in a multicellular organism and delivered to another cell type in the same organism. Such fusion protein sequences can be designed with or without specific protease sites such that a desired peptide sequence is amenable to subsequent removal.

The expressed huntingtin protein can be isolated and purified from the medium of the host in accordance with conventional conditions, such as extraction, precipitation, chromatography, affinity chromatography, electrophoresis, or the like. For example, affinity purification with anti-huntingtin antibody can be used. A protein having the amino acid sequence shown in FIG. 3 can be made, or a shortened peptide of this sequence can be made, and used to raised antibodies using methods well known in the art. These antibodies can be used to affinity purify or quantitate huntingtin protein from any desired source.

If it is necessary to extract huntingtin protein from the intracellular regions of the host cells, the host cells can be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation.

II. Use Of Huntingtin For Diagnostic And Treatment Purposes

It is to be understood that although the following discussion is specifically directed to human patients, the teachings are also applicable to any animal that expresses huntingtin and in which alteration of huntingtin, especially the amplification of CAG repeat copy number, leads to a defect in huntingtin gene (structure or function) or huntingtin protein (structure or function or expression), such that clinical manifectations such as those seen in Huntington's disease patients are found.

It is also to be understood that the methods referred to herein are applicable to any patient suspected of developing/ having Huntington's disease, whether such condition is manifest at a young age or at a more advanced age in the patient's life. It is also to be understood that the term "patient" does not imply that symptoms are present, and patient includes any individual it is desired to examine or treat using the methods of the invention.

The diagnostic and screening methods of the invention are especially useful for a patient suspected of being at risk for developing Huntington's disease based on family history, or a patient in which it is desired to diagnose or eliminate the presence of the Huntington's disease condition as a causative agent behind a patient's symptoms.

It is to be understood that to the extent that a patient's symptoms arise due to the alteration of the CAG repeat copy numbers in the huntingtin gene, even without a diagnosis of Huntington's disease, the methods of the invention can identify the same as the underlying basis for such condition.

According to the invention, presymptomatic screening of an individual in need of such screening for their likelihood of developing Huntington's disease is now possible using DNA encoding the huntingtin gene of the invention, and specifically, DNA having the sequence of the normal human huntingtin gene. The screening method of the invention allows a presymptomatic diagnosis, including prenatal diagnosis, of the presence of an aberrant huntingtin gene in such individuals and thus an opinion concerning the likelihood that such individual would develop or has developed Huntington's disease or symptoms thereof. This is especially valuable for the identification of carriers of altered huntingtin gene alleles where such alleles possess an increased number of CAG repeats in their huntingtin gene, for example, from individuals with a family history of Huntington's disease. Especially useful for the determination of the number of CAG repeats in the patient's huntingtin gene is the use of PCR to amplify such region or DNA blotting techniques.

For example, in the method of screening, a tissue sample would be taken from such individual, and screened for (I) the presence of the "normal" human huntingtin gene, especially for the presence of a "normal" range of 11–34 CAG copies in such gene. The human huntingtin gene can be characterized based upon, for example, detection of restriction digestion patterns in 'normal' versus the patient's DNA, including RFLP analysis, using DNA probes prepared against the huntingtin sequence (or a functional fragment thereof) taught in the invention. Similarly, huntingtin mRNA can be characterized and compared to normal huntingtin mRNA (a) levels and/or (b) size as found in a human population not at risk of developing Huntington's disease using similar probes. Lastly, huntingtin protein can be (a) detected and/or (b) quantitated using a biological assay for huntingtin, for example, using an immunological assay and anti-huntingtin antibodies. When assaying huntingtin protein, the immunological assay is preferred for its speed. Methods of making antibody against the huntingtin are well known in the art.

An (1) aberrant huntingtin DNA size pattern, such as an aberrant huntingtin RFLP, and/or (2) aberrant huntingtin mRNA sizes or levels and/or (3) aberrant huntingtin protein levels would indicate that the patient has developed or is at risk for developing a huntingtin-associated symptom such as a symptom associated with Huntington's disease.

The screening and diagnostic methods of the invention do not require that the entire huntingtin DNA coding sequence be used for the probe. Rather, it is only necessary to use a fragment or length of nucleic acid that is sufficient to detect the presence of the huntingtin gene in a DNA preparation from a normal or affected individual, the absence of such gene, or an altered physical property of such gene (such as a change in electrophoretic migration pattern).

Prenatal diagnosis can be performed when desired, using any known method to obtain fetal cells, including amniocentesis, chorionic villous sampling (CVS), and fetoscopy. Prenatal chromosome analysis can be used to determine if the portion of chromosome 4 possessing the normal huntingtin gene is present in a heterozygous state, and PCR amplification or DNA blotting utilized for estimating the size of the CAG repeat in the huntingtin gene.

The huntingtin DNA can be synthesized, especially, the CAG repeat region can be amplified and, if desired, labeled with a radioactive or nonradioactive reporter group, using techniques known in the art (for example, see Eckstein, F., Ed., *Oligonucleotides and Analogues: A Practical Approach*, IRS Press at Oxford University Press, New York, 1992); and Kricka, L. J., Ed., *Nonisotopic DNA Probe Techniques*, Academic Press, San Diego, (1992)).

In one method of treating Huntington's disease in a patient in need of such treatment, functional huntingtin DNA is provided to the cells of such patient, preferably prior to such symptomatic state that indicates the death of many of the patient's neuronal cells which it is desired to target with the method of the invention. The replacement huntingtin DNA is provided in a manner and amount that permits the expression of the huntingtin protein provided by such gene, for a time and in a quantity sufficient to treat such patient. Many vector systems are known in the art to provide such delivery to human patients in need of a gene or protein missing from the cell. For example, adenovirus or retrovirus systems can be used, especially modified retrovirus systems and especially herpes simplex virus systems. Such methods are provided for, in, for example, the teachings of Breakefield, X. A. et al., *The New Biologist* 3:203–218 (1991); Huang, Q. et al., *Experimental Neurology* 115:303–316 (1992), WO93/03743 and WO90/09441 each incorporated herein fully by reference. Methods of antisense strategies are known in the art (see, for example, *Antisense Strategies*, Baserga, R. et al., Eds., Annals of the New York Academy of Sciences, volume 660, 1992).

In another method of treating Huntington's disease in a patient in need of such treatment, a gene encoding an expressible sequence that transcribes huntingtin antisense RNA is provided to the cells of such patient, preferably prior to such symptomatic state that indicates the death of many of the patient's neuronal cells which it is desired to target with the method of the invention. The replacement huntingtin antisense RNA gene is provided in a manner and amount that permits the expression of the antisense RNA provided by such gene, for a time and in a quantity sufficient to treat such patient, and especially in an amount to inhibit translation of the aberrant huntingtin mRNA that is being expressed in the cells of such patient. As above, many vector systems are known in the art to provide such delivery to human patients in need of a gene or protein which is altered in the patients' cells. For example, adenovirus or retrovirus systems can be used, especially modified retrovirus systems and especially herpes simplex virus systems. Such methods are provided for, in, for example, the teachings of Breakefield, X. A. et al., *The New Biologist* 3:203–218 (1991); Huang, Q. et al., *Experimental Neurology* 115:303–316 (1992), WO93/03743 and WO90/09441 each incorporated herein fully by reference.

Delivery of a DNA sequence encoding a functional huntingtin protein, such as the amino acid encoding sequence of FIG. 4, will effectively replace the altered huntingtin gene of the invention, and inhibit, and/or stop and/or regress the symptoms that are the result of the interference to huntingtin gene expression due to an increased number of CAG repeats, such as 37 to 86 repeats in the huntingtin gene as compared to the 11–34 CAG repeats found in human populations not at risk for developing Huntington's disease.

Because Huntington's disease is characterized by a loss of neurons that is most severe in the caudate and putamen regions of the brain, the method of treatment of the invention is most effective when the replacement huntingtin gene is provided to the patient early in the course of the disease, prior to the loss of many neurons due to cell death. For that reason, presymptomatic screening methods according to the invention are important in identifying those individuals in need of treatment by the method of the invention, and such treatment preferably is provided while such individual is presymptomatic.

In a further method of treating Huntington's disease in a patient in need of such treatment such method provides an antagonist to the aberrant huntingtin protein in the cells of such patient.

Although the method is specifically described for DNA-DNA probes, it is to be understood that RNA possessing the same sequence information as the DNA of the invention can be used when desired.

For diagnostic assays, huntingtin antibodies are useful for quantitating and evaluating levels of huntingtin protein, and are especially useful in immunoassays and diagnostic kits.

In another embodiment, the present invention relates to an antibody having binding affinity to an huntingtin polypeptide, or a binding fragment thereof. In a preferred embodiment, the polypeptide has the amino acid sequence set forth in SEQ ID NO:6, or mutant or species variation thereof, or at least 7 contiguous amino acids thereof (preferably, at least 10, 15, 20, or 30 contiguous amino acids thereof). Those which bind selectively to huntingtin would be chosen for use in methods which could include, but should not be limited to, the analysis of altered huntingtin expression in tissue containing huntingtin.

The antibodies of the present invention include monoclonal and polyclonal antibodies, as well fragments of these antibodies. Antibody fragments which contain the idiotype of the molecule can be generated by known techniques. For example, such fragments include but are not limited to: the F(ab')$_2$ fragment; the Fab' fragments, and the Fab fragments.

Of special interest to the present invention are antibodies to huntingtin (or their functional derivatives) which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988). General reviews of "humanized" chimeric antibodies are provided by Morrison, S. L. (*Science*, 229:1202–1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988)).

In another embodiment, the present invention relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1–21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the an can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.* 18:315 (1970); Bayer et al., *Meth. Enzym.* 62:308 (1979); Engval et al., *Immunol.* 109:129 (1972); Goding, *J. Immunol Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10 (1986); Jacoby et al., *Meth. Enzym.* 34 Academic Press, New York (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In *Synthetic Peptides, A User's Guide*, W. H. Freeman, New York, pp. 289–307 (1992), and Kaspczak et al., *Biochemistry* 28:9230-8 (1989).

Anti-peptide peptides can be generated in one of two fashions. First, the anti-peptide peptides can be generated by replacing the basic amino acid residues found in the huntingtin peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

The manner and method of carrying out the present invention can be more fully understood by those of skill by reference to the following examples, which examples are not intended in any manner to limit the scope of the present invention or of the claims directed thereto.

EXAMPLES

The gene causing Huntington's disease has been mapped in 4p16.3 but has previously eluded identification. The invention uses haplotype analysis of linkage disequilibrium to spotlight a small segment of 4p16.3 as the likely location of the defect. A new gene, huntingtin (ITIS), isolated using cloned "trapped" exons from a cosmid contig of the target area contains a polymorphic trinucleotide repeat that is expanded and unstable on HD chromosomes. A $(CAG)_n$ repeat longer than the normal range of about 11 to about 34 copies was observed on HD chromosomes from all 75 disease families examined, comprising a wide range of ethnic backgrounds and 4p16.3 haplotypes. The $(CAG)_n$ repeat, which varies from 37 to at least 86 copies on HD chromosomes appears to be located within the coding sequence of a predicted about 348 kDa protein that is widely expressed but unrelated to any known gene. Thus, the Huntington's disease mutation involves an unstable DNA segment, similar to those described in fragile X syndrome and myotonic dystrophy, acting in the context of a novel 4p16.3 gene to produce a dominant phenotype.

The following protocols and experimental details are referenced in the examples that follow.

HD Cell Lines. Lymphoblast cell lines from HD families of varied ethnic backgrounds used for genetic linkage and disequilibrium studies (Conneally et al., *Genomics* 5:304–308 (1989); MacDonald et al., *Nature Genet.* 1:99–103 (1992)) have been established (Anderson and Gusella, *In Vitro* 20:856–858 (1984)) in the Molecular Neurogenetics Unit, Massachusetts General Hospital, over the past 13 years. The Venezuelan HD pedigree is an extended kindred of over 10,000 members in which all affected individuals have inherited the HD gene from a common founder (Gusella et al., *Nature* 306:234–238 (1983); Gusella et al., *Science* 225:1320–1326 (1984); Wexler et al., *Nature* 326:194–197 (1987)).

DNA/RNA Blotting. DNA was prepared from cultured cells and DNA blots prepared and hybridized as described (Gusella et al., *Proc. Natl. Acad. Sci. USA* 76:5239–5243 (1979); Gusella et al., *Nature* 306:234–238 (1983)). RNA was prepared and Northern blotting performed as described in Taylor et al., *Nature Genet.* 3:223–227 (1992).

Construction of Cosmid Contig. The initial construction of the cosmid contig was by chromosome walking from cosmids L19 and BJ56 (Allitto et al., *Genomics* 9:104–112 (1991); Lin et al., *Somat. Cell Mol. Genet.* 17:481–488 (1991)). Two libraries were employed, a collection of Alu-positive cosmids from the reduced cell hybrid H39-8C10 (Whaley et al., *Som. Cell Mol. Genet.* 17:83–91 (1991)) and an arrayed flow-sorted chromosome 4 cosmid library (NM87545) provided by the Los Alamos National Laboratory. Walking was accomplished by hybridization of whole cosmid DNA, using suppression of repetitive and vector sequences, to robot-generated high density filter grids (Nizetic, D. et al., *Proc. Natl. Acad. Sci. USA* 88:3233–3237 (1991); Lehrach, H. et al., in *Genome Analysis: Genetic and Physical Mapping*, Volume 1, Davies, K. E. et al., Ed., Cold Spring Harbor Laboratory Press, 1991, pp. 39–81). Cosmids L1C2, L69F7, L228B6 and L83D3 were first identified by hybridization of YAC clone YGA2 to the same arrayed library (Bates et al., *Nature Genet.* 1:180–187 (1992); Baxendale et al., *Nucleic Acids Res.* 19:6651 (1991)). HD cosmid GUS72-2130 was isolated by standard screening of a GUS72 cosmid library using a single-copy probe. Cosmid overlaps were confirmed by a combination of clone-to-clone and clone-to-genomic hybridizations, single-copy probe hybridizations and restriction mapping.

cDNA Isolation and Characterization. Exon probes were isolated and cloned as described (Buckler et al., *Proc. Natl. Acad. Sci. USA* 88:4005–4009 (1991)). Exon probes and cDNAs were used to screen human lambda ZAPII cDNA libraries constructed from adult frontal cortex, fetal brain, adenovirus transformed retinal cell line RCA, and liver RNA. cDNA clones, PCR products and trapped exons were sequenced as described (Sanger et al., *Proc. Natl. Acad. Sci. USA* 74:5463–5467 (1977)). Direct cosmid sequencing was performed as described (McClatchey et al., *Hum. Mol. Genet.* 1:521–527 (1992)). Database searches were performed using the BLAST network service of National Center for Biotechnology Information (Altschul et al., *J. Mol. Biol.* 215:403–410 (1990)).

PCR Assay of the $(CAG)_n$ Repeat. Genomic primers (SEQ ID NO:3 and SEQ ID NO:4) flanking the $(CAG)_n$ repeat are:

5' ATG AAG GCC TTC GAG TCC CTC AAG TCC TTC 3' and

5' AAA CTC ACG GTC GGT GCA GCG GCT CCT CAG 3'.

PCR amplification was performed in a reaction volume of 25 µl using 50 ng of genomic DNA, 5 µg of each primer, 10 mM Tris, pH 8.3, 5 mM KCl, 2 mM $MgCl_2$, 200 µM dNTPs, 10% DMSO, 0.1 unit Perfectmatch (Stratagene), 2.5 µCi $^{32}$P-dCTP (Amersham) and 1.25 units Taq polymerase (Boehringer Mannheim). After heating to 94° C. for 1.5 minutes, the reaction mix was cycled according to the following program: 40×[1'@94° C.;1'@60° C.;2'@72° C.]. 5 µl of each PCR reaction was diluted with an equal volume of 95% formamide loading dye and heat denatured for 2 min. at 95° C. The products were resolved on 5% denaturing polyacrylamide gels. The PCR product from this reaction using cosmid L191F1 $(CAG_{18})$ as template was 247 bp. Allele sizes were estimated relative to a DNA sequencing ladder, the PCR products from sequenced cosmids, and the invariant background bands often present on the gel. Estimates of allelic variation were obtained by typing unrelated individuals of largely Western European ancestry, and normal parents of affected HD individuals from various pedigrees.

Typing of HD and normal chromosomes in Examples 5–8. HD chromosomes were derived from symptomatic individuals and "at risk" individuals known to be gene carriers by linkage marker analysis. All HD chromosomes were from members of well-characterized HD families of varied ethnic backgrounds used previously for genetic linkage and disequilibrium studies (MacDonald, M. E., et al., *Nature Genet.* 1:99–103 (1992); Conneally, P. M., et al., *Genomics* 5:304–308 (1989)). Three of the 150 families used were large pedigrees, each descended from a single founder. The large Venezuelan HD pedigree is an extended kindred of over 13,000 members from which we typed 75 HD chromosomes (Gusella, J. F., et al., *Nature* 306:234–238 (1983); Wexler, N. S., et al., *Nature* 326:194–197 (1987)). Two other large families that have been described previously as Family Z and Family D, provided 25 and 35 HD chromosomes, respectively (Folstein, S. E., et al., *Science* 229:776–779 (1985)). Normal chromosomes were taken from married-ins in the HD families and from unrelated normal individuals from non-HD families. The DNA tested for all individuals except four was prepared from lymphoblastoid cell lines or fresh blood (Gusella, J. F., et al., *Nature* 306:234–238 (1983); Anderson and Gusella, *In Vitro* 20:856–858 (1984)). In the exceptional cases, DNA was prepared from frozen cerebellum. No difference in the characteristics of the PCR products were observed between lymphoblastoid, fresh blood, or brain DNAs. For five members of the Venezuelan pedigree aged 24–30, we also prepared DNA by extracting pelleted sperm from semen samples. The length of the HD gene $(CAG)_n$ repeat for all DNAs was assessed using polymerase chain reaction amplification.

Statistical analysis as set forth in Examples 5–8. Associations between repeat lengths and onset age were assessed by Pearson correlation coefficient and by multivariate regression to assess higher order associations. Comparisons of the distributions of repeat length for all HD chromosomes and those for individual families were made by analysis of variance and t-test contrasts between groups. The 95% confidence bands were computed around the regression line utilizing the general linear models procedure of SAS (SAS Institute Inc., SAS/STAT User's Guide, Version 6, Fourth Edition, Volume 2 (SAS Institute Inc., Cary, N.C., pp. 846, 1989)).

Hybridization as Set Forth in Example 9. Northern blots (Clontech polyA$^+$) were hybridized with $^{32}$P-labeled (Feinberg et al., *Anal. Biochem.* 137:266–267 (1984)) human cDNA clone IT15B.1 (The Huntington's Disease Collaborative Research Group, *Cell* 72:971–983 (1993)) spanning nt 5345–10366 of the composite IT15 cDNA sequence (GenBank L12392). Hybridization conditions were: 50% formamide, 10% dextran sulfate, 0.8M NaCl, 5× Denhardt's, 50 mM Tris pH 7.5, 0.5% SDS, 100 µg/ml sheared single stranded fish DNA and 0.1% sodium pyrophosphate. Filters were hybridized for 48 hours at 42° C., then washed in 0.5× SSC, 0.1% SDS at 65° C.

The PCC4 embryonal carcinoma phage cDNA library (Stratagene) was hybridized with a pool of $^{32}$P-labeled (Feinberg et al., *Anal. Biochem.* 137:266–267 (1984)) human PCR and cDNA probes representing nt 933–1899 and 3028–10366. The 129 genomic phage library was screened similarly using a pair of probes flanking the CAG and CCG repeats prepared by PCR amplification from PCC4-8. The following primer pairs were used to amplify segments 5' and 3' to the repeats, respectively: primer set 1, 5'GAAAAGCTGATGAAGGCT3' (SEQ ID NO: 7) and 5'CTGCTGAAACGACTTGAG3' (SEQ ID NO: 8); primer set 2, 5'CACCGCCGCTGCCAGGTC3' (SEQ ID NO: 9) and 5'GGTCGGTGCAGCGGTTCC3' (SEQ ID NO: 10). Hybridization and washing were performed as above except 40% formamide, 1M NaCl, and 1× Denhardt's were used and washing was at room temperature.

DNA Sequencing as Set Forth in Example 9. Double stranded cDNA clones (1 µg), the 129-1 genomic phage clone (40 µg) and six pBSKII subclones (1 µg) of PCR product from *M. spretus* were sequenced by dideoxy chain termination (Sanger et al., *Proc. Natl. Acad. Sci. USA* 74:5463–5467 (1977) using custom primers (Biosearch Cyclone) and 7-deazaguanosine/sequenase 2.0 (USB). Sequence comparisons with the human gene were performed using the GCG package (Genetics Computer Group, Program Manual for the GCG Package, Version Apr. 7, 1991, 575 Science Drive, Madison, Wisc. (1991)).

Polymorphism Analysis as Set Forth in Example 9. Genomic mouse DNA (200 ng) was amplified using the following primers flanking the CAG-CCG repeat region: 5'CTGATGAAGGCTTTCGAGTCGCTCAAGTCG3' (SEQ ID NO: 11) and 5'CCTTCTTTGGTCGGTGCAGCG-GTTCCTCTG3' (SEQ ID NO: 12). Reaction conditions were 200 µM dNTPs 10% DMSO, 1 µCi $^{32}$P dATP, 2 units Taq polymerase (Boehringer/Mannheim) and the buffer supplied by the manufacturer. The cycling program was: 1×2'@94° C.; 30× (1'@94° C.; 1'@60° C.; 1'@72° C.). Labeled PCR products were displayed on 6% denaturing polyacrylamide gels.

For subcloning of the M. spretus PCR product the above primers were resynthesized with (CUA)4 and (CAU)4, respectively on the 5' ends. After amplification, the product was cut from low-melt agarose and subcloned using uracil DNA glycosylase (UDG) (gibco/BRL) into pBSKII modified by digestion with EcoRV and PCR amplification using primers 5'AGUAGUAGUAGAUCAAGCTTATC-GATACC3' (SEQ ID NO: 13) and 5'AUGAUGAUGAUGAUCGAATTCCTGCAGCC3' (SEQ ID NO: 14).

Cell Lines as Set Forth in Example 10. Cell lines from normal individuals, from HD heterozygotes and homozygotes and from the balanced t(4;12) carrier were established by EBV transformation of blood lymphocytes (Anderson & Gusella, In Vitro 20:856–858 (1984)). Somatic cell hybrids have been described previously (Smith, B. et al., Am. J. Hum. Genet. 42:335–344 (1988); Lin, C. S. et al., Somat. Cell Mol. Genet. 17:481–488 (1991)).

Exon Amplification as Set Forth in Example 10. The exon amplification procedure was used to isolate coding sequences from a contig cosmid spanning the location of the HD gene (Baxendale, S. et al., Nature Genet. 4:181–186 (1993)). Exon products were obtained from either BamHI-BglII digests cloned into the first generation pSPL1 vector or by BamHI-BglII or PstI digests cloned into the second generation pSPL3 as described (Buckler, A. J. et al., Proc. Natl. Acad. Sci. USA 88:4005–4009 (1991)). PCR amplified exon products were cloned into pBSKII and sequenced using the double stranded template by dideoxy chain termination (Sanger & Coulson, Proc. Natl. Acad. Sci. USA 74:5463–5467 (1977)).

Exon-Intron Structure as Set Forth in Example 10. Exon-intron boundaries were sequenced directly from cosmid DNA using specific primers designed from the IT15 cDNA (McClatchey, A. I., Hum. Mol. Genet. 1:521–527 (1992)). Placement of the boundaries was achieved by comparison of the genomic and cDNA sequences. Some exon-intron boundaries were confirmed by sequencing of random cosmid subclones. To place exons on the physical map, 60 ng of two oligomers (21–23 base pairs each) corresponding to sequences at the edges of each exon were end-labeled with γ-$^{32}$-dATP using T4 polynucleotide kinase, and were hybridized independently at 42° C. to nylon filter membrane Southern blots of cosmid DNAs digest with EcoRI, followed by washing in 6× SSC at room temperature for 15 minutes (Gusella, J. F. et. al., Nature 306:234–238 (1983)). Oligonucleotides for PCR, DNA sequencing and hybridization were synthesized using an automated DNA synthesizer (Applied Biosystems).

Blot Analyses as Set Forth in Example 10. DNA was prepared from cultured cells and Southern blots were pre-pared and hybridized as described (Gusella, J. F. et al., Nature 306:234–238 (1983); Gusella, J. F. et al., Proc. Natl. Acad. Sci. USA 76:5239–5243 (1979)). Northern blots were purchased from Clontech Laboratories, Inc. and were hybridized using the conditions provided by the manufacturer. Probes for Southern and Northern analyses were labeled with α-$^{32}$-dATP by the random priming method (Feinberg & Vogelstein, Anal. Biochem. 137:266–267 (1984)).

Scanning for Polymorphism as Set Forth in Example 10. To scan for polymorphism, first strand cDNA was prepared by oligo(dT) priming of 1 µg of lymphoblast mRNA using cloned MuLV reverse transcriptase (BRL) as described (Buckler, A. J. et al., Proc. Natl. Acad. Sci. USA 88:4005–4009 (1991); Ambrose, C. et al., Hum. Mol. Genet. 1:697–703 (1992)). The composite IT15 sequence 3' to the CAG was then amplified by PCR in overlapping segments of ~1 kb using specific primer sets based on the cDNA sequence. Each PCR produce was directly sequenced (Sanger & Coulson, Proc. Natl. Acad. Sci. USA 74:5463–5467 (1977)) and was also used as template for production of ~200–300 bp $^{32}$P-labeled PCR products for SSCP analysis. PCR reactions, direct sequencing and SSCP analysis were all carried out as described previously (Ambrose, C. et al., Hum. Mol. Genet. 1:697–703 (1992)). A few PCR products which were refractory to direct sequencing were subcloned into pBSKII. Several independent subclones were then sequenced for each product.

Example 1

Application of Exon Amplification to Obtain Trapped Cloned Exons

Figure 1:
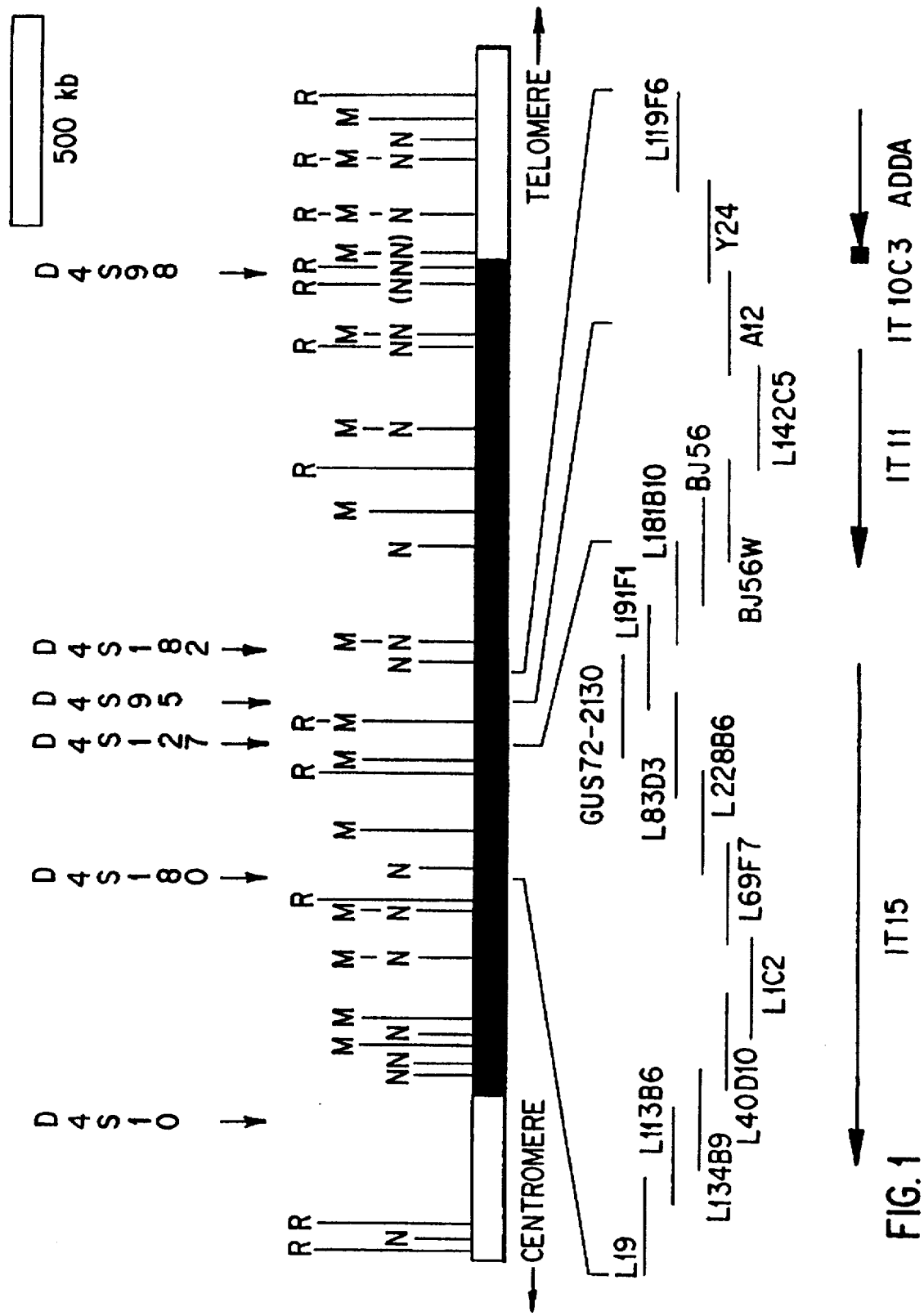
FIG. 1. Long-range restriction map of the HD candidate region. A partial long range restriction map of 4p16.3 is shown (adapted from Lin et al., Somat. *Cell Mol. Genet.* 17:48–88 (1991)). The HD candidate region determined by recombination events is depicted as a hatched line between D4S10 and D4S98. The portion of the HD candidate region implicated as the site of the defect by linkage disequilibrium haplotype analysis (MacDonald et al., *Nature Genet.* 1:99–103 (1992) is shown as a filled box. Below the map schematic, the region from D4S180 to D4S182 is expanded to show the cosmid contig (averaging 40 kb/cosmid). The genomic coverage and where known the transcriptional orientation (arrow 5' to 3') of the huntingtin (IT 15), IT11, IT10C3 and ADDA genes is also shown. Locus names above the map denote selected polymorphic markers that have been used in HD families. The positions of D4S127 and D4S95 which form the core of haplotype in the region of maximum disequilibrium are also shown in the cosmid contig. Restriction sites are given for Not I (N), Mlu I (M) and Nru I (R). Sites displaying complete digestion are shown in boldface while sites subject to frequent incomplete digestion are shown as lighter symbols. Brackets around the "N" symbols indicate the presence of additional clustered Not I sites.

The HD candidate region defined by discrete recombination events in well-characterized families spans 2.2 Mb between D4S10 and D4S98 as shown in FIG. 1. The 500 kb segment between D4S180 and D4S182 displays the strongest linkage disequilibrium with HD, with about ⅓ of disease chromosomes sharing a common haplotype, anchored by multi-allele polymorphisms at D4S127 and D4S95 (MacDonald et al., Nature Genet. 1:99–103 (1992)). Sixty-four overlapping cosmids spanning about 480 kb from D4S180 to a location between D4S95 and D4S182 have been isolated by a combination of information from YAC (Baxendale et al., Nucleic Acids Res. 19:6651 (1991)) and cosmid probe hybridization to high density filter grids of a chromosome 4 specific library, as well as additional libraries covering this region. Sixteen of these cosmids providing the complete contig are shown in FIG. 1. We have previously used exon amplification to identify ADDA, the α-adducin locus, IT10C3, a novel putative transporter gene, and IT11, a novel G protein-coupled receptor kinase gene in the region distal to D4S127 (FIG. 1).

We have now applied the exon amplification technique to cosmids from the region of the contig proximal to D4S127. This procedure produces "trapped" exon clones, which can represent single exons, or multiple exons spliced together and is an efficient method of obtaining probes for screening cDNA libraries. Individual cosmids were processed, yielding 9 exon clones in the region from cosmids L134B9 to L181B10.

Figure 2:
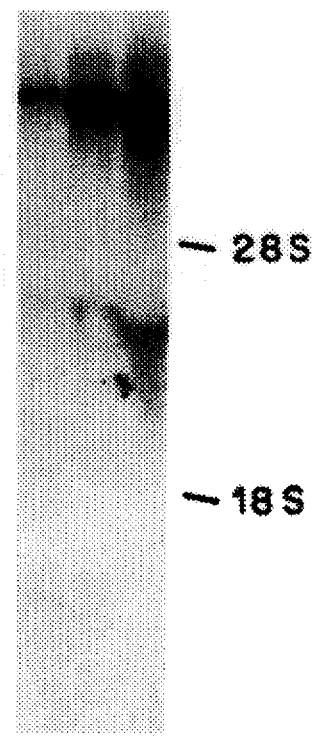
FIG. 2. Northern blot analysis of the huntingtin (IT15) transcript. Results of the hybridization of IT15A to a Northern blot of RNA from normal (lane 1) and HD homozygous (lane 2 and 3) lymphoblasts are shown. A single RNA of about 11 kb was detected in all three samples, with slight apparent variations being due to unequal RNA concentrations. The HD homozygotes are independent, deriving from the large an American family (lane 2) and the large Venezuelan family (lane 3), respectively. The Venezuelan HD chromosome has a 4p16.3 haplotype of "5 2 2" defined by a $(GT)_n$ polymorphism at D4S127 and VNTR and TaqI RFLPs at D4S95. The American homozygote carries the most common 4p16.3 haplotype found on HD chromosomes: "2 11 1" (MacDonald et al., *Nature Genet.* 1:99–103 (1992)).

Two non-overlapping cDNAs were initially isolated using exon probes. IT15A was obtained by screening a transformed adult retinal cell cDNA library with exon clone DL118F5-U. IT16A was isolated by screening an adult frontal cortex cDNA library with a pool of three exon clones, DL83D3-8, DL83D3-1, and DL228B6-3. By Northern blot analysis, we discovered that IT15A and IT16A are in fact different portions of the same large approximately 10–11 kb transcript. FIG. 2 shows an example of a Northern blot containing RNA from lymphoblastoid cell lines representing a normal individual and 2 independent homozygotes for HD chromosomes of different haplotypes. The same approximately 10–11 kb transcript was also detected in RNA from a variety of human tissues (liver, spleen, kidney, muscle and various regions of adult brain).

Figure 3:
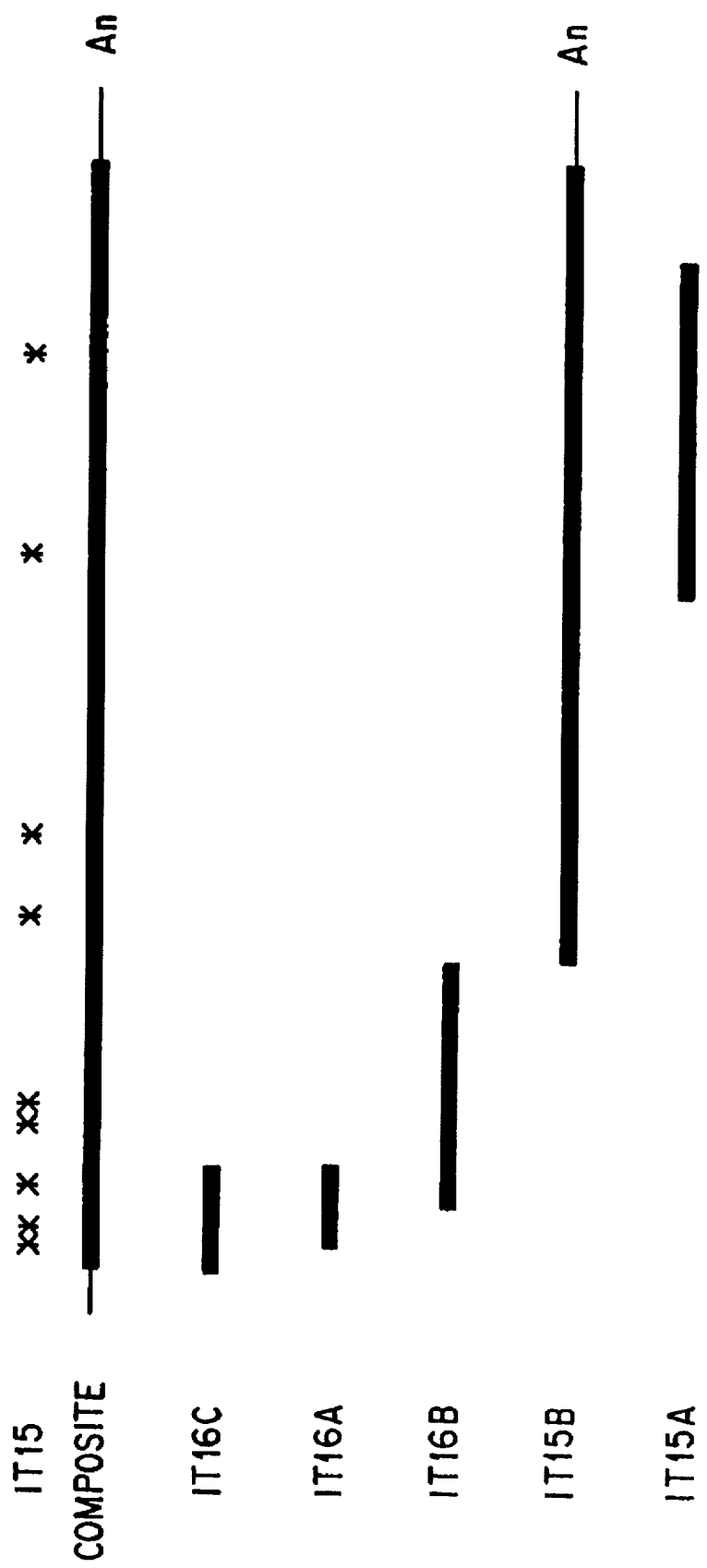
FIG. 3. Schematic of cDNA clones defining the IT15 transcript. Five cDNAs are represented under a schematic of the composite IT15 sequence. The thin line corresponds to untranslated regions. The thick line corresponds to coding sequence, assuming initiation of translation at the first Met codon in the open reading frame. Stars mark the positions of the following exon clones 5' to 3': DL83D3-8, DL83D3-1, DL228B6-3, DL228B6-5, DL228B6-13, DL69F7-3, DL178H4-6, DL118F5-U and DL134B9-U4.

IT15A and IT16A were used to "walk" in a number of human tissue cDNA libraries in order to obtain the full-length transcript. FIG. 3 shows a representation of 5 cDNA clones which define the IT15 transcript, under a schematic of the composite sequence derived as described in the legend. FIG. 3 also displays the locations on the composite sequence of the 9 trapped exon clones.

The composite sequence of IT15, containing the entire predicted coding sequence, spans 10,366 bases including a tail of 18 A's as shown in FIG. 4. An open reading frame of 9,432 bases begins with a potential initiator methionine codon at base 316, located in the context of an optimal translation initiation sequence. An in-frame stop codon is located 240 bases upstream from this site. The protein product of IT15 is predicted to be a 348 kDa protein containing 3,144 amino acids. Although the first Met codon in the long open reading frame has been chosen as the probably initiator codon, we cannot exclude that translation does not actually begin at a more 3' Met codon, producing a smaller protein.

Example 2

Polymorphic Variation of the $(CAG)_n$ Trinucleotide Repeat

Near its 5' end, the IT15 sequence contains 21 copies of the triplet CAG, encoding glutamine (FIG. 5). When this sequence was compared with genomic sequences that are known to surround simple sequence repeats (SSRs) in 4p16.3, it was found that normal cosmid L191F1 had 18 copies of the triplet indicating that the $(CAG)_n$ repeat is polymorphic (FIG. 5). Primers from the genomic sequence flanking the repeat were chosen to establish a PCR assay for this variation. In the normal population, this SSR polymorphism displays at least 17 discrete alleles (Table 1) ranging from about 11 to about 34 repeat units. Ninety-eight percent of the 173 normal chromosomes tested contained repeat lengths between 11 and 24 repeats. Two chromosomes were detected in the 25–30 repeat range and 2 normal chromosomes had 33 and 34 repeats respectively. The overall heterozygosity on normal chromosome was 80%. Based on sequence analysis of three clones, it appears that the variation is based entirely on the $(CAG)_n$, but the potential for variation of the smaller downstream $(CCG)_7$ which is also included in the PCR product, is also present.

example 3

Instability of the Trinucleotide Repeat on HD chromosomes

Sequence analysis of cosmid GUS72-2130, derived from a chromosome with the major HD haplotype (see below), revealed 48 copies of the trinucleotide repeat, far greater than the largest normal allele (FIG. 5). When the PCR assay was applied to HD chromosomes, a pattern strikingly different from the normal variation was observed. HD heterozygotes contained one discrete allelic product in the normal size range, and one PCR product of much larger size, suggesting that the $(CAG)_n$ repeat on HD chromosomes is expanded relative to normal chromosomes.

FIG. 6 shows the patterns observed when the PCR assay was performed on lymphoblast DNA from a selected nuclear family in a large Venezuelan HD kindred. In this family, DNA marker analysis has shown previously that the HD chromosome was transmitted from the father (lane 2) to seven children (lanes 3, 5, 6, 7, 8, 10 and 11). The three normal chromosomes present in this mating yielded a PCR product in the normal size range (AN1, AN2, AN3) that was inherited in a Mendelian fashion. The HD chromosome in the father yielded a diffuse, "fuzzy"-appearing PCR product slightly smaller than the 48 repeat product of the non-Venezuelan HD cosmid. Except for the DNA in lane 5 which did not PCR amplify and in lane 11 which displayed only a single normal allele, each of the affected children's DNAs yielded a fuzzy PCR product of a different size (AE), indicating instability of the HD chromosome $(CAG)_n$ repeat. Lane 6 contained an HD-specific product slightly smaller than or equal to that of the father's DNA. Lanes 3, 7, 10 and 8, respectively, contained HD-specific PCR products of progressively larger size. The absence of an HD-specific PCR product in lane 11 suggested that this child's DNA possessed a $(CAG)_n$ repeat that was too long to amplify efficiently. This was verified by Southern blot analysis in which the expanded HD allele was easily detected and estimated to contain up to 100 copies of the repeat. Notably, this child had juvenile onset of HD at the very early age of 2 years. The onset of HD in the father was in his early 40s, typical of most adult HD patients in this population. The onset ages of children represented by lanes 3, 7, 10 and 8 were 26, 25, 14 and 11 years, respectively, suggesting a rough correlation between age at onset of HD and the length of the $(CAG)_n$ repeat on the HD chromosome. In keeping with this trend, the offspring represented in lane 6 with the fewest repeats remained asymptomatic when last examined at age of 30.

FIG. 7 shows PCR analysis for a second sibship from the Venezuelan pedigree in which both parents are HD heterozygotes carrying the same HD chromosome based on DNA marker studies. Several of the offspring are HD homozygotes (lanes 6+7, 10+11, 13+14, 17+18, 23+24) as reported previously (Wexler et al., Nature 326:194–197 (1987)). Each parent's DNA contained one allele in the normal range (AN1, AN2) which was transmitted in a Mendelian fashion. The HD-specific products (AE) from the DNA of both parents and children were all much larger than the normal allelic products and also showed extensive variation in mean size. A neurologic diagnosis for the offspring in this pedigree was not provided to maintain the blind status of investigators involved in the ongoing Venezuela HD project, although age of onset again appears to parallel repeat length. Paired samples under many of the individual symbols represent independent lymphoblast lines initiated at least one year apart. The variance between paired samples was not as great as between the different individuals, suggesting that the major differences in size of the PCR products resulted from meiotic transmission. Of special note is the result obtained in lanes 13 and 14. This HD homozygote's DNA yielded one PCR product larger and one smaller than the HD-specific PCR products of both parents.

To date, we have tested 75 independent HD families, representing all different reported in MacDonald et al., Nature Genet. 1:99–103 (1992)) and a wide range of ethnic backgrounds. In all 75 cases, a PCR product larger than the normal size range was produced from the HD chromosome.

The sizes of the HD-specific products ranged from 42 repeat copies to more than 66 copies, with a few individuals failing to yield a product because of the extreme length of the repeat. In these cases, Southern blot analysis revealed an increase in the length of an EcoRI fragment with the largest allele approximating 100 copies of the repeat. FIG. 8 shows the variation detected in members of an American family of Irish ancestry in which the major HD haplotype is segregating. Cosmid GUS72-2130 was cloned from the HD homozygous individual whose DNA was amplified in lane 2. As was observed in the Venezuelan HD pedigree (FIGS. 6 and 7), which segregates the disorder with a different 4p16.3 haplotype, the HD-specific PCR products for this family display considerable size variation.

Example 4

New Mutations to HD

The mutation rate in HD has been reported to be very low. To test whether the expansion of the $(CAG)_n$ repeat is the mechanism by which new HD mutations occur, two pedigrees with sporadic cases of HD have been examined in which intensive searching failed to reveal a family history of the disorder. In these cases, pedigree information sufficient to identify the same chromosomes in both the affected individual and unaffective relatives was gathered. FIGS. 9 and 10 show the results of PCR analysis of the $(CAG)_n$ repeat in these families. The chromosomes in each family were assigned an arbitrary number based on typing for a large number of RFLP and SSR markers in 4p16.3 defining distinct haplotypes and the presume HD chromosome is starred.

In family #1, HD first appeared in individual II-3 who transmitted the disorder to III-1 along with chromosome 3*. This same chromosome was present in II-2, an elderly unaffected individual. PCR analysis revealed that chromosome 3* from II-2 produced a PCR product at the extreme high end of the normal range (about 36 CAG copies). However, the $(CAG)_n$ repeat on the same chromosome in II-3 and III-1 had undergone sequential expansions to about 44 and about 46 copies, respectively. A similar result was obtained in Family #2, where the presumed HD mutant III-2 had a considerably expanded repeat relative to the same chromosome in II-1 and III-1 (about 49 vs. about 33 CAG copies). In both family #1 and family #2, the ultimate HD chromosome displays the marker haplotype characteristic of ⅓ of all HD chromosomes, suggesting that this haplotype may be predisposed to undergoing repeat expansion.

Discussion

The discovery of an expanded, unstable trinucleotide repeat on HD chromosomes within the IT15 gene is the basis for utilizing this gene as the HD gene of the invention. These results are consistent with the interpretation that HD constitutes the latest example of a mutational mechanism that may prove quite common in human genetic disease. Elongation of a trinucleotide repeat sequence has been implicated previously as the cause of three quite different human disorders, the fragile X syndrome, myotonic dystrophy and spino-bulbar muscular atrophy. The initial observations of repeat expansion in HD indicate that this phenomenon shares features in common with each of these disorders.

In the fragile X syndrome, expression of a constellation of symptoms that includes mental retardation and a fragile site at Xq27.3 is associated with expansion of a $(CGG)_n$ repeat thought to be in the 5' untranslated region of the FMRI gene (Fu et al., *Cell* 67:1047–1058 (1991); Kremer et al., *Science* 252:1711–1714 (1991); Verkerk et al., *Cell* 65:904–914 (1991)). In myotonic dystrophy, a dominant disorder involving muscle weakness with myotonia that typically present in early adulthood, the unstable trinucleotide repeat, $(CTG)_n$, is located in the 3' untranslated region of the mysotonin protein kinase gene (Aslanidis et al., *Nature* 355:548–551 (1992); Brook et al., *Cell* 68:799–808 (1992); Buxton et al., *Nature* 355:547–548 (1992); Fu et al., *Science* 255:1256–1259 (1992); Harley et al., *Lancet* 339:1125–1128 (1992); Mahadevan et al., *Science* 255:1253–1255 (1992)). The unstable $(CAG)_n$ repeat in HD may be within the coding sequence of the IT15 gene, a feature shared with spino-bulbar muscular atrophy, an X-linked recessive adult-onset disorder of the motor neurons caused by expansion of a $(CAG)_n$ repeat in the coding sequence of the androgen receptor gene (LaSpada et al., *Nature* 352:77–79 (1991)). The repeat length in both the fragile X syndrome and myotonic dystrophy tends to increase in successive generations, sometimes quite dramatically. Occasionally, decreases in the average repeat length are observed (Fu et al., *Science* 255:1256–1259 (1992); Yu et al., *Am. J. Hum. Genet.* 50:968–980 (1992); Brunet et al., *N. Engl. J. Med.*:476–480 (1993)). The HD trinucleotide repeat is also unstable, usually expanding when transmitted to the next generation, but contracting on occasion. In HD, as in the other disorders, change in copy number occurs in the absence of recombination. Compared with the fragile X syndrome, myotonic dystrophy, and HD, the instability of the disease allele in spino-bulbar muscular atrophy is more limited, and dramatic expansions of repeat length have not been seen (Biancalana et al., *Hum. Mol. Genet.* 1:255–258 (1992)).

Expansion of the repeat length in myotonic dystrophy is associated with a particular chromosomal haplotype, suggesting the existence of a primordial predisposing mutation (Harley et al., *Am. J. Hum. Genet.* 49:68–75 (1991); Harley et al., *Nature* 355:545–546 (1992); Ashizawa, *Lancet* 338:642–643 (1991); and Epstein (1991)). In the fragile X syndrome, there may be a limited number of ancestral mutations that predispose to increases in trinucleotide repeat number (Richards et al., *Nature Genet.* 1:257–260 (1992); Oudet et al., *Am. J. Hum. Genet.* 52:297–304 (1993)). The linkage disequilibrium analysis used to identify IT15 indicates that there are several haplotypes associated with HD, but that at least ⅓ of HD chromosomes are ancestrally related (MacDonald et al., *Nature Genet.* 1:99–103 (1992)). These data, combined with the reported low rate of new mutation to HD (Harper, *J. Med. Genet.* 89:365–376 (1992)), suggest that expansion of the trinucleotide repeat may only occur on select chromosomes. The analysis of two families presented herein, in which new mutation was supposed to have occurred, is consistent with the view that there may be particular normal chromosomes that have the capacity to undergo expansion of the repeat into the HD range. In each of these families, a chromosome with a $(CAG)_n$ repeat length in the upper end of the normal range was segregating on a chromosome whose 4p16.3 haplotype matched the most common haplotype seen on HD chromosomes and the clinical appearance of HD in these two cases was associated with expansion of the trinucleotide repeat.

The recent application of haplotype analysis to explore the linkage disequilibrium on HD chromosomes pointed to a portion of a 2.2 Mb candidate region defined by the majority of recombination events described in HD pedigrees (MacDonald et al., *Nature Genet.* 1:99–103 (1992)). Previously, the search for the gene was confounded by three matings in which the genetic inheritance pattern was inconsistent with the remainder of the family (MacDonald et al.,

*Neuron* 3:183–190 (1989b); Prichard et al., *Am. J. Hum. Genet.* 50:1218–1230 (1992)). These matings produced apparently affected HD individuals despite the inheritance of only normal alleles for markers throughout 4p16.3, effectively excluding inheritance of the HD chromosome present in the rest of the pedigree. Using PCR assay disclosed above, each of these families was tested and it was determined that like other HD kindreds, an expanded allele segregates with HD in affected individuals of all three pedigrees. However, an expanded allele was not present in those specific individuals with the inconsistent 4p16.3 genotypes. Instead, these individuals displayed the normal alleles expected based on analysis of other markers in 4p16.3. It is conceivable that these inconsistent individuals do not, in fact, have HD, but some other disorder. Alternatively, they might represent genetic mosaics in which the HD allele is more heavily represented and/or more expanded in brain tissue than in the lymphoblast DNA used for genotyping.

The capacity to monitor directly the size of the trinucleotide repeat in individuals "at risk" for HD provides significant advantages over current methods, eliminating the need for complicated linkage analyses, facilitating genetic counseling, and extending the applicability of presymptomatic and prenatal diagnosis to "at risk" individuals with no living affected relatives. However, it is of the utmost importance that the current internationally accepted guidelines and counseling protocols for testing those "at risk" continue to be observed, and that samples from unaffected relatives should not be tested inadvertently or without full consent. In the series of patients examined in this study, there is an apparent correlation between repeat length and age of onset of the disease, reminiscent of that reported in myotonic dystrophy (Harley et al., *Lancet* 339:1125–1128 (1992); Tsilfidis et al., *Nature Genet.* 1:192–195 (1992)). The largest HD trinucleotide repeat segments were found in juvenile onset cases, where there is a known preponderance of male transmission (Merrit et al., *Excerpta Medica*, Amsterdam, pp. 645–650 (1969)).

The expression of fragile X syndrome is associated with direct inactivation of the FMR1 gene (Pierretti et al., *Cell* 66:817–822 (1991); DeBoulle et al., *Nature Genet.* 3:31–35 (1993)). The recessive inheritance pattern of spino-bulbar muscular atrophy suggests that in this disorder, an inactive gene product is produced. In myotonic dystrophy, the manner in which repeat expansion leads to the dominant disease phenotype is unknown. There are numerous possibilities for the mechanism of pathogenesis of the expanded trinucleotide repeat in HD. Without intending to be held to this theory, nevertheless notice can be taken that since Wolf-Hirschhorn patients hemizygous for 4p16.3 do not display features of HD, and IT15 mRNA is present in HD homozygotes, the expanded trinucleotide repeat does not cause simple inactivation of the gene containing it. The observation that the phenotype of HD is completely dominant, since homozygotes for the disease allele do not differ clinically from heterozygotes, has suggested that HD results from a gain of function mutation, in which either the mRNA product or the protein product of the disease allele would have some new property, or be expressed inappropriately (Wexler et al., *Nature* 326:194–197 (1987); Myers et al., *Am. J. Hum. Genet.* 45:615–618 (1989)). If the expanded trinucleotide repeat were translated, the consequences on the protein product would be dramatic, increasing the length of the poly-glutamine stretch near the N-terminus. It is possible, however, that despite the presence of an upstream Met codon, the normal translational start occurs 3' to the (CAG)$_n$ repeat and there is no poly-glutamine stretch in the protein product. In this case, the repeat would be in the 5' untranslated region and might be expected to have its dominant effect at the mRNA level. The presence of an expanded repeat might directly alter regulation, localization, stability or translatability of the mRNA containing it, and could indirectly affect its counterpart from the normal allele in HD heterozygotes. Other conceivable scenarios are that the presence of an expanded repeat might alter the effective translation start site for the HD transcript, thereby truncating the protein, or alter the transcription start site for the IT15 gene, disrupting control of mRNA expression. Finally, although the repeat is located within the IT15 transcript, the possibility that it leads to HD by virtue of an action on the expression of an adjacent gene cannot be excluded.

Despite this final caveat, it is consistent with the above results and most likely that the trinucleotide repeat expansion causes HD by its effect, either at the mRNA or protein level, on the expression and/or structure of the protein product of the IT15 gene, which has been named huntingtin. Outside of the region of the triplet repeat, the IT15 DNA sequence detected no significant similarity to any previously reported gene in the GenBank database. Except for the stretches of glutamine and proline near the N-terminus, the amino acid sequence displayed no similarity to known proteins, providing no conspicuous clues to huntingtin's function. The poly-glutamine and poly-proline region near the N-terminus detect similarity with a large number of proteins which also contain long stretches of these amino acids. It is difficult to assess the significance of such similarities, although it is notable that many of these are DNA binding proteins and that huntingtin does have a single leucine zipper motiff at residue 1,443. Huntingtin appears to be widely expressed, and yet cell death in HD is confined to specific neurons in particular regions of the brain.

TABLE 1

COMPARISON OF HD AND NORMAL REPEAT SIZES

| RANGE OF ALLELE SIZES (# REPEATS) | NORMAL CHROMOSOMES NUMBER AND FREQUENCY | | HD CHROMOSOMES NUMBER AND FREQUENCY | |
|---|---|---|---|---|
| ≧48 | 0 | 0 | 44 | 0.59 |
| 42–47 | 0 | 0 | 30 | 0.41 |
| 30–41 | 2 | 0.01 | 0 | 0 |
| 25–30 | 2 | 0.01 | 0 | 0 |
| ≦24 | 169 | 0.98 | 0 | 0 |
| TOTAL | 173 | 1.00 | 74 | 1.0 |

Example 5

Distribution of Trinucleotide Repeat Lengths on Normal and HD Chromosomes

The number of copies of the HD triplet repeat has been examined in a total of 425 HD chromosomes from 150 independent families and compared with the copy number of the HD triplet repeat of 545 normal chromosomes. The results are displayed in FIG. 11. Two non-overlapping distributions of repeat length were observed, wherein the upper end of the normal range and the lower end of the HD range were separated by 3 repeat units. The normal chromosomes displayed 24 alleles producing PCR products ranging from 11 to 34 repeat units, with a median of 19 units (mean 19.71, s.d. 3.21). The HD chromosomes yielded 54 discrete PCR products corresponding to repeat lengths of 37 to 86 units, with a median of 45 units (mean 46.42, s.d. 6.68).

Of the HD chromosomes, 134 and 161 were known to be maternally or paternally-derived, respectively. To investigate whether the sex of the transmitting parent might influence the distribution of repeat lengths, these two sets of chromosomes were plotted separately in FIG. 12. The maternally-derived chromosomes displayed repeat lengths ranging from 37 to 73 units, with a median of 44 (mean 44.93, s.d. 5.14). The paternally-derived chromosomes had 37 to 86 copies of the repeat unit, with a median of 48 units (mean 49.14, s.d. 8.27). However, a higher proportion of the paternally-derived HD chromosomes had repeat lengths greater than 55 units (16% vs. 2%), suggesting the possibility of a differential effect of paternal versus maternal transmission.

The data set used excluded chromosomes from a few clinically diagnosed individuals who have previously been shown not to have inherited the HD chromosome by DNA marker linkage studies (MacDonald, M. E., et al., *Neuron* 3:183–190 (1989); Pritchard, C., et al., *Am. J. Hum. Genet.* 50:1218–1230 (1992)). These individuals have repeat lengths well within the normal range. Their disease manifestations have not been explained, and they may represent phenocopies of HD. Regardless of the mechanism involved, the occurrence at low frequency of such individuals within known HD families must be considered if diagnostic conclusions are based solely on repeat length.

The control data set also excludes a number of chromosomes from phenotypically normal individuals who are related to "spontaneous" cases of HD or "new mutations". Chromosomes from these individuals who are not clinically affected and have no family history of the disorder cannot be designated as HD. However, these chromosomes cannot be classified as unambiguously normal because they are essentially the same chromosome as that of an affected relative, the diagnosed "spontaneous" HD proband, except with respect to repeat length. The lengths of repeat found on these ambiguous chromosomes (34–38 units) span the gap between the control and HD distributions, confounding a decision on the status of any individual with a repeat in the high normal to low HD range.

Example 6

Instability of the Trinucleotide Repeat

The data in FIG. 11 combine repeat lengths from 150 different HD families representing many potentially independent origins of the defect. To examine the variation in repeat lengths on sets of HD chromosomes known to descend from a common founder, the data from three large HD kindreds (Gusella, J. F., et al., *Nature* 306:234–238 (1983); Wexler, N. S., et al., *Nature* 326:194–197 (1987); Folstein, S. E., et al., *Science* 229:776–779 (1985)) with different 4p16.3 haplotypes (MacDonald, M. E., et al., *Nature Genet.* 1:99–103 (1992)), typed for 75, 25 and 35 individuals, respectively, were separated. Despite the single origin of the founder HD chromosome within each pedigree, members of the separate pedigrees display a wide range of repeat lengths (FIG. 13). This instability of the HD chromosome repeat is most prominent in members of a large Venezuelan HD kindred (panel A) in which the common HD ancestor has produced 10 generations of descendants, numbering over 13,000 individuals. The distribution of repeat lengths in this sampling of the Venezuelan pedigree (median 46, mean 48.26, s.d. 9.3) is not significantly different from that of the larger sample of HD chromosomes from all families. Panels B and C display results for two extended families in which HD was introduced more recently than in the Venezuelan kindred. These families have been reported to exhibit different age of onset distributions and varied phenotypic features of HD (Folstein, S. E., et al., *Science* 229:776–779 (1985)). Both revealed extensive repeat length variation, with a median of 41 and 49 repeat units, respectively. The distribution of repeat lengths in the members of the family in Panel B was significantly different from the distribution of all HD chromosome repeat lengths (p<0.0001), with a smaller mean of 42.04 repeat units (s.d. 2.82). The repeat distribution from HD chromosomes of Panel C was also significantly different from the total data set (p<0.004), but with a higher mean of 49.80(s.d. 5.86).

Example 7

Parental Source Effects on Repeat Length Variation

For 62 HD chromosomes in FIG. 11, the length of the trinucleotide repeat also could be examined on the corresponding parental HD chromosome. In 20 of 25 maternal transmissions, and in 31 of 37 paternal transmissions, the repeat length was altered, indicating considerable instability. A similar phenomenon was not observed for normal chromosomes, where more than 500 meiotic transmissions revealed no changes in repeat length, although the very existence of such a large number of normal alleles suggests at least a low degree of instability.

FIG. 14 shows the relationship between the repeat lengths on the HD chromosomes in the affected parent and corresponding progeny. For the 20 maternally-inherited chromosomes on which the repeat length was altered, 13 changes were increases in length and 7 were decreases. Both increases and decreases involved changes of less than 5 repeat units and the overall correlation between the mother's repeat length and that of her child was r=0.95 (p<0.0001). The average change in repeat length in the 25 maternal transmissions was an increase of 0.4 repeats.

On paternally-derived chromosomes, the 31 transmissions in which the repeat length changes comprised 26 length increases and 5 length decreases. Although the decreases in size were only slightly smaller than those observed on maternally-derived chromosomes, ranging from 1 to 3 repeat units, the increases were often dramatically larger. Thus, the correlation of the repeat length in the father with that of his offspring was only r=0.35 (p<0.04). The average change in the 37 paternal transmissions was an increase of 9 repeat units. The maximum length increase observed through paternal transmission was 41 repeat units, a near doubling of the parental repeat.

For both male and female transmissions, there was no correlation between the size of the parental repeat and either the magnitude or frequency of changes.

To determine whether the variation in the length of the repeat observed through male transmission of HD chromosomes is reflected in the male germ cells, we amplified the repeat from sperm DNA and from DNA of the corresponding lymphoblast from 5 HD gene carriers. The results, shown in FIG. 15, reveal striking differences between the lymphoblast and sperm DNA for the HD chromosome repeat, but not for the repeat on the normal chromosome. All the sperm donors are members of the Venezuelan HD family and range in age from 24 to 30 years. Individuals 1 and 2 are siblings with HD chromosome repeat lengths based on lymphoblast DNA of 45 and 52, respectively. Individuals 3 and 4 are also siblings, with HD repeat lengths of 46 and 49, respectively. Individual 5, from a different sibship than either of the other two pairs, has an HD repeat of 52 copies.

In all 5 cases, the PCR amplification of sperm DNA and lymphoblast DNA yielded identical products from the normal chromosome. However, in comparison with lymphoblast DNA, the HD gene from sperm DNA yielded a diffuse array of products. In 3 of the 5 cases (2,4 and 5), the diffuse array spread to much larger allelic products than the corresponding lymphoblast product. Subject 2 showed the greatest range of expansion, with the sperm DNA product extending to over 80 repeat units. Interestingly, the 3 individuals displaying the greatest variation have the longest repeats and are currently symptomatic. The other two donors have shorter repeat lengths in the HD range, and remain at risk at this time.

The striking difference in the high repeat length range (>55) between HD chromosomes transmitted from the father and those transmitted from the mother indicated a potential parental source effect. When this was examined directly, the HD chromosome repeat length changed in about 85% of transmissions. Most changes involved a fluctuation of only a few repeat units, with larger increases occurring only in male transmissions. The greater size increases in male transmission appear to be caused by particular instability of the HD trinucleotide repeat during male gametogenesis, based on the amplification of the repeat from sperm DNA.

Example 8

Relationship Between Repeat Length and Age of Onset

Increased repeat length might correlate with a reduced age of onset of HD. Accordingly, age of onset data was determined for 234 of the individuals represented in FIG. 11. FIG. 16 displays the repeat lengths found on the HD and normal chromosomes of these individuals relative to their age of onset. Indeed, age of onset is inversely correlated with the HD repeat length. A Pearson correlation coefficient of r=−0.75, p<0.0001 was obtained assuming a linear relationship between age of onset and repeat length. When a polynomial function was used, a better fit was obtained ($R^2$=0.61, F=121.45), suggesting a higher order association between age of onset and repeat length.

There is considerable variation in the age of onset associated with any specific number of repeat units, particularly for trinucleotide repeats in the 37–52 unit zone (88% of HD chromosomes) here onset ranged from 15 to 75 years. In this range, a linear relationship between age of onset and repeat length provided as good a fit as a higher order relationship. The 95% confidence interval surrounding the predicted regression line was estimated at ±18 years. In the 37 to 52 unit range, the association of repeat length to onset age is only half as strong as in the overall distribution (r=0.40, p<0.0001), indicating that much of the predictive power is contributed by repeats longer than 52 units. In this increased range, onset is likely to be very young and consequently not relevant to most persons seeking testing.

For the 178 cases in the 37–52 repeat unit range for which it was possible to subdivide the data set based on parental origin of the HD gene, multivariate regression analysis suggested a significant effect of parental origin on age of onset (p<0.05) independent of repeat length in this range. HD gene carriers from maternal transmissions had an average age of onset two years later than those from paternal transmissions.

In both univariate and multivariate analyses, no association between age of onset and the repeat length on the normal chromosome was detected, either in the total data set, or when it was subdivided into chromosomes of maternal or paternal origin.

Example 9

The Mouse Huntington's Disease Gene Homologue (Hdh)

A. Northern Blot Analysis of Hdh Expression

The HD gene is expressed in all human tissues tested to date as two different mRNAs of 10.5 and 13.5 kb that encode the same huntingtin protein, but differ in their 3' untranslated regions (UTRs) due to alternative polyadenylation (Lin et al., *Hum. Mol. Genet.* 2:1541–1545 (1993)). In DNA blot analyses used to map the Hdh locus on Chr 5, it was determined that the mouse gene is sufficiently conserved to be easily detected using a human probe. FIG. 17 displays the results of hybridizing a human HD probe to Northern blots containing polyA+RNA from a variety of mouse tissues. The pattern of expression is remarkably similar to the expression of HD in man, with two different RNAs also of 10.5 and 13.5 kb. These RNAs are expressed in all tissues tested, but at varying ratios. As in man, mouse brain RNA displays the highest proportion of the larger transcript. A novel band of variable intensity is also seen on the mouse Northern blots at ~7 kb. This signal is removed by stringent washing suggesting the possibility of a related locus.

B. Isolation of Overlapping cDNA Clones for Hdh

To permit direct comparison of the human and mouse homologoues, a mouse PCC4 embryonal carcinoma cDNA library was screened, with a pool of cDNA and PCR probes spanning almost the entire published composite IT15 sequence of 10,355 bp (GenBank #L12392) to isolate overlapping clones representing the Hdh mRNAs. A summary of the cDNAs obtained is displayed in FIG. 18. Three cDNA clones provided overlapping sequence coverage from a few bases 3' to the initiator ATG codon through the entire coding sequence. Clone PCC4-3 also possessed a polyA tail attached to a 3' UTR similar in length to that of the shorter of the two human transcripts. The larger mouse Hdh transcript, like that in man, is possibly generated by alternative polyadenylation.

The 5' UTR and the first few bases of coding sequence were not recovered in any cDNA clones. To obtain these sequences, a genomic clone was isolated by screening a 129 phage library with probes from the 5' end of PCC4-8. Direct sequencing of the phage insert provided Hdh sequence from 89 bp upstream of the initiator ATG through the first 44 bases of the coding sequence.

C. Composite Hdh cDNA and Huntingtin Sequences

The composite DNA sequence generated from the clones shown in FIG. 18 spans 9998 nucleotides (nt) and has been deposited in GenBank, with accession #L28827 (SEQ ID NO:15). The putative initiator ATG codon at nt 90 and the TGA stop codon at nt 9447 bracket an open reading frame (SEQ. ID NO:15) that predicts a mouse huntingtin protein of 3,119 amino acids (SEQ. ID NO:16). Like human huntingtin, mouse huntingtin has a region with stretches polyglutamine and polyproline near its N-terminus. Across the coding sequence 5' (nt 90–143) and 3' (nt 267–9446) to the glutamine/proline-rich region, respectively, the DNA sequence is 90% and 86% identical to the human cDNA. In the 89 nt of 5' UTR, identity to the human sequence declines to 67%, with the mouse sequence having an insert of 7 bases 48 nt upstream from the ATG. The 552 nt of 3' UTR is less conserved overall (64%) with many gaps required to match the sequences from the two species. Interestingly, however, the 75 nt segment immediately upstream from the site of polyA addition shows 90% identity in man and mouse, perhaps indicative of a common structural basis for alternative polyadenylation at this site.

At the protein level, human and mouse huntingtin are 100% and 91% identical N-terminal and C-terminal to the glutamine/proline-rich region, respectively. The mouse protein is shorter than the human protein, owing largely to a smaller glutamine/proline-rich region. The remainder of the mouse protein displays 238 conservative amino acid substitutions, 29 non-conservative substitutions, 5 residue deletions and 1 residue addition relative to its human counterpart.

Features of DNA encoding the glutamine/proline-rich region of human huntingtin are the polymorphic CAG repeat that is expanded on disease chromosomes, and the adjacent polymorphic CCG repeat. In man, the polyglutamine stretch varies from 13 to 36 residues, and is encoded almost entirely by CAG except for a penultimate CAA codon. The mouse gene encodes 7 consecutive glutamines in an imperfect repeat with a CAA codon flanked on 5' and 3' sides by 2 and 4 CAG codons, respectively. In both species, the glutamine stretch is followed by a segment with runs of proline with the occasional glutamine or other amino acid residue interspersed. In man, the CCG repeat located just downstream from the polymorphic CAG repeat is also polymorphic (Rubinsztein et al., Nature Genet. 5:214–215 (1993)).

D. Polymorphisms of a CCG Repeat in Hdh

To determine whether the repeat sequences displayed polymorphism in the mouse comparable to that on human chromosomes, the corresponding region was amplified from various strains of laboratory mouse and from M. spretus. A typical result is shown in FIG. 19, in which 129 (represented by clone PCC4-8), C57BL/6J and CBA/J all yield an identical product. The shorter product generated from M. spretus was sequenced for comparison with PCC4-8. The difference in length is not due to any change in CAG number, but rather to a decrease of one CCG in the M. spretus. Thus, the CAG repeat is not only shorter in mouse than in man, it also does not display any evidence of significant length variation.

E. Discussion

The mouse Hdh gene is located on Chr 5, in a region of synteny conservation with human chromosome 4 (Cheng et al., Genomics 4:419–426 (1989)). Although the genomic structure of Hdh is unknown, the human HD gene contains 67 exons, spread across 180 kb of 4p16.3. The human and mouse genes are extremely similar, showing a overall amino acid identity of more than 90% over most of the predicted protein. A comparison of the differences indicates that they are not confined to alterations affecting a few exons, but are found throughout the gene. However, neither are they equally distributed. The regions encompassing amino acids 373–403, 567–641, 1684–1717, and 2136–2374 seem particularly rich in amino acid substitutions in contrast to segments such as residues 60–372, and 1190–1637. The latter might indicate the locations of critical functional domains of huntingtin.

More extensive differences are found in the DNA of the 5' and particularly the 3' UTRs, suggesting less stringent selective pressures overall on these sequences. However, the relatively high level of conservation of the DNA sequence immediately upstream from one site of polyA addition in man indicates that this segment may be involved in regulating alternative polyadenylation. Although the existence of alternative polyadenylation has not been demonstrated unequivocally in the mouse, the ubiquitous expression of two Hdh RNAs comparable in size to the human HD RNAs supports this supposition.

Lin et al. (Lin et al., Hum. Mol. Genet. 3:85–92 (1994)) has also reported a cDNA sequence for mouse Hdh spanning 9992 bp, also encoding a huntingtin protein of 3119 residues. However, the composite cDNA sequence reported herein has notable differences. These are best compared at the protein level, where the two sequences differ at 28 residues spread across the entire protein, from position 2 to position 3096. In 24 of these cases, the mouse huntingtin sequence described herein matches the amino acid sequence found in man. In the remaining 4 cases, Lin et al. (Lin et al., Hum. Mol. Genet. 3:85–92 (1994)) matches the human sequence. Our 3' UTR sequence has seven mismatches, additions, or deletions of single bases compared to Lin et al. (Lin et al., Hum. Mol. Genet. 3:85–92 (1994)). In addition, both of the clones PCC4-3 and PCC4-5 described herein contain a stretch of 35 bp not present in Lin et al.'s sequence. Lin et al. also found that in their cDNA clones the CCG repeat beginning at codon 32 varies between C57BL6 and random outbred laboratory mice, displaying 3 and 4 repeat units, respectively. While the amplification described herein of genomic DNA agrees with the site of this polymorphism, it does not yield the same strain-specific pattern. In the experiments described herein, all 3 strains of laboratory mice, including 129, C57BL/6J and CBA/J, possessed 4 CCG units while only M. spretus revealed 3 CCGs.

Finally, Lin et al. (Lin et al., Hum. Mol. Genet. 3:85–92 (1994)) reported the identification of a putative alternative splicing event that removed nt 4562 to 6091, and therefore amino acids 1522 to 2001 from the protein. An examination of FIG. 18 reveals that this segment begins in exon 35 and ends in exon 44 of the human gene. Thus, unless the exon structure of the mouse gene differs radically from that of the human gene, the clone isolated by Lin et al. (Lin et al., Hum. Mol. Genet. 3:85–92 (1994)) cannot be explained by simple alternative splicing. Indeed, these authors suggest that the same variant sequence is also expressed in man. For this to occur would require a complex change, including the recognition of a segment in exon 35 as a splice donor, the use of a different sequence in exon 44 as a splice acceptor, and the bypassing of conventional splicing signals in exons 36–44. Alternatively, the sequence reported by Lin et al. could have resulted from a cloning artefact.

Human huntingtin is predicted to be a large protein of greater than ~3,130 amino acids that does not display significant homology to any known protein. The high level of conservation of mouse huntingtin (91% identify) suggests that there are tight evolutionary constraints on its sequence. The decline in DNA sequence conservation upstream from the putative initiator ATG suggests that the coding sequence indeed begins as predicted, and includes the polyglutamine segment encoded by the CAG repeat.

The fact that mouse huntingtin also contains a short stretch of polyglutamine argues for a role of this segment in the normal function of the protein. However, there must be considerable leeway in the fulfillment of this role and of the role of the adjacent polyproline stretch, given the extensive CAG repeat variation on normal human chromosomes. The failure to observe similar variation in the mouse gene, with the exception of one codon change in a CCG repeat, may indicate a stronger selective pressure for maintaining the length of these repeats in the model organism. Alternatively, the variation in the human repeats may indicate that a greater mean length, the particular chromosomal context in which they are found, or species differences in characteristics of the replication process produce a higher mutation rate in man.

Because RNA is produced at normal levels from the HD allele and heterozygous disruption of the gene by translocation does not produce any phenotype the expanded CAG mutation does not entail simple cis-inactivation of the HD gene (although its effects on adjacent genes remain to be determined). The dominant nature of the HD phenotype (Wexler et al., *Nature* 326:194–197 (1987); Myers et al., *Am. J. Hum. Genet.* 45:615–618 (1989)) indicates that the effect of the expanded repeat must include either trans-inactivation of the normal product or conference of a new property on the abnormal product. Both of these possibilities seem more likely to operate at the protein than at the RNA level, particularly since initial antibody studies of huntingtin have not revealed grossly altered expression in HD (Hoogeveen et al., *Hum. Mol. Genet.* 2:2069–2073 (1993)). The small size and apparent stability of the CAG repeat in mouse is consistent with the absence of an HD-like disorder in this model organism. However, the overall conservation of the Hdh gene suggests that genetic manipulation in the mouse, either to produce homozygous "knock-outs" or to introduce an expanded CAG repeat, provides a reasonable hope of resolving the mechanistic issues and of generating an accurate animal model of HD.

Example 10

Exon-Intron Structure of the HD Gene

In the initial search for the HD gene, exons from cosmids spanning a region of 4p16.3 that displayed a common haplotype on approximately ⅓ of HD chromosomes were cloned (MacDonald, M. E. et al., *Nature Genet.* :199–103 (1992)). Initially, the first generation exon amplification system developed by Buckler, A. J. et al. (*Proc. Natl. Acad. Sci. USA* 88:4005–4009 (1991)) was employed to produce cloned exons from individual cosmids isolated by sequential walking steps from D4S180 and D4S156 (Baxendale, S. et al., *Nature Genet.* 4:181–186 (1993)). These exons were used to identify the IT15 cDNA clones (MacDonald, M. E. et al., *Cell* 72:971–983 (1993)).

To determine intron-exon junctions, DNA primers located every 200–300 bp in the cDNAs were used to directly sequence the corresponding cosmid DNAs and designed new primers as needed based on the evolving knowledge of the exon structure. As this work progressed, a second-generation vector system that eliminated false-positive products, and allowed cloning of genomic DNA with multiple restriction enzymes was applied in multiple experiments to saturate the region with cloned exons. The products obtained in this system have the additional advantage that 5'-3' orientation is immediately discernible. To position all exons on the physical map, two primers from each exon were hybridized to EcoRI digests of all overlapping cosmids from the region, representing an average 3-fold redundancy.

The composite IT15 cDNA sequence corresponds to a genomic segment of 180 kb and is encoded in 67 exons as shown in FIG. 20. The internal exons ranged in size from 48 bp to 341 bp with an average of 138 bp. All cloned, sequenced exons are aligned with the composite cDNA sequence in FIG. 20, and together constitute 36% of the transcript. Of the 65 internal exons, 27 were trapped by exon amplification using PstI or BamHI-BglII digests, 15 as single exon products and 12 as multiple adjacent exons spliced together in the amplification procedure. The minimum and maximum sized exons were both represented in this collection, which averaged 139 bp/exon, indicating no apparent size bias in the procedure.

A codon loss polymorphism in IT15

To search for DNA changes other than the trinucleotide repeat expansion that might also be associated with HD, the normal and HD transcripts were compared by sequence analysis of partial cDNA clones and by single strand conformational polymorphism analysis (SSCP) of PCR products from first strand cDNA (Orita, M. et al., *Genomics* 5:874–879 (1989)). Sequencing of individual normal cDNAs revealed four single base pair differences from the consensus sequence, at positions 1849 (C to G, Leu to Val), 2372 (C to G, Ser to Cys), 4034 (G to A, Arg to Lys), and 8677 (A to G, Ile to Val) (See: SEQ ID No:5). No sequence differences other than the CAG repeat length were found exclusively in the HD cDNAs.

For SSCP analysis, two HD homozygotes of different haplotypes, both alleles from a single normal individual, and the normal sequence represented in a corresponding cDNA clone were scanned. Variant SSCP bands were detected in exons 58, 60 and 67. The exon 67 difference involved a choice of either C or T at position 9809 of the composite cDNA sequence (SEQ ID No:5). This change occurred in the 3' untranslated region and both forms were represented on at least one normal and one HD allele. The exon 60 difference was found only on one of the normal alleles.

The exon 58 difference (FIG. 21A) was present in the HD homozygote representing the most common disease haplotype, but absent from an HD homozygote of another haplotype (MacDonald, M. E. et al. *Nature Genet.* 1:99–103 (1992); Myers, R. H. et al., *Am. J. Hum. Genet.* 45:615–618 (1989)). Sequence analysis of multiple cloned PCR products revealed the loss of a single codon from a run of our consecutive GAG (Glu) codons at positions 2642–2645 of the predicted amino acid sequence ((SEQ ID No:6). For convenience, this change is referred to as Δ2642. A genomic PCR assay for Δ2642 was developed in order to scan additional HD and normal chromosomes to test its disease specificity ((FIG. 21B). This analysis revealed that the codon loss represents a normal, infrequent polymorphism with allele frequencies of 0.93 and 0.07 for presence or absence or codon 2642, respective (N=175 normal chromosomes). The Δ2642 change showed linkage disequilibrium with HD ($\chi^2$=37.47, 1 d.f., p<0.0001), where the codon loss was represented on 38% of disease chromosomes (N=80 independent HD chromosomes).

Both HD alleles are expressed

The Δ2642 polymorphism provided a ready means to assay whether both alleles of the HD gene are expressed in the cells of affected individuals. FIG. 22 shows the analysis of two independent preparations of first strand cDNA from lymphoblast lines of four unrelated HD patients, two of whom were heterozygous for the polymorphism, with the codon loss segregating with the disease chromosome. Both of these individuals clearly expressed both the normal and disease alleles. Similar results have been observed in RNA from normal individuals, HD heterozygotes and HD homozygotes using the CAG repeat assay.

Expression of the HD mRNA

The pathology of HD appears to be confined to the brain. However, the expression of the IT15 transcript is not confined to this tissue. FIGS. 23 and 24 show a Northern blot survey of 15 adult and 5 fetal tissue RNAs, respectively. Hybridization with an IT15 probe revealed two RNA species that were present in all tissues tested but varied in relative abundance. The size of these RNAs were estimated as 13.5 kb and 10.5 kb with the latter being the more abundant in most tissues. Interestingly, the apparent ratio of larger to the smaller transcript was greatest in fetal and adult brain. By contrast, the larger transcript was barely detectable in adult liver and colon.

The smaller RNA species probably corresponds to the composite cDNA sequence (SEQ ID No:5), and the larger could result either from alternative splicing or from alternative polyadenylation. The SSCP analysis of first strand cDNA had failed to yield any evidence of extensive alternative splicing, and an exon 2 probe detected both RNA species. Therefore, a genomic probe was prepared from the region of cosmid L120D5 located immediately downstream from the sequence at the site of the polyA tail in cDNA clone IT15B (Baxendale, S. et al., Nature Genet. 4:181–186 (1993)). Hybridization of this second probe to the Northern blots is also shown in FIGS. 23 and 24. The extended 3' probe detected only the larger of the two IT15 RNA species suggesting that this transcript arises by use of a downstream polyA addition site. Thus, screening of additional cDNA libraries, particularly from fetal brain, would likely yield a cDNA containing an additional ~3kb of 3' untranslated region contiguous with the current exon 67 sequence.

A balanced translocation disrupting the HD gene

The HD gene search produced a panel of somatic cell hybrid lines dissecting 4p into several regions (Smith, B. et al., Am. J. Hum. Genet. 42:335–344 (1988); Lin, C. S. et al., Somat. Cell Mol. Genet. 17:481–488 (1991)). One of the chromosomes from this panel has a t(4p16.3;12p13.3) with a breakpoint between D4S180 and D4S127 (McKeown, C. et al., J. Med. Genet. 24:410–412 (1987)). To establish whether this chromosome bisects the HD gene, exon probes were hybridized to genomic blots of DNA from a lymphoblast cell line (CV066) with the balanced translocation and from a hybrid line (HHW1071) containing only the region of 4p16.3 between the translocation breakpoint and the 4p telomere as part of the der(12) chromosome. Exons 41–67 are absent from the hybrid, indicating that the breakpoint maps between exons 40 and 41. Indeed, the EcoRI and HindIII fragments containing exon 40 are altered in size in CV066 and in HHW1071 (FIG. 25) positioning the t(4;12) breakpoint within the HD gene as depicted in FIG. 20.

The CV066 lymphoblast line was derived from a balanced carrier of the t(4;12) who was first identified as the mother of a Wolf-Hirschhorn child produced by transmission of only the der(4) chromosome (McKeown, C. et al., J. Med. Genet. 24:410–412 (1987)). Therefore, this woman possesses one intact HD gene which will produce a normal product, and a bisected HD gene which at best could produce a partial protein, or partial fusion protein. This balanced translocation is not associated with any detectable abnormal phenotype either in the woman or in one of her offspring. Thus, heterozygous disruption of the HD gene does not have catastrophic consequences for development or cause juvenile HD. Moreover, this translocation makes it unlikely that the expanded CAG repeat in HD acts by simply inactivating the allele containing it. At age 46, the woman, who possesses only one intact copy of this locus, is already beyond the age of onset of the majority of HD cases and does not display any signs of the disorder. She has also passed the balanced translocation to one offspring who is similarly phenotypically normal.

Discussion

The number of exons comprising the HD gene is one of the highest report to date for any human locus. However, the exons are arrayed across a relatively compact genomic region of 180 kb. The initial identification and detailed analysis of this locus was aided tremendously by the development of the exon amplification procedure (Buckler, A. J. et al., Proc. Natl. Acad. Sci. USA 88:4005–4009 (1991)). Cloned trapped exons provided probes for the isolation of cDNA clones and multiple sequenced, oriented entry points for aligning the cDNA. The knowledge of the cosmid of origin of each trapped exon included in a cDNA clone gave an immediate assessment of genomic coverage, and provided the basis for complete sequence analysis and rapid determination of exon-intron junctions. The fact that 42% of the internal exons susceptible to exon amplification were recovered as cloned segments demonstrates that it is remarkably easy to isolate a significant portion of a gene using this procedure. In fact, only two of several possible enzyme combinations for cloning the genomic DNA were employed. It is likely that many of the exons that were missed could be isolated using an alternative restriction digest with the same vector system. Thus, exon amplification appears to be an excellent means of saturating a particular genomic region with expressed sequences and quickly relating the corresponding transcripts to the physical map.

The HD gene is expressed in every tissue tested to date, with at least two alternative forms that differ in the extent of their 3' untranslated region. There might be alternative splicing of the transcript in some tissues, but RNA-PCR SSCP analysis of lymphoblastoid cell RNA failed to reveal any evidence of alternative forms within the coding sequence. Moreover, the exon trapping did not yield any other putative exons from this region that could be a part of a transcript from these gene. Finally, all of the overlapping cDNAs so far isolated from brain and other tissues have been colinear, except when they contain unspliced intronic sequence. Thus, if alternative splicing occurs it is unlikely to be extensive unless it is restricted to a specific cell type not yet explored.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A purified protein comprising an amino acid sequence corresponding to a mammalian huntingtin protein.

2. The purified protein according to claim 1 having the amino acid sequence shown in SEQ ID NO: 6.

* * * * *